(12) United States Patent
Karp et al.

(10) Patent No.: US 7,645,881 B2
(45) Date of Patent: Jan. 12, 2010

(54) METHODS FOR TREATING HEPATITIS C

(75) Inventors: Gary Mitchell Karp, Princeton Junction, NJ (US); Guangming Chen, Bridgewater, NJ (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 159 days.

(21) Appl. No.: 11/180,779

(22) Filed: Jul. 14, 2005

(65) Prior Publication Data

US 2006/0019976 A1 Jan. 26, 2006

Related U.S. Application Data

(60) Provisional application No. 60/589,876, filed on Jul. 22, 2004.

(51) Int. Cl.
*C07D 513/02* (2006.01)
(52) U.S. Cl. .................................................... 546/114
(58) Field of Classification Search ................... 546/114
See application file for complete search history.

(56) References Cited

U.S. PATENT DOCUMENTS

| | | | |
|---|---|---|---|
| 4,788,206 A | 11/1988 | Guthrie et al. | |
| 4,874,756 A | 10/1989 | Mertens et al. | |
| 5,072,003 A | 12/1991 | Behrend et al. | |
| 5,190,942 A | 3/1993 | Poss | |
| 5,215,980 A | 6/1993 | Jones | |
| 5,217,996 A | 6/1993 | Ksander | |
| 5,354,759 A | 10/1994 | Oku et al. | |
| 5,369,120 A | 11/1994 | Woodruff | |
| 5,413,999 A | 5/1995 | Vacca et al. | |
| 5,474,994 A | 12/1995 | Leonardi et al. | |
| 5,527,819 A | 6/1996 | Williams et al. | |
| 5,559,127 A | 9/1996 | Hartman et al. | |
| 5,605,896 A | 2/1997 | Leonardi et al. | |
| 5,633,388 A | 5/1997 | Diana et al. | |
| 5,639,906 A | 6/1997 | London et al. | |
| 5,681,954 A | 10/1997 | Yamamoto et al. | |
| 5,693,643 A | 12/1997 | Gilbert et al. | |
| 5,714,496 A | 2/1998 | Brown et al. | |
| 5,880,137 A | 3/1999 | Miller et al. | |
| 5,922,898 A | 7/1999 | Miller et al. | |
| 5,958,086 A | 9/1999 | Adam et al. | |
| 5,977,090 A | 11/1999 | Slusher et al. | |
| 5,985,910 A | 11/1999 | Miller et al. | |
| 6,030,785 A | 2/2000 | Katze et al. | |
| 6,057,093 A | 5/2000 | Han et al. | |
| 6,124,311 A | 9/2000 | Chandrasekhar et al. | |
| 6,132,966 A | 10/2000 | Draper | |
| 6,194,599 B1 | 2/2001 | Miller et al. | |
| 6,221,902 B1 | 4/2001 | Malamas et al. | |
| 6,326,392 B1 | 12/2001 | Gast et al. | |
| 6,335,445 B1 | 1/2002 | Chabrier de Lassauniere et al. | |
| 6,358,992 B1 | 3/2002 | Pamukcu et al. | |
| 6,376,529 B1 | 4/2002 | Tang et al. | |
| 6,380,166 B1 | 4/2002 | Miller et al. | |
| 6,384,022 B1 | 5/2002 | Jackson et al. | |
| 6,555,555 B1 | 4/2003 | Konishi et al. | |
| 6,589,570 B1 | 7/2003 | Thyagarajan | |
| 6,589,954 B1 | 7/2003 | Mavunkel et al. | |
| 6,685,931 B1 | 2/2004 | Grint et al. | |
| 6,690,975 B2 | 2/2004 | Yamamoto et al. | |
| 6,974,870 B2 * | 12/2005 | Cywin et al. ................. | 546/114 |
| 2002/0055651 A1 | 5/2002 | Moran et al. | |
| 2002/0091116 A1 | 7/2002 | Zhu et al. | |
| 2002/0099054 A1 | 7/2002 | Conner et al. | |
| 2002/0099080 A1 | 7/2002 | Gagliardi et al. | |
| 2002/0103210 A1 | 8/2002 | Furuya et al. | |
| 2002/0143022 A1 | 10/2002 | Pamukcu et al. | |
| 2002/0169101 A1 | 11/2002 | Gonzalez et al. | |
| 2002/0169107 A1 | 11/2002 | Rajagopalan et al. | |
| 2003/0004119 A1 | 1/2003 | Ganguly et al. | |
| 2003/0050320 A1 | 3/2003 | Hashimoto et al. | |
| 2003/0078420 A1 | 4/2003 | Chabrier de Lassauniere et al. | |
| 2003/0096825 A1 | 5/2003 | Wang et al. | |
| 2003/0176433 A1 | 9/2003 | Beaulieu et al. | |
| 2003/0176697 A1 | 9/2003 | Overman et al. | |
| 2003/0199689 A1 | 10/2003 | Nazare et al. | |
| 2003/0220377 A1 | 11/2003 | Chesworth | |

(Continued)

FOREIGN PATENT DOCUMENTS

CA 2099060 12/1993

(Continued)

OTHER PUBLICATIONS

Leistner et al. STN Accession No. 1992:235578 Document No. 116:235578; Abstract of Pharmazie (1992), 47(1), 11-14.*

(Continued)

*Primary Examiner*—D. Margaret Seaman
*Assistant Examiner*—Nizal S Chandrakumar
(74) *Attorney, Agent, or Firm*—Hoffmann & Baron, LLP

(57) ABSTRACT

In accordance with the present invention, compounds that can inhibit viral replication, preferably Hepatitis C Virus (HCV) replication, have been identified, and methods for their use provided. In one aspect of the invention, compounds useful in the treatment or prevention of a viral infection are provided. In another aspect of the invention, compounds useful in the treatment or prevention of HCV infection are provided.

12 Claims, 1 Drawing Sheet

U.S. PATENT DOCUMENTS

| | | |
|---|---|---|
| 2003/0232866 A1 | 12/2003 | Watterson et al. |
| 2003/0236391 A1 | 12/2003 | Klunk et al. |
| 2004/0044059 A1 | 3/2004 | Pinney et al. |
| 2004/0059131 A1 | 3/2004 | Dell et al. |
| 2004/0067996 A1 | 4/2004 | Sheppeck |
| 2004/0180945 A1 | 9/2004 | Artico et al. |
| 2005/0026969 A1 | 2/2005 | Cheng et al. |
| 2005/0075242 A1 | 4/2005 | Holtcamp et al. |
| 2005/0075384 A1 | 4/2005 | Sheppeck et al. |
| 2005/0085529 A1 | 4/2005 | Brown et al. |
| 2005/0113283 A1 | 5/2005 | Solow-Cordero et al. |
| 2005/0119318 A1 | 6/2005 | Hudyma et al. |
| 2005/0123560 A1 | 6/2005 | Sinnott |
| 2005/0227291 A1 | 10/2005 | Kinsella |

FOREIGN PATENT DOCUMENTS

| | | | |
|---|---|---|---|
| CN | 1333206 A | | 1/2002 |
| DE | 25 26 317 A1 | | 1/1976 |
| DE | 29 09 779 | | 9/1980 |
| DE | 258014 | * | 6/1988 |
| DE | 258015 | * | 6/1988 |
| DE | 258016 | * | 6/1988 |
| DE | 37 06 427 A1 | | 9/1988 |
| DE | 41 39 851 A1 | | 6/1992 |
| DE | 41 29 603 A1 | | 3/1993 |
| DE | 44 37 262 A1 | | 4/1995 |
| DE | 44 37 265 A1 | | 4/1995 |
| DE | 196 48 793 A1 | | 5/1998 |
| DE | 198 38 705 A1 | | 3/2000 |
| DE | 199 46 289 A1 | | 3/2001 |
| EP | 0 196 096 A2 | | 10/1986 |
| EP | 0 290 153 A1 | | 11/1988 |
| EP | 0 318 902 A2 | | 6/1989 |
| EP | 0 387 201 A1 | | 9/1990 |
| EP | 0 406 734 A2 | | 1/1991 |
| EP | 0 414 386 A1 | | 2/1991 |
| EP | 0 425 434 A2 | | 5/1991 |
| EP | 0 427 225 A1 | | 5/1991 |
| EP | 0 430 186 A1 | | 6/1991 |
| EP | 0 436 199 A1 | | 7/1991 |
| EP | 0 471 372 A1 | | 2/1992 |
| EP | 0 480 204 A1 | | 4/1992 |
| EP | 0 488 532 | | 6/1992 |
| EP | 0 497 659 | | 8/1992 |
| EP | 0 527 458 A1 | | 2/1993 |
| EP | 0 527 704 A2 | | 2/1993 |
| EP | 0 528 762 A1 | | 2/1993 |
| EP | 0 530 149 | | 3/1993 |
| EP | 0 548 798 A1 | | 6/1993 |
| EP | 0 553 682 A1 | | 8/1993 |
| EP | 0 556 949 | | 8/1993 |
| EP | 0 558 245 A1 | | 9/1993 |
| EP | 0 502 424 B1 | | 1/1994 |
| EP | 0 586 331 A2 | | 3/1994 |
| EP | 0 617 968 A1 | | 10/1994 |
| EP | 0 622 356 A1 | | 11/1994 |
| EP | 0 624 584 A1 | | 11/1994 |
| EP | 0 628 559 | | 12/1994 |
| EP | 0 630 895 A1 | | 12/1994 |
| EP | 0 639 573 | | 2/1995 |
| EP | 0 657 508 A1 | | 6/1995 |
| EP | 0 697 172 | | 2/1996 |
| EP | 0 708 091 | | 4/1996 |
| EP | 0 714 955 A1 | | 6/1996 |
| EP | 0 716 855 A2 | | 6/1996 |
| EP | 0 719 837 A2 | | 7/1996 |
| EP | 0 802 183 | | 10/1997 |
| EP | 0 802 184 | | 10/1997 |
| EP | 0 826 743 A2 | | 3/1998 |
| EP | 1 118 323 | | 7/2001 |
| EP | 1 120 114 | | 8/2001 |
| EP | 1 125 582 | | 8/2001 |
| EP | 1 149 579 | | 10/2001 |
| EP | 1 177 787 | | 2/2002 |
| EP | 1 192 945 | | 4/2002 |
| EP | 1 199 069 | | 4/2002 |
| EP | 1 226 823 | | 7/2002 |
| EP | 1 314 733 A1 | | 5/2003 |
| EP | 1 457 485 A1 | | 9/2004 |
| EP | 1 532 980 | | 5/2005 |
| EP | 1 574 502 A1 | | 9/2005 |
| FR | 2 854 159 | | 10/2004 |
| FR | 2 865 208 | | 7/2005 |
| GB | 2 282 808 A | | 4/1995 |
| GB | 2 292 149 A | | 2/1996 |
| JP | 57-085055 A2 | | 5/1982 |
| JP | 01273040 | | 10/1989 |
| JP | 3-32801 | | 2/1991 |
| JP | 3-43744 | | 2/1991 |
| JP | 4-319959 | | 11/1992 |
| JP | 5-58997 | | 3/1993 |
| JP | 06-236010 | | 8/1994 |
| JP | 6-306077 | | 11/1994 |
| JP | 8-157461 | | 6/1996 |
| JP | 8-183260 | | 7/1996 |
| JP | 8-244353 | | 9/1996 |
| JP | 9-20083 | | 1/1997 |
| JP | 9-169729 | | 6/1997 |
| JP | 9-258399 | | 10/1997 |
| JP | 10-45512 | | 2/1998 |
| JP | 11-302177 | | 11/1999 |
| JP | 2000-63354 | | 2/2000 |
| JP | 2001-55332 | | 2/2001 |
| JP | 2001-64166 | | 3/2001 |
| JP | 2001-64205 | | 3/2001 |
| JP | 2001-151751 | | 6/2001 |
| JP | 2001-206845 | | 7/2001 |
| JP | 2001-242165 | | 9/2001 |
| JP | 3246259 | | 11/2001 |
| JP | 2002-3368 | | 1/2002 |
| JP | 2002105081 | * | 4/2002 |
| JP | 2003-300875 | | 10/2003 |
| JP | 2004-61583 | | 2/2004 |
| JP | 2004-327313 | | 11/2004 |
| JP | 2005-2346 | | 1/2005 |
| JP | 2005-82701 | | 3/2005 |
| JP | 2005-194198 | | 7/2005 |
| JP | 2005194198 | | 7/2005 |
| JP | 2005-225872 | | 8/2005 |
| KR | 93-12108 | | 12/1993 |
| WO | WO 92/15579 | | 9/1992 |
| WO | 93/14758 | | 8/1993 |
| WO | WO 93/18030 | | 9/1993 |
| WO | WO 93/18765 | | 9/1993 |
| WO | WO 93/18766 | | 9/1993 |
| WO | WO 93/19067 | | 9/1993 |
| WO | WO 94/04153 | | 3/1994 |
| WO | WO 94/04535 | | 3/1994 |
| WO | WO 94/08583 | | 4/1994 |
| WO | WO 94/08962 | | 4/1994 |
| WO | WO 94/11378 | | 5/1994 |
| WO | WO 94/14435 | | 7/1994 |
| WO | WO 94/14438 | | 7/1994 |
| WO | WO 94/14763 | | 7/1994 |
| WO | WO 94/14771 | | 7/1994 |
| WO | WO 94/26746 | | 11/1994 |
| WO | WO 95/02583 | | 1/1995 |
| WO | WO 95/07910 | | 3/1995 |
| WO | WO 95/14003 | | 5/1995 |
| WO | WO 95/32710 | | 12/1995 |
| WO | WO 95/33720 | | 12/1995 |
| WO | WO 96/10012 | | 4/1996 |
| WO | WO 96/16054 | | 5/1996 |

| | | | | | | |
|---|---|---|---|---|---|---|
| WO | WO 96/26207 | 8/1996 | | WO | WO 02/30879 A2 | 4/2002 |
| WO | WO 96/32379 | 10/1996 | | WO | WO 02/36203 A2 | 5/2002 |
| WO | WO 96/40650 | 12/1996 | | WO | WO 02/36562 | 5/2002 |
| WO | WO 96/41800 | 12/1996 | | WO | WO 02/36580 A2 | 5/2002 |
| WO | WO 97/14419 | 4/1997 | | WO | WO 02/42292 | 5/2002 |
| WO | WO 97/45410 | 4/1997 | | WO | WO 02/48099 A1 | 6/2002 |
| WO | WO 98/13044 | 4/1998 | | WO | WO 02/051805 A1 | 7/2002 |
| WO | WO 98/22457 | 5/1998 | | WO | WO 02/053534 A1 | 7/2002 |
| WO | WO 98/25883 | 6/1998 | | WO | WO 02/055496 A1 | 7/2002 |
| WO | WO 98/48797 | 11/1998 | | WO | WO 02/059088 | 8/2002 |
| WO | WO 99/06836 | 2/1999 | | WO | WO 02/059120 | 8/2002 |
| WO | WO 99/11634 | 3/1999 | | WO | WO 02/060374 A2 | 8/2002 |
| WO | WO 99/13714 | 3/1999 | | WO | WO 02/060447 A1 | 8/2002 |
| WO | WO 99/18096 | 4/1999 | | WO | WO 02/066477 A2 | 8/2002 |
| WO | WO 99/23072 | 5/1999 | | WO | WO 02/070462 A1 | 9/2002 |
| WO | WO 99/24027 | 5/1999 | | WO | WO 02/070469 A2 | 9/2002 |
| WO | WO 99/26946 | 6/1999 | | WO | WO 02/070510 A2 | 9/2002 |
| WO | WO 99/33849 | 7/1999 | | WO | WO 02/072549 | 9/2002 |
| WO | WO 99/43651 | 9/1999 | | WO | WO 02/074742 | 9/2002 |
| WO | WO 99/50237 | 10/1999 | | WO | WO 02/076926 | 10/2002 |
| WO | WO 99/58520 | 11/1999 | | WO | WO 02/083134 A1 | 10/2002 |
| WO | WO 99/59581 | 11/1999 | | WO | WO 02/053545 A1 | 11/2002 |
| WO | WO 99/59969 | 11/1999 | | WO | WO 02/053565 A1 | 11/2002 |
| WO | WO 99/61426 | 12/1999 | | WO | WO 02/089811 | 11/2002 |
| WO | WO 99/64035 | 12/1999 | | WO | WO 02/096426 A1 | 12/2002 |
| WO | WO 99/64415 | 12/1999 | | WO | WO 02/098424 | 12/2002 |
| WO | WO 00/15645 | 3/2000 | | WO | WO 03/000254 A1 | 1/2003 |
| WO | WO 00/28991 | 5/2000 | | WO | WO 03/000690 A1 | 1/2003 |
| WO | WO 00/29384 | 5/2000 | | WO | WO 03/004458 A1 | 1/2003 |
| WO | WO 00/35886 | 6/2000 | | WO | WO 03/005025 A1 | 1/2003 |
| WO | WO 00/43393 | 7/2000 | | WO | WO 03/006447 A2 | 1/2003 |
| WO | 00/61586 | 10/2000 | | WO | 03/010140 A2 | 2/2003 |
| WO | WO 00/73269 A2 | 12/2000 | | WO | WO 03/010141 | 2/2003 |
| WO | WO 01/19798 A2 | 3/2001 | | WO | WO 03/022214 A2 | 3/2003 |
| WO | WO 01/19839 | 3/2001 | | WO | WO 03/048101 A1 | 6/2003 |
| WO | WO 01/21589 A2 | 3/2001 | | WO | WO 03/053359 A2 | 7/2003 |
| WO | WO 01/21609 | 3/2001 | | WO | WO 03/053368 A2 | 7/2003 |
| WO | WO 01/23353 | 4/2001 | | WO | WO 03/053938 A1 | 7/2003 |
| WO | WO 01/23390 A2 | 4/2001 | | WO | WO 03/053941 A2 | 7/2003 |
| WO | WO 01/44182 | 6/2001 | | WO | WO 03/055447 A2 | 7/2003 |
| WO | WO 01/47883 A1 | 7/2001 | | WO | WO 03/059269 A2 | 7/2003 |
| WO | WO 01/55111 A1 | 8/2001 | | WO | WO 03/062392 A2 | 7/2003 |
| WO | WO 01/55136 | 8/2001 | | WO | WO 03/064539 A1 | 8/2003 |
| WO | WO 01/55137 | 8/2001 | | WO | WO 03/066629 A2 | 8/2003 |
| WO | WO 01/55138 | 8/2001 | | WO | WO 03/074047 | 9/2003 |
| WO | WO 01/55139 | 8/2001 | | WO | WO 03/082265 | 10/2003 |
| WO | WO 01/55144 | 8/2001 | | WO | WO 03/087092 | 10/2003 |
| WO | WO 01/58859 A1 | 8/2001 | | WO | WO 03/091211 | 11/2003 |
| WO | WO 01/64678 A2 | 9/2001 | | WO | WO 03/097036 A1 | 11/2003 |
| WO | WO 01/68585 A1 | 9/2001 | | WO | WO 03/099276 A1 | 12/2003 |
| WO | WO 01/74773 A2 | 10/2001 | | WO | WO 2004/003103 A1 | 1/2004 |
| WO | WO 01/83451 A1 | 11/2001 | | WO | WO 2004/012736 A1 | 2/2004 |
| WO | WO 01/85687 A1 | 11/2001 | | WO | WO 2004/013135 | 2/2004 |
| WO | WO 01/90105 | 11/2001 | | WO | WO 2004/014912 | 2/2004 |
| WO | WO 02/00651 A2 | 1/2002 | | WO | WO 2004/022057 A1 | 3/2004 |
| WO | WO 02/03975 | 1/2002 | | WO | WO 2004/024060 A2 | 3/2004 |
| WO | WO 02/03976 | 1/2002 | | WO | WO 2004/024655 A2 | 3/2004 |
| WO | WO 02/03977 | 1/2002 | | WO | WO 2004/024896 A2 | 3/2004 |
| WO | WO 02/03986 | 1/2002 | | WO | WO 2004/030630 | 4/2004 |
| WO | WO 02/03987 | 1/2002 | | WO | WO 2004/035047 A1 | 4/2004 |
| WO | WO 02/03988 | 1/2002 | | WO | WO 2004/035522 A1 | 4/2004 |
| WO | WO 02/03989 | 1/2002 | | WO | WO 2004/035525 A1 | 4/2004 |
| WO | WO 02/03990 | 1/2002 | | WO | WO 2004/035571 | 4/2004 |
| WO | WO 02/03991 | 1/2002 | | WO | WO 2004/037788 | 5/2004 |
| WO | WO 02/03992 | 1/2002 | | WO | WO 2004/037791 A1 | 5/2004 |
| WO | WO 02/04418 | 1/2002 | | WO | WO 2004/041256 | 5/2004 |
| WO | WO 02/06226 A1 | 1/2002 | | WO | WO 2004/041781 A1 | 5/2004 |
| WO | WO 02/13802 | 2/2002 | | WO | 2004/050035 A2 | 6/2004 |
| WO | WO 02/16333 A2 | 2/2002 | | WO | WO 2004/064759 | 8/2004 |
| WO | WO 02/16353 | 2/2002 | | WO | WO 2004/064925 | 8/2004 |
| WO | WO 02/26696 A1 | 4/2002 | | WO | WO 2004/065367 | 8/2004 |
| WO | WO 02/26703 A1 | 4/2002 | | WO | WO 2004/074447 | 9/2004 |
| WO | WO 02/30358 | 4/2002 | | WO | WO 2004/082638 | 9/2004 |

| | | |
|---|---|---|
| WO | WO 2004/083195 A1 | 9/2004 |
| WO | WO 2004/087714 A1 | 10/2004 |
| WO | WO 2004/093871 | 11/2004 |
| WO | WO 2004/093912 A1 | 11/2004 |
| WO | WO 2004/094409 | 11/2004 |
| WO | WO 2004/096210 | 11/2004 |
| WO | WO 2004/099168 A2 | 11/2004 |
| WO | WO 2004/099170 A2 | 11/2004 |
| WO | WO 2004/099171 A2 | 11/2004 |
| WO | WO 2004/099192 A2 | 11/2004 |
| WO | WO 2004/099239 A1 | 11/2004 |
| WO | WO 2004/111056 A2 | 12/2004 |
| WO | WO 2005/003086 A2 | 1/2005 |
| WO | WO 2005/003131 A1 | 1/2005 |
| WO | WO 2005/009389 | 2/2005 |
| WO | WO 2005/013950 A2 | 2/2005 |
| WO | WO 2005/013976 | 2/2005 |
| WO | WO 2005/013977 | 2/2005 |
| WO | WO 2005/014000 | 2/2005 |
| WO | WO 2005/014045 | 2/2005 |
| WO | WO 2005/014543 A1 | 2/2005 |
| WO | WO 2005/016862 A1 | 2/2005 |
| WO | WO 2005/018531 | 3/2005 |
| WO | WO 2005/020899 A2 | 3/2005 |
| WO | WO 2005/020921 A1 | 3/2005 |
| WO | WO 2005/021505 | 3/2005 |
| WO | WO 2005/028502 | 3/2005 |
| WO | WO 2005/034941 | 4/2005 |
| WO | WO 2005/034943 | 4/2005 |
| WO | WO 2005/039489 A2 | 5/2005 |
| WO | WO 2005/042018 | 5/2005 |
| WO | WO 2005/055940 A2 | 6/2005 |
| WO | WO 2005058312 A1 * | 6/2005 |
| WO | WO 2005/061519 A1 | 7/2005 |
| WO | WO 2005/062676 A1 | 7/2005 |
| WO | WO 2005/066180 A1 | 7/2005 |
| WO | 2005/076861 A2 | 8/2005 |
| WO | WO 2005/072132 A2 | 8/2005 |
| WO | WO 2005/077122 A2 | 8/2005 |
| WO | WO 2005/077969 | 8/2005 |
| WO | WO 2005/080335 | 9/2005 |
| WO | WO 2005/080388 A1 | 9/2005 |
| WO | WO 2005/082895 A1 | 9/2005 |
| WO | WO 2005/082905 A1 | 9/2005 |
| WO | WO 2005/086754 A2 | 9/2005 |
| WO | WO 2005/090282 | 9/2005 |
| WO | WO 2005/092855 | 10/2005 |
| WO | WO 2005/107747 | 11/2005 |
| WO | WO 2005/112519 | 11/2005 |
| WO | WO 2005/113529 | 12/2005 |
| WO | WO 2006/024699 | 3/2006 |
| WO | WO 2006/041874 | 4/2006 |
| WO | WO 2006/049013 | 5/2006 |
| WO | WO 2006/050236 | 5/2006 |
| WO | WO 2006/057354 | 6/2006 |
| WO | WO 2006/083458 | 8/2006 |

OTHER PUBLICATIONS

Bohm et al. STN Accession No. 1992:235578 Document No. 116:235578; Abstract of Pharmazie (1992) 47(12), 897-901.*
Elgemeie et. al. STN Accession No. 1994:54466 Document No. 120:54466; Abstract of Journal of Chemical Research, Synopses (1993), (7), 256-7).*
Frolova et al. STN Accession No. 1996:396582 Document No. 125:167833; Abstract of Izvestiya Akademii Nauk, Seriya Khimicheskaya (1996),(4), 938-942.*
Dyachenko et. al. STN Accession No. 1996:756686 Document No. 126:74777; Abstract of Khimiya Geterotsiklicheskikh Soedinenii (1996), (9), 1232-1234.*
Frolova et. al. STN Accession No. 1997:73192 Document No. 126:131360; Abstract of Izvestiya Akademii Nauk, Seriya Khimicheskaya (1996),(11), 2719-2721.*

Quintela et al. STN Accession No. 2003:236103 Document No. 139:197457; Abstract of Journal of Medicinal Chemistry (1999), 42(22), 4720-4724.*
Al-Omran, STN Accession No. 2000:825367 Document No. 134:131488; Abstract of Journal of Heterocyclic Chemistry (2000), 37(5), 1219-1223.*
Paronikyan et al. STN Accession No. 1998:173599 Document No. 128:243969; Abstract of Khimiko-Farmatsevticheskii Zhurnal (1997), 31(10), 34-36.*
Sharanin et. al. STN Accession No. 1985:113330 Document No. 102:113330; Abstract of Zhurnal Organicheskoi Khimii (1984), 20(9), Nov. 2002.*
Vieweg et al. STN Accession #: 1993:449330, Document #: 119:49330, Abstract of Pharmazie (1993), 48(1), 26-30.*
Baronikyan et al. STN Accession No. 2003:74658 Document No. 1139:292172. Abstract of Hayastani Kimiakan Handes (2002), 55(4), 67-71 Coden: KZARF3; ISSN: 1561-4190.*
Leistner et al. STN Accession No. 1993:80893; Document No. 118:80893. Abstract of Pharmazie (1992), 47(9), 682-6).*
Leistner et al. STN Accession No. 1992:235578; Document No. 116:235578. Abstract of Pharmazie (1992), 47(1), 11-14.*
Attaby et al., "Synthesis and Antimicrobial Evaluation of Several New Pyridine, Thienopyridine and Pyridothienopyrazole Derivatives", *Phosphorus, Sulfur and Silicon*, 149:49-64 (1999).
International Search Report, PCT/US2005/024882 (mailed Jan. 17, 2006).
Perola et al., "Successful Virtual Screening of a Chemical Database for Farnesyltransferase Inhibitor Leads", *J. Med. Chem.*, 43(3):401-408 (2000).
Ali et al., "Human La Antigen is Required for the Hepatitis C Virus Internal Ribosome Entry Site-mediated Translation", *J Biol Chem*, 275(36):27531-27540 (2000).
Ali et al., "Interaction of Polypyrimidine Tract-Binding Protein with the 5' Noncoding Region of the Hepatitis C Virus RNA Genome and its Functional Requirement in Internal Initiation of Translation", *J Virol*, 69(10):6367-6375 (1995).
Ali et al., "The La Antigen Binds 5' Noncoding Region of the Hepatitis C Virus RNA in the Context of the Initiator AUG Codon and Stimulates Internal Ribosome Entry Site-Mediated Translation", *Proc Natl Acad Sci USA*, 94:2249-2254 (1997).
Anwar et al., "Demonstration of Functional Requirement of Polypyrimidine Tract-binding Protein by SELEX RNA during Hepatitis C Virus Internal Ribosome Entry Site-mediated Translation Initiation", *J Biol Chem*, 275(44):34231-34235 (2000).
Beales et al., "The Internal Ribosome Entry Site (IRES) of Hepatitis C Virus Visualized by Electron Microscopy", *RNA*, 7:661-670 (2001).
Belsham et al., "A Region of the 5' Noncoding Region of Foot-and-Mouth Disease Virus RNA Directs Efficient Internal Initiation of Protein Synthesis within Cells: Involvement with the Role of L Protease in Translational Control", *J Virol*, 64(11):5389-5395 (1990).
Belsham et al., "Translation Initiation on Picornavirus RNA", p. 869-900, Cold Spring Harbor Laboratory Press, New York (2000).
Blight et al., "Efficient Initiation of HCV RNA Replication in Cell Culture", *Science*, 290:1972-1974 (2000).
Blight et al., "Highly Permissive Cell Lines for Subgenomic and Genomic Hepatitis C Virus RNA Replication", *J Virol*, 76(24):13001-13014 (2002).
Boni et al., "Hepatitis C Virus Core Protein Acts as a *trans*-Modulating Factor on Internal Translation Initiation of the Viral RNA", *J Biol Chem*, 280(18):17737-17748 (2005).
Borovjagin et al., "Pyrimidine Tract Binding Protein Strongly Stimulates in vitro Encephalomyocarditis Virus RNA Translation at the Level of the Preinitiation Complex Formation" *FEBS Lett*, 351:291-302 (1994).
Brown et al., "Secondary Structure of the 5' Nontranslated Regions of Hepatitis C Virus and Pestivirus Genomic RNAs", *Nucleic Acids Res*, 20(19):5041-5045 (1992).
Buck et al., "The Human Immunodeficiency Virus Type 1 *gag* Gene Encodes an Internal Ribosome Entry Site", *J Virol*, 75(1):181-191 (2001).
Bukh et al. "Sequence Analysis of the 5' Noncoding Region of Hepatitis C Virus", *Proc Natl Acad Sci USA*, 89:4942-4946 (1992).

Bukh et al., "Sequence Analysis of the Core Gene of 14 Hepatitis C Virus Genotypes", *Proc Natl Acad Sci USA*, 91:8239-8243 (1994).

Buratti et al., "Functional Analysis of the Interaction Between HCV 5'UTR and Putative Subunits of Eukaryotic Translation Initiation Factor eIF3", *Nucleic Acids Res*, 26(13)3179-3187 (1998).

Chappell et al., "A Mutation in the c-*myc*-IRES Leads to Enhanced Internal Ribosome Entry in Multiple Myeloma: A Novel Mechanism of Oncogene De-Regulation", *Oncogene*, 19:4437-4440 (2000).

Chung et al., "Hepatitis C Virus Replication is Directly Inhibited by IFN-α in a Full-Length Binary Expression System", *Proc Natl Acad Sci USA*, 98(17):9847-9852 (2001).

Coldwell et al., "Initiation of Apaf-1 Translation by Internal Ribosome Entry", *Oncogene*, 19:899-905 (2000).

Créancier et al., "Fibroblast Growth Factor 2 Internal Ribosome Entry Site (IRES) Activity Ex Vivo and in Transgenic Mice Reveals a Stringent Tissue-specific Regulation", *J Cell Biol*, 150(1):275-281 (2000).

Das et al., "Inhibition of Internal Entry Site (IRES)-Mediated Translation by a Small Yeast RNA: a Novel Strategy to Block Hepatitis C Virus Protein Synthesis" *Front Biosci*, (3)d1241-1252 (1998).

Dever, "Gene-Specific Regulation by General Translation Factors", *Cell*, 108:545-556 (2002).

Dumas et al., "A Promoter Activity is Present in the DNA Sequence Corresponding to the Hepatitis C Virus 5' UTR", *Nucleic Acids Res*, 31(4):1275-1281 (2003).

Fukushi et al., "Complete 5' Noncoding Region is Necessary for the Efficient Internal Initiation of Hepatitis C Virus RNA", *Biochem Biophys. Res Commun.*, 199(2):425-432 (1994).

Fukushi et al., "The Sequence Element of the Internal Ribosome Entry Site and a 25-Kilodalton Cellular Protein Contribute to Efficient Internal Initiation of Translation of Hepatitis C Virus RNA", *J Virol*, 71(2):1662-1666 (1997).

Fukushi et al., "Specific Interaction of a 25-Kilodalton Cellular Protein, a 40S Ribosomal Subunit Protein, with the Internal Ribosome Entry Site of Hepatitis C Virus Genome", *Virus Genes*, 19(2):153-161 (1999).

Fukushi et al., "Ribosomal Protein S5 Interacts with the Internal Ribosomal Entry Site of Hepatitis C Virus", *J Biol Chem*, 276(24):20824-20826 (2001).

Funkhouser et al., "Hepatitis A Virus Translation is Rate-Limiting for Virus Replication in MRC-5 Cells", *Virology*, 254:268-278 (1999).

Glass et al., "Identification of the Hepatitis A Virus Internal Ribosome Entry Site: In vivo and in vitro Analysis of Bicistronic RNAs Containing the HAV 5' Noncoding Region", *Virology*, 193:842-852 (1993).

Gordon et al., "A Phase II, 12-Week Study of ISIS 14803, an Antisense Inhibitor of HCV for the Treatment of Chronic Hepatitis C" AASLD Abst., 795, *Hepatology*, 36:362A (2002).

Gosert et al., "Transient Expression of Cellular Polypyrimidine-Tract Binding Protein Stimulates Cap-Independent Translation Directed by Both Picornaviral and Flaviviral Internal Ribosome Entry Sites In Vivo", *Mol Cell Biol*, 20(5):1583-1595 (2000).

Gray et al., "Control of Translation Initiation in Animals", *Annu Rev Cell Dev Biol*, 14:399-458 (1998).

Griffith et al., "An Unusual Internal Ribosome Entry Site in the Herpes Simplex Virus Thymidine Kinase Gene", *Proc Natl Acad Sci USA*, 102(27):9667-72 (2005).

Guo et al., "Effect of Alpha Interferon on the Hepatitis C Virus Replicon", *J Virol*, 75(18):8516-8523 (2001).

Hahm et al., "Heterogeneous Nuclear Ribonucleoprotein L Interacts with the 3' Border of the Internal Ribosomal Entry Site of Hepatitis C Virus", *J Virol*, 72(11):8782-8788 (1998).

Haller et al., "Attenuation Stem-Loop Lesions in the 5' Noncoding Region of Poliovirus RNA: Neuronal Cell-Specific Translation Defects", *J Virol*, 70(3):1467-1474 (1996).

He et al., "The Regulation of Hepatitis C Virus (HCV) Internal Ribosome-Entry Site-Mediated Translation by HCV Replicons and Nonstructural Proteins", *J Gen Virol*, 84:535-543 (2003).

Hellen et al., "Translation of Hepatitis C Virus RNA", *J Viral Hepat*, 6:79-87 (1999).

Hellen et al., "A Cytoplasmic 57-kDa Protein that is Required for Translation of Picornavirus RNA by Internal Ribosomal Entry is Identical to the Nuclear Pyrimidine Tract-Binding Protein", *Proc Natl Acad Sci USA*, 90:7642-7646 (1993).

Hendrix et al., "Direct Observation of Aminoglycoside-RNA Interactions by Surface Plasmon Resonance" *Journal of the American Chemical Society*, 119(16):3641-8 (1997).

Holcik et al., "Functional Characterization of the X-Linked Inhibitor of Apoptosis (XIAP) Internal Ribosome Entry Site Element: Role of La Autoantigen in XIAP Translation", *Mol Cell Biol*, 20(13):4648-4657 (2000).

Holcik et al., "A new Internal-Ribosome-Entry-Site Motif Potentiates XIAP-Mediated Cytoprotection", *Nat Cell Biol*, 1:190-192 (1999).

Honda et al., "A Phylogenetically Conserved Stem-Loop Structure at the 5' Border of the Internal Ribosome Entry Site of Hepatitis C Virus is Required for Cap-Independent Viral Translation", *J Virol*, 73(2):1165-1174 (1999).

Honda et al., "Stability of a Stem-Loop Involving the Initiator AUG Controls the Efficiency of Internal Initiation of Translation on Hepatitis C Virus RNA", *RNA*, 2:955-968 (1996).

Honda et al., "Structural Requirements for Initiation of Translation by Internal Ribosome Entry within Genome-Length Hepatitis C Virus RNA", *Virology*, 222:31-42 (1996).

Honda et al., "Natural Variation in Translational Activities of the 5' Nontranslated RNAs of Hepatitis C Virus Genotypes 1a and 1b: Evidence for a Long-Range RNA-RNA Interaction Outside of the Internal Ribosomal Entry Site", *J Virol*, 73(6):4941-4951 (1999).

Huez et al., "New Vascular Endothelial Growth Factor Isoform Generated by Internal Ribosome Entry Site-Driven CUG Translation Initiation", *Mol Endocrinol.*, 15(12):2197-2210 (2001).

Huez et al., "Two Independent Internal Ribosome Entry Sites Are Involved in Translation Initiation of Vascular Endothelial Growth Factor mRNA", *Mol Cell Biol*, 18(11):6178-6190 (1998).

Ikeda et al., "Selectable Subgenomic and Genome-Length Dicistronic RNAs Derived from an Infectious Molecular Clone of the HCV-N Strain of Hepatitis C Virus Replicate Efficiently in Cultured Huh7 Cells" *J Virol*, 76(6):2997-3006 (2002).

Irvine et al., "MDCK (Madin-Darby Canine Kidney) Cells: A Tool for Membrane Permeability Screening", *J Pharm Sci*, 88(1):28-33 (1999).

Isoyama et al., "Lower Concentration of La Protein Required for Internal Ribosome Entry on Hepatitis C Virus RNA than on Poliovirus RNA", *J Gen Virol*, 80(9):2319-2327 (1999).

Ito et al., "An Internal Polypyrimidine-Tract-Binding Protein-Binding Site in the Hepatitis C Virus RNA Attenuates Translation, Which is Relieved by the 3'-Untranslated Sequence", *Virology* 254:288-296 (1999).

Jang et al., "A Segment of the 5' Nontranslated Region of Encephalomyocarditis Virus RNA Directs Internal Entry of Ribosomes during In Vitro Translation", *J Virol*, 62(8):2636-2643 (1988).

Jubin et al., "Hepatitis C Virus Internal Ribosome Entry Site (IRES) Stem Loop IIId Contains a Phylogenetically Conserved GGG Triplet Essential for Translation and IRES Folding", *J Virol*, 74(22):10430-10437 (2000).

Kalliampakou et al., "Mutational Analysis of the Apical Region of Domain II of the HCV IRES", *FEBS Lett*, 511:79-84 (2002).

Kaminski et al., "Direct Evidence that Polypyrimidine Tract Binding Protein (PTB) is Essential for Internal Initiation of Translation of Encephalomyocarditis Virus RNA", *RNA*, 1:924-938 (1995).

Kamoshita et al., "Genetic Analysis of Internal Ribosomal Entry Site on Hepatitis C Virus RNA: Implication for Involvement of the Highly Ordered Structure and Cell Type-Specific Transacting Factors", *Virology*, 233:9-18 (1997).

Kato et al., "Hepatitis C Virus NS4A and NS4B Proteins Suppress Translation In Vivo", *J Med Virol*, 66:187-199 (2002).

Kieft et al., "The Hepatitis C Virus Internal Ribosome Entry Site Adopts an Ion-dependent Tertiary Fold", *J Mol Biol*, 292:513-529 (1999).

Kieft et al., "Mechanism of Ribosome Recruitment by Hepatitis C IRES RNA", *RNA*, 7:194-206 (2001).

Klinck et al., "A Potential RNA Drug Target in the Hepatitis C Virus Internal Ribosomal Entry Site", *RNA*, 6:1423-1431 (2000).

Kolupaeva et al., "An Enzymatic Footprinting Analysis of the Interaction of 40S Ribosomal Subunits with the Internal Ribosomal Entry Site of Hepatitis C Virus", *J Virol*, 74(14):6242-6250 (2000).

Kolupaeva et al., "Structural Analysis of the Interaction of the Pyrimidine Tract-Binding Protein with the Internal Ribosomal Entry Site of Encephalomyocarditis Virus and Foot-and-Mouth Disease Virus RNAs", *RNA*, 2:1199-1212 (1996).

Kolupaeva et al., "Translation Eukaryotic Initiation Factor 4G Recognizes a Specific Structural Element within the Internal Ribosome Entry Site of Encephalomyocarditis Virus RNA", *J Biol Chem*, 273(29):18599-18604 (1998).

Kozak, "Initiation of Translation in Prokaryotes and Eukaryotes", *Gene*, 234:187-208 (1999).

Krüger et al., "Involvement of Proteasome α-Subunit PSMA7 in Hepatitis C Virus Internal Ribosome Entry Site-Mediated Translation", *Mol Cell Biol*, 21(24): 8357-8364 (2001).

La Monica et al., "Differences in Replication of Attenuated and Neurovirulent Polioviruses in Human Neuroblastoma Cell Line SH-SY5Y", *J Virol*, 63(5):2357-2360 (1989).

Le et al., "Unusual Folding Regions and Ribosome Landing Pad within Hepatitis C Virus and Pestivirus RNAs", *Gene*, 154:137-143 (1995).

Lerat et al., "Cell Type-Specific Enhancement of Hepatitis C Virus Internal Ribosome Entry Site-Directed Translation due to 5' Nontranslated Region Substitutions Selected during Passage of Virus in Lymphoblastoid Cells", *J Virol*, 74(15):7024-7031 (2000).

Li et al., "A Heterocyclic Inhibitor of the Rev-RRE Complex Binds to RRE as a Dimer", *Biochemistry*, 40:1150-1158 (2001).

Li et al., "Amino Acids 1-20 of the Hepatitis C Virus (HCV) Core Protein Specifically Inhibit HCV IRES-Dependent Translation in HepG2 Cells, and Inhibit Both HCV IRES- and Cap-Dependent Translation in HuH7 and CV-1 Cells", *J Gen Virol*, 84:815-825 (2003).

Lipinski, "Drug-Like Properties and the Causes of Poor Solubility and Poor Permeability", *J Pharm Tox Meth*, 44:235-249 (2000).

Llinàs-Brunet, "NS3 Serine Protease Inhibitors as Potential Antiviral Agents for the Treatment of Hepatitis C Virus Infections", The 3rd Internatl Antiviral & Vaccine Discovery & Development Summit, Princeton, NJ (Mar. 13-14, 2002).

Lohmann et al., "Mutations in Hepatitis C Virus RNAs Conferring Cell Culture Adaptation", *J Virol*, 75(3):1437-1449 (2001).

Lohmann et al., "Replication of Subgenomic Hepatitis C Virus RNAs in a Hepatoma Cell Line", *Science*, 285:110-113 (1999).

Lopez et al., "IRES Interaction with Translation Initiation Factors: Functional Characterization of Novel RNA Contacts with eIF3, eIF4B, and eIF4GII", *RNA*, 7:1213-1226 (2001).

Lopez et al., "Interaction of the eIF4G Initiation Factor with the Aphthovirus IRES is Essential for Internal Translation Initiation In Vivo", *RNA*, 6:1380-1392 (2000).

Lu et al., "Poliovirus Chimeras Replicating Under the Translational Control of Genetic Elements of Hepatitis C Virus Reveal Unusual Properties of the Internal Ribosomal Entry Site of Hepatitis C Virus", *Proc Natl Acad Sci USA*, 93:1412-1417 (1996).

Lukavsky et al., "Structures of Two RNA Domains Essential for Hepatitis C Virus Internal Ribosome Entry Site Function", *Nat Struct Bio*, 7(12):1105-1110 (2000).

Lyons et al., "Hepatitis C Virus Internal Ribosome Entry Site RNA Contains a Tertiary Structural Element in a Functional Domain of Stem-Loop II", *Nucleic Acids Res*, 29(12):2535-2541 (2001).

Lukavsky et al., "Structure of HCV IRES Domain II Determined by NMR", *Nat Struct Biol*, 10(12):1033-1038 (2003).

Macejak et al., "Inhibition of Hepatitis C Virus (HCV)-RNA-Dependent Translation and Replication of a Chimeric HCV Poliovirus Using Synthetic Stabilized Ribozymes", *Hepatology*, 31:769-76 (2000).

Macejak et al., "Enhanced Antiviral Effect in Cell Culture of Type I Interferon and Ribozymes Targeting HCV RNA", *J Viral Hepatitis*, 8:400-405 (2001).

Macejak et al., "Internal Initiation of Translation Mediated by the 5' Leader of a Cellular mRNA", *Nature*, 353:90-94 (1991).

Major et al., "Hepatitis C Viruses.", p. 1127-1161. In D. Knipe and P. Howley (eds.), Fields Virology, vol. 1, 4th Ed. Lippincott Williams and Wilkins, Philadelphia, PA (2001).

Manns et al., "Peginterferon alfa-2b Plus Ribavirin Compared with Interferon Alfa-2b Plus Ribavirin for Initial Treatment of Chronic Hepatitis C: A Randomised Trial", *The Lancet*, 358:958-965 (2001).

Martinez-Salas et al., "Functional Interactions in Internal Translation Initiation Directed by Viral and Cellular IRES Elements", *J Gen Virol*, 82:973-984 (2001).

Mazur et al., "A Thermodynamic and Structural Analysis of DNA Minor-groove Complex Formation", *J Mol Biol*, 300:321-337 (2000).

McHutchison et al., "Combination Therapy With Interferon Plus Ribavirin for the Initial Treatment of Chronic Hepatitis C", *Semin Liver Dis*, 19 Suppl 1:57-65 (1999).

McHutchison et al., "Hepatic HCV RNA Before and After Treatment With Interferon Alone or Combined With Ribavirin", *Hepatology*, 35(3):688-693 (2002).

Meerovitch et al., "A Cellular Protein that Binds to the 5'-Noncoding Region of Poliovirus RNA: Implications for Internal Translation Initiation", *Genes Dev*, 3:1026-1034 (1989).

Meerovitch et al., "La Autoantigen Enhances and Corrects Aberrant Translation of Poliovirus RNA in Reticulocyte Lysate", *J Virol*, 67(7): 3798-3807 (1993).

Mercer et al., "Hepatitis C Virus Replication in Mice with Chimeric Human Livers", *Nature Medicine*, 7(8):927-933 (2001).

Michel et al., "Eukaryotic Initiation Factor 4G-Poly(A) Binding Protein Interaction Is Required for Poly(A) Tail-Mediated Stimulation of Picornavirus Internal Ribosome Entry Segment-Driven Translation but Not for X-Mediated Stimulation of Hepatitis C Virus Translation", *Mol Cell Biol*, 21(13): 4097-4109 (2001).

Mitchell et al., "Protein Factor Requirements of the Apaf-1 Internal Ribosome Entry Segment: Roles of Polypyrimidine Tract Binding Protein and Upstream of N-ras", *Mol Cell Biol*, 21(10):3364-3374 (2001).

Moriguchi, et al., "Simple Method of Calculating Octanol/Water Partition Coefficient", *Chem Pharm Bull*, 40(1):127-130 (1992).

Nanbru et al., "Alternative Translation of the Proto-oncogene c-*myc* by an Internal Ribosome Entry Site", *J Biol Chem*, 272(51):32061-32066 (1997).

Niepmann et al., "Functional Involvement of Polypyrimidine Tract-Binding Protein in Translation Initiation Complexes with the Internal Ribosome Entry Site of Foot-and-Mouth Disease Virus", *J Virol*, 71(11):8330-8339 (1997).

Odreman-Macchioli et al., "Mutational Analysis of the Different Bulge Regions of Hepatitis C Virus Domain II and Their Influence on Internal Ribosome Entry Site Translational Ability", *J Biol Chem*, 276(45):41648-41655 (2001).

Odreman-Macchioli et al., "Influence of Correct Secondary and Tertiary RNA Folding on the Binding of Cellular Factors to the HCV IRES", *Nucleic Acids Res*, 28(4):875-885 (2000).

Ohlmann et al., "An Internal Ribosome Entry Segment Promotes Translation of the Simian Immunodeficiency Virus Genomic RNA", *J Biol Chem*, 275(16):11899-11906 (2000).

Otto et al., "The Pathway of HCV IRES-Mediated Translation Initiation", *Cell*, 119:369-380 (2004).

Pain, "Initiation of Protein Synthesis in Eukaryotic Cells", *Eur J Biochem*, 236:747-771 (1996).

Pelletier et al., "Internal Initiation of Translation of Eukaryotic mRNA Directed by a Sequence Derived from Poliovirus RNA", *Nature*, 334:320-325 (1988).

Pelletier et al., "Internal Binding of Eucaryotic Ribosomes on Poliovirus RNA: Translation in HeLa Cell Extracts", *J Virol*, 63(1):441-444 (1989).

Pestova et al., "Eukaryotic Ribosomes Require Initiation Factors 1 and 1A to Locate Initiation Codons", *Nature* 394:854-859 (1998).

Pestova et al., "A Prokaryotic-Like Mode of Cytoplasmic Eukaryotic Ribosome Binding to the Initiation Codon During Internal Translation Initiation of Hepatitis C and Classical Swine Fever Virus RNAs", *Genes Dev*, 12: 67-83 (1998).

Pestova et al., "Functional Dissection of Eukaryotic Initiation Factor 4F: the 4A Subunit and the Central Domain of the 4G Subunit Are Sufficient To Mediate Internal Entry of 43S Preinitiation Complexes", *Mol Cell Biol*, 16(12):6870-6878 (1996).

Peytou et al., "Synthesis and Antiviral Activity of Ethidium-Arginine Conjugates Directed Against the TAR RNA of HIV-1", *J Med Chem*, 42(20):4042-53 (1999).

Pietschmann et al., "Persistent and Transient Replication of Full-Length Hepatitis C Virus Genomes in Cell Culture", *J Virol*, 76(8):4008-4021 (2002).

Pietschmann et al., "Characterization of Cell Lines Carrying Self-Replicating Hepatitis C Virus RNAs", *J Virol*, 75(3):1252-1264 (2001).

Poole et al., "Pestivirus Translation Initiation Occurs by Internal Ribosome Entry", *Virology*, 206:750-754 (1995).

Pringle, "Virus Taxonomy—1999. The Universal System of Virus Taxonomy, Updated to Include the New Proposals Ratified by the International Committee on Taxonomy of Viruses During 1998", *Arch Virol*, 144/2:421-429 (1999).

Psaridi et al., "Mutational Analysis of a Conserved Tetraloop in the 5' Untranslated Region of Hepatitis C Virus Identifies a Novel RNA Element Essential for the Internal Ribosome Entry Site Function", *FEBS Lett*, 453:49-53 (1999).

Reynolds et al., "Internal Initiation of Translation of Hepatitis C Virus RNA: The Ribosome Entry Site is at the Authentic Initiation Codon", *RNA*, 2:867-878 (1996).

Reynolds et al., "Unique Features of Internal Initiation of Hepatitis C Virus RNA Translation", *EMBO J*, 14(23):6010-6020 (1995).

Rijnbrand et al., "Almost the Entire 5' Non-Translated Region of Hepatitis C Virus is Required for Cap-Independent Translation", *FEBS Lett*, 365:115-119 (1995).

Rijnbrand et al., "Internal Ribosome Entry Site-Mediated Translation in Hepatitis C Virus Replication", *Curr Top Microbiol Immunol*, 242:85-116 (2000).

Rijnbrand et al., "The Influence of Downstream Protein-Coding Sequence on Internal Ribosome Entry on Hepatitis C Virus and Other Flavivirus RNAs", *RNA*, 7:585-597 (2001).

Rijnbrand et al., "The Influence of AUG Codons in the Hepatitis C Virus 5' Nontranslated Region on Translation and Mapping of the Translation Initiation Window", *Virology*, 226:47-56 (1996).

Sachs et al., "Starting at the Beginning, Middle, and End: Translation Initiation in Eukaryotes", *Cell*, 89:831-838 (1997).

Saito et al., "Hepatitis C Virus Infection is Associated with the Development of Hepatocellular Carcinoma", *Proc Natl Acad Sci USA*, 87:6547-6549 (1990).

Schultz et al., "Mutations within the 5' Nontranslated RNA of Cell Culture-Adapted Hepatitis A Virus Which Enhance Cap-Independent Translation in Cultured African Green Monkey Kidney Cells", *J Virol*, 70(2):1041-1049 (1996).

Shimazaki et al., "Inhibition of Internal Ribosomal Entry Site-Directed Translation of HCV by Recombinant IFN-α Correlates With a Reduced La Protein", *Hepatology*, 35(1):199-208 (2002).

Simmonds, "Variability of Hepatitis C Virus", *Hepatology*, 21(2):570-583 (1995).

Sinha Roy et al., "Direct Interaction of a Vancomycin Derivative with Bacterial Enzymes Involved in Cell Wall Biosynthesis", *Chem Biol*, 8:1095-1106 (2001).

Sizova et al., "Specific Interaction of Eukaryotic Translation Initiation Factor 3 with the 5' Nontranslated Regions of Hepatitis C Virus and Classical Swine Fever Virus RNAs", *J Virol*, 72(6):4775-4782 (1998).

Smith, "Design of Drugs Through a Consideration of Drug Metabolism and Pharmacokinetics", *Eur J Drug Metab Pharm*, 3:193-199 (1994).

Smith et al., "Variation of the Hepatitis C Virus 5' Non-Coding Region: Implications for Secondary Structure, Virus Detection and Typing", *J Gen Virol*, 76(7):1749-1761 (1995).

Sonenberg et al., "Translational Control of Gene Expression", Cold Spring Harbor. Cold Spring Harbor Laboratory Press, New York (2000).

Spahn et al., "Hepatitis C Virus IRES RNA-Induced Changes in the Conformation of the 40s Ribosomal Subunit", *Science*, 291:1959-1962 (2001).

Spatzenegger et al., "Clinical Importance of Hepatic Cytochrome P450 in Drug Metabolism", *Drug Metab Rev* 27(3):397-417 (1995).

Subkhankulova et al., "Internal Ribosome Entry Segment-Mediated Initiation of c-Myc Protein Synthesis Following Genotoxic Stress", *Biochem J*, 359:183-192 (2001).

Tang et al., "Alterations to Both the Primary and Predicted Secondary Structure of Stem-Loop IIIc of the Hepatitis C Virus 1b 5' Untranslated Region (5'UTR) Lead to Mutants Severely Defective in Translation Which Cannot Be Complemented in *trans* by the Wild-Type 5'UTR Sequence", *J Virol*, 73(3):2359-2364 (1999).

Thiel et al., "Internal Ribosome Entry in the Coding Region of Murine Hepatitis Virus mRNA 5", *J Gen Virol.*, 75(11):3041-3046 (1994).

Tsukiyama-Kohara et al., "Internal Ribosome Entry Site within Hepatitis C Virus RNA", *J Virol*, 66(3):1476-1483 (1992).

Vagner et al., "Alternative Translation of Human Fibroblast Growth Factor 2 mRNA Occurs by Internal Entry of Ribosomes", *Mol Cell Biol*, 15(1):35-44 (1995).

Varaklioti et al., "Mutational Analysis of Two Unstructured Domains of the 5' Untranslated Region of HCV RNA", *Biochem Biophys. Res Commun.*, 253:678-685 (1998).

Wang et al., "An RNA Pseudoknot is an Essential Structural Element of the Internal Ribosome Entry Site Located Within the Hepatitis C Virus 5' Noncoding Region", *RNA*, 1:526-537 (1995).

Wang et al., "Translation of Human Hepatitis C Virus RNA in Cultured Cells is Mediated by an Internal Ribosome-Binding Mechanism", *J Virol*, 67(6):3338-3344 (1993).

Wang et al., "A Conserved Helical Element is Essential for Internal Initiation of Translation of Hepatitis C Virus RNA", *J Virol*, 68(11):7301-7307 (1994).

Wang et al., "Screening poly(dA/dT) cDNAs for Gene Identification", *PNAS USA*, 97(8):4162-7 (2000).

Wang et al., "Core Protein-Coding Sequence, but Not Core Protein, Modulates the Efficiency of Cap-Independent Translation Directed by the Internal Ribosome Entry Site of Hepatitis C Virus", *J Virol*, 74(23):11347-11358 (2000).

Wimmer et al., "Genetics of Poliovirus", *Annu Rev Genet*, 27:353-436 (1993).

Wong et al., "Cost-Effectiveness of 24 or 48 Weeks of Interferon α-2b Alone or With Ribavirin as Initial Treatment of Chronic Hepatitis C", *Am J Gastroenterol*, 95(6):1524-1530 (2000).

Zhao et al., "Genetic Analysis of a Poliovirus/Hepatitis C Virus Chimera: New Structure for Domain II of the Internal Ribosomal Entry Site of Hepatitis C Virus", *J Virol*, 75(8):3719-3730 (2001).

Zhao et al., "Poliovirus/Hepatitis C Virus (Internal Ribosomal Entry Site-Core) Chimeric Viruses: Improved Growth Properties through Modification of a Proteolytic Cleavage Site and Requirement for Core RNA Sequences but Not for Core-Related Polypeptides", *J Virol*, 73(2):1546-1554 (1999).

Ahlquist et al., "Host Factors in Positive-Strand RNA Virus Genome Replication", *Journal of Virology*, 77(15):8181-8186 (2003).

Almerico et al., "Glycosidopyrroles Part 3. Effect of the Benzocondesnation on Acyclic Derivatives: 1-(2-hydroxyethoxy) Methylindoles as Potential Antiviral Agents", *II Farmaco*, 53:409-414 (1998).

Almerico et al., "Glycosidopyrroles. part 4. 1-β-D-ribofuranosyl-pyrroles and Indoles as Potential Antiviral agents", *ARKIVOC*, 1(4):486-496 (2000).

Cacchi et al., "2-Aryl and 2-Heteroaryl Indoles from 1-Alkynes and o-Iodotrifluoroacetanilide through a Domino Copper-Catalyzed Coupling-Cyclization Process", *Organic Letters*, 5(21):3843-3846 (2003).

Carson et al., "The Synthesis and Properties of 2-p-Dimthylaminophenyl-1,3,3-trimethyl-3H-indolium Salts", *Journal of the Chemical Society*, 5819-5825 (1965).

Chikvaidze et al., "Synthesis and Antimicrobial Activity of New Derivatives of 2-Phenylindone", *Pharmaceutical Chemistry Journal*, 28(10):751-755 (1994).

Danilova et al., "Synthesis and Transformations of Aminoethyl Derivatives of Cyclic β-Diketones", *Zhurnal Obshchei Khimii*, 1(9):1708-9 (1965).

Dhar et al., "3-Cyanoindole-Based Inhibitors of Inosine Monophosphate Dehydrogenase: Synthesis and Initial Structure-Activity Relationships", *Bioorganic & Medicinal Chemistry Letters*, 13:3557-3560 (2003).

Font et al., "Indoles and Pyridazino[4,5-*b*]indoles as Nonnucleoside Analog Inhibitors of HIV-1 Reverse Transcriptase", *Eur J Med Chem*, 30:963-971 (1995).

Germain Sanit-Ruf et al., "Analogues Méso-Hétérocycliques du dihydro-9,10 anthracéne. XII—Sur quelques Indoes Dérivés de la Dibenzo-p-Dioxine", *Notes*, 1069-1071 (1975).

Patent Abstracts of Japan of vol. 2003, No. 12 J1.

Patent Abstracts of Japan of JP 01273040 A published Oct. 31, 1989.

Patent Abstracts of Japan of JP 06236010 A published Aug. 23, 1994.

Patent Abstracts of Japan of JP 09169729 A published Jun. 30, 1997.

Terent'ev et al., "Synthesis of Derivatives of 5-Methoxyinodle", *Doklady Akademii Nauk SSSR*, 114:560-563 (1957).

Wang et al., "Alpha Interferon Induces Distinct Translational Control Programs to Suppress Hepatitis C Virus RNA Replication", *Journal of Virology*, 77(7):3898-3912 (2003).

International Search Report for International Application No. PCT/US2005/024881, mailed Feb. 3, 2006.

* cited by examiner

US 7,645,881 B2

METHODS FOR TREATING HEPATITIS C

CROSS REFERENCE TO RELATED APPLICATION

This application claims the benefit of U.S. Provisional Application No. 60/589,876, filed Jul. 22, 2004, which application is herein incorporated by reference in its entirety.

GOVERNMENT SUPPORT

The present invention was made with U.S. Government support under DHHS Grant No. 5R44 AI054029-03. The U.S. Government has certain rights in the invention.

FIELD OF THE INVENTION

The present invention relates to methods for treating Hepatitis C using thienopyridine compounds that modify translational control of Hepatitis C virus.

BACKGROUND OF THE INVENTION

An estimated 170 million people worldwide are reported to be infected with hepatitis C virus (HCV), the causative agent of hepatitis C. Seventy to eighty percent of HCV infections lead to chronic liver infection, which in turn may result in severe liver disease, including liver fibrosis, cirrhosis, and hepatocellular carcinoma (115).

HCV constitutes the Hepacivirus genus of the family Flaviviridae (106), and contains a positive-stranded 9.6 kb RNA genome. The features of the HCV genome include a 5'-untranslated region (UTR) that encodes an internal ribosome entry site (IRES) that directs the translation of a single open reading frame (ORF) encoding a polyprotein of 3,010 amino acids. The HCV ORF is followed by a 3'-UTR of variable length, depending on the HCV variant, that encodes the sequences required for the initiation of antigenomic strand synthesis (79).

The HCV IRES and 3'-UTR both contain regions of RNA structures that are required for genome translation and replication. The HCV polyprotein is posttranslationally processed into at least 10 mature viral proteins, including the structural proteins core (putative nucleocapsid), E1 and E2 and the nonstructural (NS) proteins NS2 to NS5B.

Three distinct elements have been shown to be involved in HCV IRES-mediated translation: (1) integrity of the global structure of HCV IRES, (2) the 3'-terminal region of the HCV genome; and (3) trans-acting cellular factors that interact with the HCV IRES element and assist in translation initiation (35).

The initiation of protein synthesis in eukaryotic cells predominantly follows the 5' cap-dependent, first AUG rule (61). However, an increasing number of viral (6, 12, 28, 31a, 50, 95, 97, 98, 105, 128) and cellular mRNAs (18, 39, 45, 78, 91, 130) have been shown to use an IRES element to direct translation initiation. In 1992, an IRES element was reported in the 5' UTR of the HCV RNA genome (129), indicating that synthesis of the viral protein is initiated in a cap-independent fashion.

A bicistronic expression system can be used to define and evaluate the function of IRES elements. This test system harbors two different reporter genes in which the 5'-proximal reporter gene is expressed by a cap dependent translation mechanism while the second reporter is expressed only if an upstream sequence inserted in the intergenic space contains an IRES sequence element. Using this system, a putative IRES in the HCV 5' UTR was unambiguously demonstrated to function as an IRES involved in translational control of viral proteins (133). In vitro translation, RNA transfection, and mutagenesis studies provided further evidence that the HCV 5' UTR contains an IRES element (23, 41, 42, 108, 129, 132, 133, 134). Both in vitro and cell-based studies demonstrated that the HCV IRES guides cellular translation initiation factors to an internal site of the viral RNA (56, 58, 120), thus functionally demonstrating the HCV IRES activity. Taken together, these results demonstrate that the HCV 5'-UTR contains an IRES element that plays an active and crucial role in the mechanism of internal initiation for HCV protein translation.

The IRES is one of the most conserved regions of the HCV genome, reflecting its essential nature for viral replication and protein synthesis (13, 118, 122). Although both 5' and 3' sequences of the IRES appear to play a role in the control of initiation of translation (42, 109, 110, 113, 136), the minimal sequence requirement for HCV IRES function has been mapped to a region between nucleotides 44-354 (40).

Biochemical probing and computer modeling indicate that the HCV IRES and its 5' sequence are folded into a distinct structure that consists of four major domains and a pseudoknot (11, 42, 122). Domain I contains a small stem-loop structure that does not appear to be a functional part of the IRES element while domains II, III, and IV contain the HCV IRES activity (43, 111). The relationships between secondary and tertiary structures of the HCV IRES and their function have recently been established (5, 55, 56, 99, 124). Both domains II and III consist of multiple stems, loops, and bulges and are important for IRES activity (23, 40, 51, 52, 54, 56, 64, 74, 75, 93, 107, 108, 110, 124, 127, 131, 139). Domain II can induce conformational changes on the ribosome that have been implicated in the decoding process (124). Domain III has the highest degree of structural conservation among the different HCV strains. It comprises the core of the flavivirus IRES and has 6 subdomains (40). Various studies have shown that subdomain IIId forms complex secondary/tertiary structures and is critical for initiation activity (55, 56, 57, 124, 129). Domain IV has one stem-loop that spans the initiation codon and is specific for the HCV IRES (41, 122), but the precise role of domain IV in IRES activity remains controversial (41, 112).

The role of the HCV IRES is to position the translational machinery near an internal initiator codon in the viral mRNA. The translation initiation mechanism of the HCV IRES differs significantly from that of 5'-cap-dependent translation initiation (7, 21, 31, 35, 81, 96, 114, 123). Most cellular capped mRNAs utilize a number of initiation factors (eIFs) that are required for the translation initiation process. The initial steps of the process require proteins that interact with the 5' cap structure and recruit the 40S ribosomal subunit to the cap-proximal region of mRNA. This complex then scans 3' of the cap, until reaching an AUG codon at which translation will initiate (21, 114). However, in the case of HCV, the IRES functionally replaces the 5' cap structure, allowing the 40S ribosomal subunit and eIF3 to bind directly to the RNA. Subdomain IIId of the HCV IRES harbors the binding site for the 40S ribosomal subunit and the only initiation factors required for translation initiation are eIF2, eIF3, and eIF4E (15, 58, 94, 100, 120, 124).

The polypyrimidine track-binding protein (PTB) and La autoantigen are noncanonical translation initiation factors that bind to HCV IRES and enhance its activity (1, 2, 3, 4, 5, 30, 48, 49, 53). PTB, a 57-kDa protein involved in RNA splicing, is also necessary for efficient IRES-mediated translation initiation of picornavirus mRNA, and some cellular mRNAs (10, 11, 36, 53, 59, 89, 92). The La autoantigen, a 52 kDa double-stranded RNA unwinding protein, also increases the activity of poliovirus and cellular IRESs (38, 85, 86). Other cellular factors involved in HCV IRES-mediated translation initiation include proteasome a-subunit PSMA7 (62), ribosomal protein S5 (26), ribosomal protein S9 (24, 25, 100), and hnRNPL (33). However, the role of these RNA-binding proteins in HCV IRES-mediated initiation of translation is unclear. Recently, it was reported that the activity of interferon (IFN) α against HCV replication might target HCV IRES-mediated translation initiation by causing a reduction of La protein levels (117). Thus, an inhibitor that blocks interaction between the IRES and the noncanonical factors might efficiently inhibit HCV replication and lack cytotoxicity.

Currently, only interferon (IFN) α and the nucleoside analogue ribavirin, in combination, are marketed for the treatment of HCV infection. However, these two agents are immunomodulators and have limited efficacy, relatively high toxicity, and high cost (80, 83, 84, 138). Although the treatment outcome is variable among the six major HCV genotypes, only about one-half of all treated patients respond to therapy, suggesting that the virus encodes protein products that may directly or indirectly attenuate the antiviral action of IFN. IFNs are naturally produced in response to virus infection, and cellular exposure to IFN leads to the induced expression of a variety of IFN-stimulated genes (ISGs), many of which have an antiviral function. ISG action can limit virus replication at multiple points within the replicative cycle.

There remains a need for a more effective means of treating patients afflicted with HCV. Specifically, a need exists for novel antiviral drugs that do not elicit cross-resistance to existing treatment modalities, and which demonstrate synergy with other anti-HCV agents. The applicants set out to identify drug candidates that inhibit HCV infection and were successful in identifying Indole compounds that are useful as anti-HCV agents. Without being limited to one theory, it is believed that the compounds of the present invention inhibit IRES-mediated initiation, elongation, and termination, i.e. translation.

The compounds of the present invention may also be useful for inhibiting translation of other cap-independent viruses that contain an IRES element. Such viruses include those of the picornavirus genus, such as poliovirus, hepatitis A virus and rhinovirus; those of the coronavirus genus, such as SARS; those of the arbovirus genus; those of the flavivirus genus, such as yellow fever, dengue, and West Nile virus, herpesviruses, such as herpes simplex virus and Kaposi's sarcoma-associated herpesvirus, or any other virus with a similar mode of replication. Furthermore, compounds of the invention may also be useful for inhibiting HIV, or any other virus with a similar mode of translation.

All documents referred to herein are incorporated by reference into the present application as though fully set forth herein.

SUMMARY OF THE INVENTION

In accordance with the present invention, compounds that inhibit HCV infection have been identified, and methods for their use provided.

In one aspect of the invention, compounds of Formula (I) are provided which are useful in the prevention and/or treatment of HCV infection. Without being limited to one theory, it is believed that the compounds of the present invention inhibit IRES-mediated initation, elongation and termination, i.e., translation. The compounds of Formula (I) may also be useful for inhibiting and/or treating other viral infections where the virus contains an IRES element. Such viruses include those of the picornavirus genus, such as poliovirus, hepatitis A virus and rhinovirus; those of the coronaviridae genus, such as SARS; those of the arbovirus genus; those of the flavivirus genus, such as yellow fever, dengue, and West Nile virus, herpesviruses, such as herpes simplex virus and Kaposi's sarcoma-associated herpesvirus, or any other virus with a similar mode of replication. Furthermore, compounds of the invention may also be useful for inhibiting HIV, or any other virus with a similar mode of translation.

In another aspect of the invention, methods are provided for the prevention and/or treatment of HCV infection.

In yet another aspect of the invention, pharmaceutical compositions comprising the compounds of the invention for the prevention and/or treatment of HCV infection are provided.

In one embodiment, the invention is directed to methods for inhibiting HCV IRES-mediated initiation and translation comprising administering an amount of at least one compound of the invention, effective for inhibiting IRES-mediated initiation and translation, to a subject in need thereof.

EXEMPLARY EMBODIMENTS

Embodiment 1.

A pharmaceutical composition for the prevention and/or treatment of Hepatitis C viral (HCV) infection comprising a therapeutically effective amount of at least one compound having the following formula:

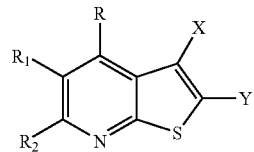

wherein:

X is:

hydrogen;

a cyano group;

an amino group;

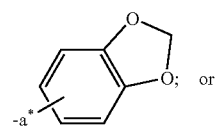

a 5- or 6-membered heteroaryl;

a $C_6$ to $C_8$ aryl, optionally substituted with:

an alkoxy group, a cyano group, or a halogen;

or X together with Y forms:

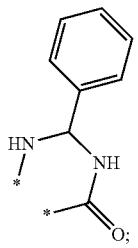

Y is:
  a halogen;
  an amino group;

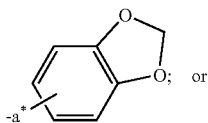

a —$SO_2R_x$, where $R_x$ is a $C_1$ to $C_6$ alkyl;
  a cyano group;
  a —$COOR_x$ group, where $R_x$ is a $C_1$ to $C_6$ alkyl;
  a $C_6$ to $C_8$ aryl, optionally substituted with:
    an alkoxy; or
    a cyano group;
  a —$COR_a$ group, where $R_a$ is:
    an amino optionally substituted with one or two $C_1$ to $C_6$ alkyls, where the alkyls are optionally substituted with a $C_6$ to $C_8$ aryl;
    a —$NHR_b$ group where $R_b$ is:
      a $C_6$ to $C_8$ aryl optionally substituted with:
        a haloalkyl; or
        a halogen
        a haloalkoxy; or
      a 5- or 6-membered heterocycle optionally substituted with a $C_1$ to $C_6$ alkyl;
    a $C_1$ to $C_6$ alkyl;
    a —$SR_x$ group, where $R_x$ is as defined above;
  a 5 or 6 membered heteroaryl optionally substituted with:
    a $C_6$ to $C_8$ aryl optionally substituted with:
      an alkoxy
      a halogen; or
      a $C_1$ to $C_6$ alkyl;
    a 5- or 6-membered heteroaryl optionally substituted with
      an alkoxy
      a halogen; or
      a $C_1$ to $C_6$ alkyl;
  a $C_1$ to $C_6$ alkyl, optionally substituted with a —$OR_c$, where $R_c$ is a $C_6$ to $C_8$ aryl optionally substituted with one or more halogens; or
  a nitro group;
  a —$NHR_d$ group, where $R_d$ is a $C_6$ to $C_8$ aryl optionally substituted with an alkoxy
  a —$NHCOR_e$ group where $R_e$ is:
    a $C_6$ to $C_8$ aryl optionally substituted with a haloalkyl;
    a $C_1$ to $C_6$ alkyl;
  or together with X forms: 0

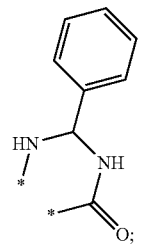

R is:
  a hydrogen
  a haloalkyl;
  a $C_1$ to $C_6$ alkyl optionally substituted with hydroxyl;
  a 5- or 6-member heteroaryl;
  a $C_6$ to $C_8$ aryl optionally substituted with one or more halogens;
  or R together with $R_1$ forms:

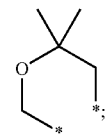

$R_1$ is:
  a hydrogen;
  a $C_6$ to $C_8$ aryl
  a $C_1$ to $C_6$ alkyl;
  a $OCOR_f$ where $R_f$ is a 5- or 6-membered heterocycle;
  an alkoxy optionally substituted with an amino group, wherein the amino group is optionally substituted with one or two $C_1$ to $C_6$ alkyls, where the alkyls are optionally substituted with an amino optionally substituted with one or two $C_1$ to $C_6$ alkyls
  an alkoxy optionally substituted with a 5 to 8 membered heterocycle optionally substituted with a $C_1$ to $C_6$ alkyl, which is optionally substituted with:
    an alkoxy, or
    an amino, optionally substituted with one or two $C_1$ to $C_6$ alkyls;
  or $R_1$ together with $R_2$ forms:

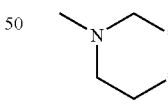 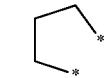 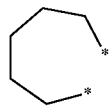 

$R_1$ together with R forms:

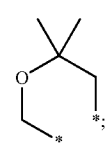

$R_2$ is:
  a $C_1$ to $C_6$ alkyl;
  a 5 or 6-membered heterocycle;

an amino optionally substituted with a $C_1$ to $C_6$ alkyl;
or $R_1$ together with $R_2$ forms:

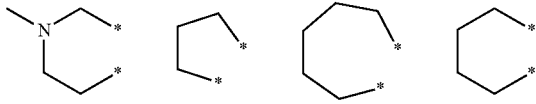

or a pharmaceutically acceptable salt thereof, together with a pharmaceutically acceptable excipient and optionally an additional anti-HCV agent.

Embodiment 2

The pharmaceutical composition of Embodiment 1, wherein said additional anti-HCV agent is selected from the group consisting of pegylated interferon, un-pegylated interferon, ribavirin or prodrugs or derivatives thereof, a glucosidase inhibitor, a protease inhibitor, a polymerase inhibitor, p7 inhibitors, an entry inhibitor, a fusion inhibitor, an anti-fibrotic, a caspase inhibitor, a drug which targets inosine monophosphate dehydrogenase inhibitors (IMPDH), synthetic thymosin alpha 1, therapeutic vaccines, immunomodulators, a helicase inhibitor, and a Toll-like receptor agonist.

Embodiment 3

The pharmaceutical composition of Embodiment 1, wherein X is an amino group or a hydrogen.

Embodiment 4

The pharmaceutical composition of Embodiment 1, wherein Y is a 5 or 6 membered heteroaryl optionally substituted with:
 a $C_6$ to $C_8$ aryl optionally substituted with:
  an alkoxy
  a halogen; or
  a $C_1$ to $C_6$ alkyl; or
 a 5- or 6-membered heteroaryl optionally substituted with
  a halogen.

Embodiment 5

The pharmaceutical composition of Embodiment 1, wherein Y is a —COORX group, where Rx is as defined above;
 a —COR$_a$ group, where R$_a$ is:
  an amino optionally substituted with one or two $C_1$ to $C_6$ alkyls, where the alkyls are optionally substituted with a $C_6$ to $C_8$ aryl;
 a —SR$_x$ group, where R$_x$ is as defined above,
 a 5 or 6 membered heteroaryl optionally substituted with:
  a $C_6$ to $C_8$ aryl optionally substituted with:
   an alkoxy
   a halogen; or
   a $C_1$ to $C_6$ alkyl;
  a 5- or 6-membered heteroaryl optionally substituted with a $C_6$ to $C_8$ aryl optionally substituted with a halogen;

Embodiment 6

The pharmaceutical composition of Embodiment 1, wherein R is a $C_1$ to $C_6$ alkyl.

Embodiment 7

The pharmaceutical compostion of Embodiment 6, wherein R is a methyl group.

Embodiment 8

The pharmaceutical composition of Embodiment 6, wherein R, $R_1$ and $R_2$ are independently $C_1$ to $C_6$ alkyl.

Embodiment 9

The pharmaceutical composition of Embodiment 6, wherein said $C_1$ to $C_6$ alkyl in R, $R_1$ and $R_2$ is independently a methyl or an ethyl.

Embodiment 10

The pharmaceutical composition of Embodiment 1, wherein $R_1$ is selected from the group consisting of
 a $C_1$ to $C_6$ alkyl; and
 an alkoxy optionally substituted with an amino group, wherein the amino group is optionally substituted with one or two $C_1$ to $C_6$ alkyls, where the alkyls are optionally substituted with an amino optionally substituted with one or two $C_1$ to $C_6$ alkyls; and
 an alkoxy optionally substituted with a 5 to 8 membered heterocycle optionally substituted with a $C_1$ to $C_6$ alkyl, which is optionally substituted with:
  an amino, optionally substituted with one or two $C_1$ to $C_6$ alkyls.

Embodiment 11

The pharmaceutical composition of Embodiment 10, wherein $R_1$ is a $C_1$ to $C_6$ alkyl.

Embodiment 12

The pharmaceutical composition of Embodiment 11, wherein $R_1$ is methyl or ethyl.

Embodiment 13

The pharmaceutical composition of Embodiment 12, wherein $R_1$ is methyl or ethyl.

Embodiment 14

The pharmaceutical composition of Embodiment 1, wherein $R_2$ is a $C_1$ to $C_6$ alkyl.

Embodiment 15

The pharmaceutical composition of Embodiment 14, wherein $R_2$ is methyl.

Embodiment 16

The pharmaceutical composition of Embodiment 1, wherein said compound is selected from the group consisting of the following compounds:

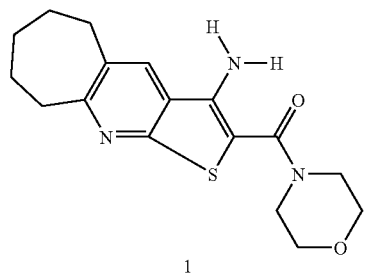
1
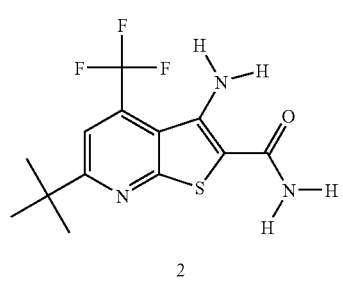
2
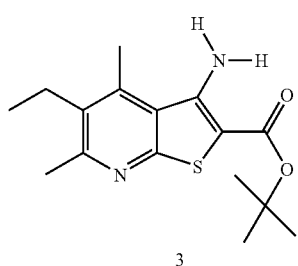
3
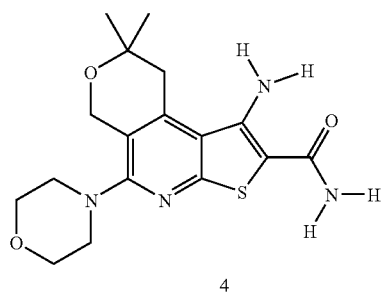
4
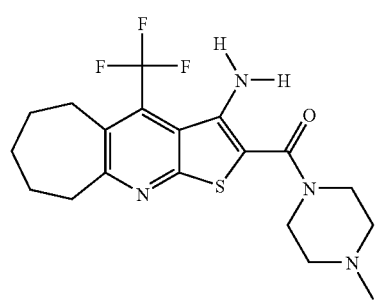
5
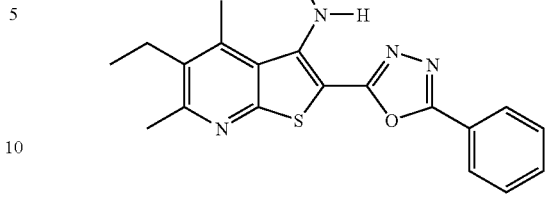
6
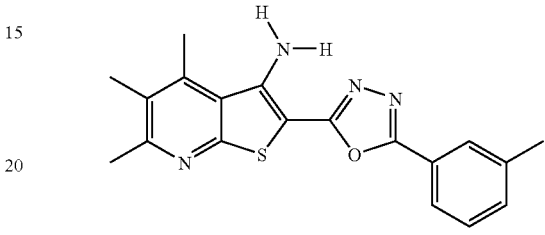
7
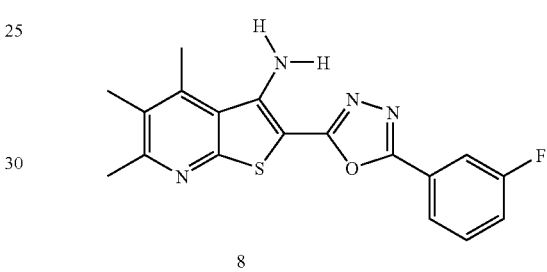
8
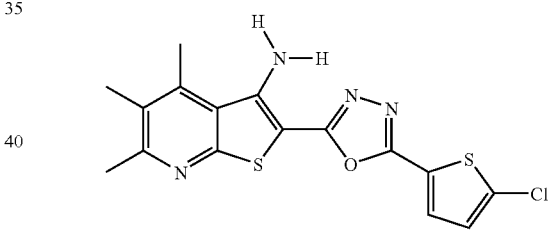
9
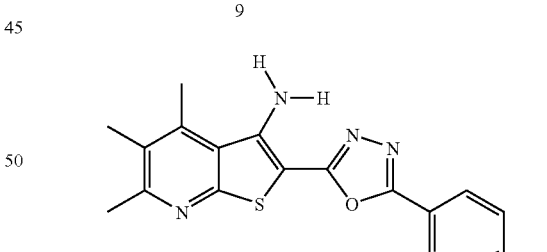
10
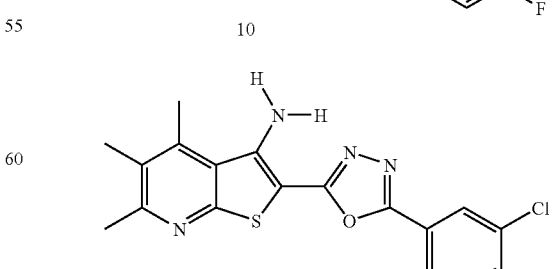
11

-continued
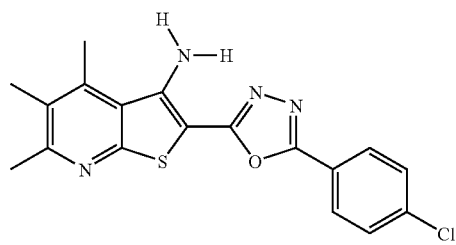
12
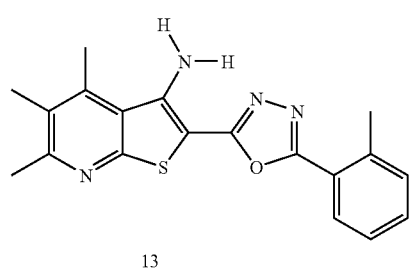
13
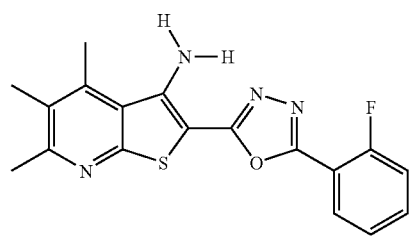
14
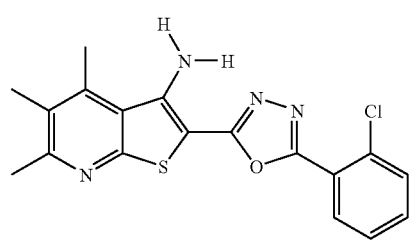
15
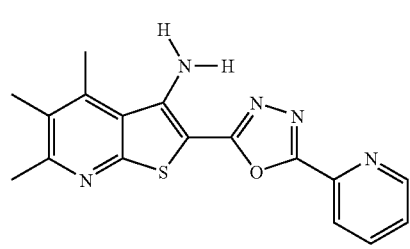
16
-continued
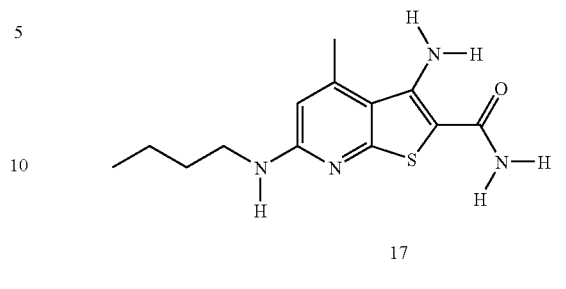
17
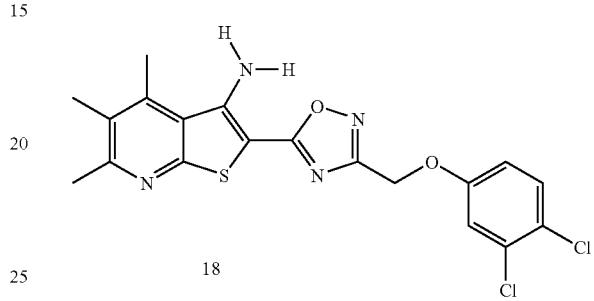
18
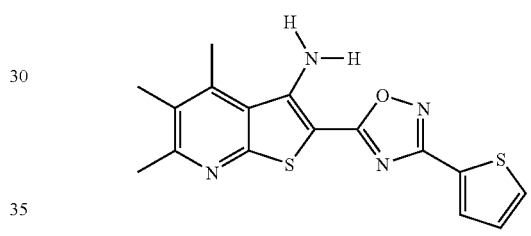
19
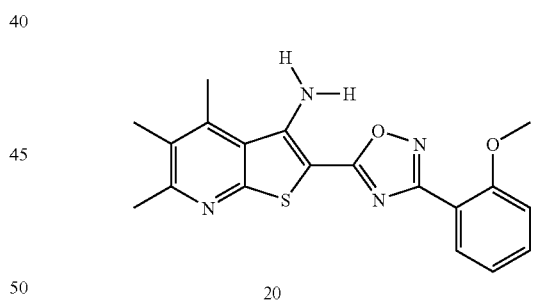
20
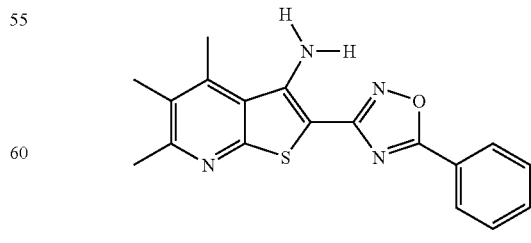
21

-continued
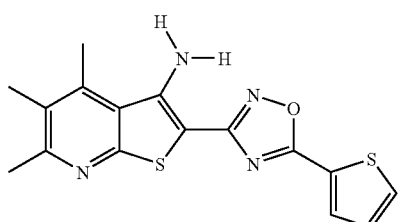
22
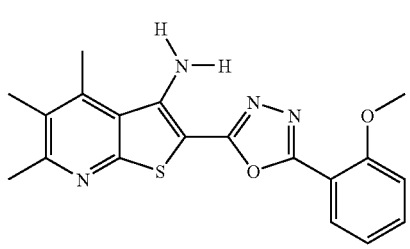
23
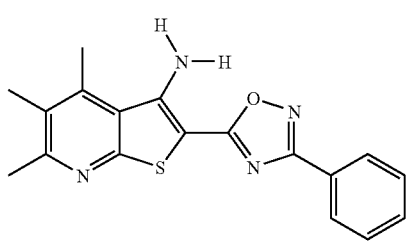
24
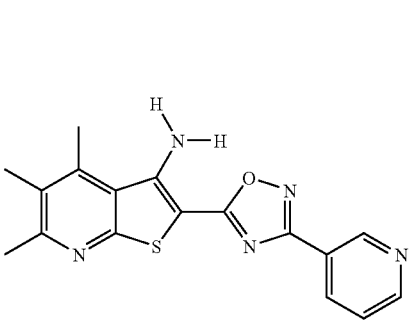
25
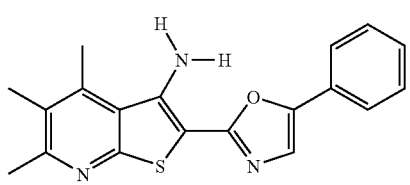
26
-continued
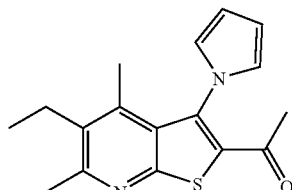
27
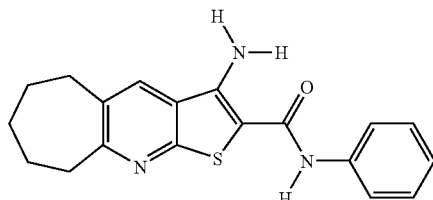
28
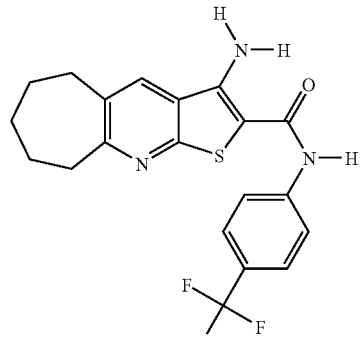
29
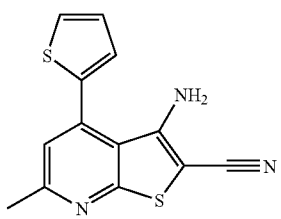
30
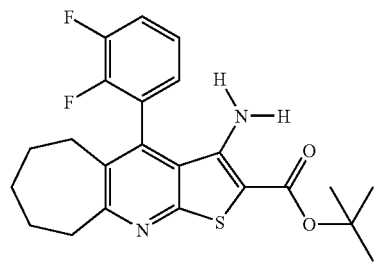
31

-continued
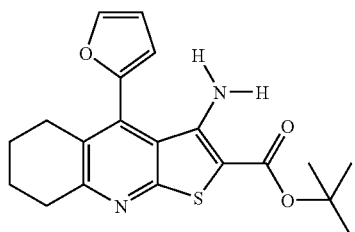
32
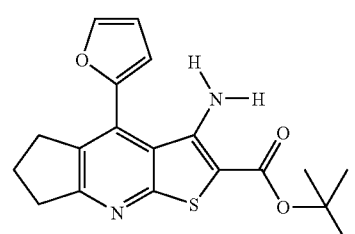
33
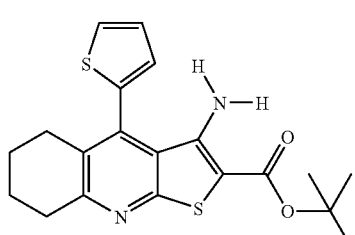
34
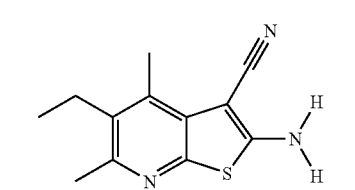
35
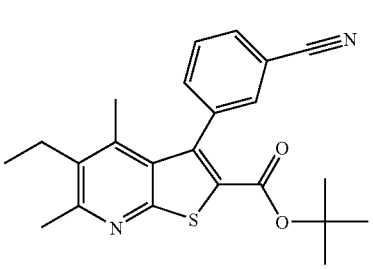
36
-continued
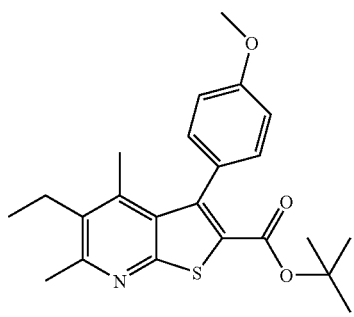
37
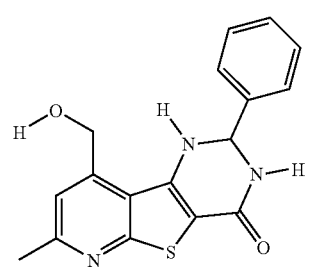
38
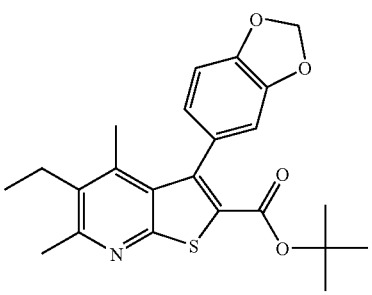
39
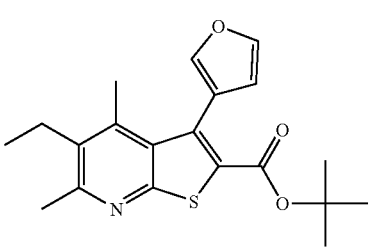
40

-continued
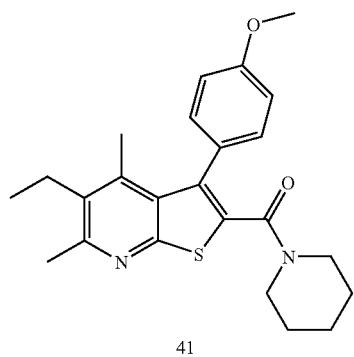
41
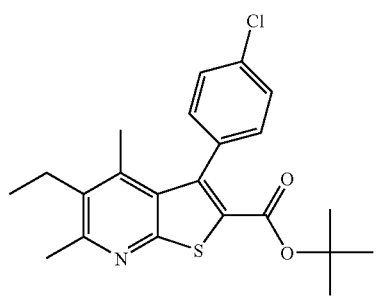
42
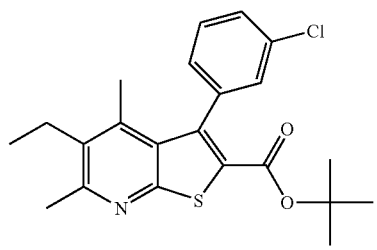
43
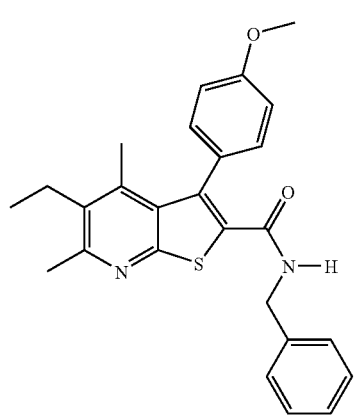
44
-continued
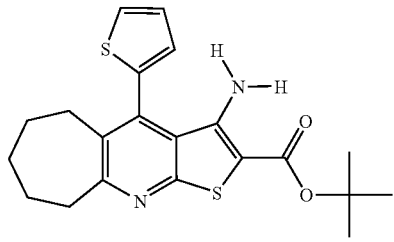
45
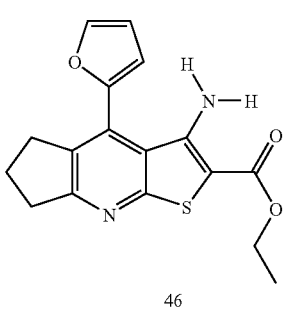
46
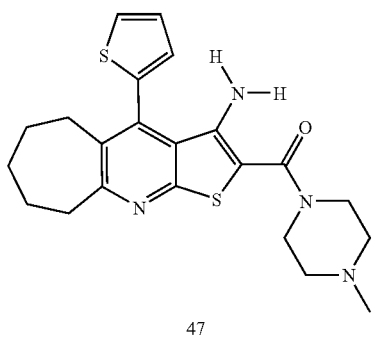
47
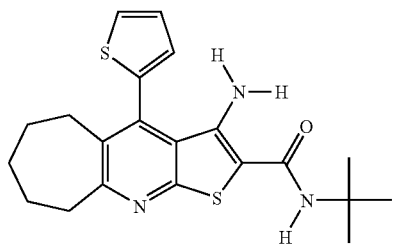
48
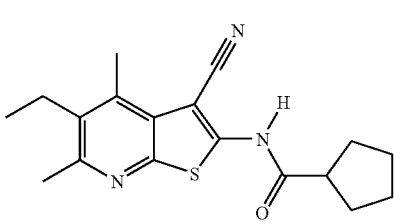
49

-continued
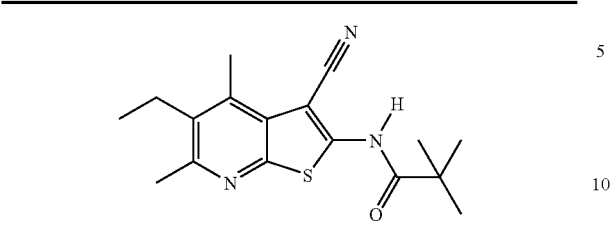
50
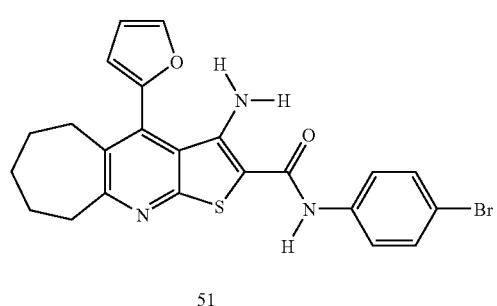
51
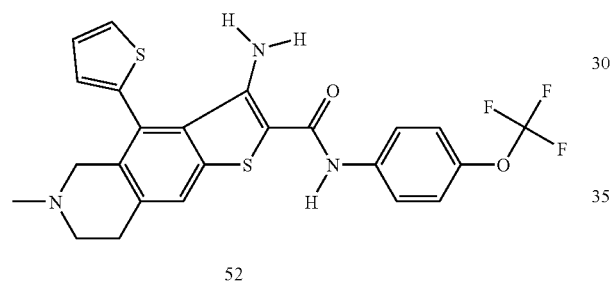
52
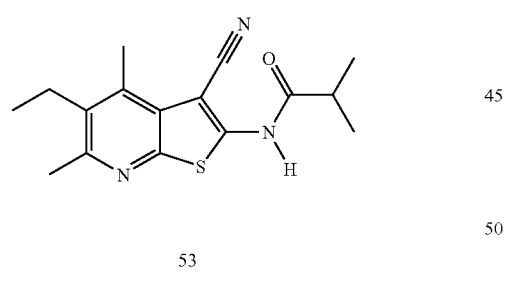
53
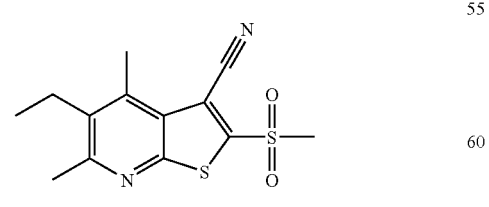
54
-continued
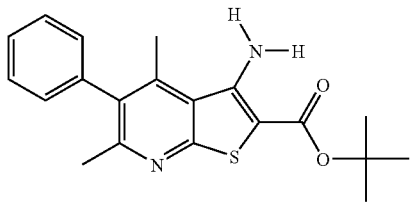
55
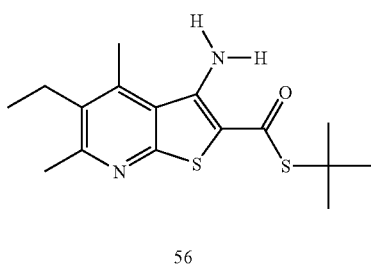
56
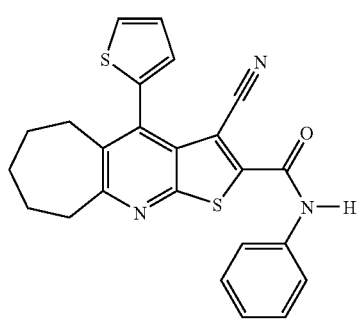
57
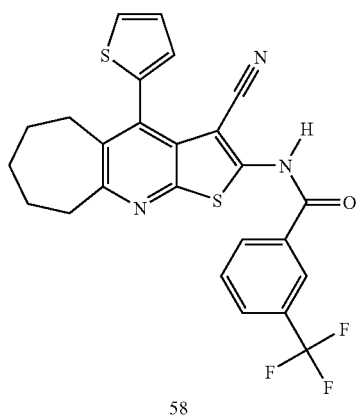
58
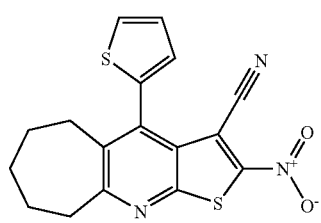
59

-continued
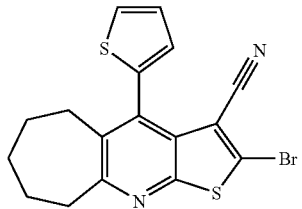
60
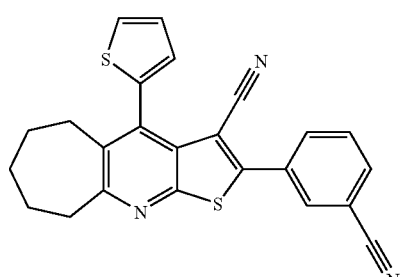
61
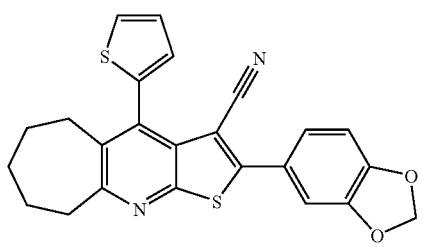
62
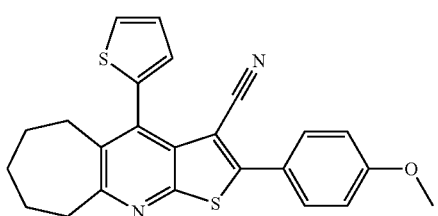
63
-continued
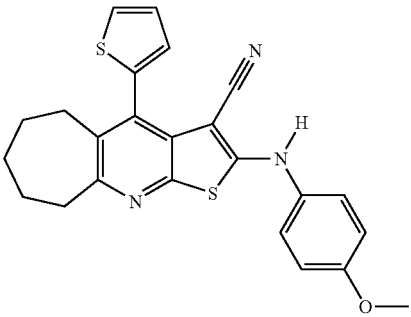
64
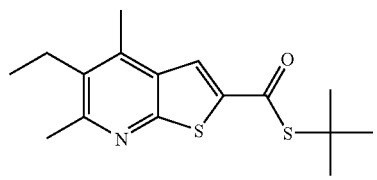
65
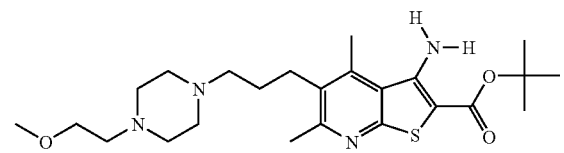
66
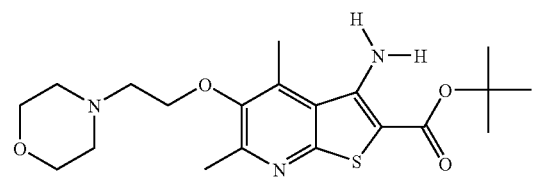
67
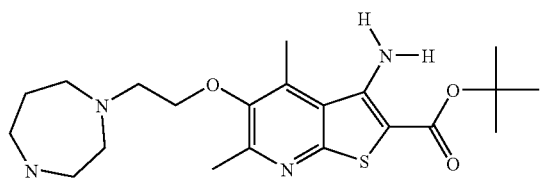
68
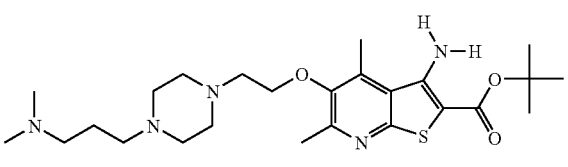
69

-continued
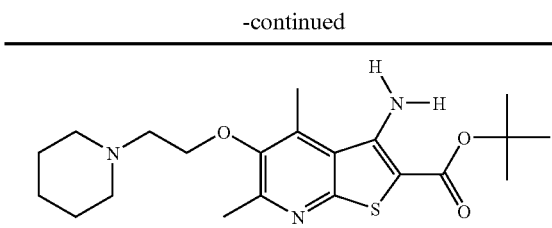
70
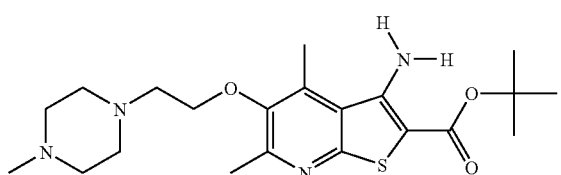
71
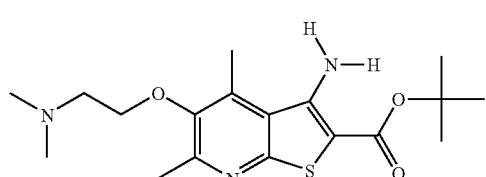
72
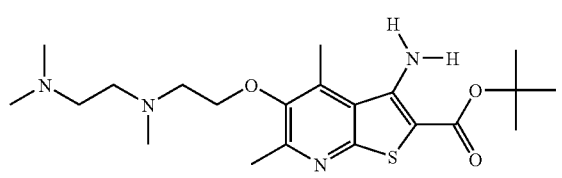
73
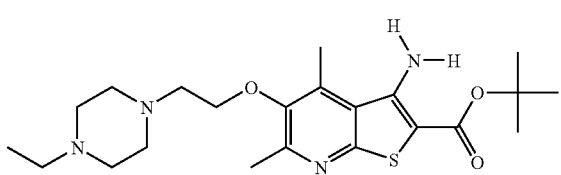
74
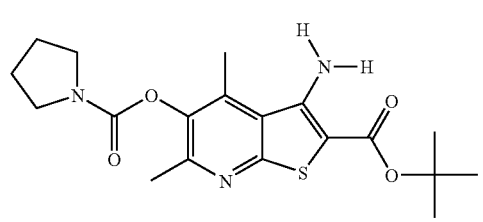
75
-continued
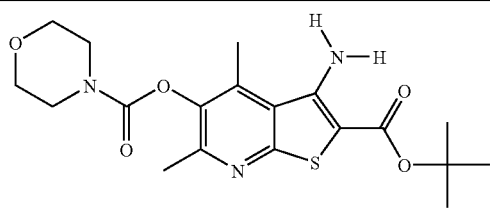
76
Embodiment 17
The pharmaceutical composition of Embodiment 1, wherein said compound is selected from the group consisting of the following compounds:
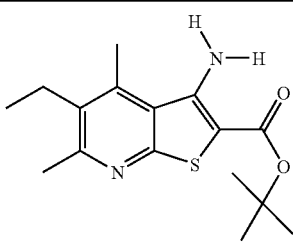
3
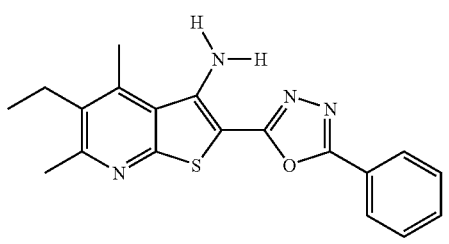
6
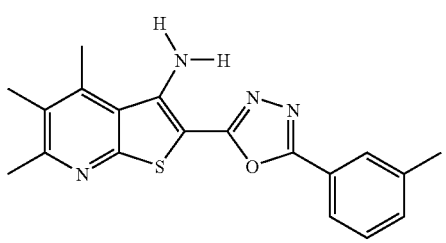
7
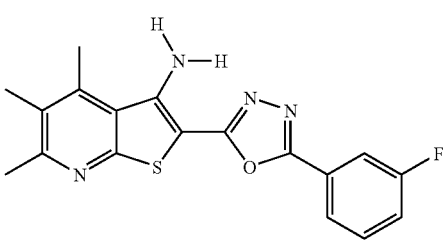
8

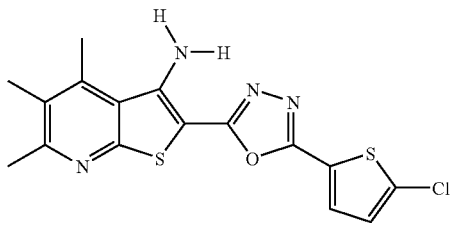
9
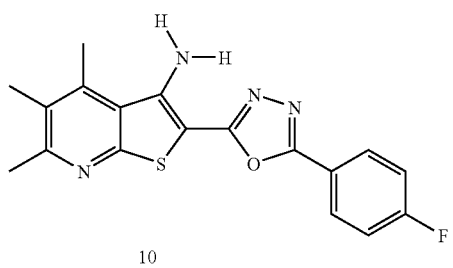
10
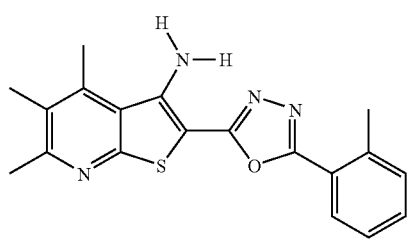
13
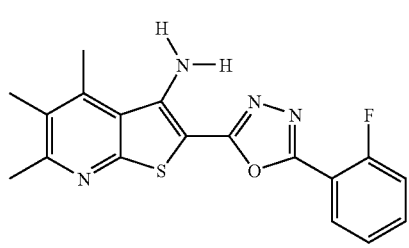
14
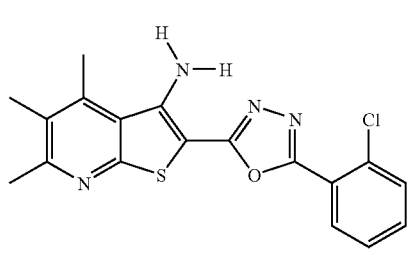
15
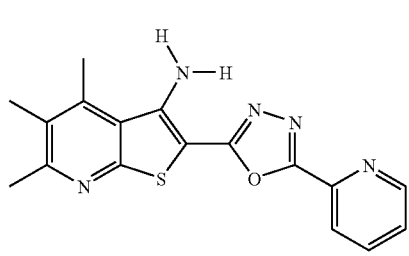
16
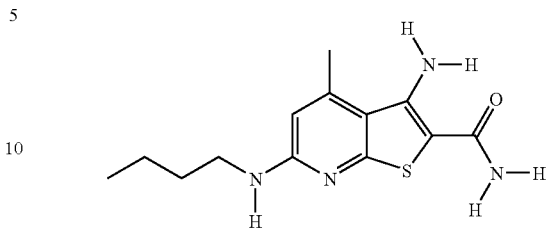
17
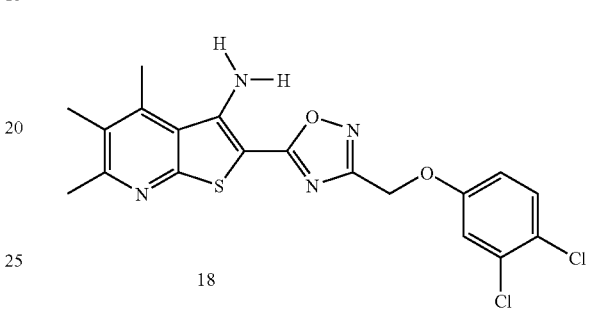
18
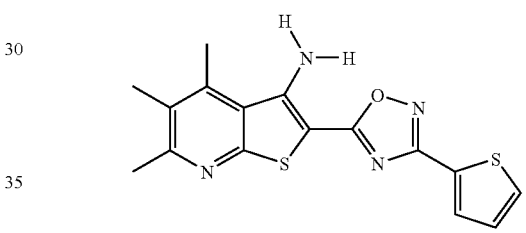
19
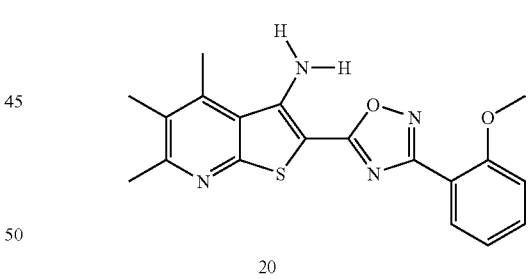
20
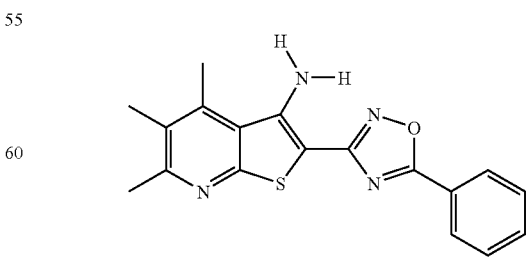
21

-continued
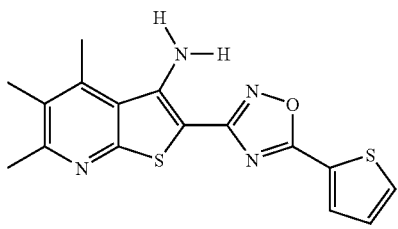
22
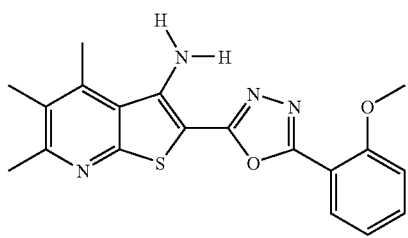
23
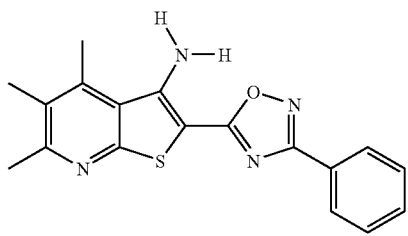
24
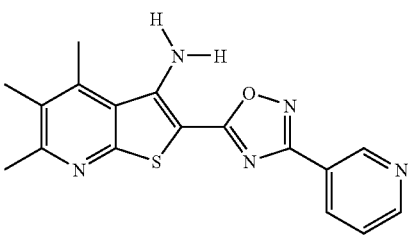
25
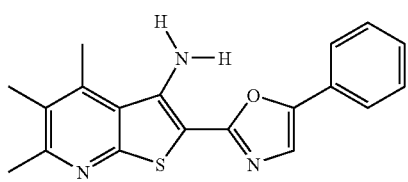
26
-continued
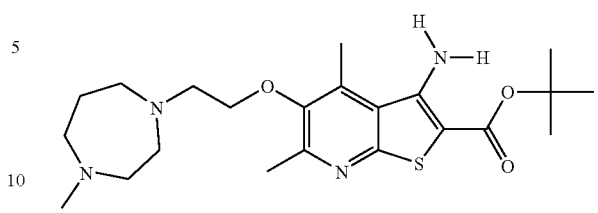
68
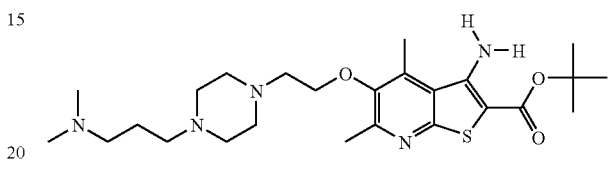
69
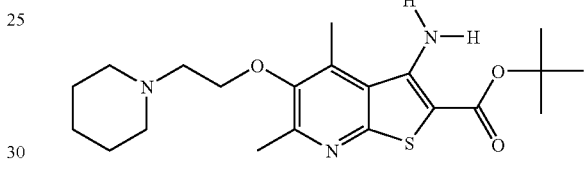
70
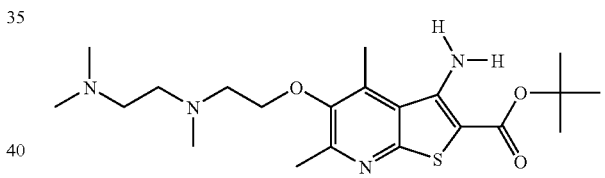
73
Embodiment 18
A pharmaceutical composition for the prevention or treatment of Hepatitis C viral (HCV) infection comprising at least one of the following compounds:
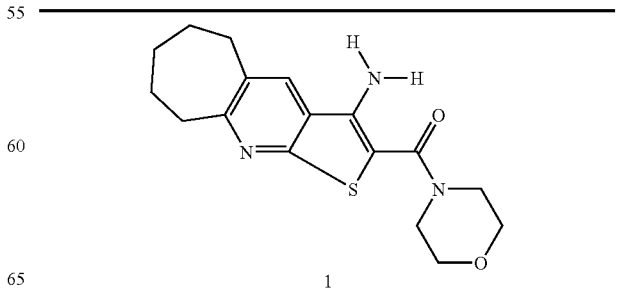
1

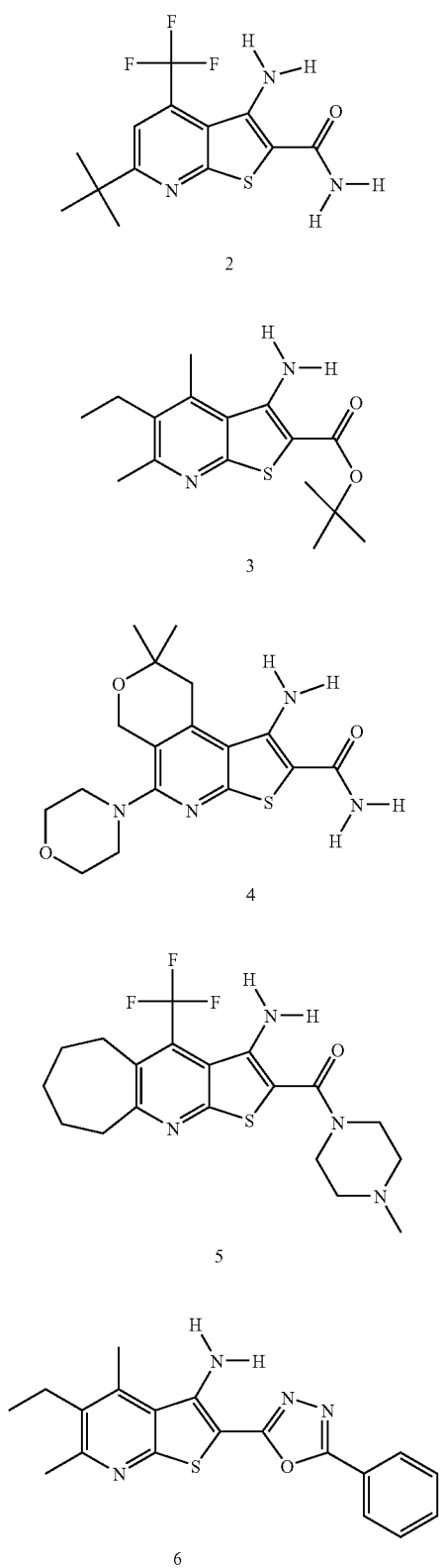
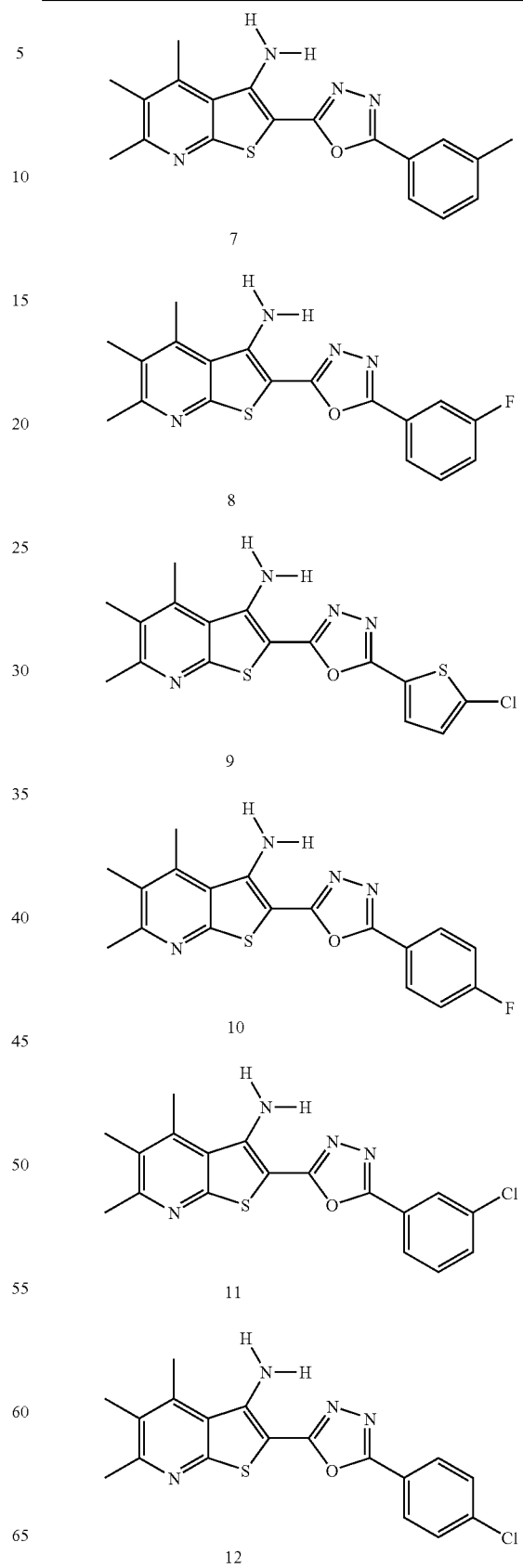

-continued
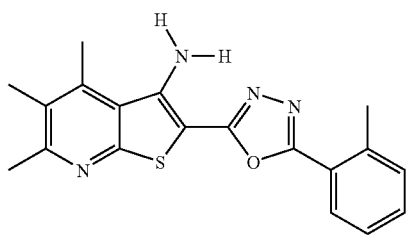
13
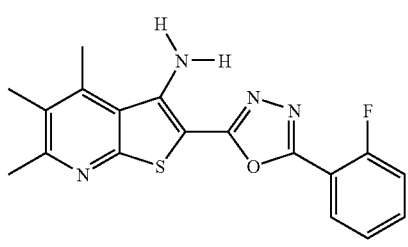
14
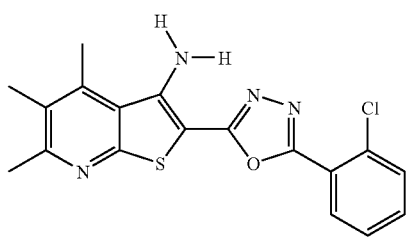
15
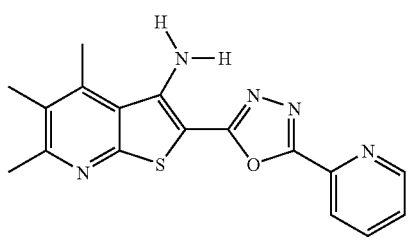
16
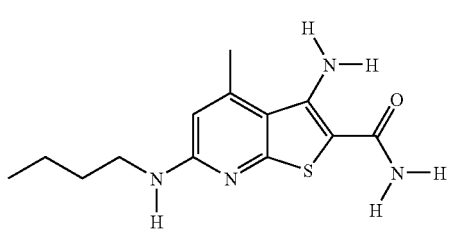
17
-continued
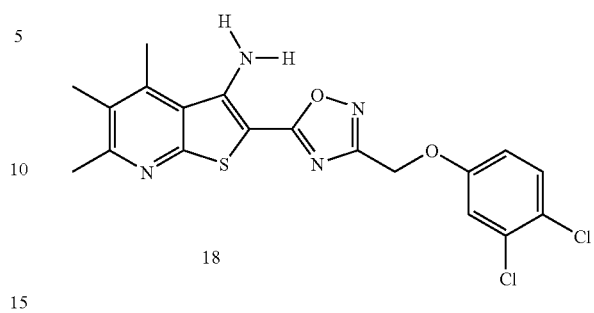
18
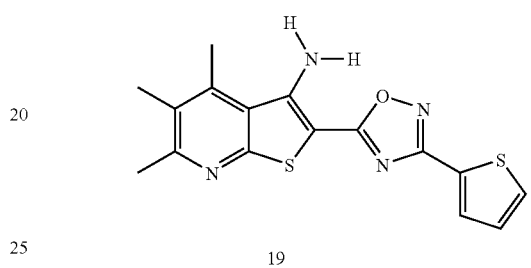
19
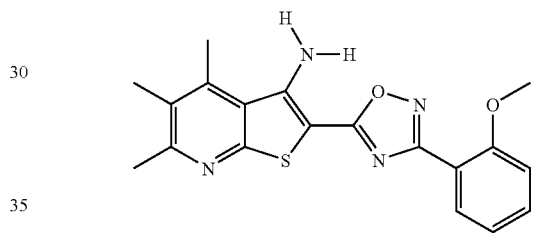
20
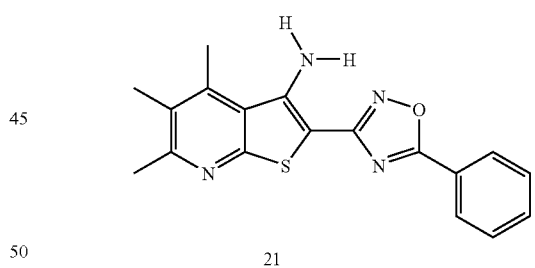
21
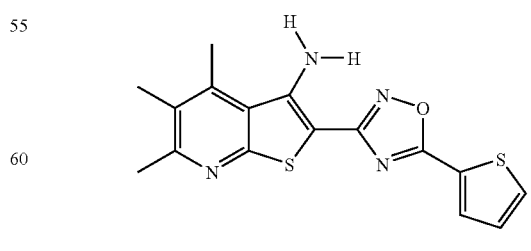
22

-continued
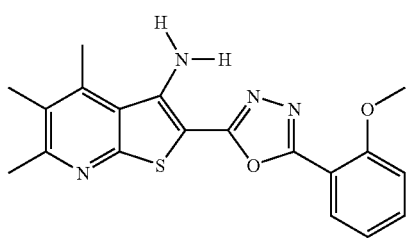
23
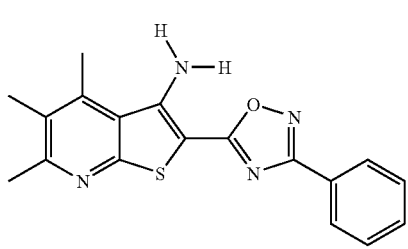
24
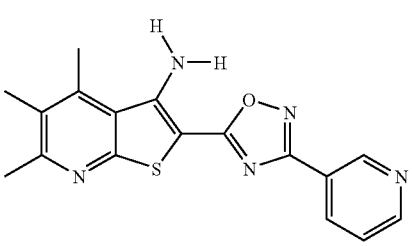
25
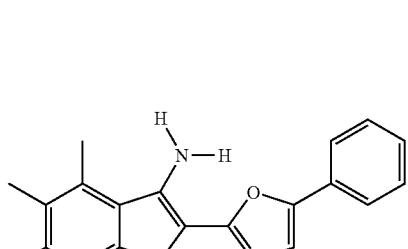
26
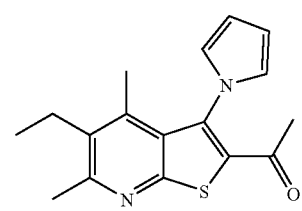
27
-continued
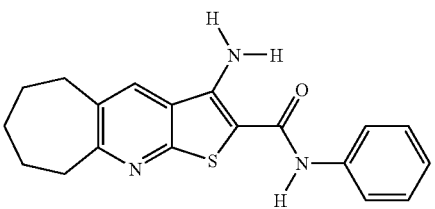
28
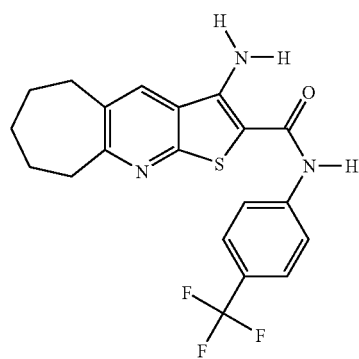
29
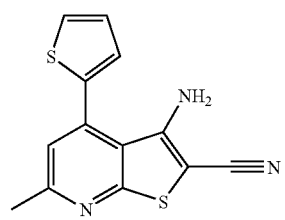
30
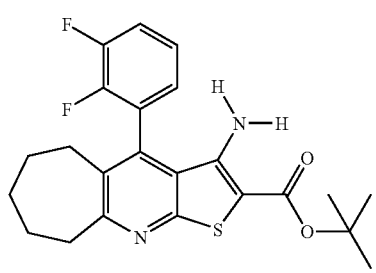
31
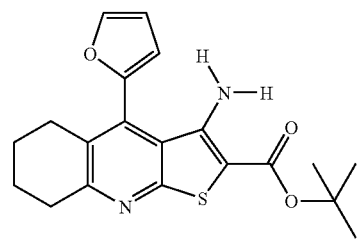
32

-continued
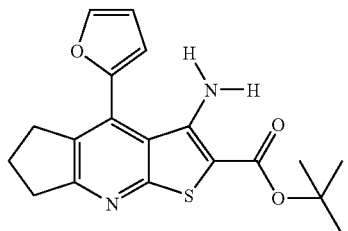
33
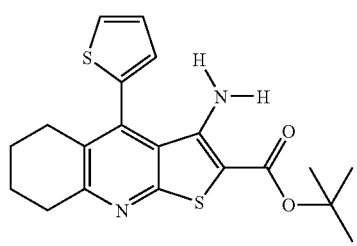
34
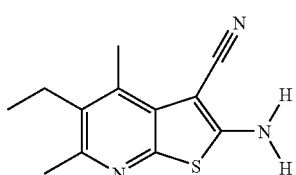
35
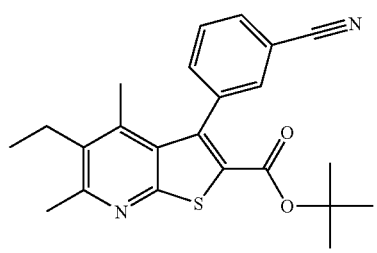
36
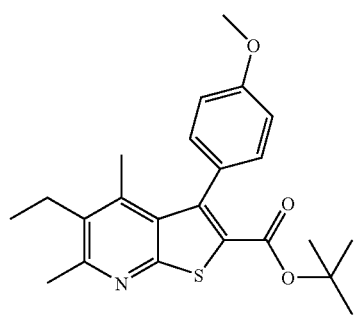
37
-continued
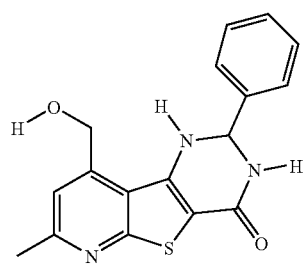
38
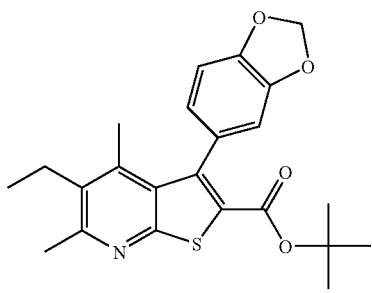
39
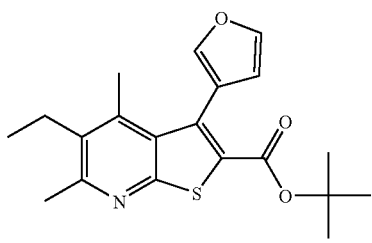
40
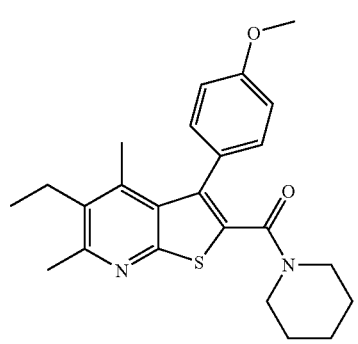
41

-continued
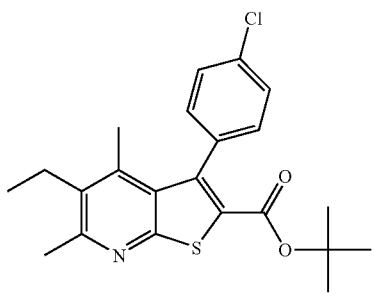
42
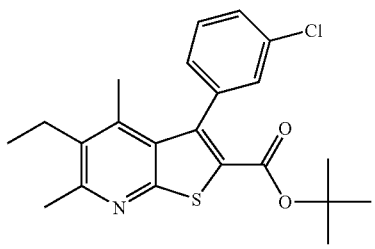
43
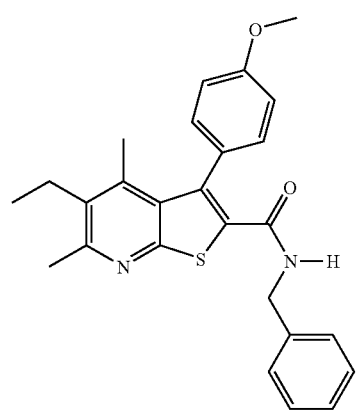
44
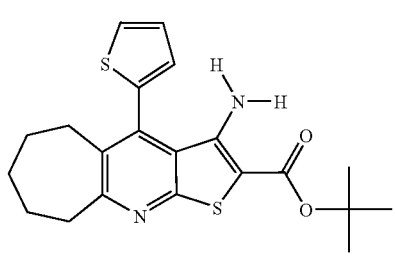
45
-continued
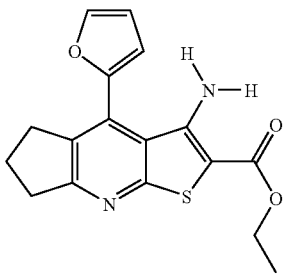
46
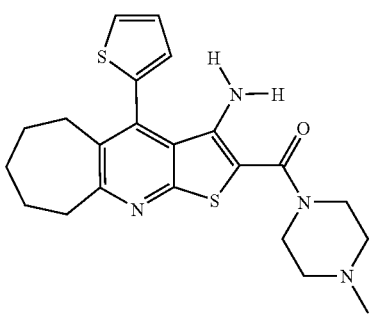
47
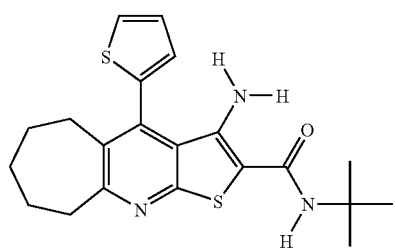
48
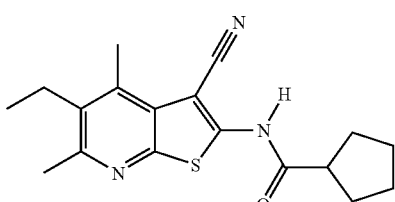
49
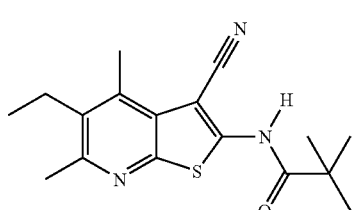
50

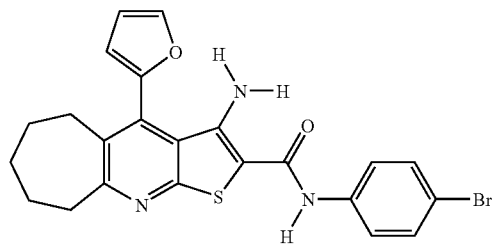
51
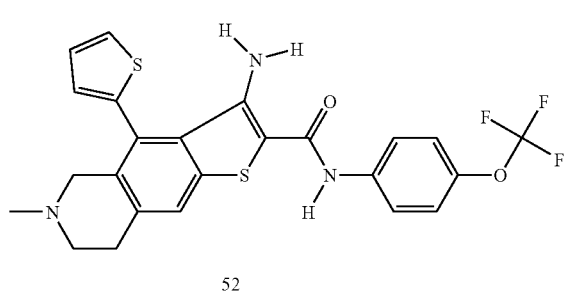
52
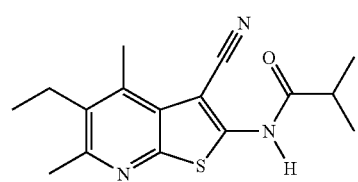
53
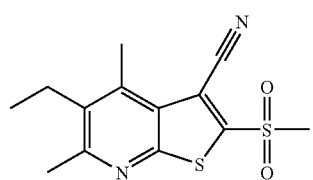
54
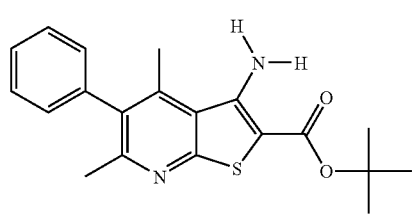
55
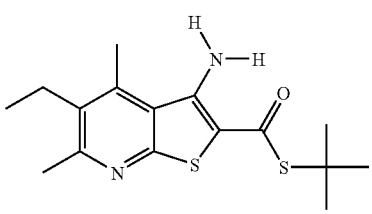
56
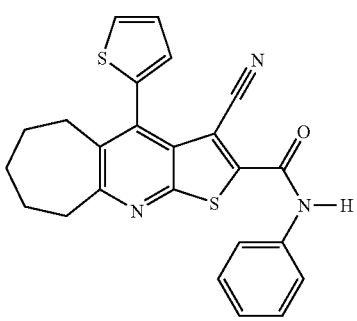
57
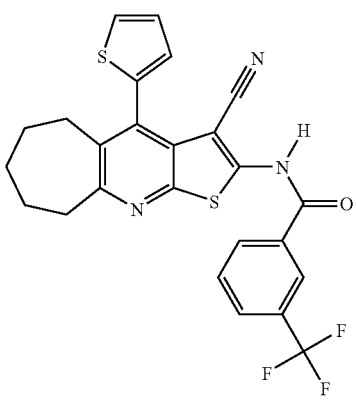
58
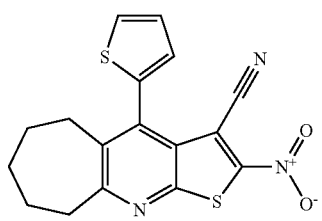
59

-continued
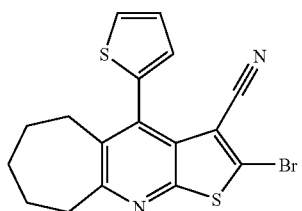
60
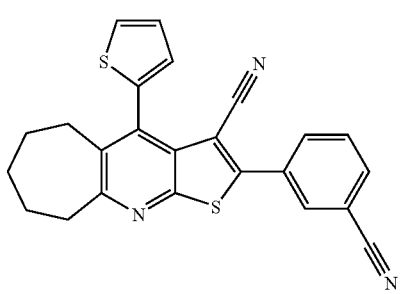
61
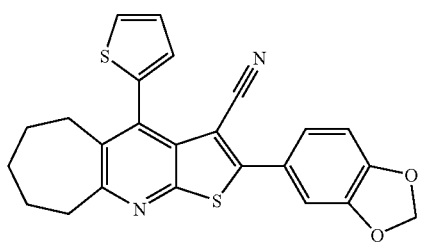
62
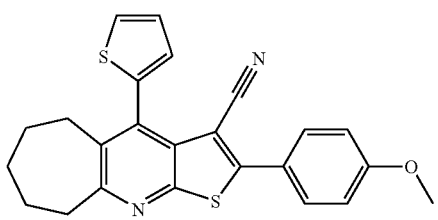
63
-continued
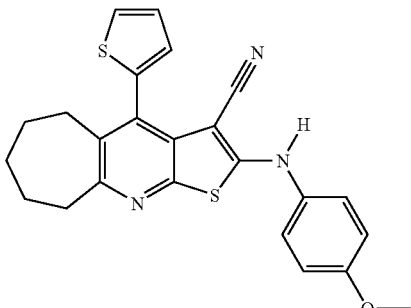
64
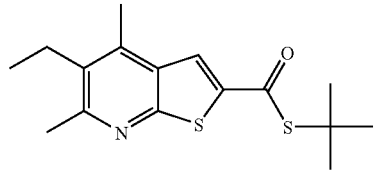
65
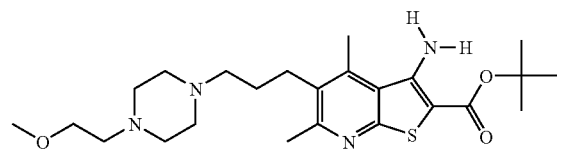
66
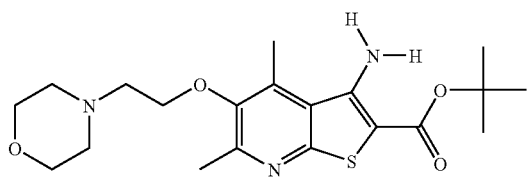
67
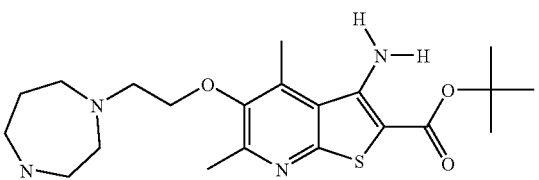
68
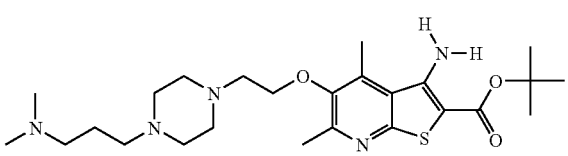
69

-continued
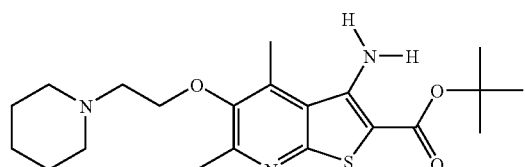
70
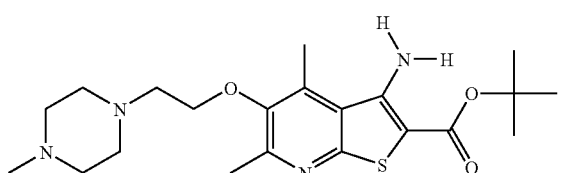
71
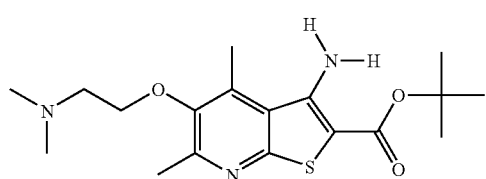
72
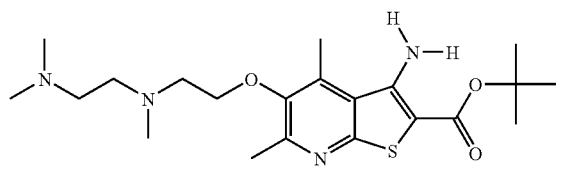
73
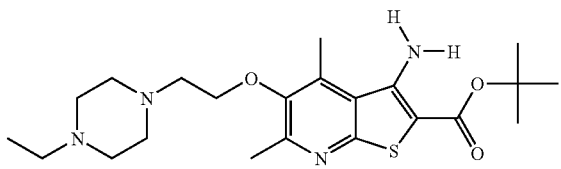
74
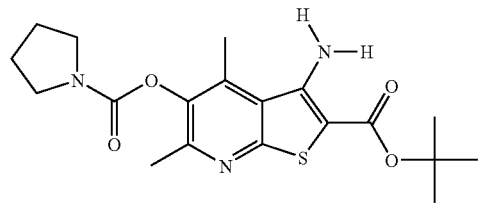
75
-continued
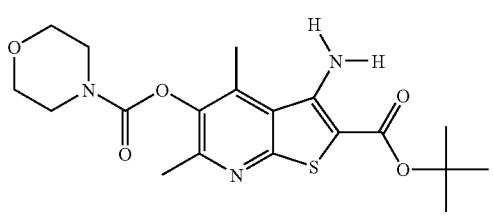
76
or a pharmaceutically acceptable salt thereof, together with a pharmaceutically acceptable excipient.
Embodiment 19
A pharmaceutical composition for the prevention or treatment of Hepatitis C viral (HCV) infection comprising at least one of the following compounds:
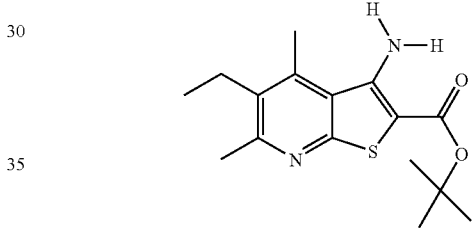
3
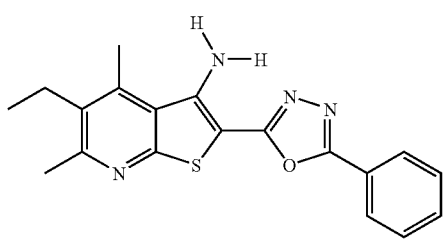
6
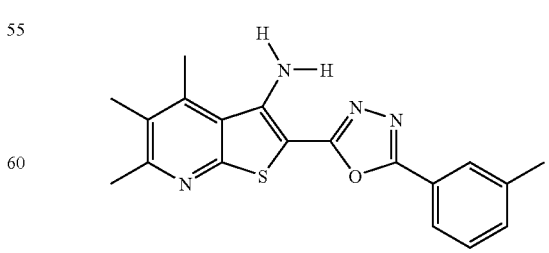
7

-continued
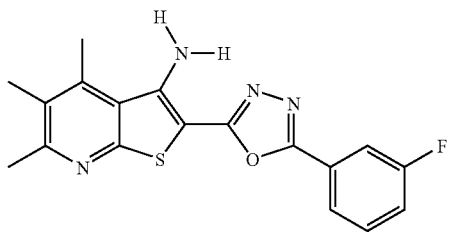
8
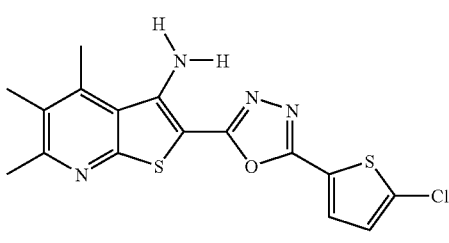
9
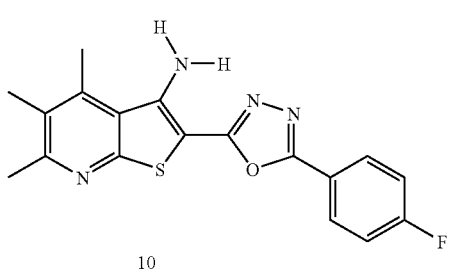
10
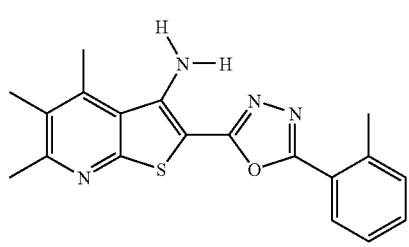
13
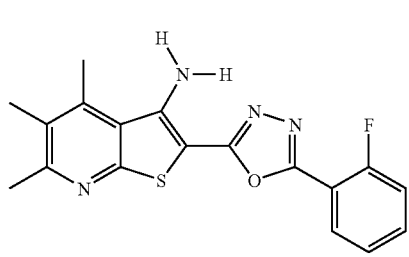
14
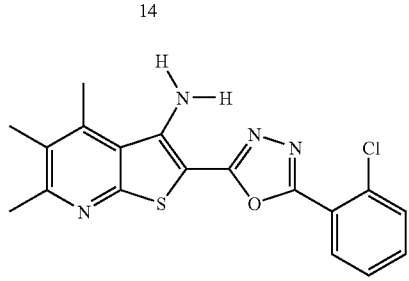
15
-continued
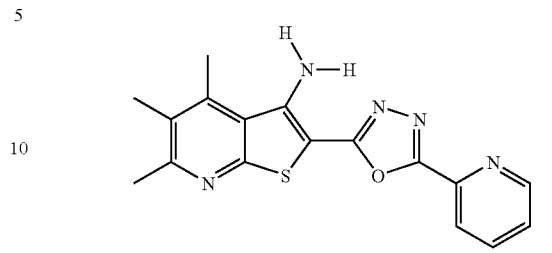
16
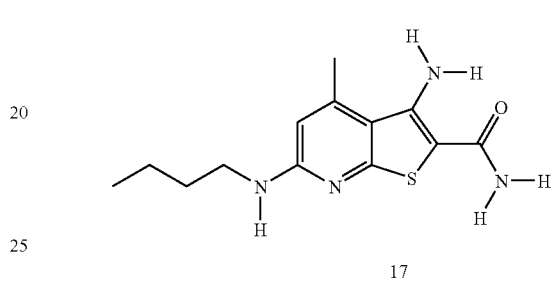
17
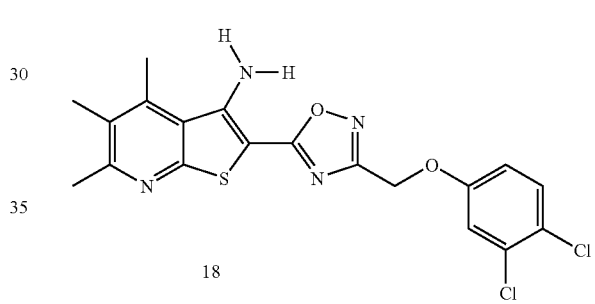
18
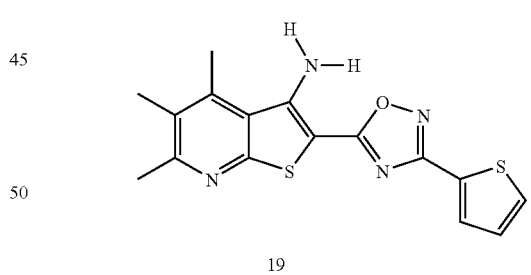
19
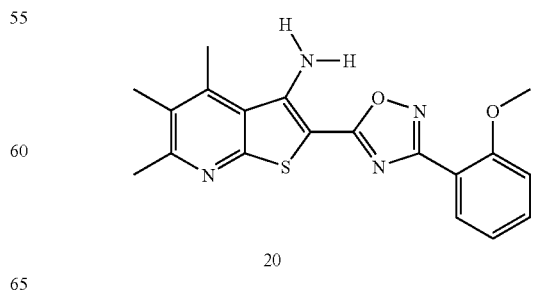
20

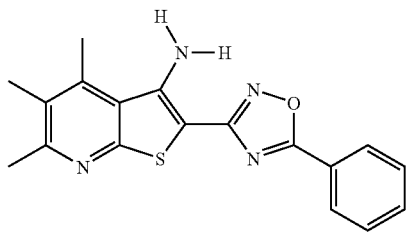

21

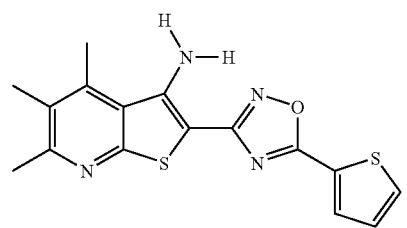

22

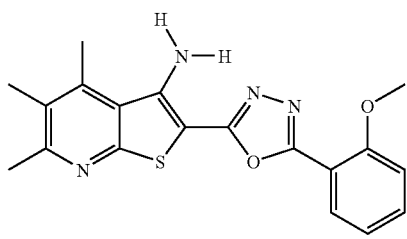

23

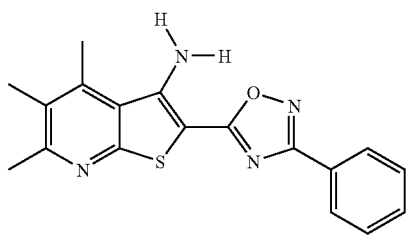

24

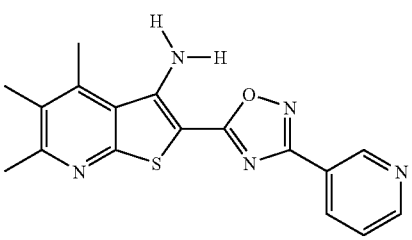

25

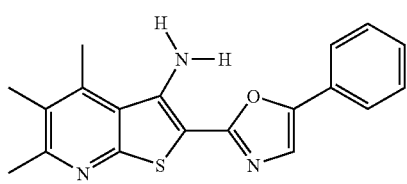

26

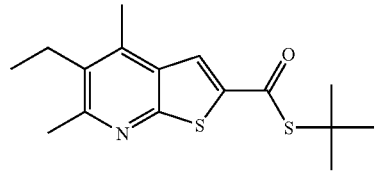

65

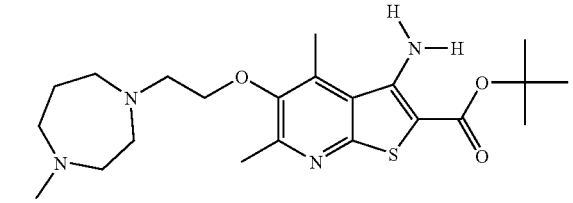

68

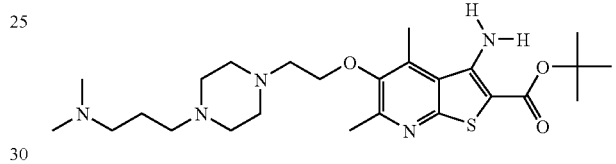

69

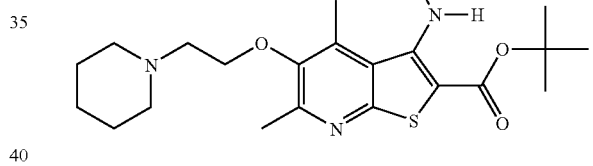

70

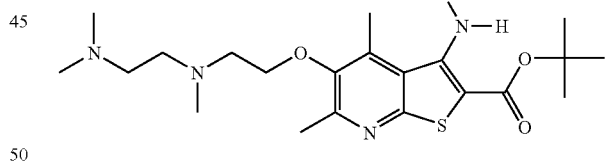

73 or a pharmaceutically acceptable salt thereof, together with a pharmaceutically acceptable Embodiment 20

The pharmaceutical composition of Embodiment 17, wherein said composition further comprises an additional anti-HCV agent selected from the group consisting of pegylated interferon, un-pegylated interferon, ribavirin or prodrugs or derivatives thereof, a glucosidase inhibitor, a protease inhibitor, a polymerase inhibitor, p7 inhibitors, and entry inhibitor, a fusion inhibitor, an anti-fibrotic, a caspase inhibitor, a drug which targets inosine monophosphate dehydrogenase inhibitors (IMPDH), synthetic thymosin alpha 1, therapeutic vaccines, immunomodulators, a helicase inhibitor, and a Toll-like receptor agonist.

Embodiment 21

A pharmaceutical composition for the prevention or treatment of Hepatitis C viral (HCV) infection comprising a compound having the following formula:

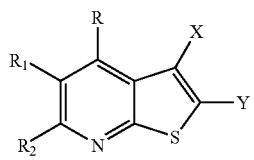

wherein
X is amino or hydrogen;
Y is
- a —COOR$_x$ group, where R$_x$ is as defined above;
- a —COR$_a$ group, where R$_a$ is:
  - an amino optionally substituted with one or two C$_1$ to C$_6$ alkyls, where the alkyls are optionally substituted with a C$_6$ to C$_8$ aryl;
- a —SR$_x$ group, where R$_x$ is as defined above;
- a 5 or 6 membered heteroaryl optionally substituted with:
  - a C$_6$ to C$_8$ aryl optionally substituted with:
    - an alkoxy
    - a halogen; or
    - a C$_1$ to C$_6$ alkyl;
  - a 5- or 6-membered heteroaryl optionally substituted with a C$_6$ to C$_8$ aryl optionally substituted with a halogen;

R is a C$_1$ to C$_6$ alkyl;
R$_1$ is a C$_1$ to C$_6$ alkyl or R$_1$ is selected from the group consisting of
- an alkoxy optionally substituted with an amino group, wherein the amino group is optionally substituted with one or two C$_1$ to C$_6$ alkyls, where the alkyls are optionally substituted with an amino optionally substituted with one or two C$_1$ to C$_6$ alkyls; and
- an alkoxy optionally substituted with a 5 to 8 membered heterocycle optionally substituted with a C$_1$ to C$_6$ alkyl, which is optionally substituted with:
  - an amino, optionally substituted with one or two C$_1$ to C$_6$ alkyls; and R$_2$ is a C$_1$ to C$_6$ alkyl or an amino optionally substituted with a C$_1$ to C$_6$ alkyl;

or a pharmaceutically acceptable salt thereof, together with an additional anti-HCV agent and a pharmaceutically acceptable excipient.

Embodiment 22

The pharmaceutical composition of Embodiment 21, wherein said additional anti-HCV agent is selected from the group consisting of pegylated interferon, un-pegylated interferon, ribavirin or prodrugs or derivatives thereof, a glucosidase inhibitor, a protease inhibitor, a polymerase inhibitor, p7 inhibitors, an entry inhibitor, a fusion inhibitor, an anti-fibrotic, a caspase inhibitor, a drug which targets inosine monophosphate dehydrogenase inhibitors (IMPDH), synthetic thymosin alpha 1, therapeutic vaccines, immunomodulators, a helicase inhibitor, and a Toll-like receptor agonist.

Embodiment 23

The pharmaceutical compostion of Embodiment 21, wherein R is a methyl group.

Embodiment 24

The pharmaceutical composition of Embodiment 21, wherein R, R$_1$ and R$_2$ are independently C$_1$ to C$_6$ alkyl. Embodiment 25. The pharmaceutical composition of Embodiment 24, wherein said C$_1$ to C$_6$ alkyl in R, R$_1$ and R$_2$ is independently a methyl or an ethyl.

Embodiment 26

The pharmaceutical composition of Embodiment 21, wherein R$_1$ is a C$_1$ to C$_6$ alkyl.

Embodiment 27

The pharmaceutical composition of Embodiment 26, wherein R$_1$ is methyl or ethyl.

Embodiment 28

The pharmaceutical composition of Embodiment 21, wherein R$_2$ is a C$_1$ to C$_6$ alkyl.

Embodiment 29

The pharmaceutical composition of Embodiment 21, wherein R$_2$ is methyl.

Embodiment 30

A method for treating a subject for a Hepatitis C viral (HCV) infection, or for preventing a subject from becoming infected with HCV, comprising administering to said subject a pharmaceutical composition comprising an HCV inhibitory amount of at least one compound having the following formula:

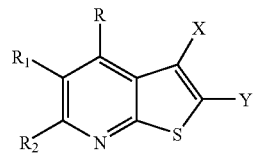

wherein:
X is:
  hydrogen;
  a cyano group;
  an amino group;

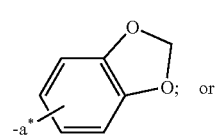

a 5- or 6-membered heteroaryl;
a $C_6$ to $C_8$ aryl, optionally substituted with:
  an alkoxy group,
  a cyano group, or
  a halogen;
or X together with Y forms: O

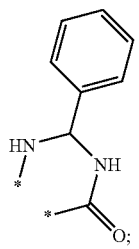

Y is:
  a halogen;
  an amino group;

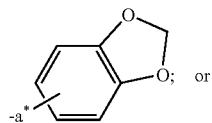

a —$SO_2R_x$, where $R_x$ is a $C_1$ to $C_6$ alkyl;
a cyano group;
a —$COOR_x$ group, where $R_x$ is a $C_1$ to $C_6$ alkyl;
a $C_6$ to $C_8$ aryl, optionally substituted with:
  an alkoxy; or
  a cyano group;
a —$COR_a$ group, where $R_a$ is:
  an amino optionally substituted with one or two $C_1$ to $C_6$ alkyls, where the alkyls are optionally substituted with a $C_6$ to $C_8$ aryl;
  a —$NHR_b$ group where $R_b$ is:
    a $C_6$ to $C_8$ aryl optionally substituted with:
      a haloalkyl; or
      a halogen
      a haloalkoxy; or
    a 5- or 6-membered heterocycle optionally substituted with a $C_1$ to $C_6$ alkyl;
    a $C_1$ to $C_6$ alkyl;
  a —$SR_x$ group, where $R_x$ is as defined above;
a 5 or 6 membered heteroaryl optionally substituted with:
  a $C_6$ to $C_8$ aryl optionally substituted with:
    an alkoxy
    a halogen; or
    a $C_1$ to $C_6$ alkyl;
  a 5- or 6-membered heteroaryl optionally substituted with
    an alkoxy
    a halogen; or
    a $C_1$ to $C_6$ alkyl;
a $C_1$ to $C_6$ alkyl, optionally substituted with a —$OR_c$, where $R_c$ is a $C_6$ to $C_8$ aryl optionally substituted with one or more halogens; or
a nitro group;
a —$NHR_d$ group, where $R_d$ is a $C_6$ to $C_8$ aryl optionally substituted with an alkoxy
a —$NHCOR_e$ group where $R_e$ is:

a $C_6$ to $C_8$ aryl optionally substituted with a haloalkyl;
a $C_1$ to $C_6$ alkyl;
or together with X forms:

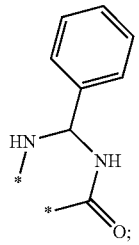

R is:
  a hydrogen
  a haloalkyl;
  a $C_1$ to $C_6$ alkyl optionally substituted with hydroxyl;
  a 5- or 6-member heteroaryl;
  a $C_6$ to $C_8$ aryl optionally substituted with one or more halogens;
or R together with $R_1$ forms:

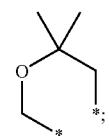

$R_1$ is:
  a hydrogen;
  a $C_6$ to $C_8$ aryl
  a $C_1$ to $C_6$ alkyl;
  a $OCOR_f$ where $R_f$ is a 5- or 6-membered heterocycle;
  an alkoxy optionally substituted with an amino group, wherein the amino group is optionally substituted with one or two $C_1$ to $C_6$ alkyls, where the alkyls are optionally substituted with an amino optionally substituted with one or two $C_1$ to $C_6$ alkyls
  an alkoxy optionally substituted with a 5 to 8 membered heterocycle optionally substituted with a $C_1$ to $C_6$ alkyl, which is optionally substituted with:
    an alkoxy, or
    an amino, optionally substituted with one or two $C_1$ to $C_6$ alkyls;
or $R_1$ together with $R_2$ forms:

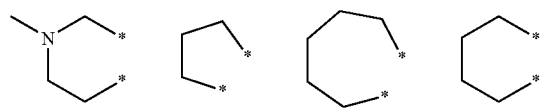

$R_1$ together with R forms:

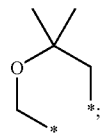

$R_2$ is:
  a $C_1$ to $C_6$ alkyl;

a 5 or 6-membered heterocycle;
an amino optionally substituted with a $C_1$ to $C_6$ alkyl;
or $R_1$ together with $R_2$ forms:

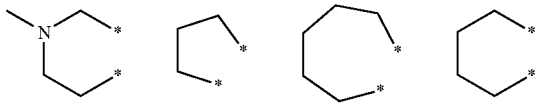

or a pharmaceutically acceptable salt thereof and a pharmaceutically acceptable excipient.

Embodiment 31

The method of Embodiment 30, wherein said method further comprises administering an additional anti-HCV agent.

Embodiment 32

The method of Embodiment 30, wherein said additional anti-HCV agent is selected from the group consisting of pegylated interferon, un-pegylated interferon, ribavirin or pro-drugs or derivatives thereof, a glucosidase inhibitor, a protease inhibitor, a polymerase inhibitor, p7 inhibitors, an entry inhibitor, a fusion inhibitor, an anti-fibrotic, a caspase inhibitor, a drug which targets inosine monophosphate dehydrogenase inhibitors (IMPDH), synthetic thymosin alpha 1, therapeutic vaccines, immunomodulators, a helicase inhibitor, and a Toll-like receptor agonist.

Embodiment 33

The method of Embodiment 30, wherein X is an amino group or a hydrogen.

Embodiment 34

The method of Embodiment 30, wherein Y is a 5 or 6 membered heteroaryl optionally substituted with:
a $C_6$ to $C_8$ aryl optionally substituted with:
an alkoxy
a halogen; or
a $C_1$ to $C_6$ alkyl; or
a 5- or 6-membered heteroaryl optionally substituted with
a halogen.

Embodiment 35

The method of Embodiment 30, wherein Y is a —$COOR_5$ group, where $R_x$ is as defined above;
a —$COR_a$ group, where $R_a$ is:
an amino optionally substituted with one or two $C_1$ to $C_6$ alkyls, where the alkyls are optionally substituted with a $C_6$ to $C_8$ aryl;
a —$SR_x$ group, where $R_x$ is as defined above;
a 5 or 6 membered heteroaryl optionally substituted with:
a $C_6$ to $C_8$ aryl optionally substituted with:
an alkoxy
a halogen; or
a $C_1$ to $C_6$ alkyl;
a 5- or 6-membered heteroaryl optionally substituted with a $C_6$ to $C_8$ aryl optionally substituted with a halogen;

Embodiment 36

The method of Embodiment 30, wherein R is a $C_1$ to $C_6$ alkyl.

Embodiment 37

The method of Embodiment 36, wherein R is a methyl group.

Embodiment 38

The method of Embodiment 30, wherein R, $R_1$ and $R_2$ are independently $C_1$ to $C_6$ alkyl.

Embodiment 39

The method of Embodiment 38, wherein said $C_1$ to $C_6$ alkyl in R, $R_1$ and $R_2$ is independently a methyl or an ethyl.

Embodiment 40

The method of Embodiment 30, wherein $R_1$ is selected from the group consisting of
a $C_1$ to $C_6$ alkyl; and
an alkoxy optionally substituted with an amino group, wherein the amino group is optionally substituted with one or two $C_1$ to $C_6$ alkyls, where the alkyls are optionally substituted with an amino optionally substituted with one or two $C_1$ to $C_6$ alkyls; and
an alkoxy optionally substituted with a 5 to 8 membered heterocycle optionally substituted with a $C_1$ to $C_6$ alkyl, which is optionally substituted with:
an amino, optionally substituted with one or two $C_1$ to $C_6$ alkyls.

Embodiment 41

The method of Embodiment 40, wherein $R_1$ is a $C_1$ to $C_6$ alkyl.

Embodiment 42

The method of Embodiment 41, wherein $R_1$ is methyl or ethyl.

Embodiment 43

The method of Embodiment 30, wherein $R_2$ is a $C_1$ to $C_6$ alkyl.

Embodiment 44

The method of Embodiment 43, wherein $R_2$ is methyl.

Embodiment 45

The method of Embodiment 30, wherein said compound is selected from the group consisting of the following compounds:

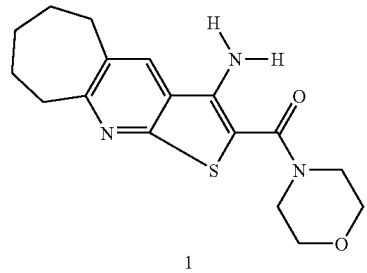
1
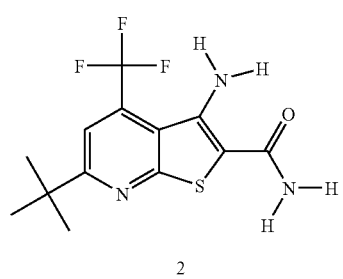
2
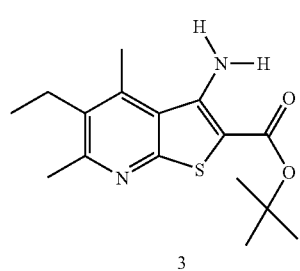
3
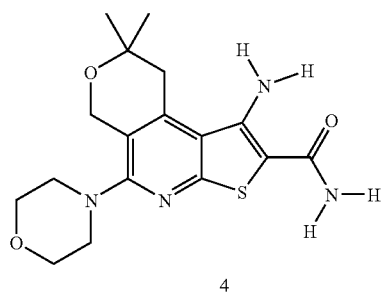
4
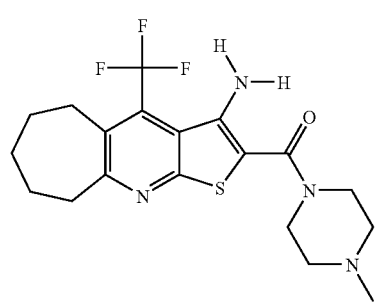
5
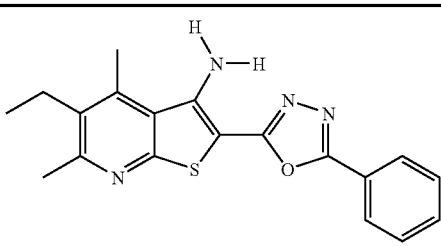
6
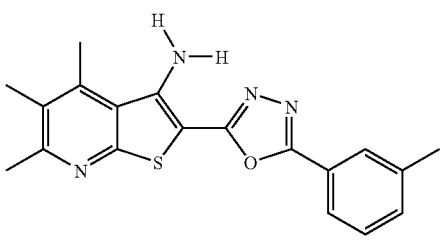
7
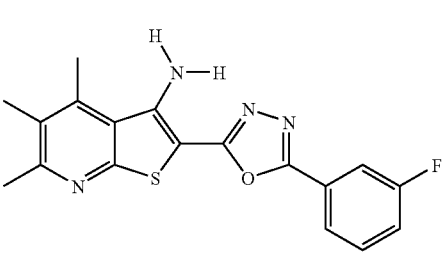
8
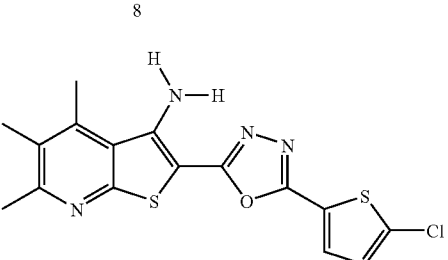
9
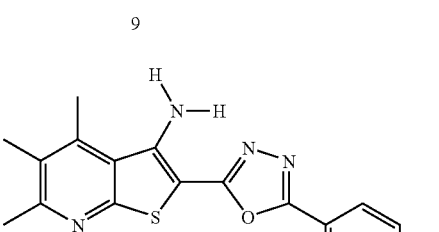
10
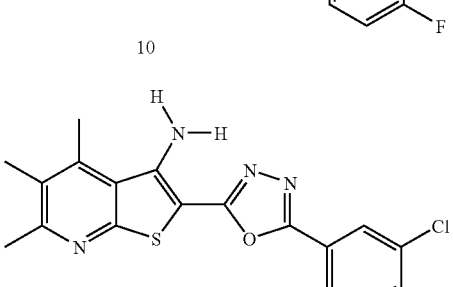
11

-continued
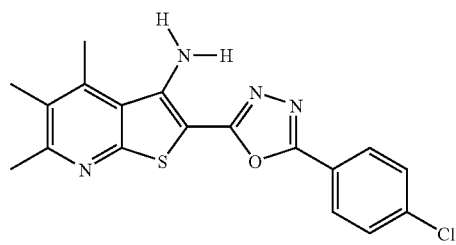
12
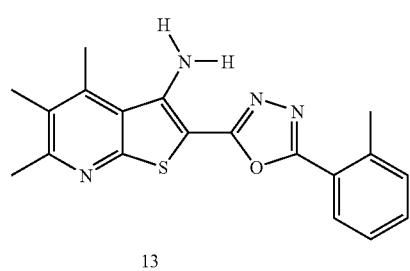
13
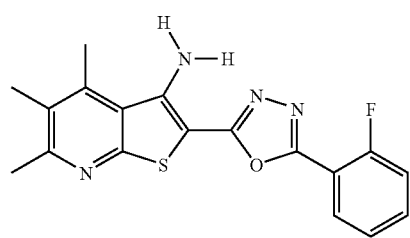
14
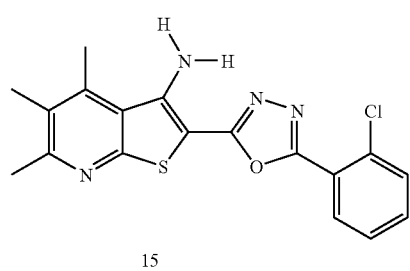
15
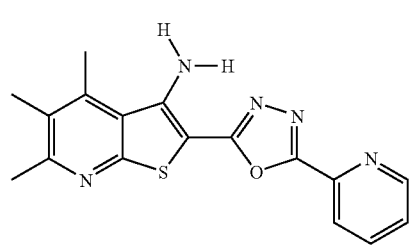
16
-continued
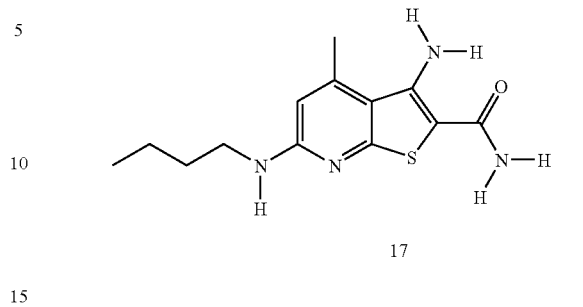
17
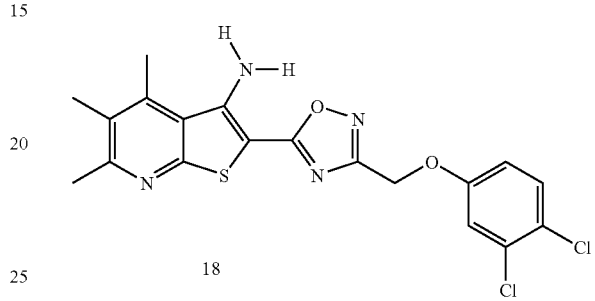
18
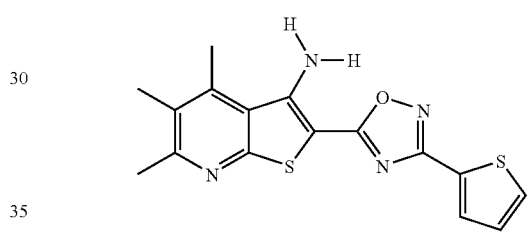
19
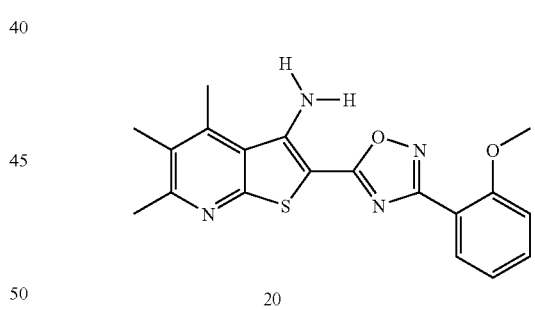
20
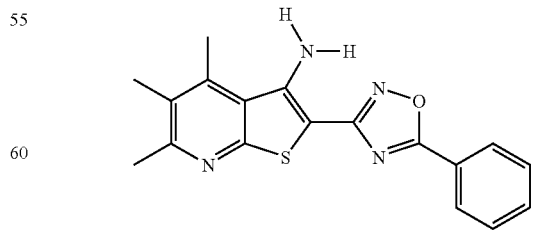
21

-continued
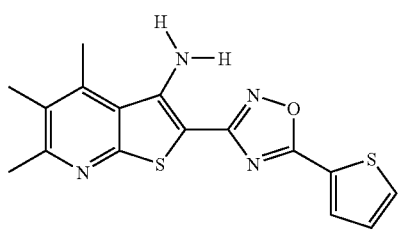
22
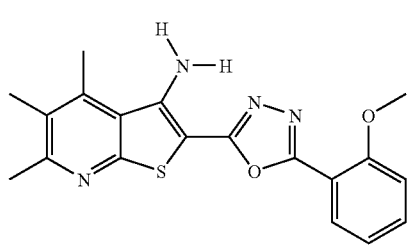
23
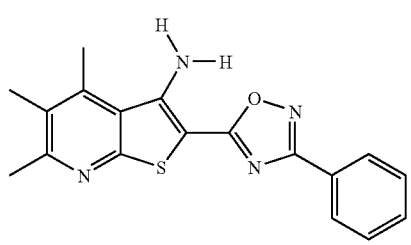
24
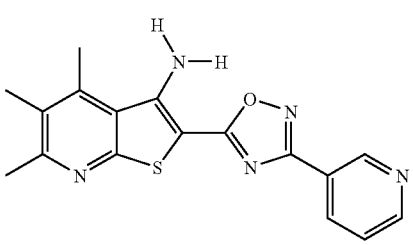
25
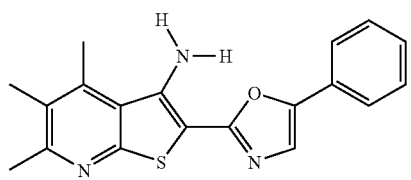
26
-continued
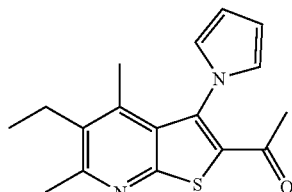
27
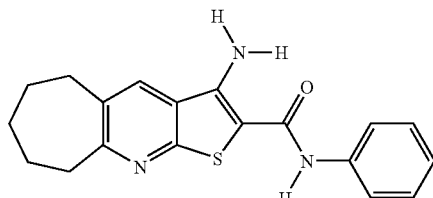
28
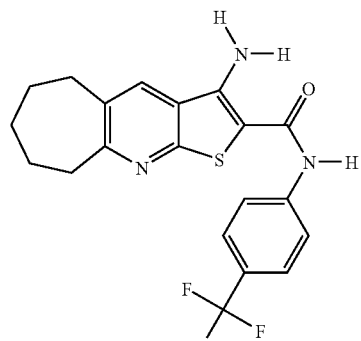
29
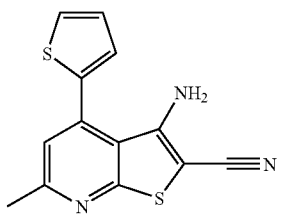
30
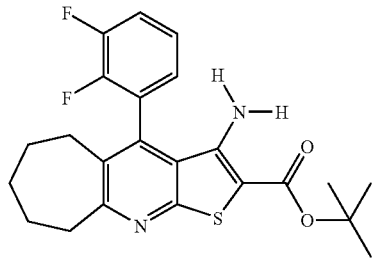
31

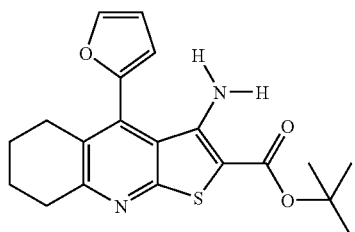
32
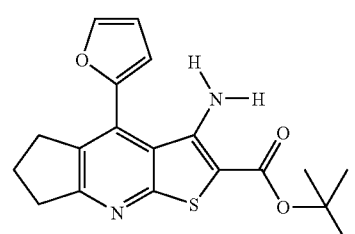
33
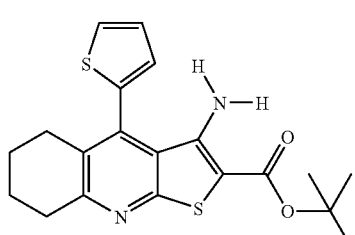
34
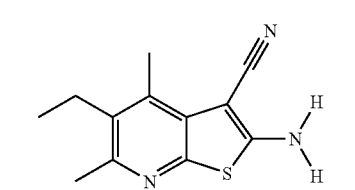
35
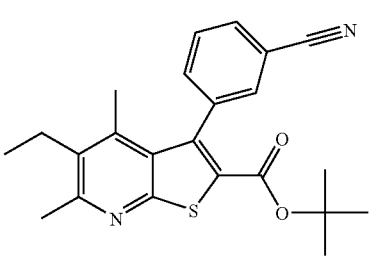
36
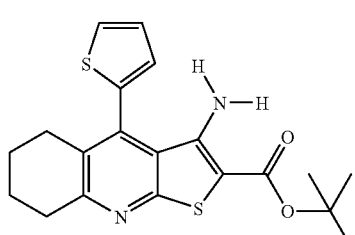
37
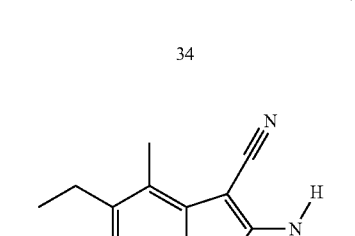
38
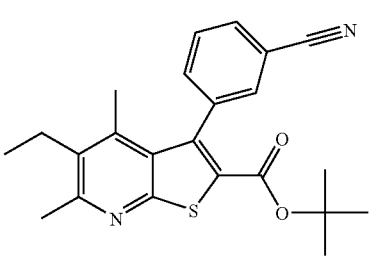
39
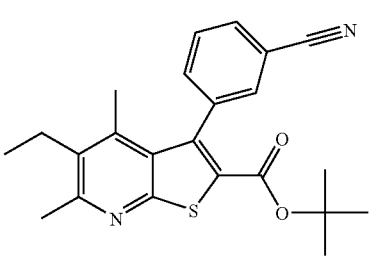
40

-continued
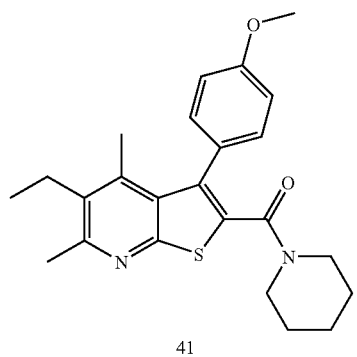
41
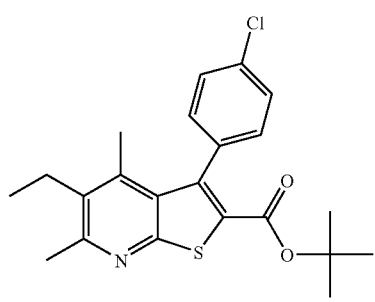
42
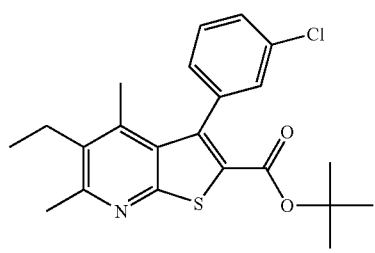
43
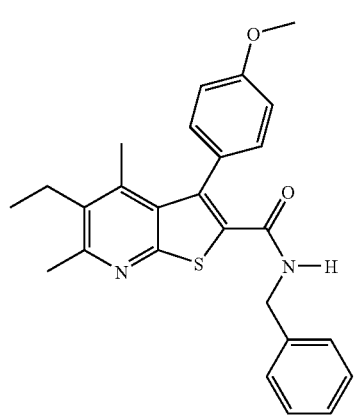
44
-continued
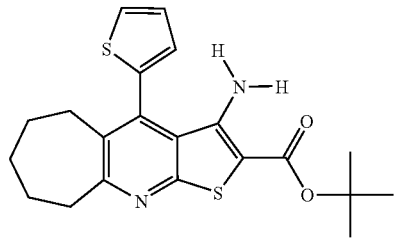
45
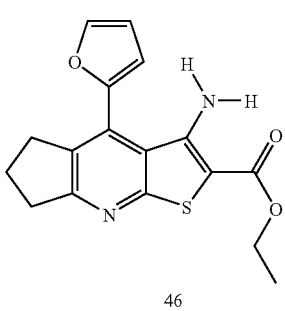
46
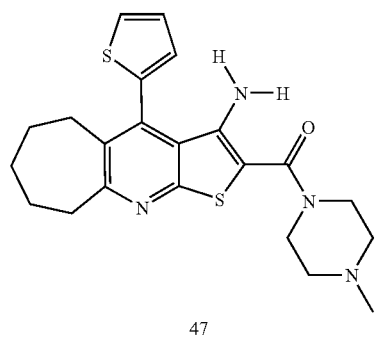
47
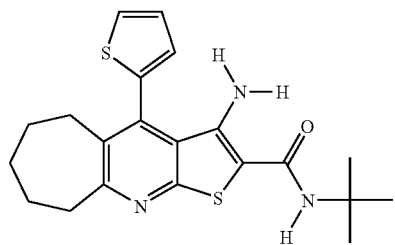
48
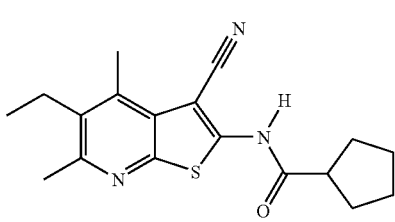
49

-continued
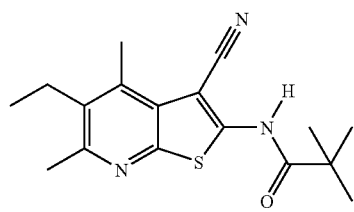
50
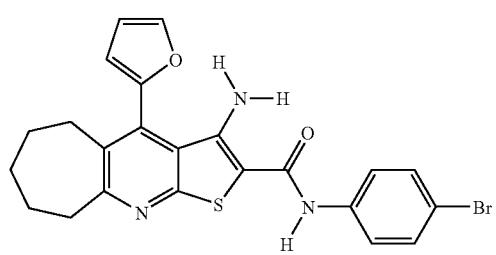
51
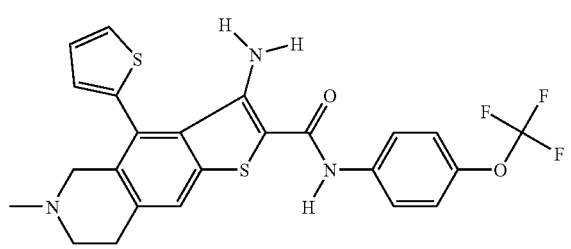
52
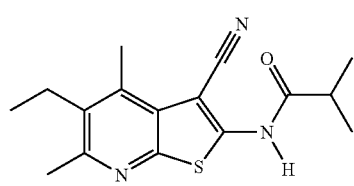
53
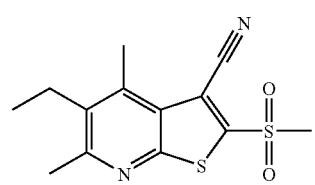
54
-continued
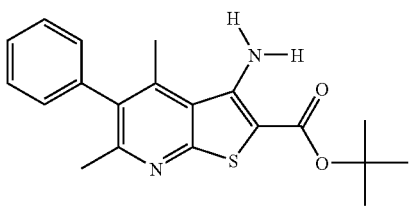
55
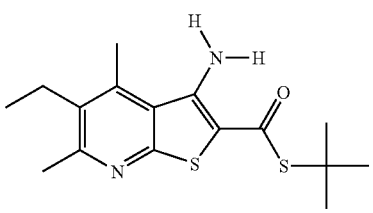
56
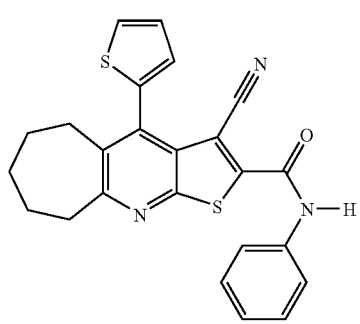
57
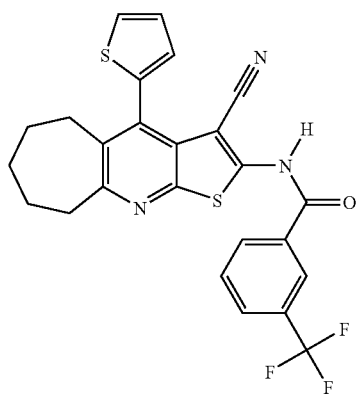
58
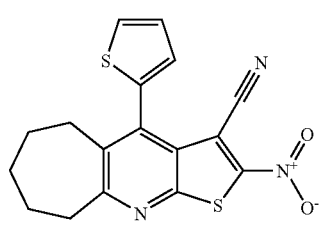
59

-continued
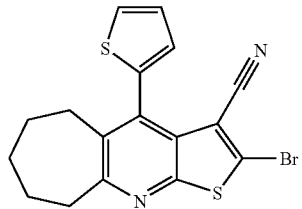
60
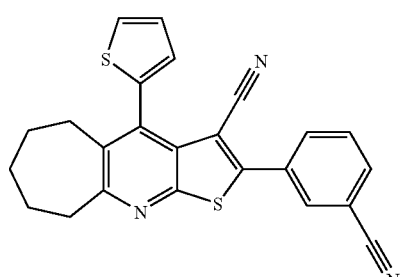
61
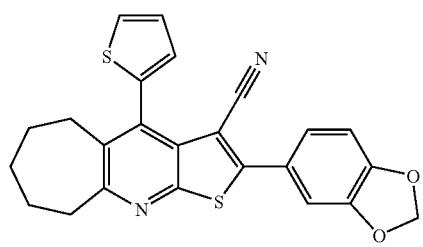
62
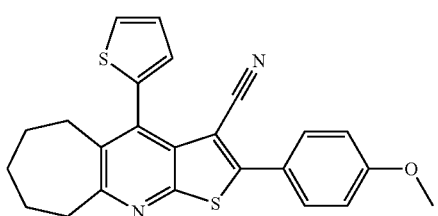
63
-continued
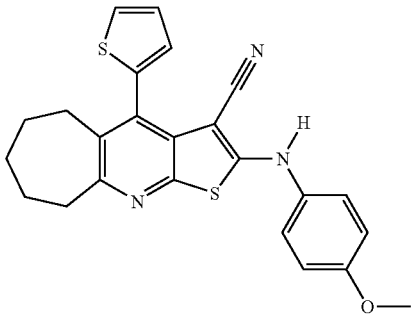
64
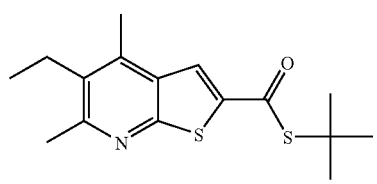
65
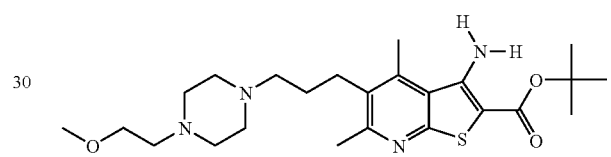
66
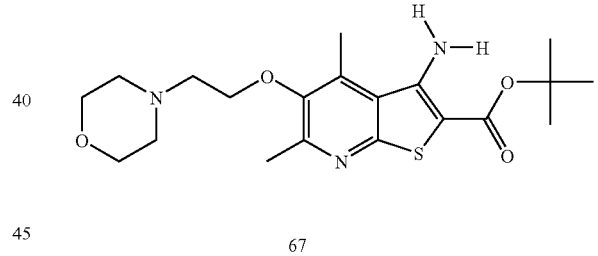
67
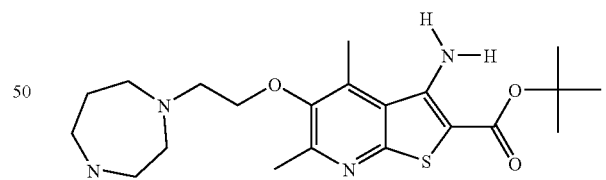
68
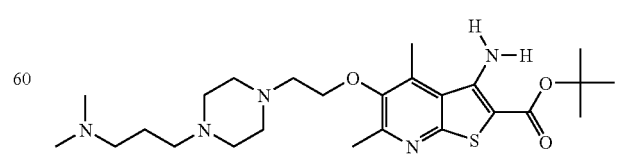
69

-continued
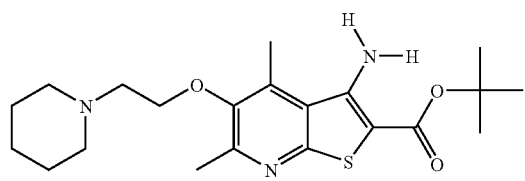
70
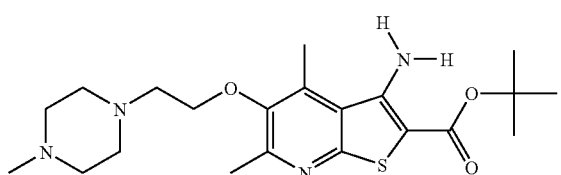
71
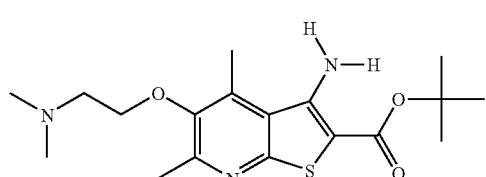
72
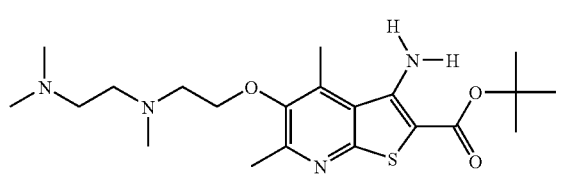
73
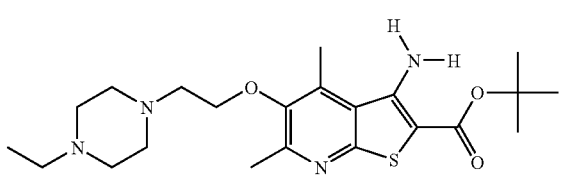
74
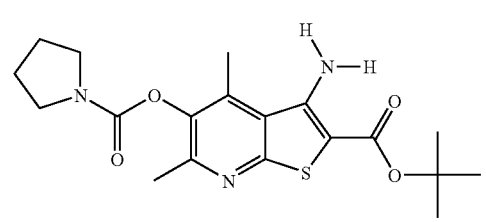
75
-continued
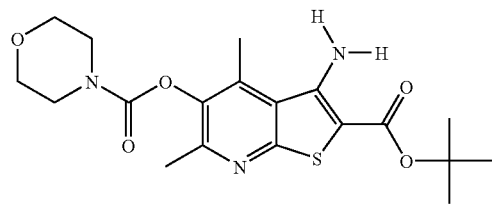
76
Embodiment 46
The method of Embodiment 30, wherein said compound is selected from the group consisting of the following compounds:
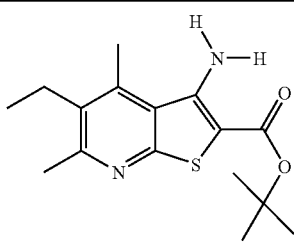
3
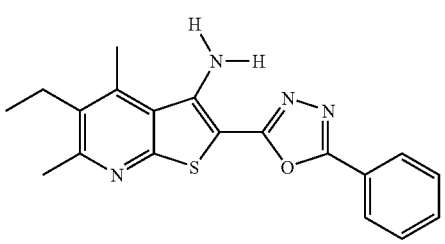
6
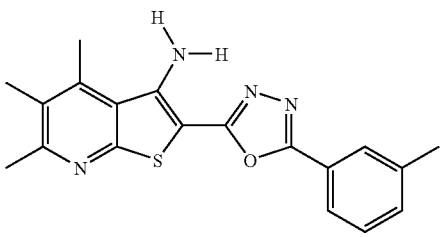
7
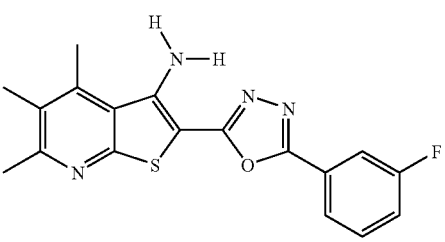
8

-continued
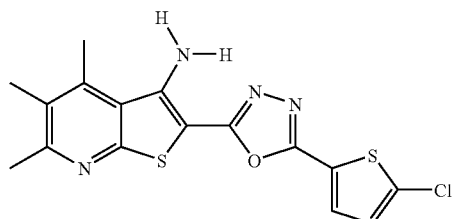
9
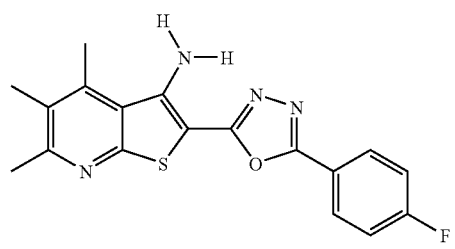
10
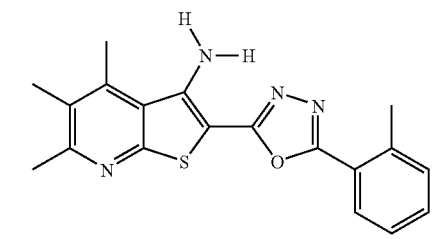
13
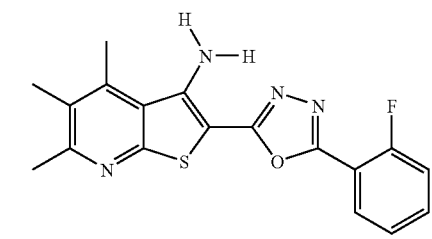
14
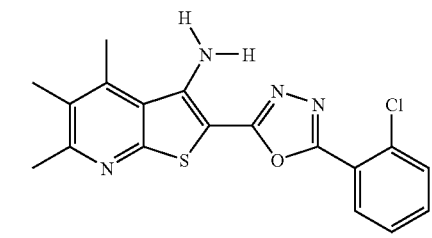
15
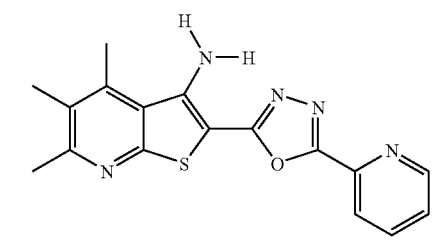
16
-continued
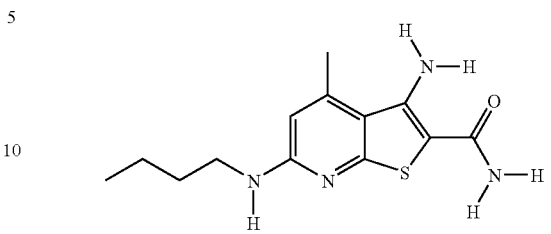
17
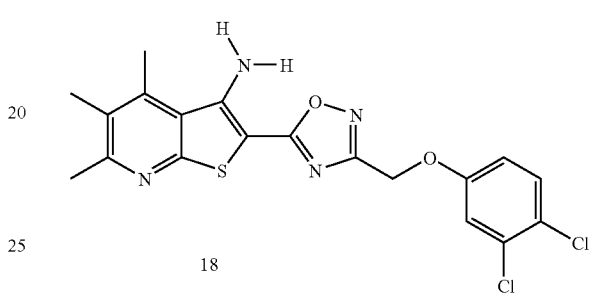
18
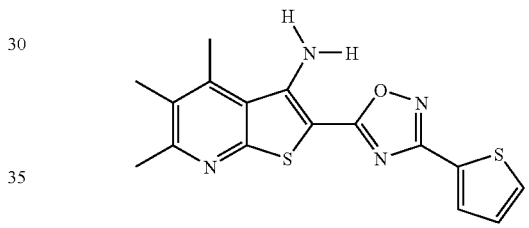
19
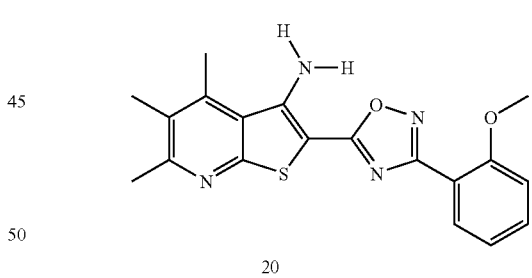
20
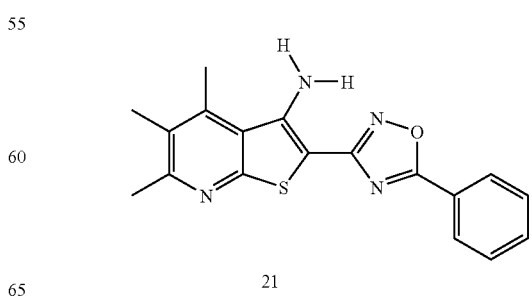
21

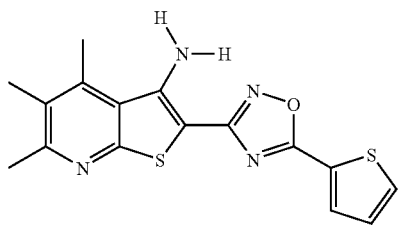
22
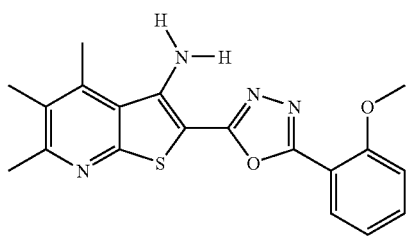
23
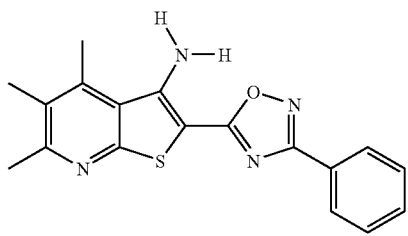
24
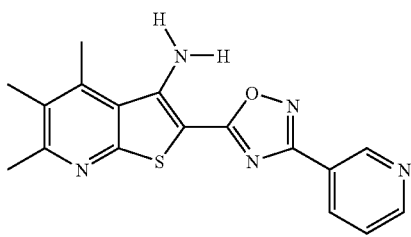
25
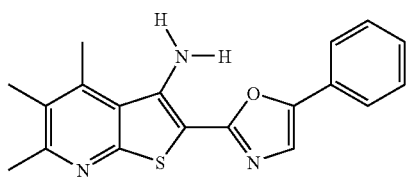
26
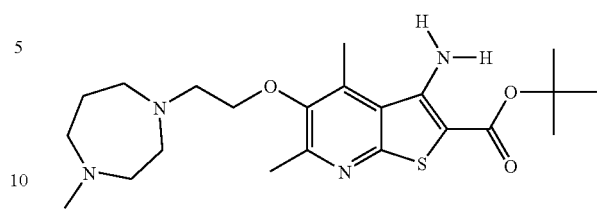
68
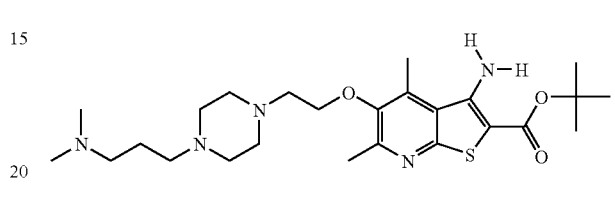
69
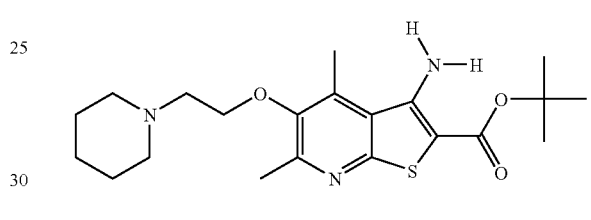
70
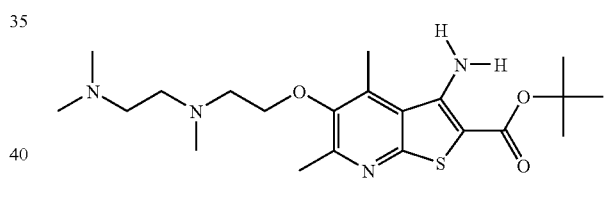
73
Embodiment 47
A pharmaceutical composition for the prevention or treatment of Hepatitis C viral (HCV) infection comprising at least one of the following compounds:
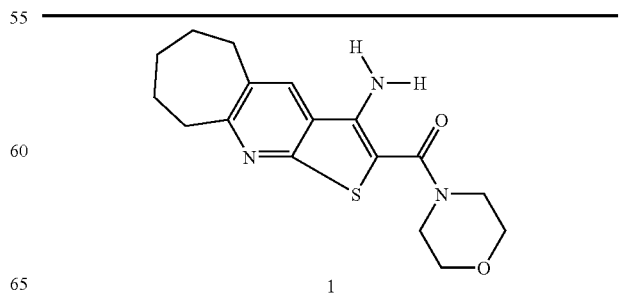
1

-continued
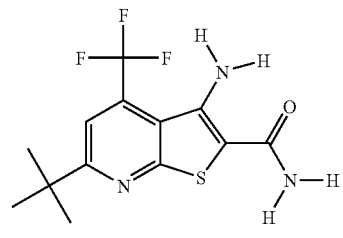
2
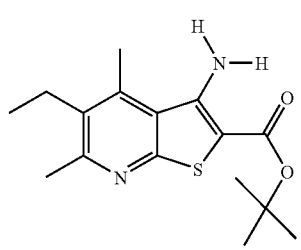
3
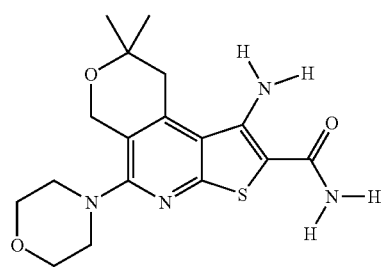
4
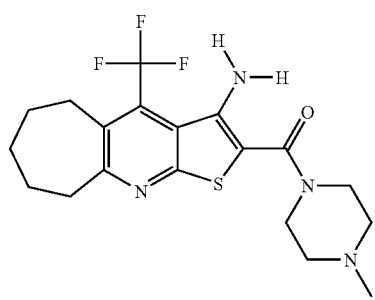
5
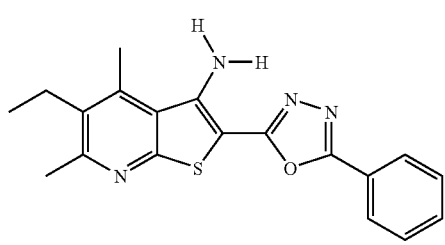
6
-continued
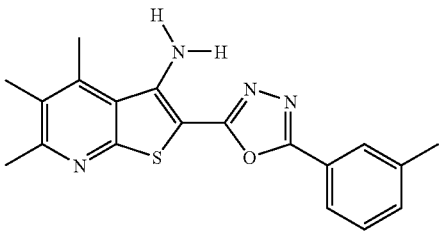
7
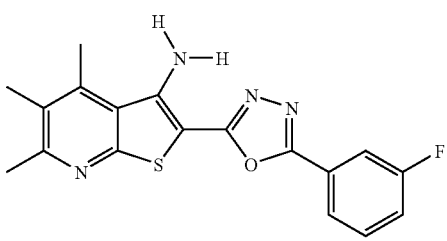
8
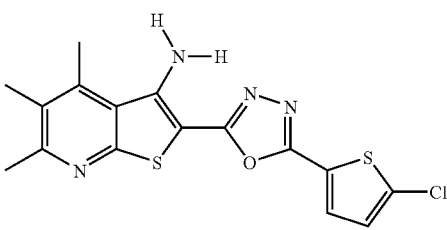
9
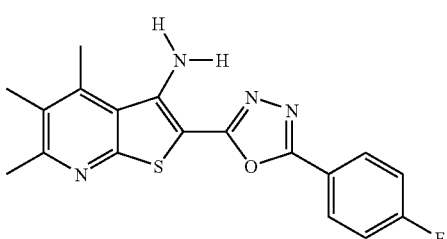
10
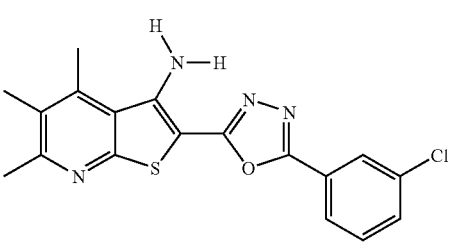
11
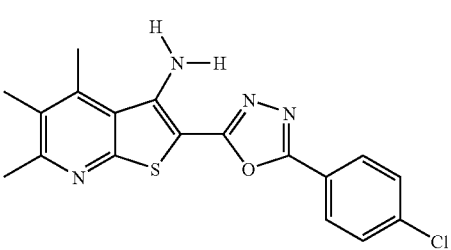
12

-continued
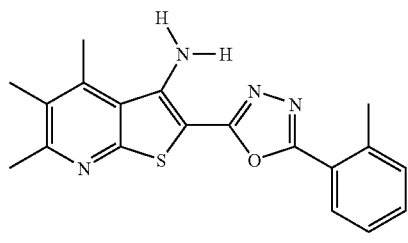
13
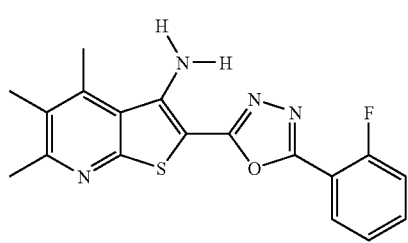
14
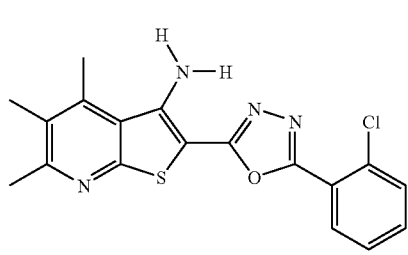
15
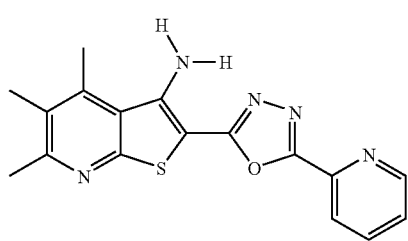
16
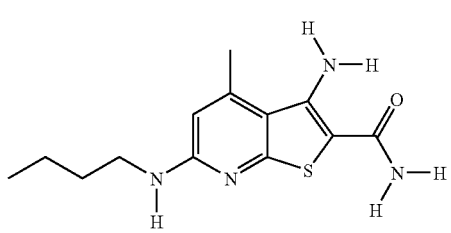
17
-continued
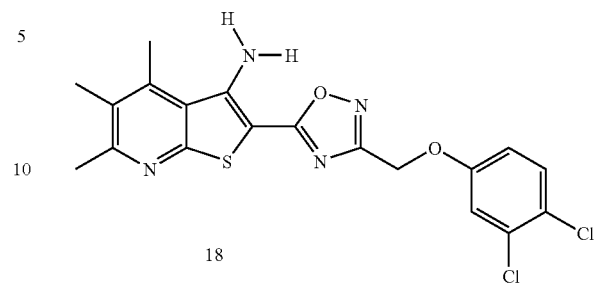
18
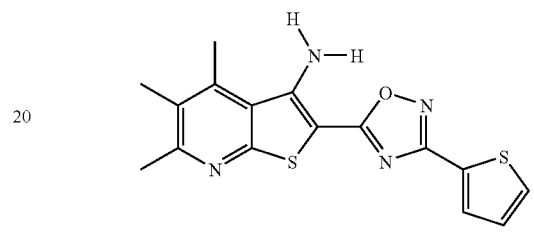
19
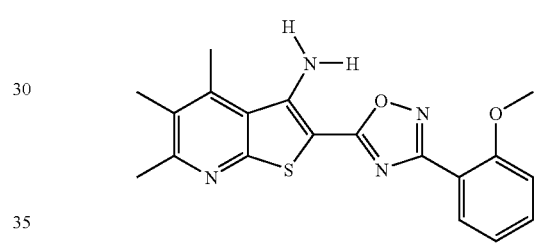
20
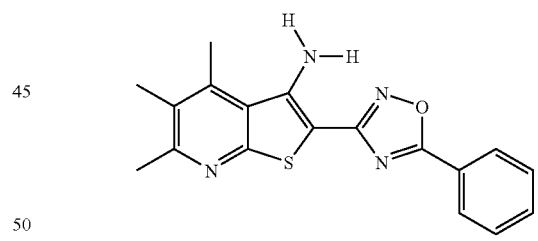
21
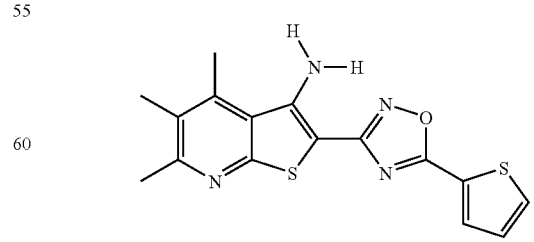
22

-continued
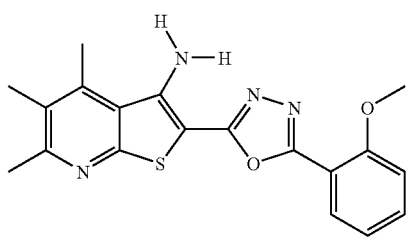
23
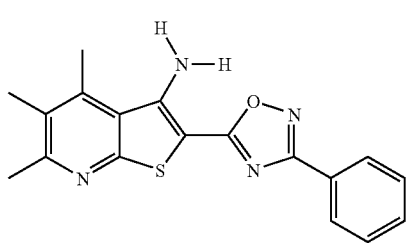
24
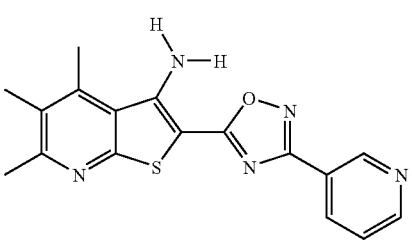
25
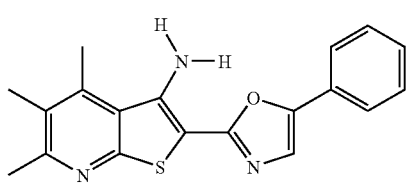
26
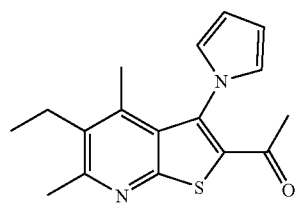
27
-continued
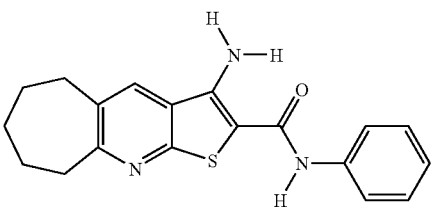
28
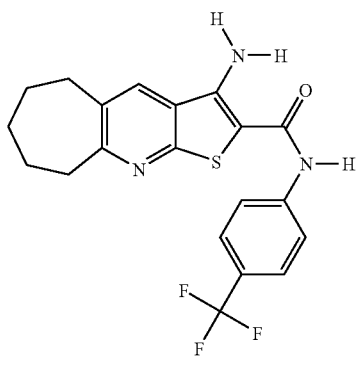
29
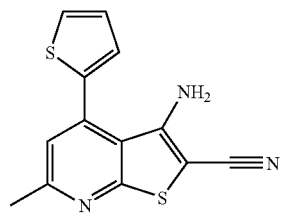
30
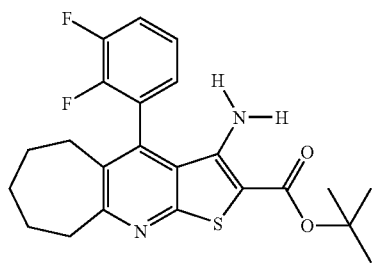
31
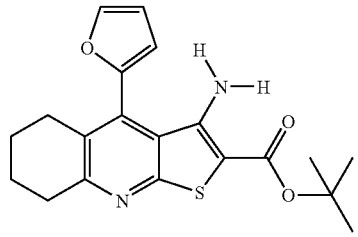
32

-continued
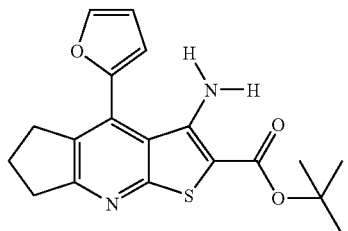
33
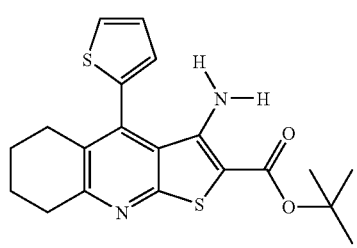
34
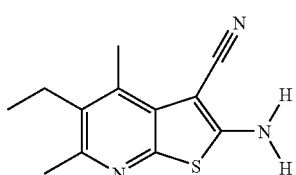
35
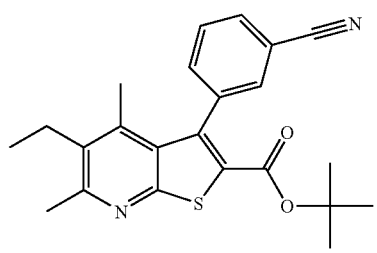
36
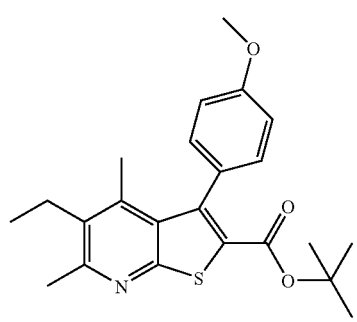
37
-continued
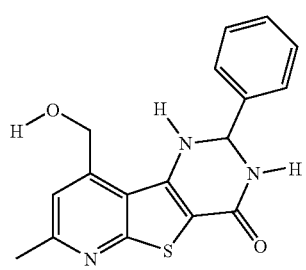
38
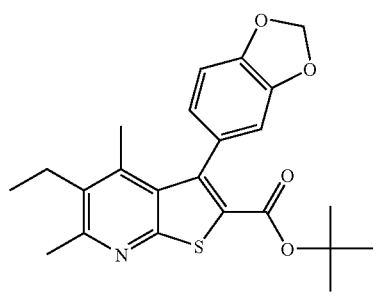
39
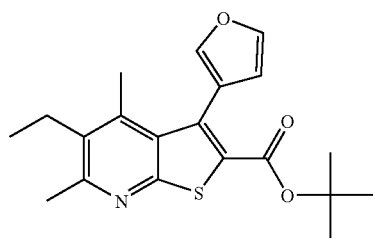
40
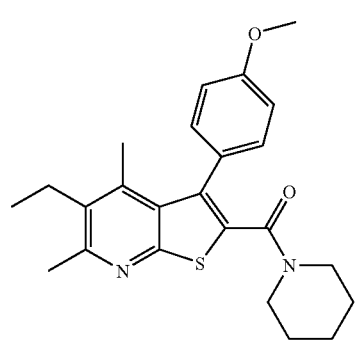
41

-continued
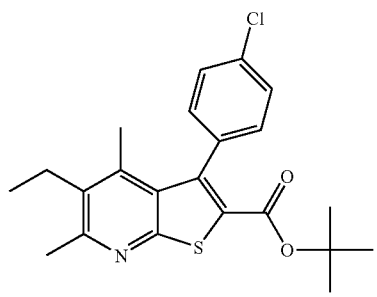
42
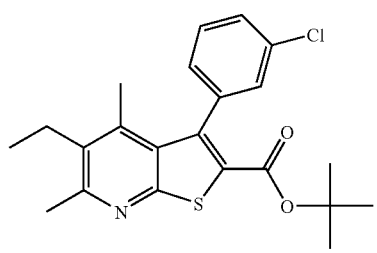
43
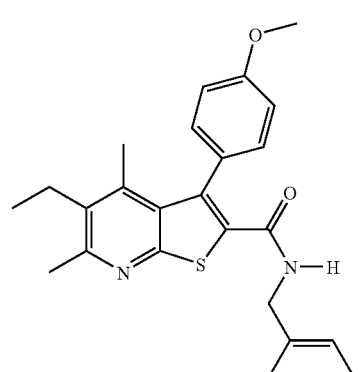
44
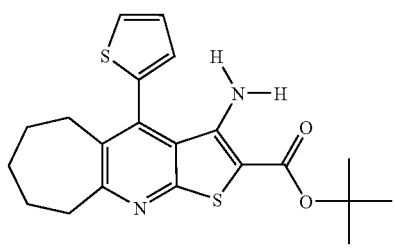
45
-continued
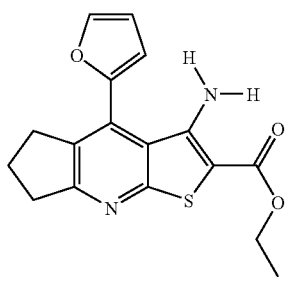
46
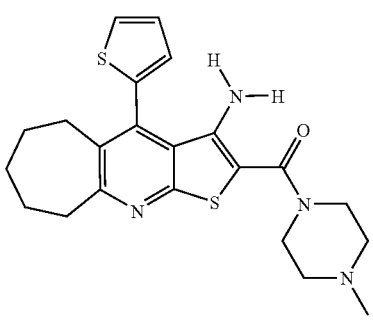
47
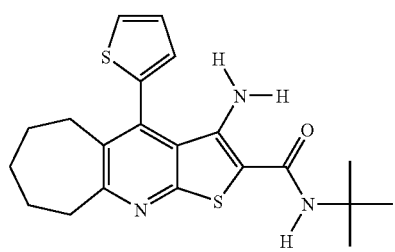
48
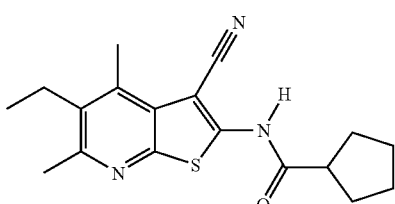
49
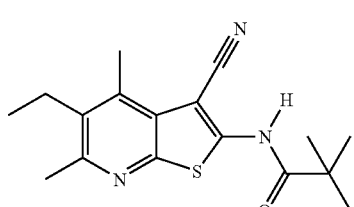
50

-continued
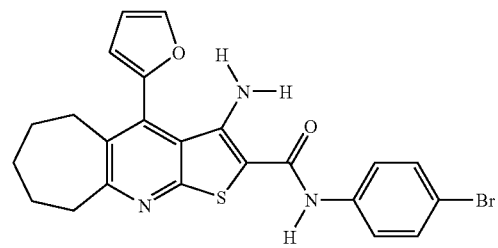
51
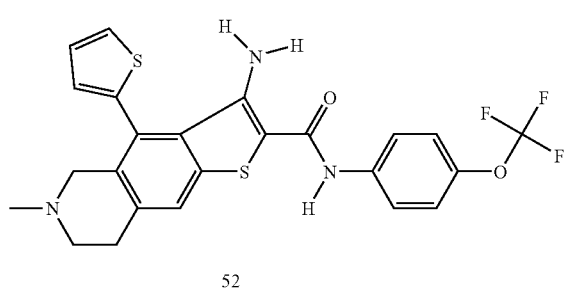
52
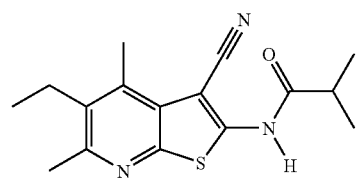
53
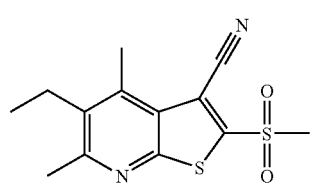
54
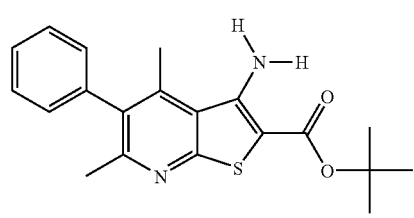
55
-continued
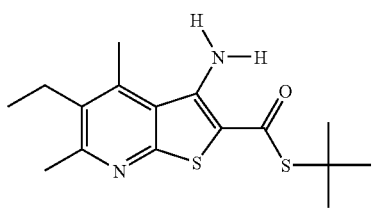
56
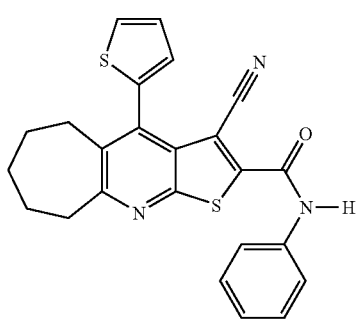
57
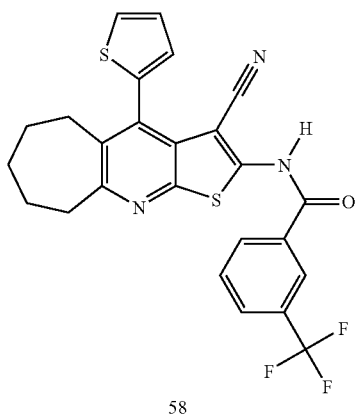
58
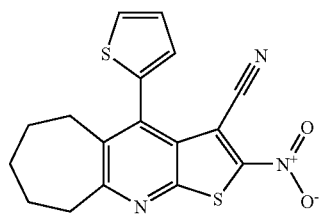
59

-continued
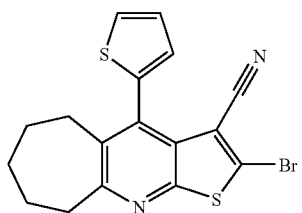
60
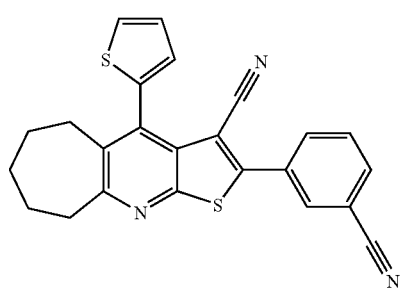
61
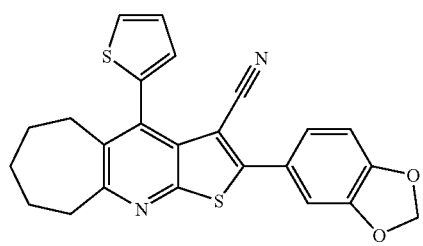
62
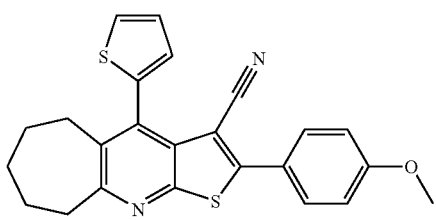
63
-continued
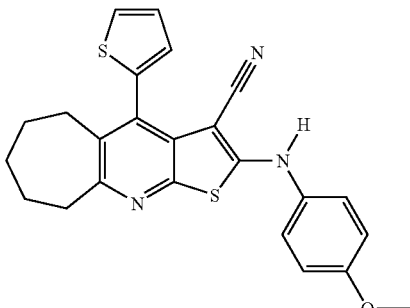
64
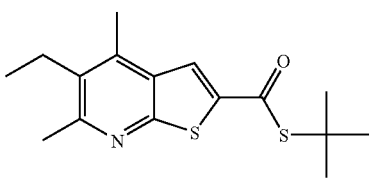
65
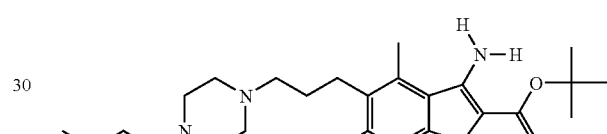
66
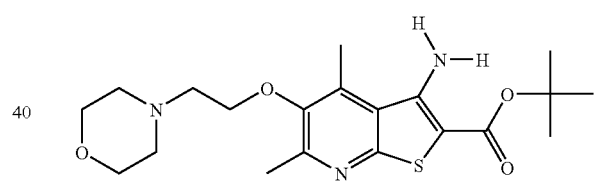
67
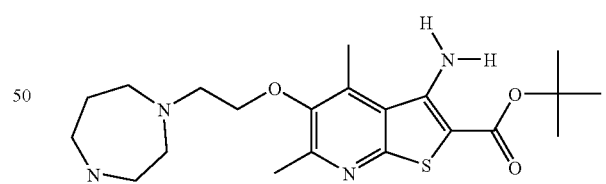
68
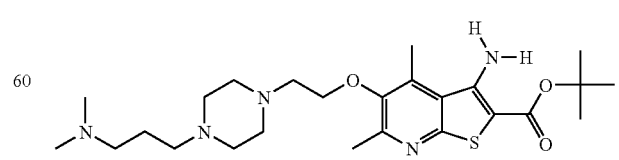
69

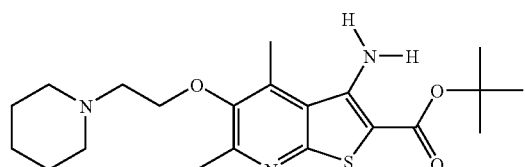
70
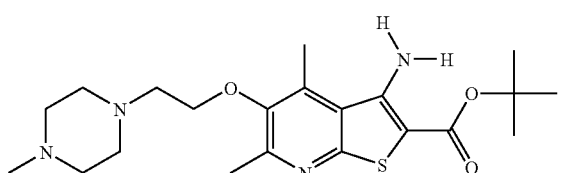
71
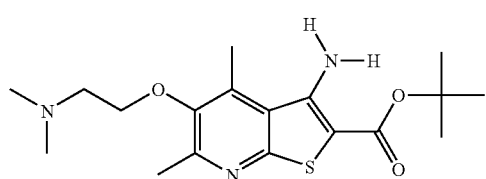
72
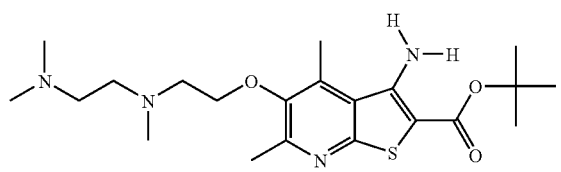
73
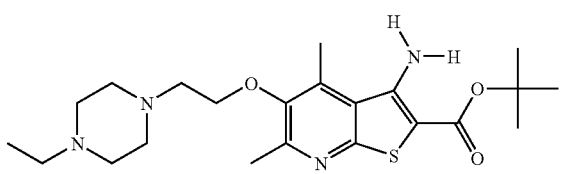
74
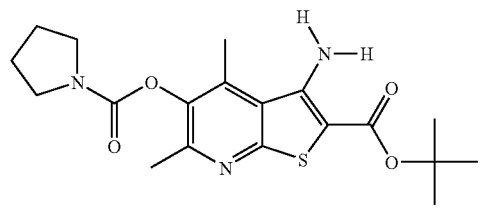
75
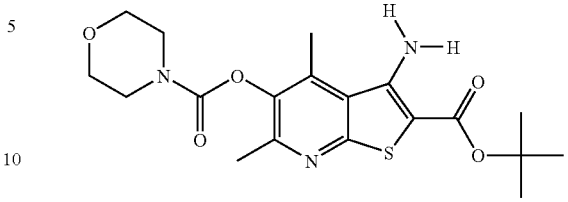
76
or a pharmaceutically acceptable salt thereof, together with a pharmaceutically acceptable excipient.
Embodiment 48
A method for the treatment of for the prevention or treatment of Hepatitis C viral (HCV) infection comprising at least one of the following compounds:
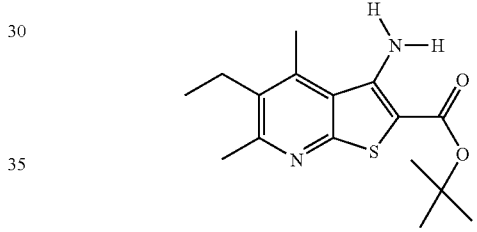
3
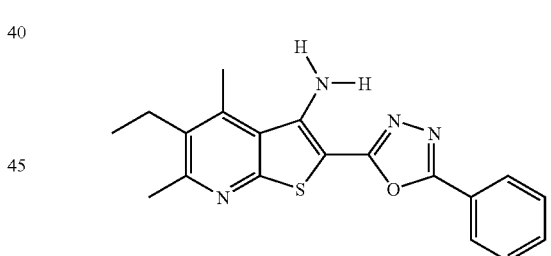
6
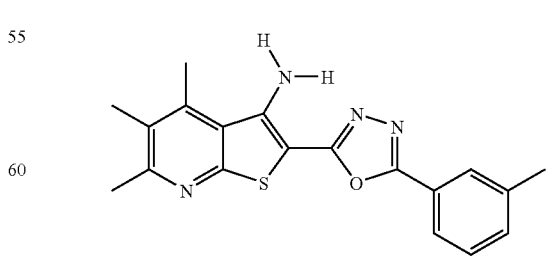
7

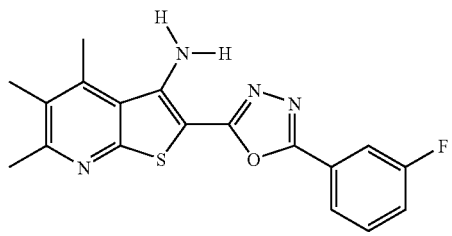
8
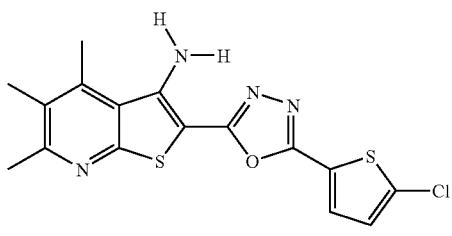
9
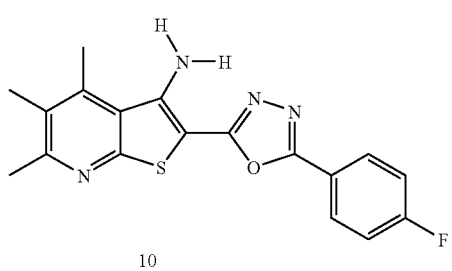
10
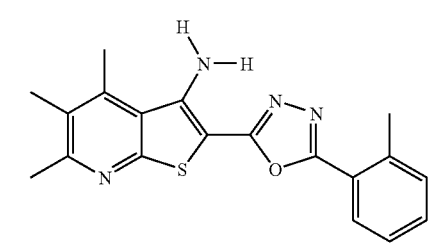
13
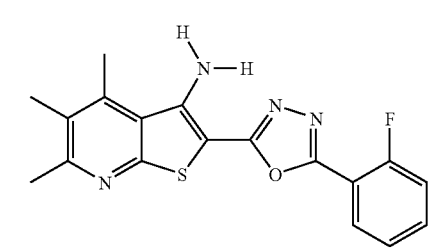
14
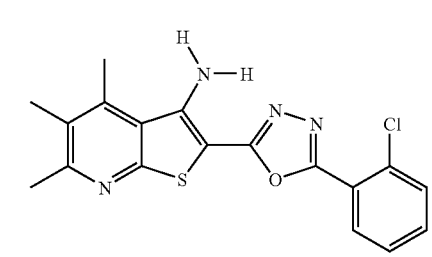
15
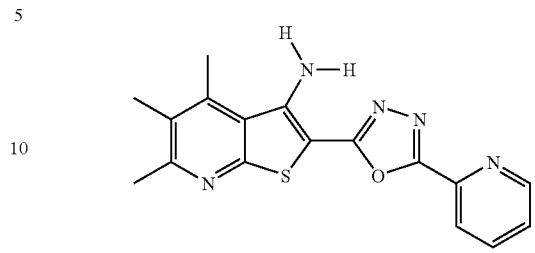
16
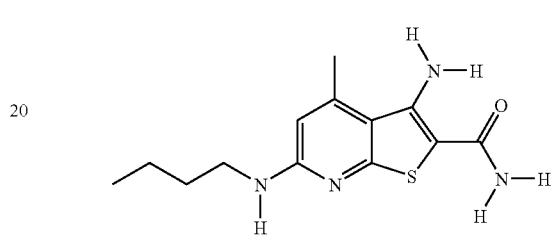
17
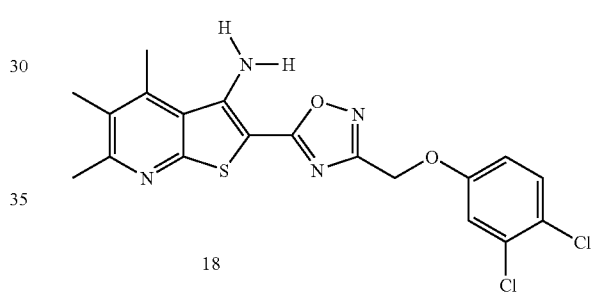
18
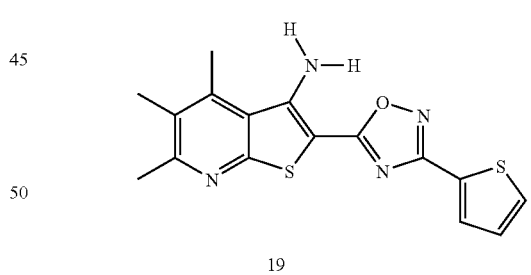
19
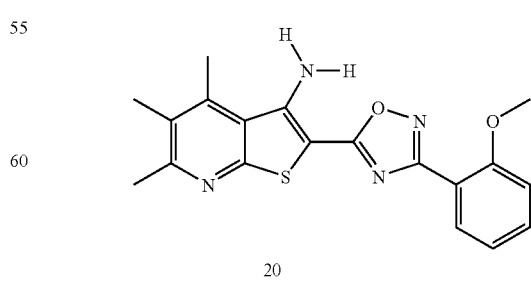
20

-continued
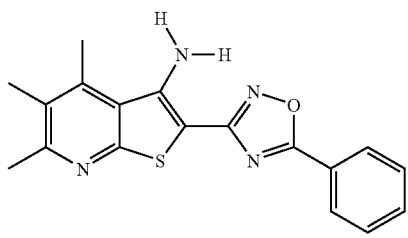
21
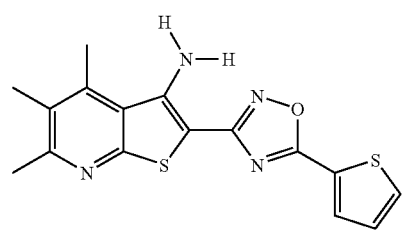
22
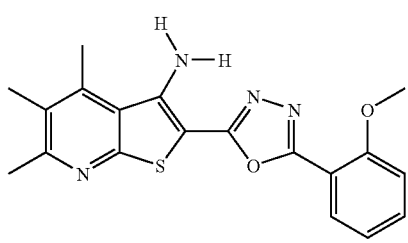
23
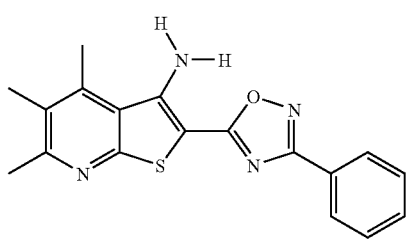
24
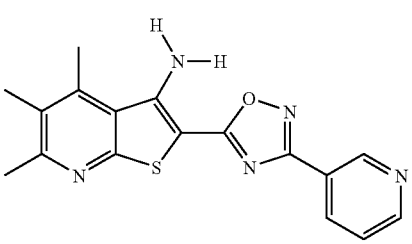
25
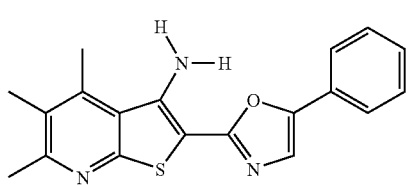
26
-continued
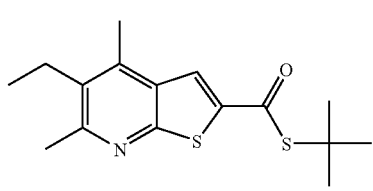
65
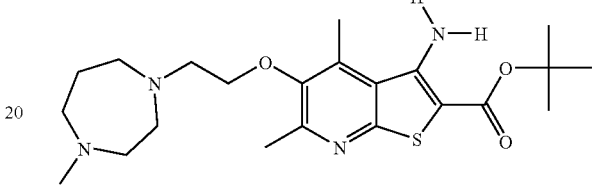
68
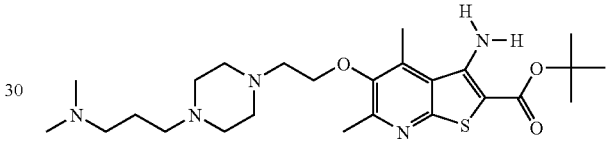
69
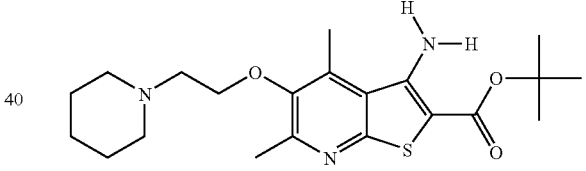
70
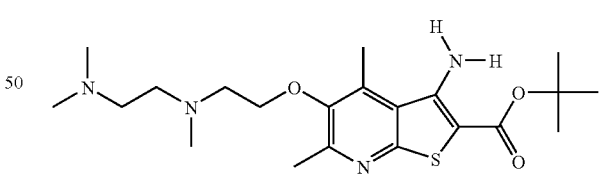
73
Embodiment 49
A method for treating a subject for a Hepatitis C viral (HCV) infection, or for preventing a subject from being infected with HCV, comprising administering to said subject a pharmaceutical composition comprising an HCV inhibitory amount of a compound having the following formula:

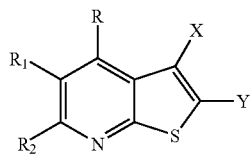

wherein

X is amino or hydrogen;

Y is
- a —COOR$_5$ group, where R$_x$ is as defined above;
- a —COR$_a$ group, where R$_a$ is:
  - an amino optionally substituted with one or two C$_1$ to C$_6$ alkyls, where the alkyls are optionally substituted with a C$_6$ to C$_8$ aryl;
- a —SR$_x$ group, where R$_x$ is as defined above;
- a 5 or 6 membered heteroaryl optionally substituted with:
  - a C$_6$ to C$_8$ aryl optionally substituted with:
    - an alkoxy
    - a halogen; or
    - a C$_1$ to C$_6$ alkyl;
  - a 5- or 6-membered heteroaryl optionally substituted with a C$_6$ to C$_8$ aryl optionally substituted with a halogen;

R is a C$_1$ to C$_6$ alkyl;

R$_1$ is a C$_1$ to C$_6$ alkyl or R$_1$ is selected from the group consisting of
- an alkoxy optionally substituted with an amino group, wherein the amino group is optionally substituted with one or two C$_1$ to C$_6$ alkyls, where the alkyls are optionally substituted with an amino optionally substituted with one or two C$_1$ to C$_6$ alkyls; and
- an alkoxy optionally substituted with a 5 to 8 membered heterocycle optionally substituted with a C$_1$ to C$_6$ alkyl, which is optionally substituted with:
  - an amino, optionally substituted with one or two C$_1$ to C$_6$ alkyls; and R$_2$ is a C$_1$ to C$_6$ alkyl or an amino optionally substituted with a C$_1$ to C$_6$ alkyl;

or a pharmaceutically acceptable salt thereof and a pharmaceutically acceptable excipient.

Embodiment 50

The method of Embodiment 49, wherein said method further comprises administering an additional anti-HCV agent.

Embodiment 51

The method of Embodiment 50, wherein said additional anti-HCV agent is selected from the group consisting of pegylated interferon, un-pegylated interferon, ribavirin or prodrugs or derivatives thereof, a glucosidase inhibitor, a protease inhibitor, a polymerase inhibitor, p7 inhibitors, an entry inhibitor, a fusion inhibitor, an anti-fibrotic, a caspase inhibitor, a drug which targets inosine monophosphate dehydrogenase inhibitors (IMPDH), synthetic thymosin alpha 1, therapeutic vaccines, immunomodulators, a helicase inhibitor, and a Toll-like receptor agonist.

Embodiment 52

A method for treating a subject for a Hepatitis C viral (HCV) infection comprising administering to said subject a pharmaceutical composition comprising an HCV inhibitory amount of at least one of the following compounds:

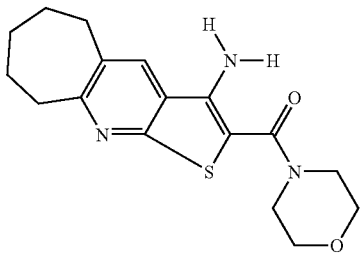

1

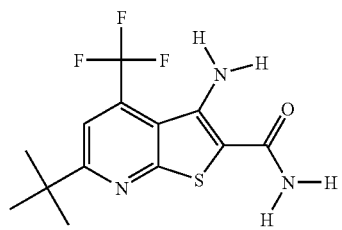

2

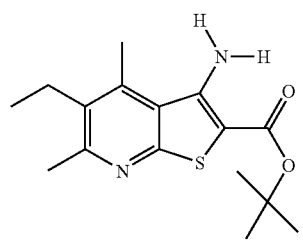

3

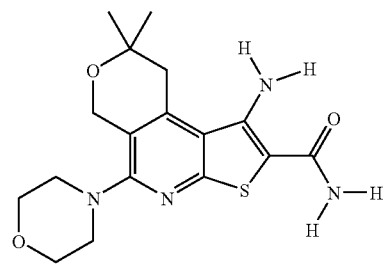

4

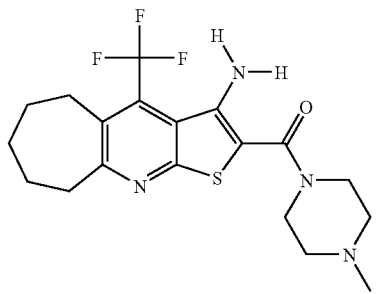

5

-continued
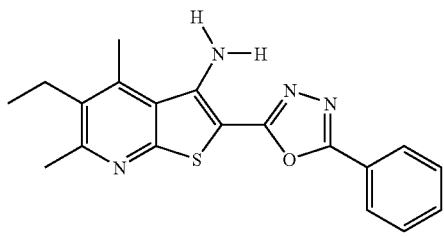
6
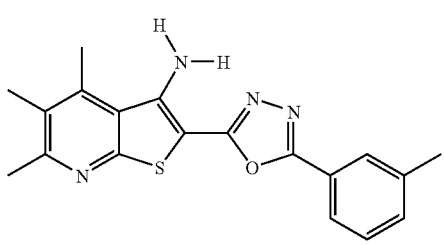
7
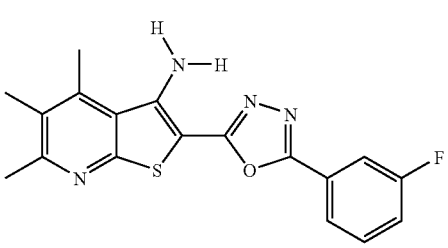
8
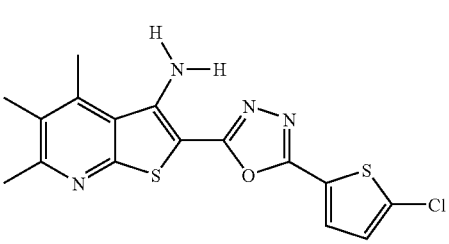
9
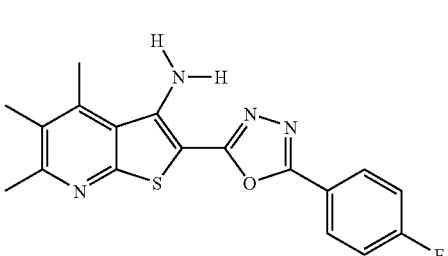
10
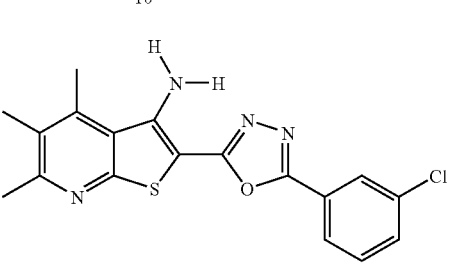
11
-continued
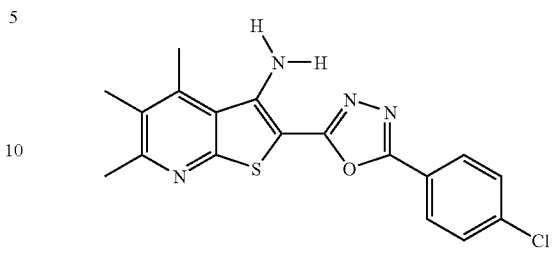
12
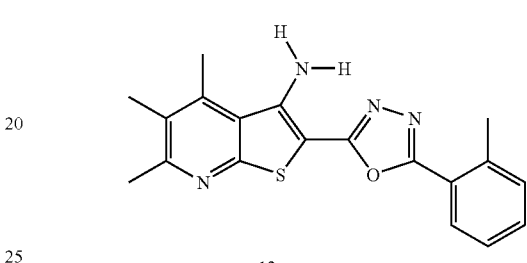
13
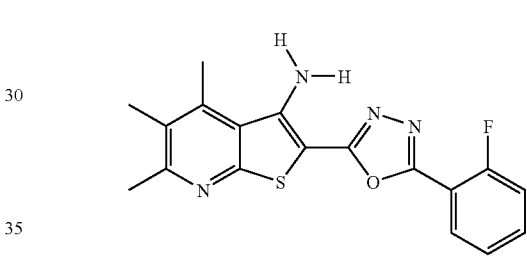
14
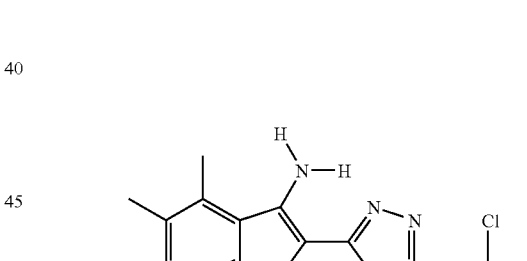
15
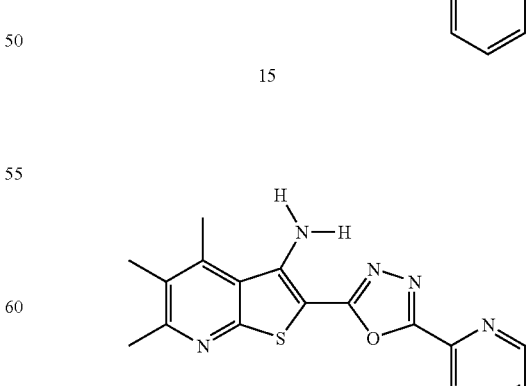
16

-continued
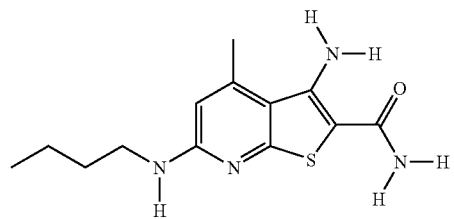
17
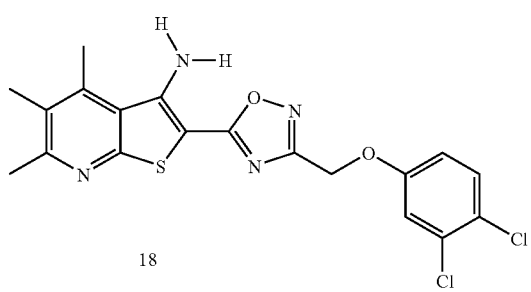
18
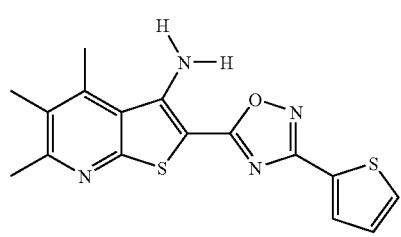
19
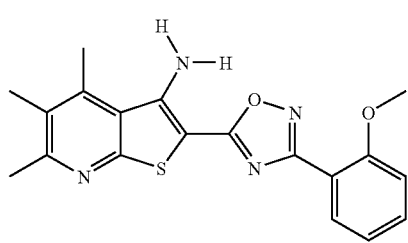
20
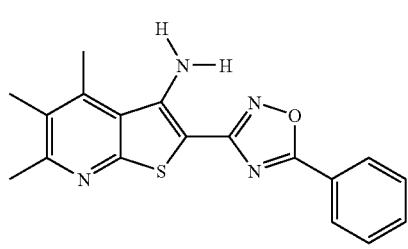
21
-continued
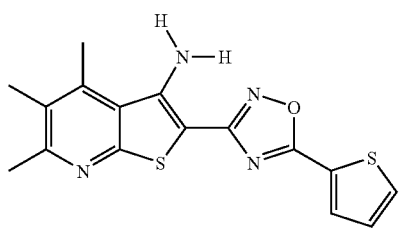
22
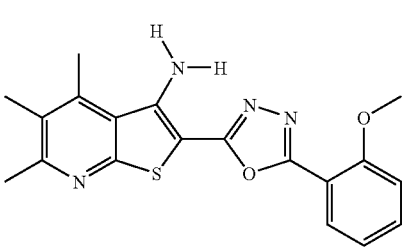
23
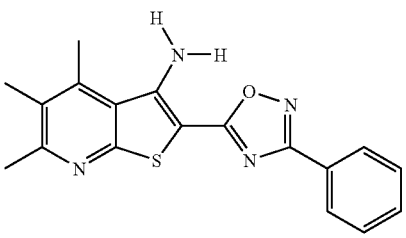
24
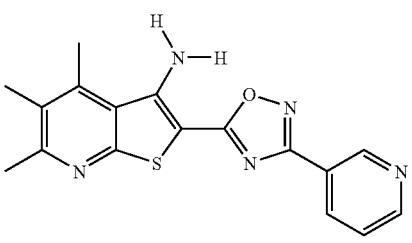
25
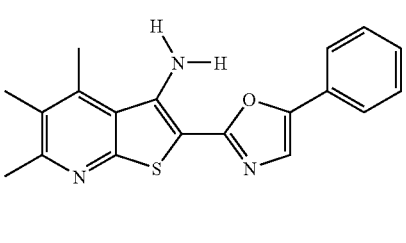
26

-continued
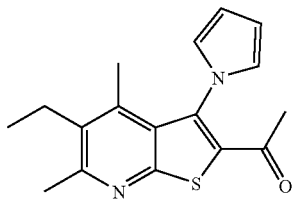
27
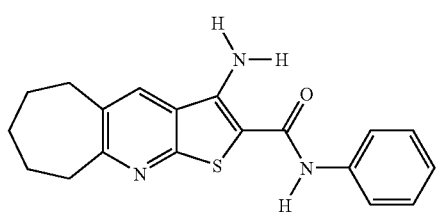
28
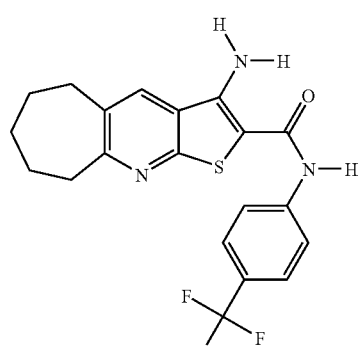
29
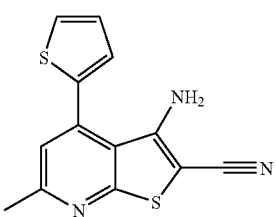
30
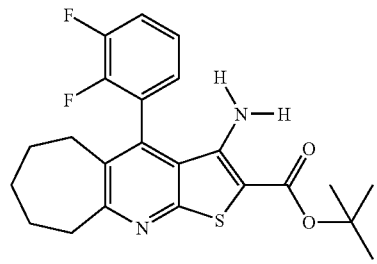
31
-continued
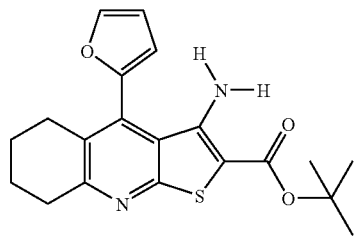
32
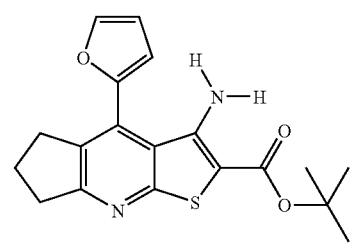
33
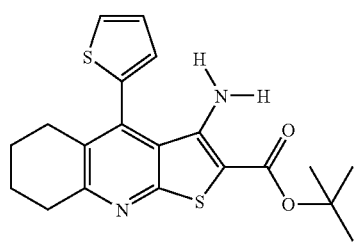
34
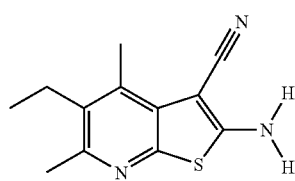
35
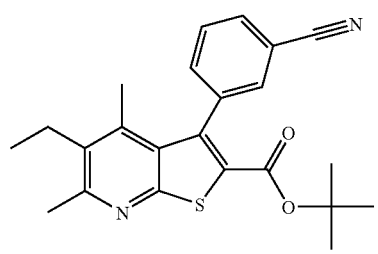
36

-continued
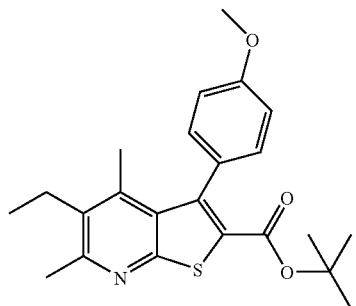
37
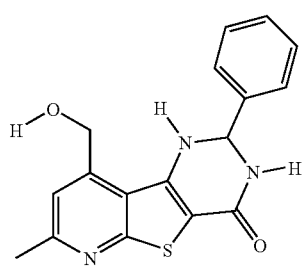
38
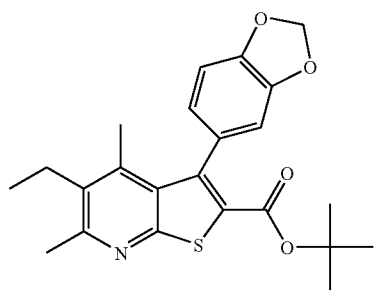
39
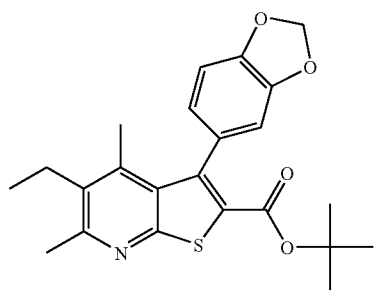
40
-continued
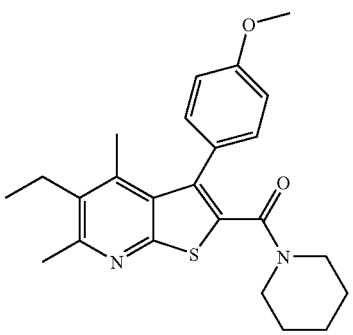
41
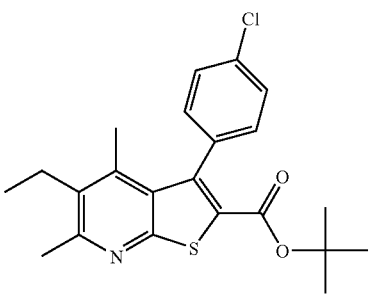
42
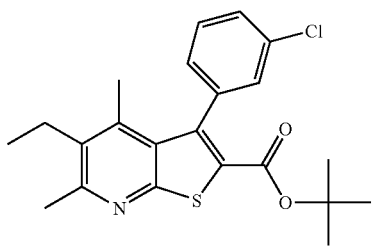
43
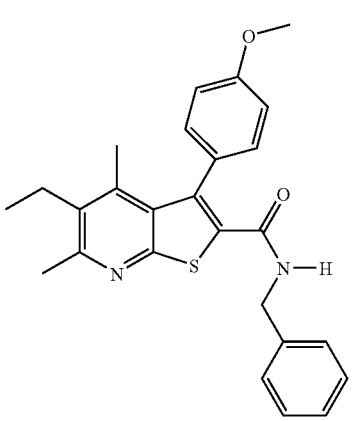
44

-continued
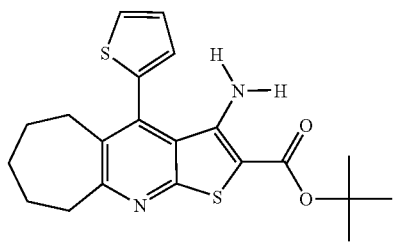
45
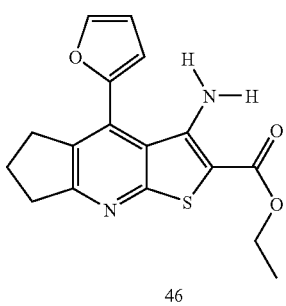
46
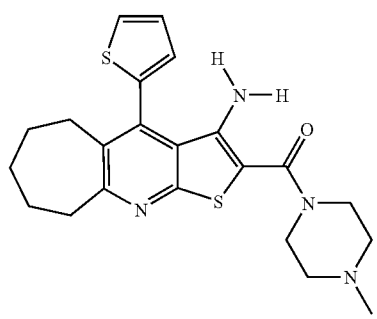
47
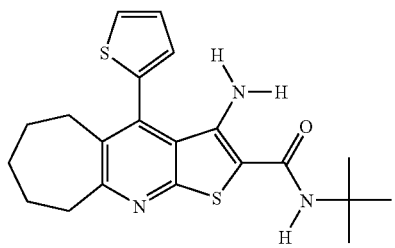
48
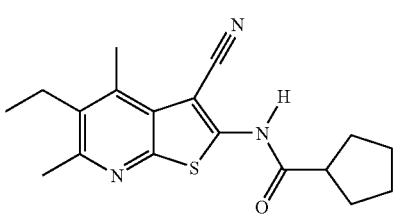
49
-continued
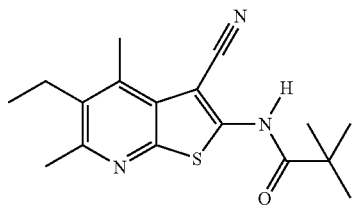
50
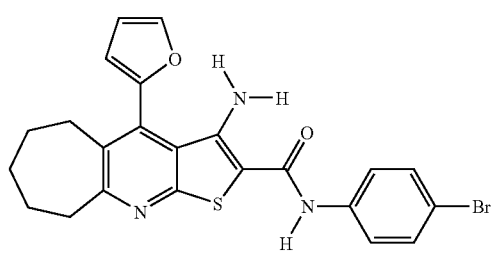
51
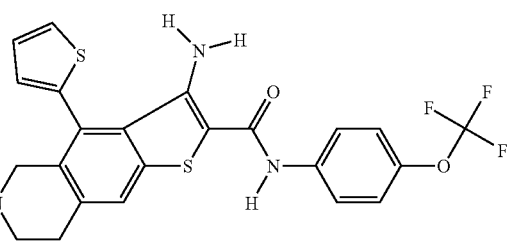
52
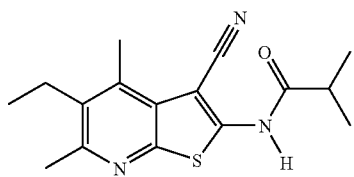
53
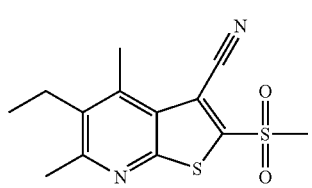
54

-continued
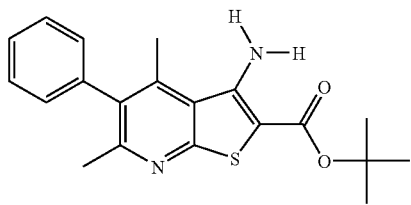
55
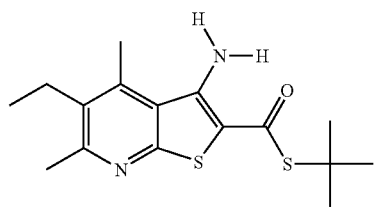
56
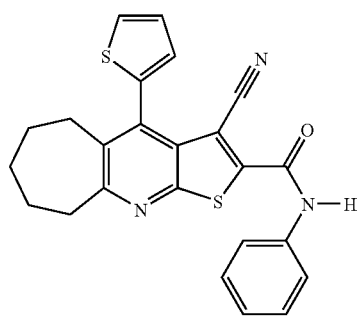
57
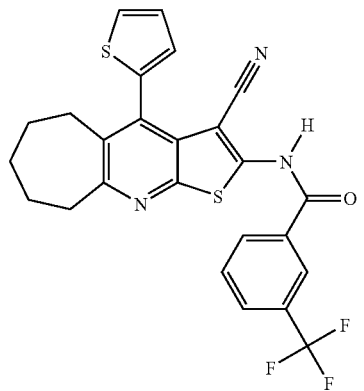
58
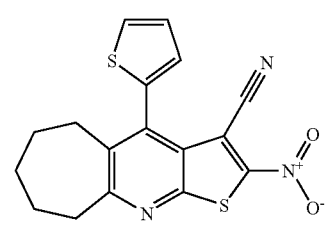
59
-continued
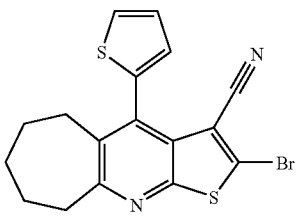
60
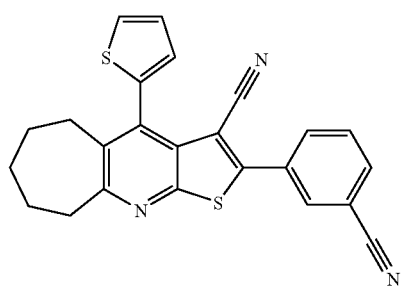
61
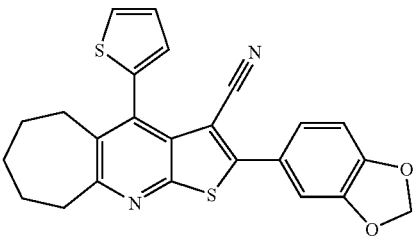
62
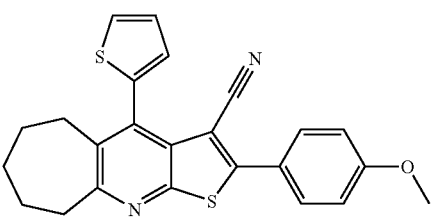
63

-continued
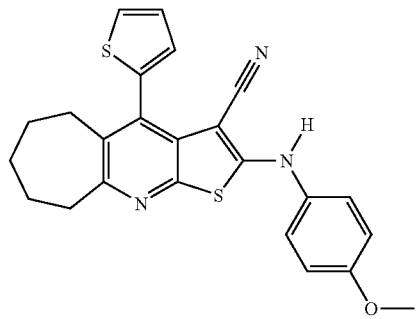
64
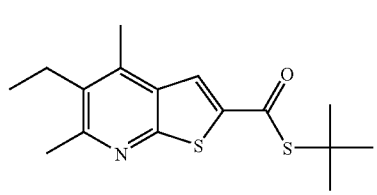
65
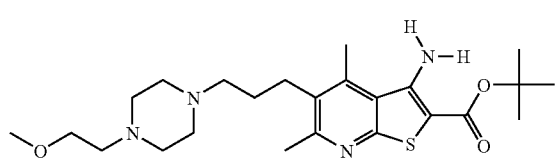
66
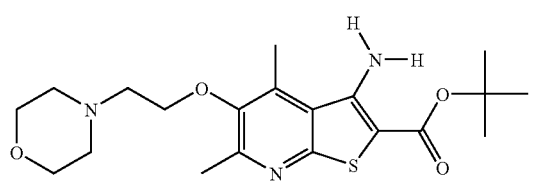
67
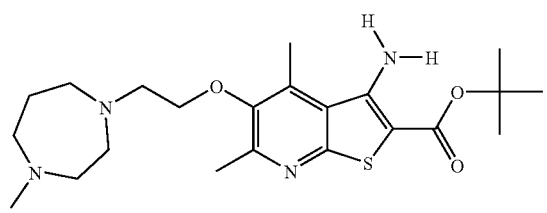
68
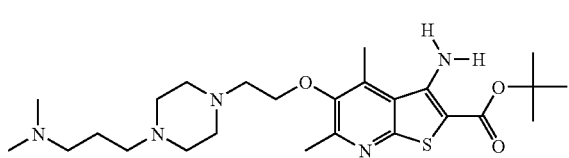
69
-continued
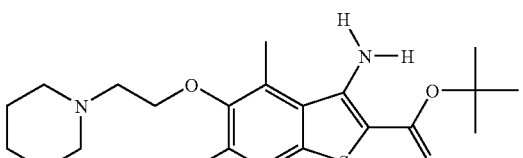
70
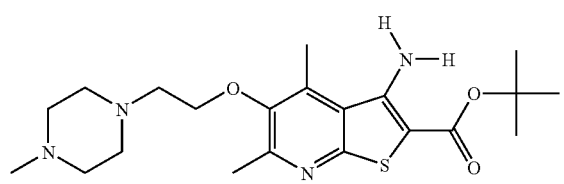
71
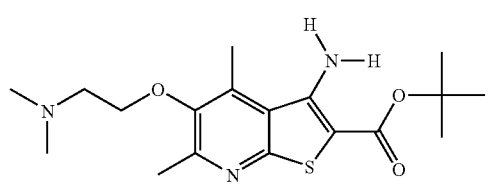
72
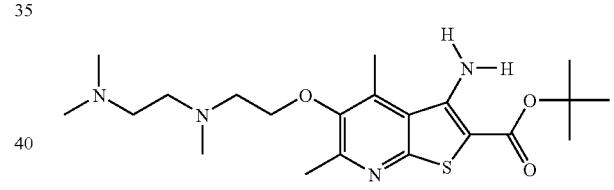
73
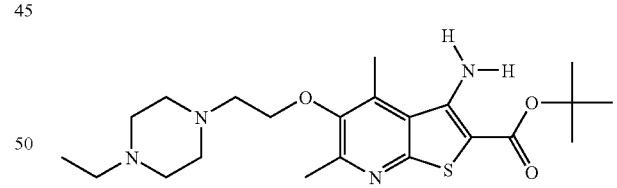
74
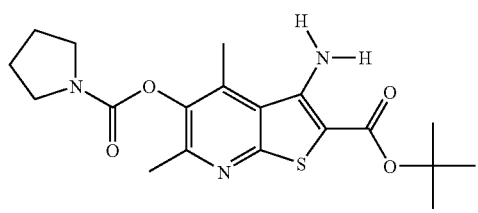
75

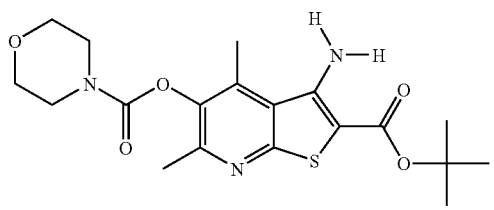
76
or a pharmaceutically acceptable salt thereof together with a pharmaceutically acceptable excipient.
Embodiment 53
A method for treating a subject for a Hepatitis C viral (HCV) infection comprising administering to said subject a pharmaceutical composition comprising an HCV inhibitory amount of at least one of the following compounds:
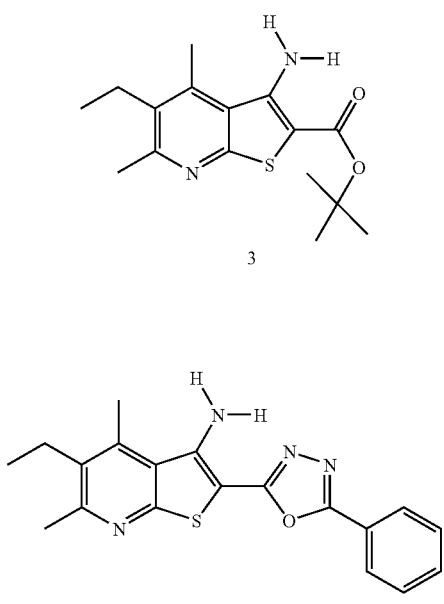
3
6
7
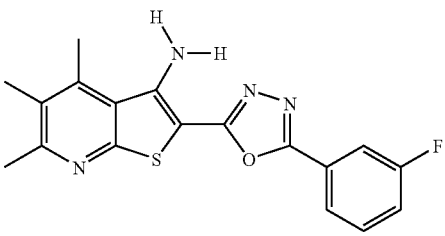
8
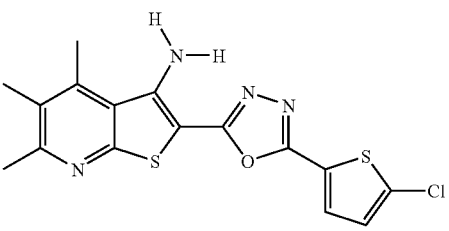
9
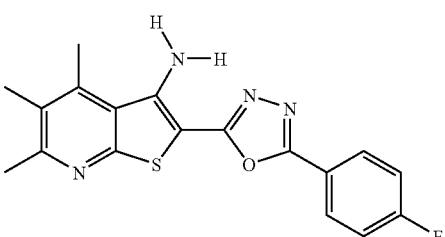
10
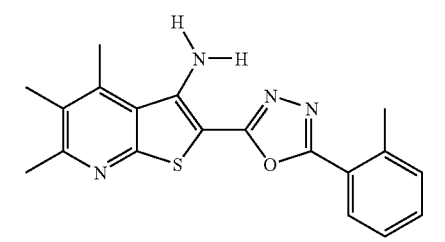
13
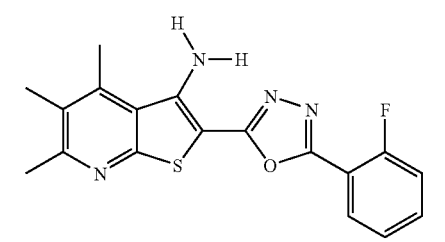
14
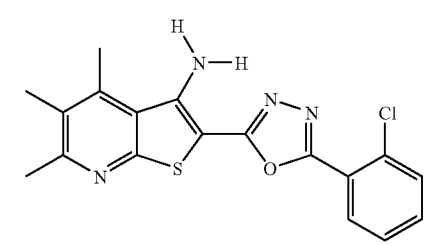
15

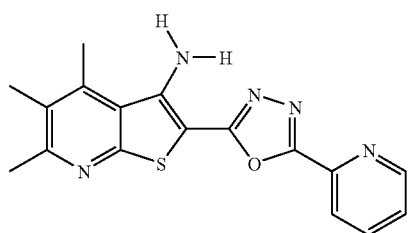
16
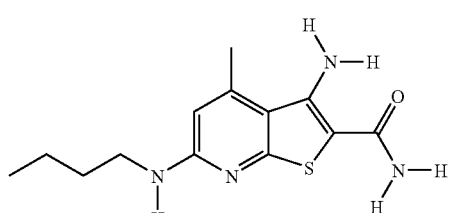
17
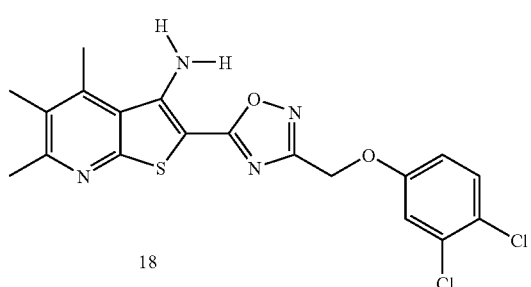
18
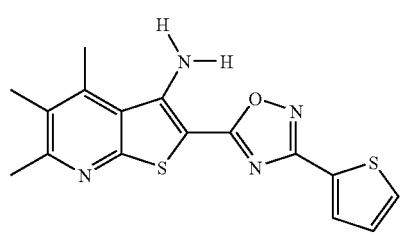
19
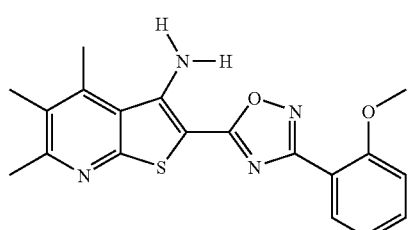
20
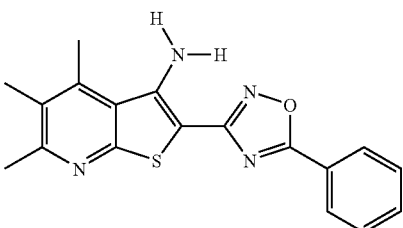
21
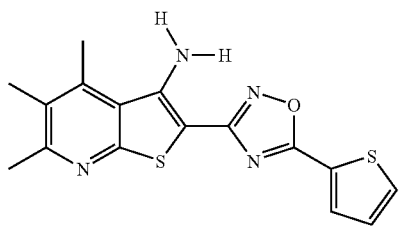
22
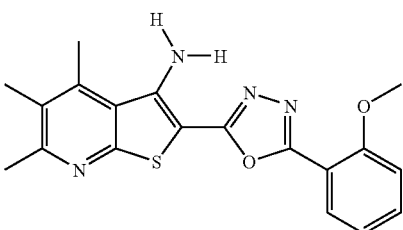
23
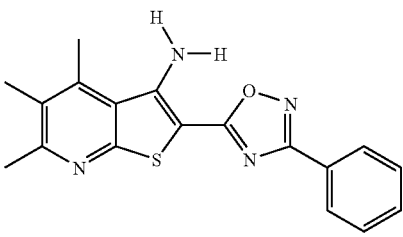
24
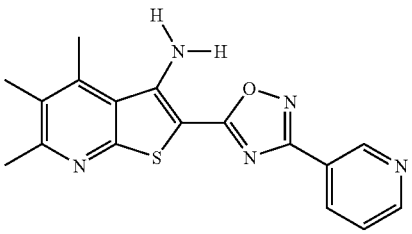
25
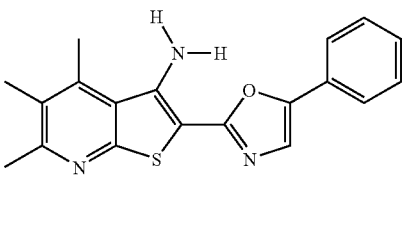
26

(IMPDH), synthetic thymosin alpha 1, therapeutic vaccines, immunomodulators, a helicase inhibitor, and a Toll-like receptor.

Embodiment 55

A compound having one of the following formulas:

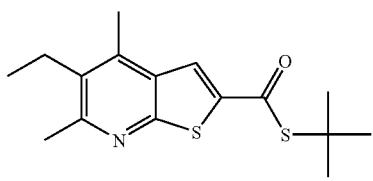
65

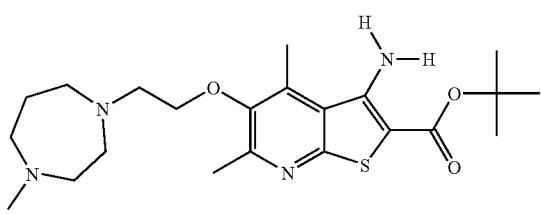
68

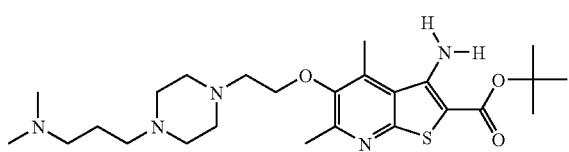
69

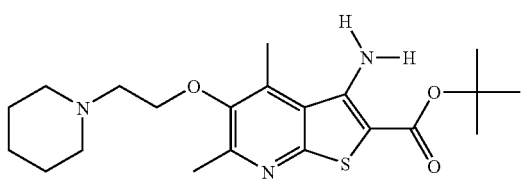
70

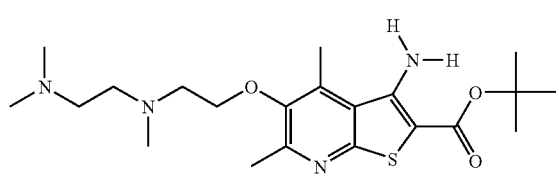
73 or a pharmaceutically acceptable salt thereof together with a pharmaceutically acceptable excipient.

Embodiment 54

The method of Embodiment 53, wherein said method further comprises administering an additional anti-HCV agent selected from the group consisting of pegylated interferon, un-pegylated interferon, ribavirin or prodrugs or derivatives thereof, a glucosidase inhibitor, a protease inhibitor, a polymerase inhibitor, p7 inhibitors, an entry inhibitor, a fusion inhibitor, an anti-fibrotic, a caspase inhibitor, a drug which targets inosine monophosphate dehydrogenase inhibitors

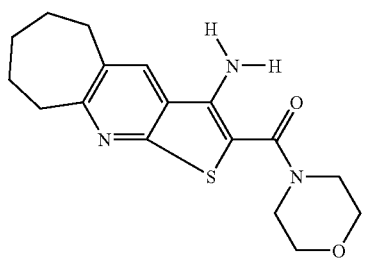
1

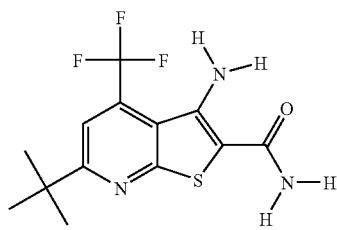
2

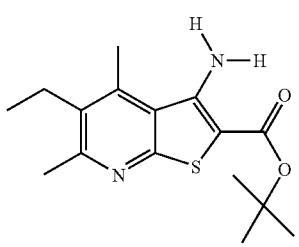
3

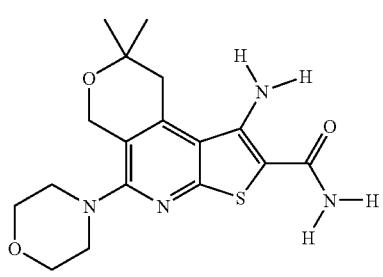
4

-continued
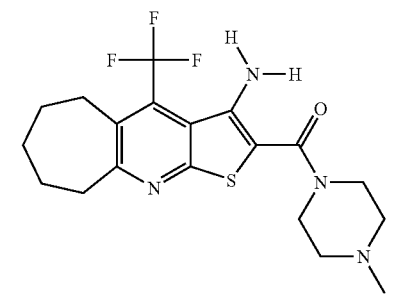
5
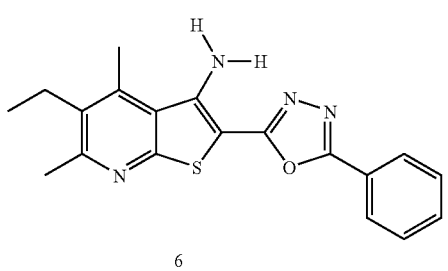
6
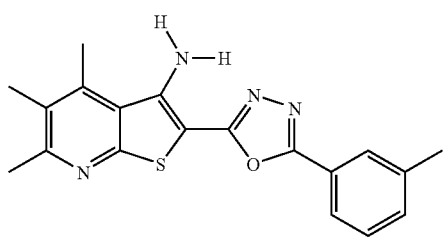
7
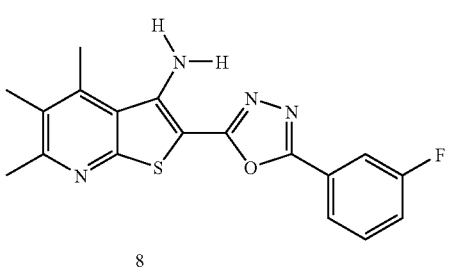
8
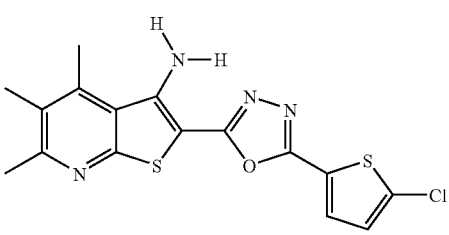
9
-continued
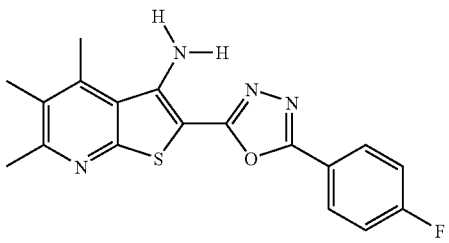
10
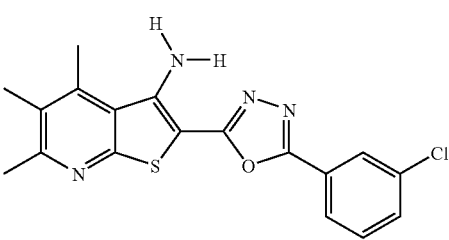
11
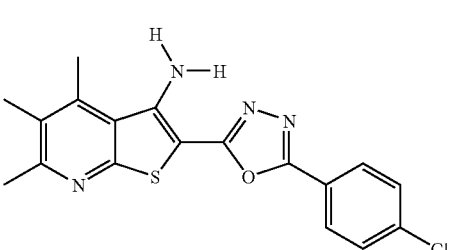
12
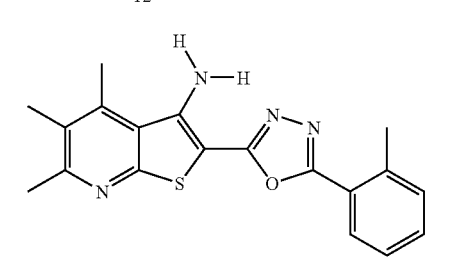
13
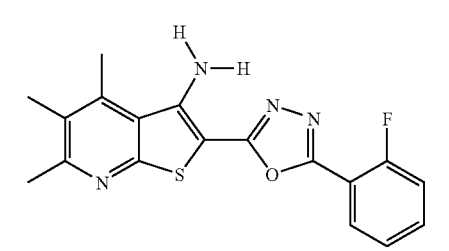
14
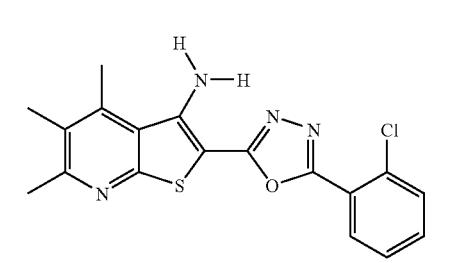
15

-continued
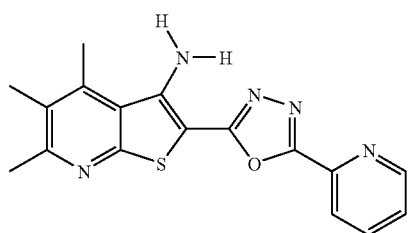
16
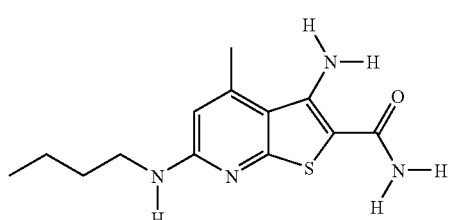
17
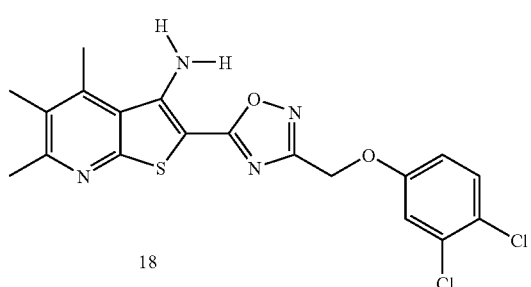
18
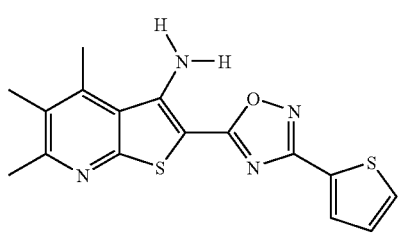
19
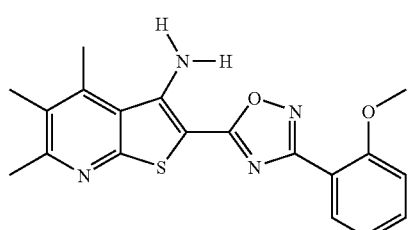
20
-continued
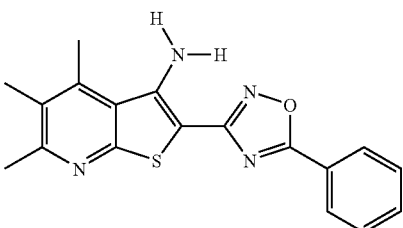
21
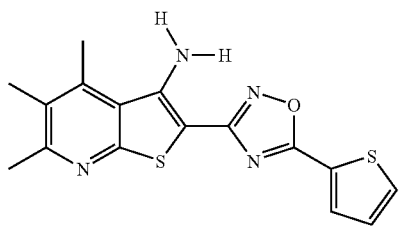
22
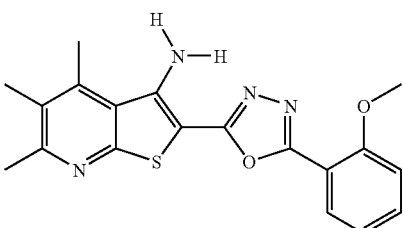
23
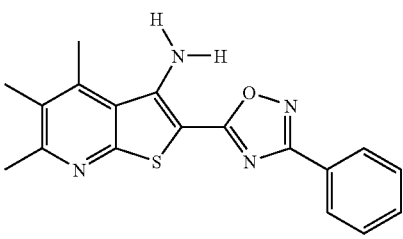
24
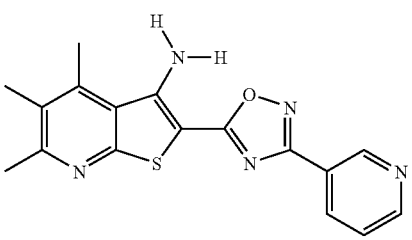
25
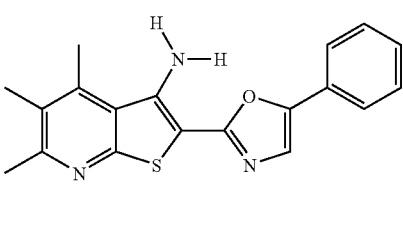
26

-continued
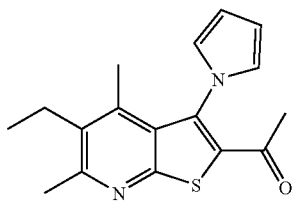
27
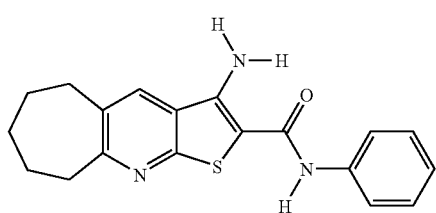
28
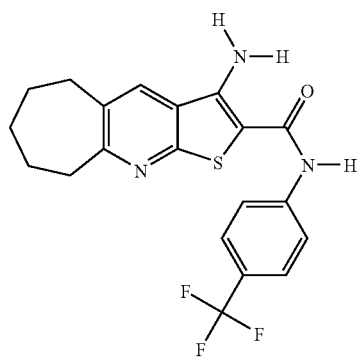
29
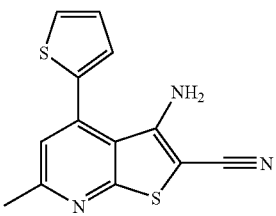
30
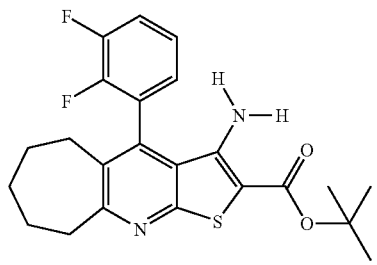
31
-continued
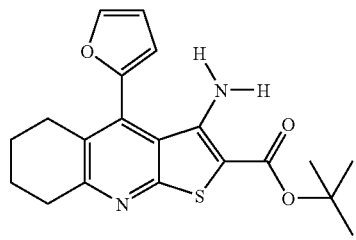
32
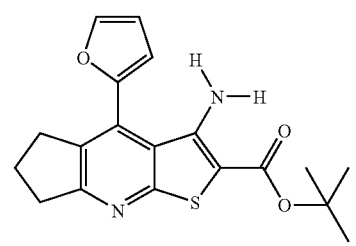
33
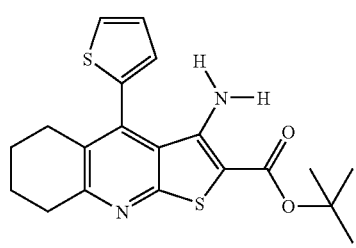
34
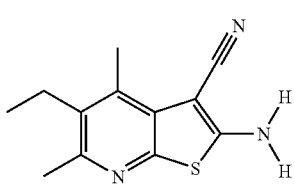
35
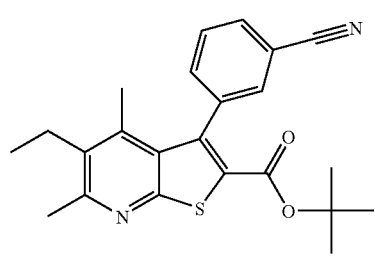
36

| 123 | 124 |
|---|---|
| -continued | -continued |
| 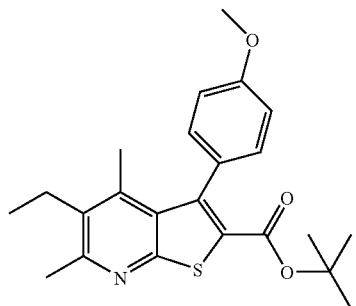<br>37 | 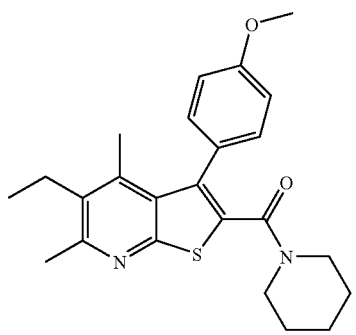<br>41 |
| 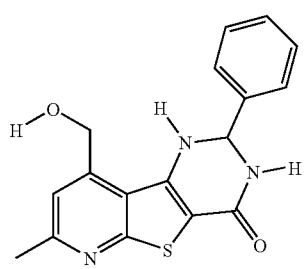<br>38 | 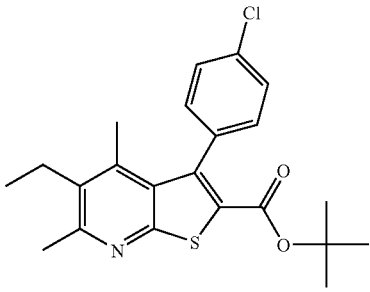<br>42 |
| 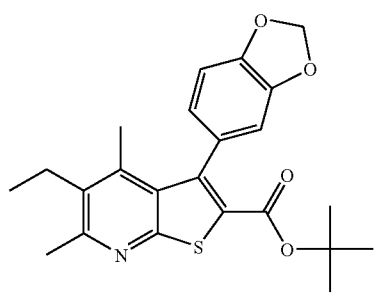<br>39 | 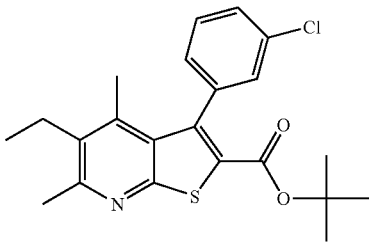<br>43 |
| 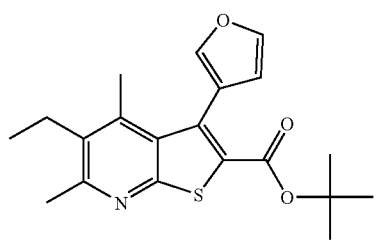<br>40 | 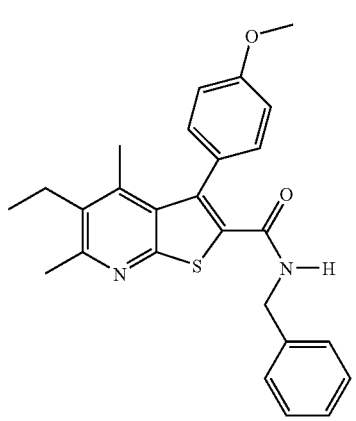<br>44 |

-continued
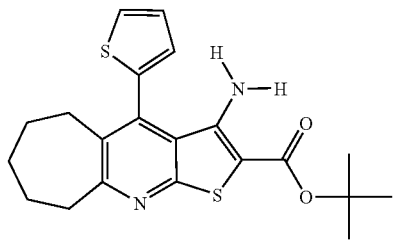
45
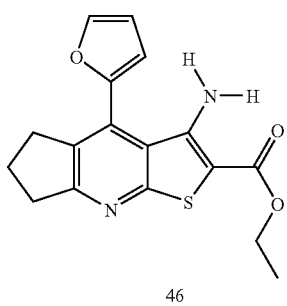
46
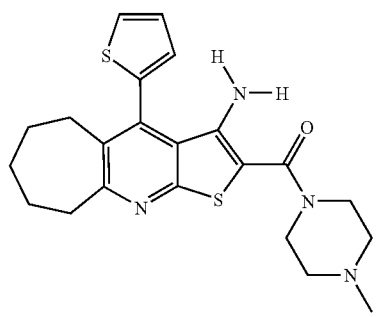
47
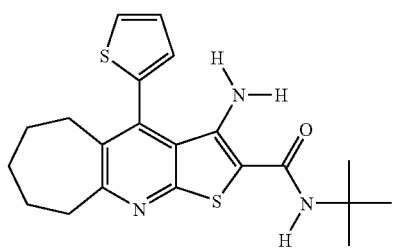
48
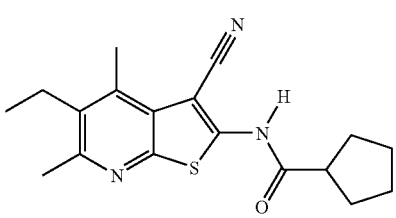
49
-continued
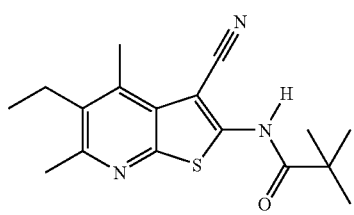
50
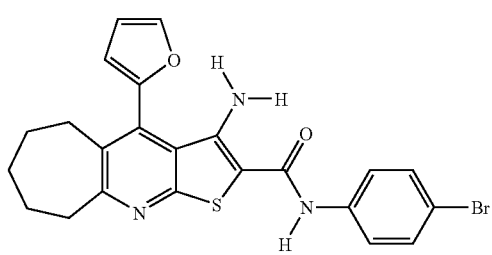
51
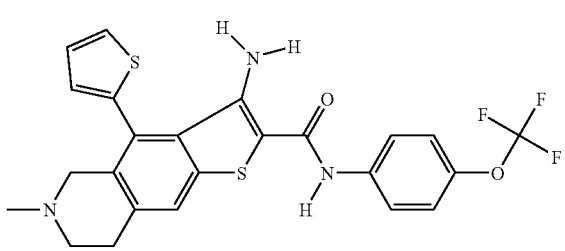
52
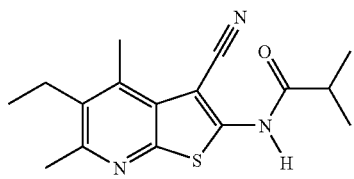
53
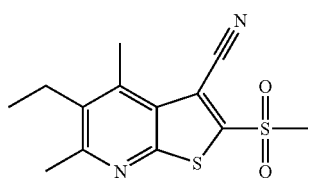
54

-continued
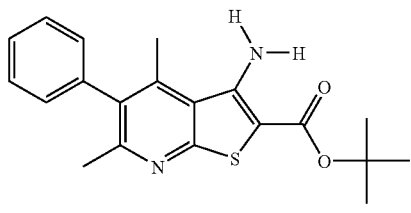
55
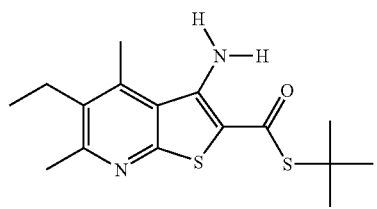
56
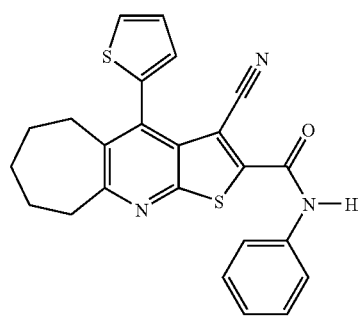
57
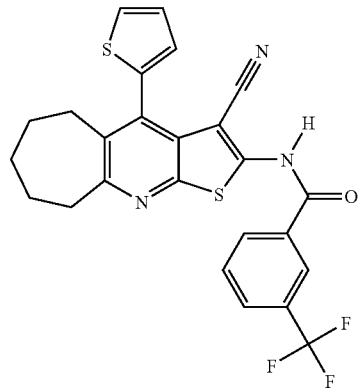
58
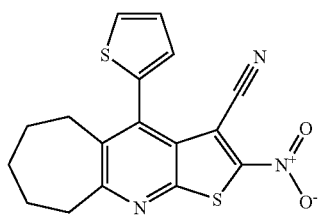
59
-continued
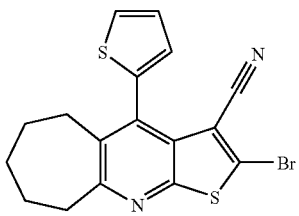
60
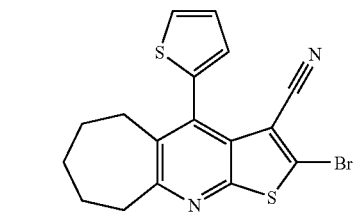
61
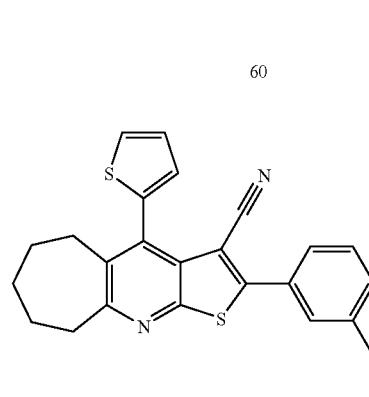
62
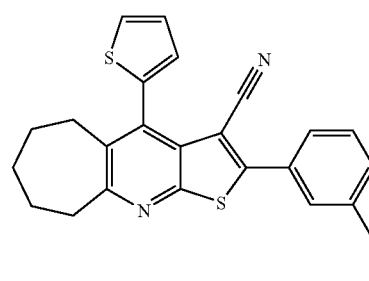
63

-continued
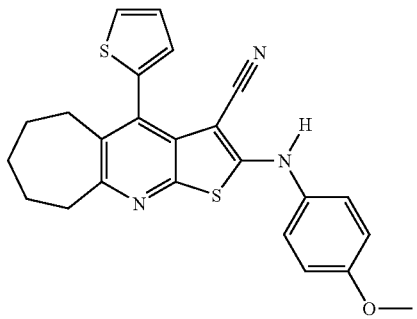
64
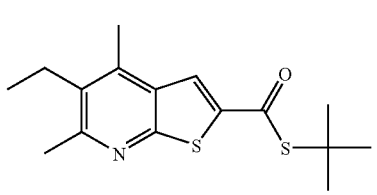
65
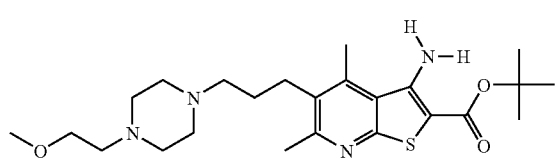
66
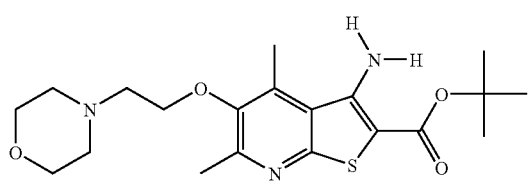
67
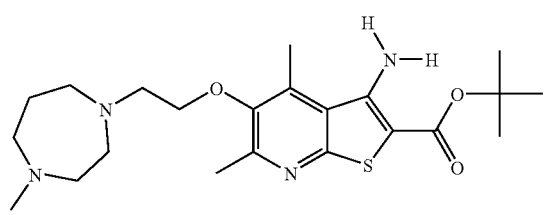
68
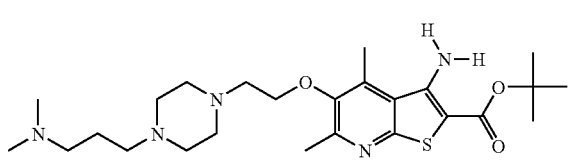
69
-continued
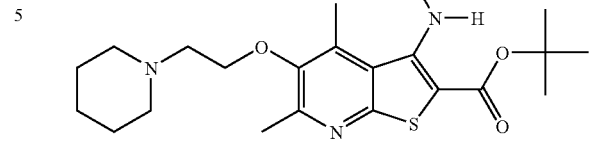
70
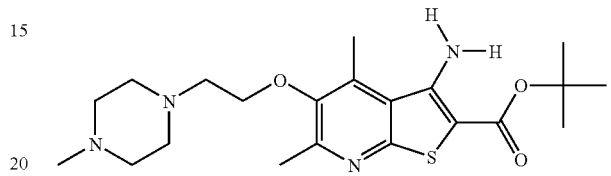
71
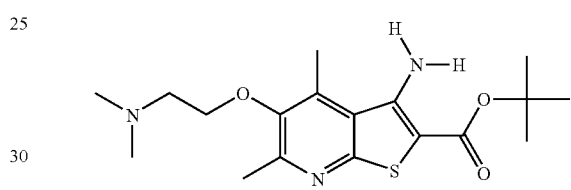
72
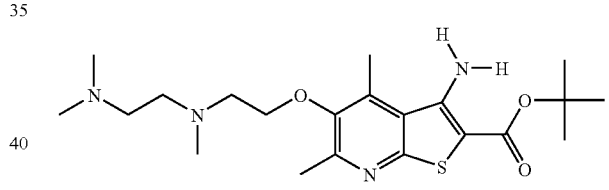
73
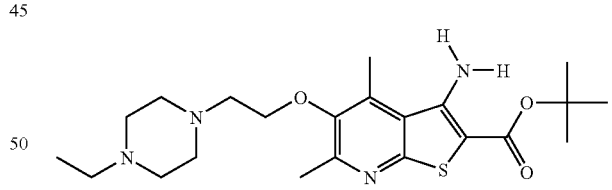
74
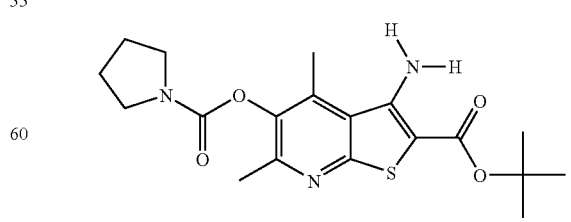
75

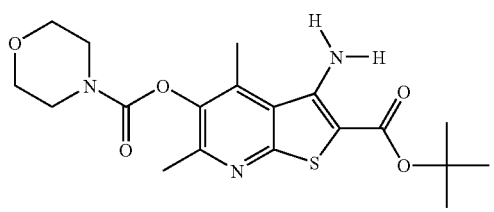
76
Embodiment 56
A compound having one of the following formulas:
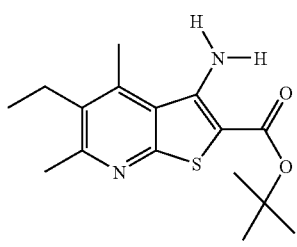
3
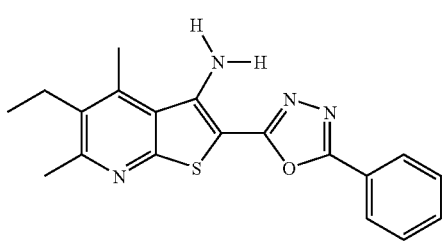
6
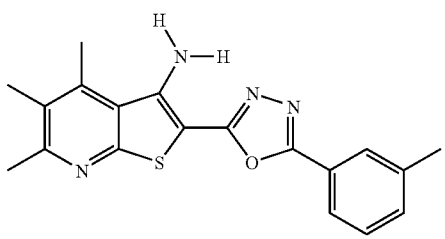
7
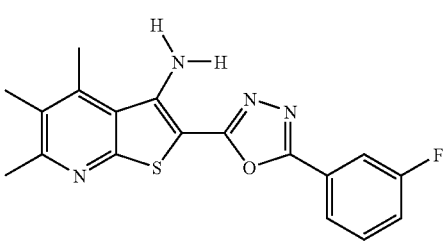
8
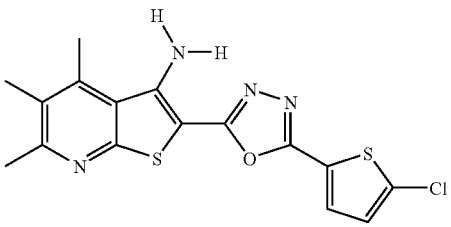
9
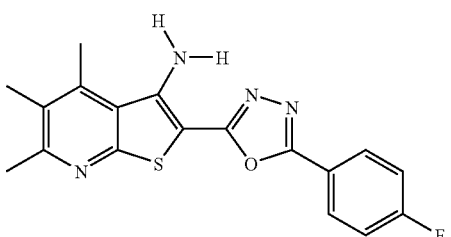
10
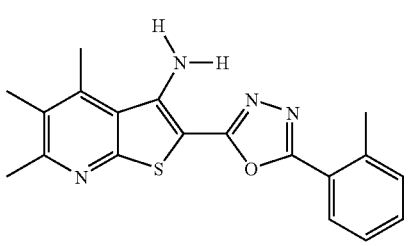
13
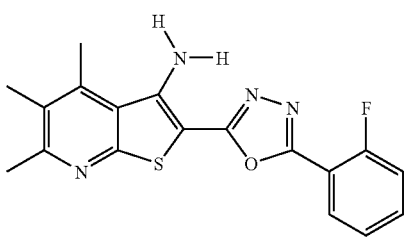
14
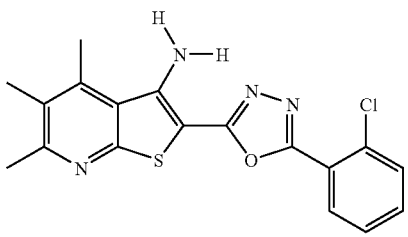
15
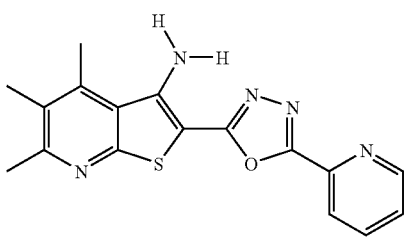
16

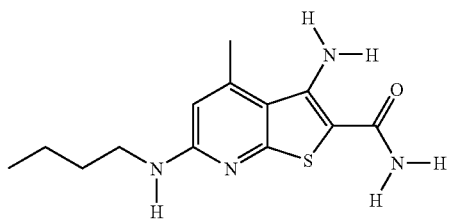
17
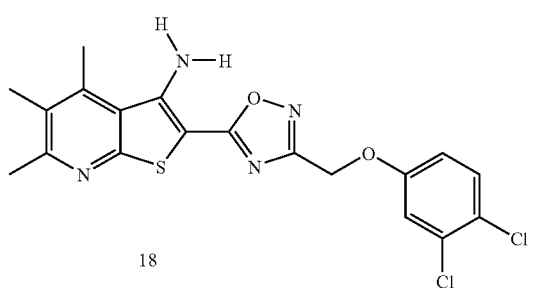
18
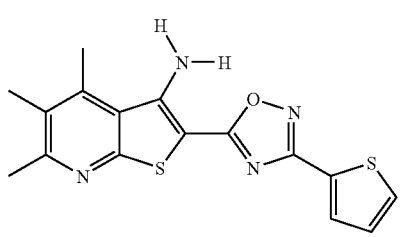
19
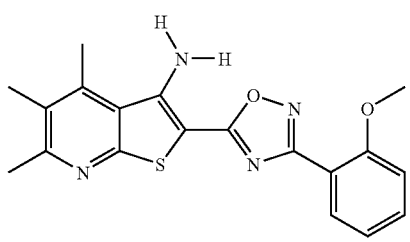
20
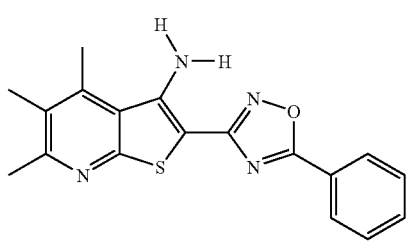
21
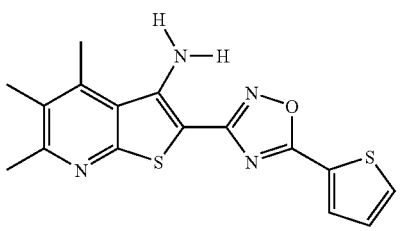
22
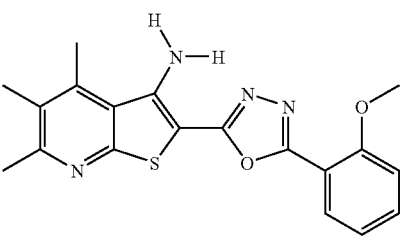
23
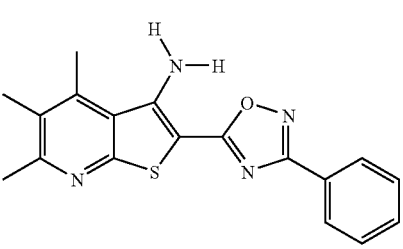
24
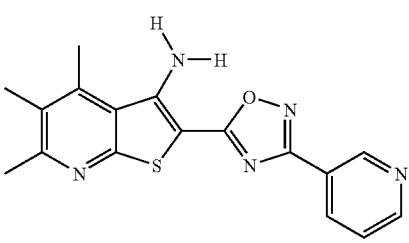
25
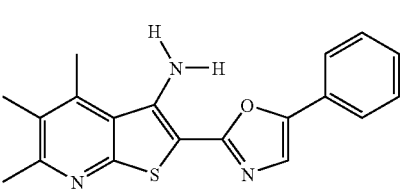
26
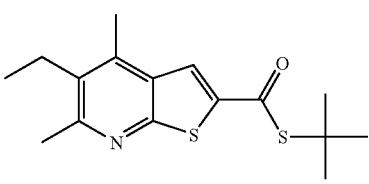

-continued

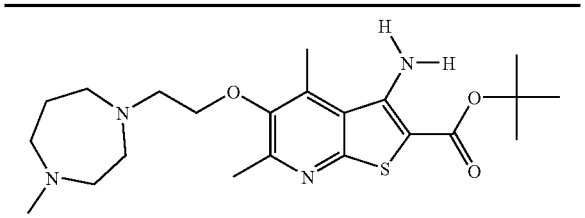

68

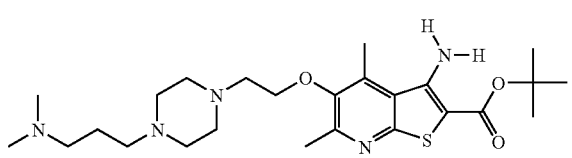

69

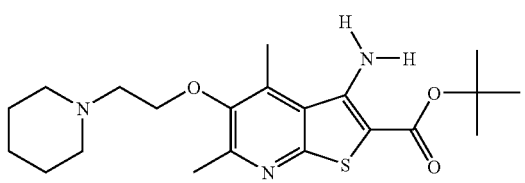

70

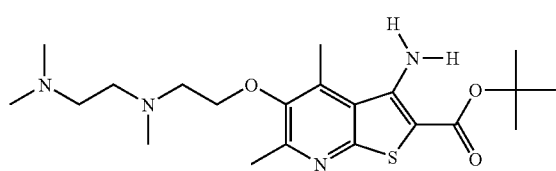

73

Embodiment 57

A method for treating or preventing infection by a virus in a subject, wherein said virus comprises an internal ribosome entry site (IRES), comprising administering to said subject a pharmaceutical composition comprising a viral inhibitory amount of at least one compound having the following formula:

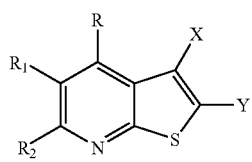

wherein:
X is:
  hydrogen;
  a cyano group;
  an amino group;

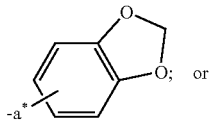

a 5- or 6-membered heteroaryl;
a $C_6$ to $C_8$ aryl, optionally substituted with:
  an alkoxy group,
  a cyano group, or
  a halogen;
or X together with Y forms:

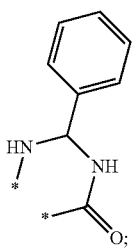

Y is:
  a halogen;
  an amino group;

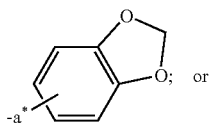

a —$SO_2R_x$, where $R_x$ is a $C_1$ to $C_6$ alkyl;
a cyano group;
a —$COOR_5$ group, where $R_x$ is a $C_1$ to $C_6$ alkyl;
a $C_6$ to $C_8$ aryl, optionally substituted with:
  an alkoxy; or
  a cyano group;
a —$COR_a$ group, where $R_a$ is:
  an amino optionally substituted with one or two $C_1$ to $C_6$ alkyls, where the alkyls are optionally substituted with a $C_6$ to $C_8$ aryl;
a —$NHR_b$ group where $R_b$ is:
  a $C_6$ to $C_8$ aryl optionally substituted with:
    a haloalkyl; or
    a halogen
    a haloalkoxy; or
  a 5- or 6-membered heterocycle optionally substituted with a $C_1$ to $C_6$ alkyl;
a $C_1$ to $C_6$ alkyl;
a —$SR_x$ group, where $R_x$ is as defined above;
a 5 or 6 membered heteroaryl optionally substituted with:
  a $C_6$ to $C_8$ aryl optionally substituted with:
    an alkoxy
    a halogen; or
    a $C_1$ to $C_6$ alkyl;
  a 5- or 6-membered heteroaryl optionally substituted with
    an alkoxy
    a halogen; or
    a $C_1$ to $C_6$ alkyl;

a $C_1$ to $C_6$ alkyl, optionally substituted with a —$OR_e$, where $R_e$ is a $C_6$ to $C_8$ aryl optionally substituted with one or more halogens; or a nitro group;

a —$NHR_d$ group, where $R_d$ is a $C_6$ to $C_8$ aryl optionally substituted with an alkoxy a —$NHCOR_e$ group where Re is:
 a $C_6$ to $C_8$ aryl optionally substituted with a haloalkyl;
 a $C_1$ to $C_6$ alkyl;

or together with X forms:

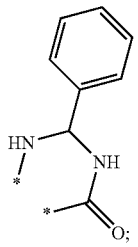

R is:
 a hydrogen
 a haloalkyl;
 a $C_1$ to $C_6$ alkyl optionally substituted with hydroxyl;
 a 5- or 6-member heteroaryl;
 a $C_6$ to $C_8$ aryl optionally substituted with one or more halogens;
 or R together with $R_1$ forms:

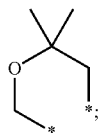

$R_1$ is:
 a hydrogen;
 a $C_6$ to $C_8$ aryl
 a $C_1$ to $C_6$ alkyl;
 a $OCOR_f$ where $R_f$ is a 5- or 6-membered heterocycle;
 an alkoxy optionally substituted with an amino group, wherein the amino group is optionally substituted with one or two $C_1$ to $C_6$ alkyls, where the alkyls are optionally substituted with an amino optionally substituted with one or two $C_1$ to $C_6$ alkyls
 an alkoxy optionally substituted with a 5 to 8 membered heterocycle optionally substituted with a $C_1$ to $C_6$ alkyl, which is optionally substituted with:
  an alkoxy, or
  an amino, optionally substituted with one or two $C_1$ to $C_6$ alkyls;
 or $R_1$ together with $R_2$ forms:

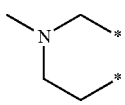

$R_1$ together with R forms:

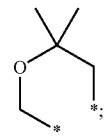

$R_2$ is:
 a $C_1$ to $C_6$ alkyl;
 a 5 or 6-membered heterocycle;
 an amino optionally substituted with a $C_1$ to $C_6$ alkyl;
 or $R_1$ together with $R_2$ forms:

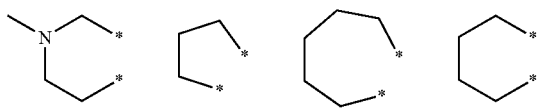

or a pharmaceutically acceptable salt thereof and a pharmaceutically acceptable excipient.

Embodiment 58

The method of Embodiment 57, wherein said pharmaceutical composition further comprises an additional anti-viral agent.

Embodiment 59

The method of Embodiment 58, wherein said additional anti-viral agent is selected from the group consisting of pegylated interferon, un-pegylated interferon, ribavirin or pro-drugs or derivatives thereof, a glucosidase inhibitor, a protease inhibitor, a polymerase inhibitor, p7 inhibitors, an entry inhibitor, a fusion inhibitor, an anti-fibrotic, a caspase inhibitor, a drug which targets inosine monophosphate dehydrogenase inhibitors (IMPDH), synthetic thymosin alpha 1, therapeutic vaccines, immunomodulators, a helicase inhibitor, and a Toll-like receptor agonist.

Embodiment 60

A method for treating or preventing infection by a virus in a subject, wherein said virus comprises an internal ribosome entry site (IRES), comprising administering to said subject a pharmaceutical composition comprising a viral inhibitory amount of at least one compound having the following formula:

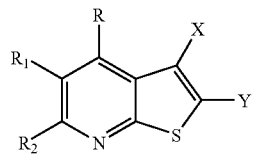

wherein
X is amino or hydrogen;
Y is
 a —$COOR_x$ group, where $R_x$ is as defined above;
 a —$COR_a$ group, where $R_a$ is:

an amino optionally substituted with one or two $C_1$ to $C_6$ alkyls, where the alkyls are optionally substituted with a $C_6$ to $C_8$ aryl;
a —$SR_x$ group, where $R_x$ is as defined above;
a 5 or 6 membered heteroaryl optionally substituted with:
a $C_6$ to $C_8$ aryl optionally substituted with:
an alkoxy
a halogen; or
a $C_1$ to $C_6$ alkyl;
a 5- or 6-membered heteroaryl optionally substituted with a $C_6$ to $C_8$ aryl optionally substituted with a halogen;
R is a $C_1$ to $C_6$ alkyl;
$R_1$ is a $C_1$ to $C_6$ alkyl or $R_1$ is selected from the group consisting of
an alkoxy optionally substituted with an amino group, wherein the amino group is optionally substituted with one or two $C_1$ to $C_6$ alkyls, where the alkyls are optionally substituted with an amino optionally substituted with one or two $C_1$ to $C_6$ alkyls; and
an alkoxy optionally substituted with a 5 to 8 membered heterocycle optionally substituted with a $C_1$ to $C_6$ alkyl, which is optionally substituted with:
an amino, optionally substituted with one or two $C_1$ to $C_6$ alkyls; and
$R_2$ is a $C_1$ to $C_6$ alkyl or an amino optionally substituted with a $C_1$ to $C_6$ alkyl;
or a pharmaceutically acceptable salt thereof, together with a pharmaceutically acceptable excipient.

Embodiment 61

The method of Embodiment 60, wherein said pharmaceutical composition further comprises an additional anti-viral agent.

Embodiment 62

The method of Embodiment 61, wherein said additional anti-viral agent is selected from the group consisting of pegylated interferon, un-pegylated interferon, ribavirin or prodrugs or derivatives thereof, a glucosidase inhibitor, a protease inhibitor, a polymerase inhibitor, p7 inhibitors, an entry inhibitor, a fusion inhibitor, an anti-fibrotic, a caspase inhibitor, a drug which targets inosine monophosphate dehydrogenase inhibitors (IMPDH), synthetic thymosin alpha 1, therapeutic vaccines, immunomodulators, a helicase inhibitor, and a Toll-like receptor agonist.

Embodiment 63

A pharmaceutical composition for affecting viral IRES activity in a subject infected with a virus, comprising at least one compound having the following formula:

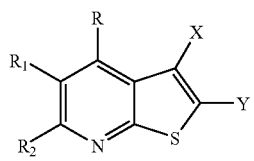

wherein:
X is:
hydrogen;
a cyano group;
an amino group;

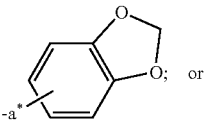

a 5- or 6-membered heteroaryl;
a $C_6$ to $C_8$ aryl, optionally substituted with:
an alkoxy group,
a cyano group, or
a halogen;
or X together with Y forms:

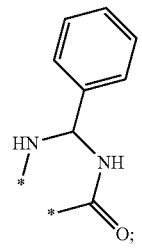

Y is:
a halogen;
an amino group;

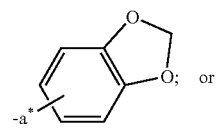

a —$SO_2R_x$, where $R_x$ is a $C_1$ to $C_6$ alkyl;
a cyano group;
a —$COOR_x$ group, where $R_x$ is a $C_1$ to $C_6$ alkyl;
a $C_6$ to $C_8$ aryl, optionally substituted with:
an alkoxy; or
a cyano group;
a —$COR_a$ group, where $R_a$ is:
an amino optionally substituted with one or two $C_1$ to $C_6$ alkyls, where the alkyls are optionally substituted with a $C_6$ to $C_8$ aryl
a —$NHR_b$ group where $R_b$ is:
a $C_6$ to $C_8$ aryl optionally substituted with:
a haloalkyl; or
a halogen
a haloalkoxy; or
a 5- or 6-membered heterocycle optionally substituted with a $C_1$ to $C_6$ alkyl;
a $C_1$ to $C_6$ alkyl;
a —$SR_x$ group, where $R_x$ is as defined above;
a 5 or 6 membered heteroaryl optionally substituted with:
a $C_6$ to $C_8$ aryl optionally substituted with:
an alkoxy
a halogen; or
a $C_1$ to $C_6$ alkyl;
a 5- or 6-membered heteroaryl optionally substituted with
an alkoxy a halogen; or
a $C_1$ to $C_6$ alkyl;
a $C_1$ to $C_6$ alkyl, optionally substituted with a —$OR_c$, where $R_c$ is a $C_6$ to $C_8$ aryl optionally substituted with one or more halogens; or
a nitro group;
a —$NHR_d$ group, where $R_d$ is a $C_6$ to $C_8$ aryl optionally substituted with an alkoxy
a —$NHCOR_e$ group where $R_e$ is:
 a $C_6$ to $C_8$ aryl optionally substituted with a haloalkyl;
 a $C_1$ to $C_6$ alkyl;
or together with X forms:

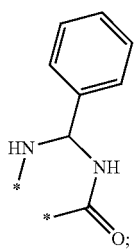

R is:
a hydrogen
a haloalkyl;
a $C_1$ to $C_6$ alkyl optionally substituted with hydroxyl;
a 5- or 6-member heteroaryl;
a $C_6$ to $C_8$ aryl optionally substituted with one or more halogens;
or R together with $R_1$ forms:

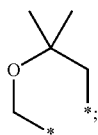

$R_1$ is:
a hydrogen;
a $C_6$ to $C_8$ aryl
a $C_1$ to $C_6$ alkyl;
a $OCOR_f$ where $R_f$ is a 5- or 6-membered heterocycle;
an alkoxy optionally substituted with an amino group, wherein the amino group is optionally substituted with one or two $C_1$ to $C_6$ alkyls, where the alkyls are optionally substituted with an amino optionally substituted with one or two $C_1$ to $C_6$ alkyls
an alkoxy optionally substituted with a 5 to 8 membered heterocycle optionally substituted with a $C_1$ to $C_6$ alkyl, which is optionally substituted with:
 an alkoxy, or
 an amino, optionally substituted with one or two $C_1$ to $C_6$ alkyls;
or $R_1$ together with $R_2$ forms:

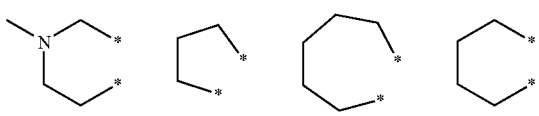

$R_1$ together with R forms:

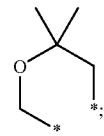

$R_2$ is:
a $C_1$ to $C_6$ alkyl;
a 5 or 6-membered heterocycle;
an amino optionally substituted with a $C_1$ to $C_6$ alkyl;
or $R_1$ together with $R_2$ forms:

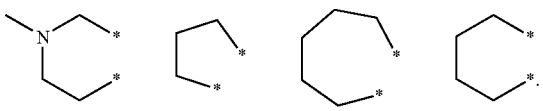

or a pharmaceutically acceptable salt thereof, together with a compound known in the art to affect IRES activity and a pharmaceutically acceptable excipient.

Embodiment 64

The pharmaceutical composition of Embodiment 50, wherein said compound known in the art to affect IRES activity affects IRES mediated translation of the viral proteins.

Embodiment 65

A pharmaceutical composition for affecting viral IRES activity in a subject infected with a virus, comprising at least one compound having the following formula:

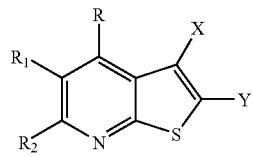

wherein
X is amino or hydrogen;
Y is
 a —$COOR_x$ group, where $R_x$ is as defined above;
 a —$COR_a$ group, where $R_a$ is:
  an amino optionally substituted with one or two $C_1$ to $C_6$ alkyls, where the alkyls are optionally substituted with a $C_6$ to $C_8$ aryl;
 a —$SR_x$ group, where $R_x$ is as defined above;
 a 5 or 6 membered heteroaryl optionally substituted with:
  a $C_6$ to $C_8$ aryl optionally substituted with:
   an alkoxy
   a halogen; or
   a $C_1$ to $C_6$ alkyl;
  a 5- or 6-membered heteroaryl optionally substituted with a $C_6$ to $C_8$ aryl optionally substituted with a halogen;
R is a $C_1$ to $C_6$ alkyl;
$R_1$ is a $C_1$ to $C_6$ alkyl or $R_1$ is selected from the group consisting of an alkoxy optionally substituted with an amino group, wherein the amino group is optionally substituted with one or two $C_1$ to $C_6$ alkyls, where the alkyls are optionally substituted with an amino optionally substituted with one or two $C_1$ to $C_6$ alkyls; and an alkoxy optionally substituted with a 5 to 8 membered heterocycle optionally substituted with a $C_1$ to $C_6$ alkyl, which is optionally substituted with:

an amino, optionally substituted with one or two $C_1$ to $C_6$ alkyls; and $R_2$ is a $C_1$ to $C_6$ alkyl or an amino optionally substituted with a $C_1$ to $C_6$ alkyl;

or a pharmaceutically acceptable salt thereof, together with a compound known in the art to affect IRES activity and a pharmaceutically acceptable excipient.

Embodiment 66

The pharmaceutical composition of Embodiment 65, wherein said compound known in the art to affect IRES activity affects IRES mediated translation of the viral proteins.

Embodiment 67

A method for affecting viral IRES activity in a subject infected with a virus, comprising administering to said subject at least one compound having the following formula:

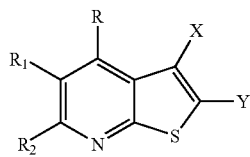

wherein:

X is:
  hydrogen;
  a cyano group;
  an amino group;

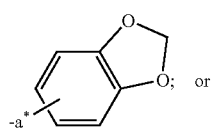

a 5- or 6-membered heteroaryl;
a $C_6$ to $C_8$ aryl, optionally substituted with:
  an alkoxy group,
  a cyano group, or
  a halogen;

or X together with Y forms

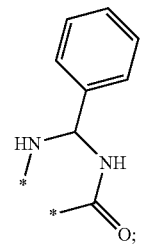

Y is:
a halogen;
an amino group;

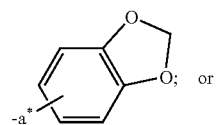

a —$SO_2R_x$, where $R_x$ is a $C_1$ to $C_6$ alkyl;
a cyano group;
a —$COOR_x$ group, where $R_x$ is a $C_1$ to $C_6$ alkyl;
a $C_6$ to $C_8$ aryl, optionally substituted with:
  an alkoxy; or
  a cyano group;
a —$COR_a$ group, where $R_a$ is:
  an amino optionally substituted with one or two $C_1$ to $C_6$ alkyls, where the alkyls are optionally substituted with a $C_6$ to $C_8$ aryl;
  a —$NHR_b$ group where $R_b$ is:
    a $C_6$ to $C_8$ aryl optionally substituted with:
      a haloalkyl; or
      a halogen
      a haloalkoxy; or
    a 5- or 6-membered heterocycle optionally substituted with a $C_1$ to $C_6$ alkyl;
  a $C_1$ to $C_6$ alkyl;
  a —$SR_x$ group, where $R_x$ is as defined above;
a 5 or 6 membered heteroaryl optionally substituted with:
  a $C_6$ to $C_8$ aryl optionally substituted with:
    an alkoxy
    a halogen; or
    a $C_1$ to $C_6$ alkyl;
  a 5- or 6-membered heteroaryl optionally substituted with
    an alkoxy
    a halogen; or
    a $C_1$ to $C_6$ alkyl;
  a $C_1$ to $C_6$ alkyl, optionally substituted with a —$OR_e$, where $R_e$ is a $C_6$ to $C_8$ aryl optionally substituted with one or more halogens; or
a nitro group;
a —$NHR_d$ group, where $R_d$ is a $C_6$ to $C_8$ aryl optionally substituted with an alkoxy
a —$NHCOR_e$ group where $R_e$ is:
  a $C_6$ to $C_8$ aryl optionally substituted with a haloalkyl;
  a $C_1$ to $C_6$ alkyl;
or together with X forms:

[structure: HN-CH(Ph)-C(=O)-NH, with * marks]

R is:
- a hydrogen
- a haloalkyl;
- a $C_1$ to $C_6$ alkyl optionally substituted with hydroxyl;
- a 5- or 6-member heteroaryl;
- a $C_6$ to $C_8$ aryl optionally substituted with one or more halogens;
- or R together with $R_1$ forms:

[structure: gem-dimethyl oxetane-like ring with * marks]

$R_1$ is:
- a hydrogen;
- a $C_6$ to $C_8$ aryl
- a $C_1$ to $C_6$ alkyl;
- a $OCOR_f$ where $R_f$ is a 5- or 6-membered heterocycle;
- an alkoxy optionally substituted with an amino group, wherein the amino group is optionally substituted with one or two $C_1$ to $C_6$ alkyls, where the alkyls are optionally substituted with an amino optionally substituted with one or two $C_1$ to $C_6$ alkyls
- an alkoxy optionally substituted with a 5 to 8 membered heterocycle optionally substituted with a $C_1$ to $C_6$ alkyl, which is optionally substituted with:
  - an alkoxy, or
  - an amino, optionally substituted with one or two $C_1$ to $C_6$ alkyls;
- or $R_1$ together with $R_2$ forms:

[structures: N-methylpiperazine-like, pyrrolidine, azepane, piperidine rings with * marks]

$R_1$ together with R forms:

[structure: gem-dimethyl oxetane-like ring with * marks]

$R_2$ is:
- a $C_1$ to $C_6$ alkyl;
- a 5 or 6-membered heterocycle;
- an amino optionally substituted with a $C_1$ to $C_6$ alkyl;
- or $R_1$ together with $R_2$ forms:

[structures: N-methylpiperazine-like, pyrrolidine, azepane, piperidine rings with * marks]

or a pharmaceutically acceptable salt thereof, together with a pharmaceutically acceptable excipient.

Embodiment 68

A method for affecting viral IRES activity in a subject infected with a virus, comprising administering to said subject at least one compound having the following formula:

[structure: thieno[2,3-b]pyridine with substituents R, $R_1$, $R_2$, X, Y]

wherein
X is amino or hydrogen;
Y is
- a —$COOR_x$ group, where $R_x$ is as defined above;
- a —$COR_a$ group, where $R_a$ is:
  - an amino optionally substituted with one or two $C_1$ to $C_6$ alkyls, where the alkyls are optionally substituted with a $C_6$ to $C_8$ aryl;
- a —$SR_x$ group, where $R_x$ is as defined above;
- a 5 or 6 membered heteroaryl optionally substituted with:
  - a $C_6$ to $C_8$ aryl optionally substituted with:
    - an alkoxy
    - a halogen; or
    - a $C_1$ to $C_6$ alkyl;
  - a 5- or 6-membered heteroaryl optionally substituted with a $C_6$ to $C_8$ aryl optionally substituted with a halogen;

R is a $C_1$ to $C_6$ alkyl;
$R_1$ is a $C_1$ to $C_6$ alkyl or $R_1$ is selected from the group consisting of
- an alkoxy optionally substituted with an amino group, wherein the amino group is optionally substituted with one or two $C_1$ to $C_6$ alkyls, where the alkyls are optionally substituted with an amino optionally substituted with one or two $C_1$ to $C_6$ alkyls; and
- an alkoxy optionally substituted with a 5 to 8 membered heterocycle optionally substituted with a $C_1$ to $C_6$ alkyl, which is optionally substituted with:
  - an amino, optionally substituted with one or two $C_1$ to $C_6$ alkyls; and $R_2$ is a $C_1$ to $C_6$ alkyl or an amino optionally substituted with a $C_1$ to $C_6$ alkyl;

or a pharmaceutically acceptable salt thereof, together with a pharmaceutically acceptable excipient.

DETAILED DESCRIPTION OF THE INVENTION

Figure 1:
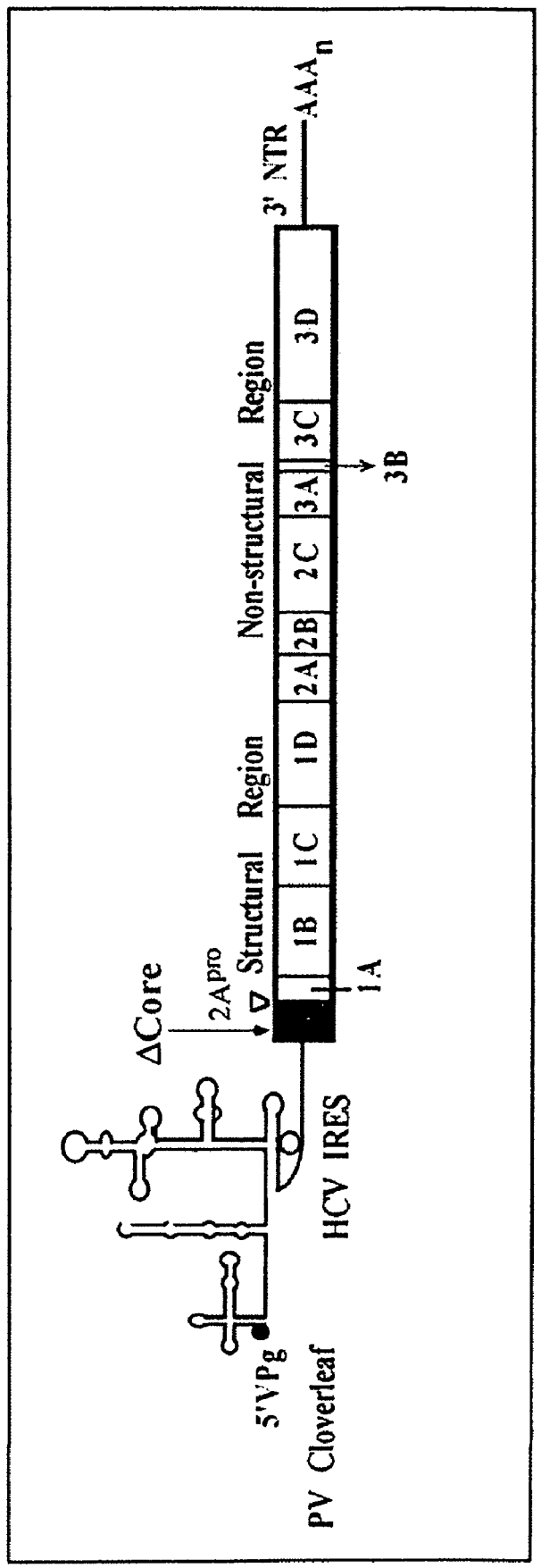
FIG. 1 illustrates the HCV-PV chimera construct. The cloverleaf-like RNA structure of PV, an essential cis-acting replication signal ending with the genome-linked protein VPg, is located at the 5' end of the genome. The solid (HCV) and open (PV) boxes depict open reading frames encoding viral polypeptides. The position of the HCV core fragment (the first 123 amino acids) gene is denoted by Δ Core. Overall, the HCV specific sequence in the HCV-PV spans from nucleotides 18 to 710. (139).

In accordance with the present invention, compounds that modify HCV translation have been identified and methods of using these compounds for preventing or treating HCV infection are provided. Without being limited to one theory, it is believed that the compounds of the present invention inhibit IRES-mediated initiation and translation. The HCV IRES directs the translation of the viral polyprotein that is post-translationally processed into at least 10 mature viral proteins, including the structural proteins core (putative nucleocapsid), E1 and E2 and the nonstructural (NS) proteins NS2 to NS5B.

A. Compounds of the Invention

In one aspect of the invention, compounds of the invention are provided which may be useful for preventing or treating HCV infection.

Preferred compounds of the present invention useful in the inhibition of HCV-IRES mediated initiation and translation include those of Formula (I) as shown below.

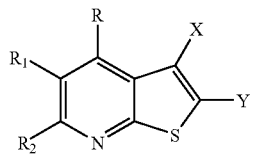

wherein:
X is:
    hydrogen;
    a cyano group;
    an amino group;

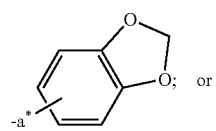

a 5- or 6-membered heteroaryl;
a $C_6$ to $C_8$ aryl, optionally substituted with:
    an alkoxy group,
    a cyano group, or
    a halogen;
or X together with Y forms:

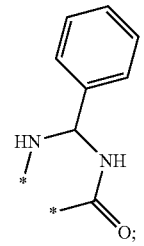

Y is:
a halogen;
an amino group;

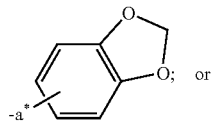

a —$SO_2R_x$, where $R_x$ is a $C_1$ to $C_6$ alkyl;
a cyano group;
a —COOR5 group, where $R_x$ is a $C_1$ to $C_6$ alkyl;
a $C_6$ to $C_8$ aryl, optionally substituted with:
    an alkoxy; or
    a cyano group;
a —$COR_a$ group, where $R_a$ is:
    an amino optionally substituted with one or two $C_1$ to $C_6$ alkyls, where the alkyls are optionally substituted with a $C_6$ to $C_8$ aryl;
    a —$NHR_b$ group where $R_b$ is:
        a $C_6$ to $C_8$ aryl optionally substituted with:
            a haloalkyl; or
            a halogen
            a haloalkoxy; or
        a 5- or 6-membered heterocycle optionally substituted with a $C_1$ to $C_6$ alkyl;
    a $C_1$ to $C_6$ alkyl;
    a —$SR_x$ group, where $R_x$ is as defined above;
a 5 or 6 membered heteroaryl optionally substituted with:
    a $C_6$ to $C_8$ aryl optionally substituted with:
        an alkoxy
        a halogen; or
        a $C_1$ to $C_6$ alkyl;
    a 5- or 6-membered heteroaryl optionally substituted with
        an alkoxy
        a halogen; or
        a $C_1$ to $C_6$ alkyl;
    a $C_1$ to $C_6$ alkyl, optionally substituted with a —$OR_c$, where $R_c$ is a $C_6$ to $C_8$ aryl optionally substituted with one or more halogens; or
a nitro group;
a —$NHR_d$ group, where $R_d$ is a $C_6$ to $C_8$ aryl optionally substituted with an alkoxy
a —$NHCOR_e$ group where $R_e$ is:
    a $C_6$ to $C_8$ aryl optionally substituted with a haloalkyl;
    a $C_1$ to $C_6$ alkyl;
or together with X forms:

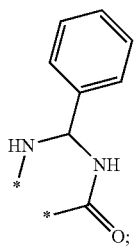

R is:
  a hydrogen
  a haloalkyl;
  a $C_1$ to $C_6$ alkyl optionally substituted with hydroxyl;
  a 5- or 6-member heteroaryl;
  a $C_6$ to $C_8$ aryl optionally substituted with one or more halogens;
  or R together with $R_1$ forms:

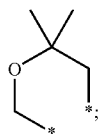

$R_1$ is:
  a hydrogen;
  a $C_6$ to $C_8$ aryl
  a $C_1$ to $C_6$ alkyl;
  a $OCOR_f$ where $R_f$ is a 5- or 6-membered heterocycle;
  an alkoxy optionally substituted with an amino group, wherein the amino group is optionally substituted with one or two $C_1$ to $C_6$ alkyls, where the alkyls are optionally substituted with an amino optionally substituted with one or two $C_1$ to $C_6$ alkyls
  an alkoxy optionally substituted with a 5 to 8 membered heterocycle optionally substituted with a $C_1$ to $C_6$ alkyl, which is optionally substituted with:
    an alkoxy, or
    an amino, optionally substituted with one or two $C_1$ to $C_6$ alkyls;
  or $R_1$ together with $R_2$ forms:

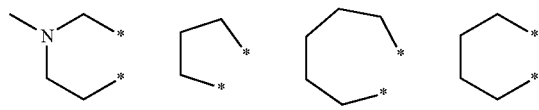

$R_1$ together with R forms:

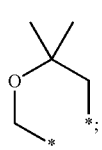

$R_2$ is:
  a $C_1$ to $C_6$ alkyl;
  a 5 or 6-membered heterocycle;
  an amino optionally substituted with a $C_1$ to $C_6$ alkyl;
  or $R_1$ together with $R_2$ forms:

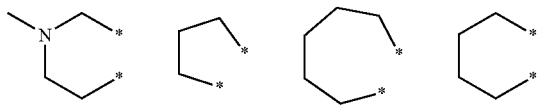

or a pharmaceutically acceptable salt thereof, together with an additional anti-HCV agent and a pharmaceutically acceptable excipient.

In another preferred embodiment, a compound or a composition of the present invention includes a compound of Formula I, wherein the compound of Formula I is not Compound 1

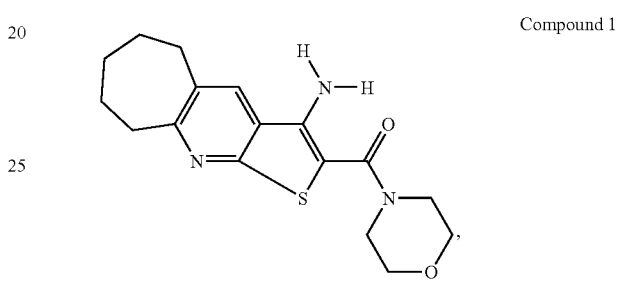

Compound 4

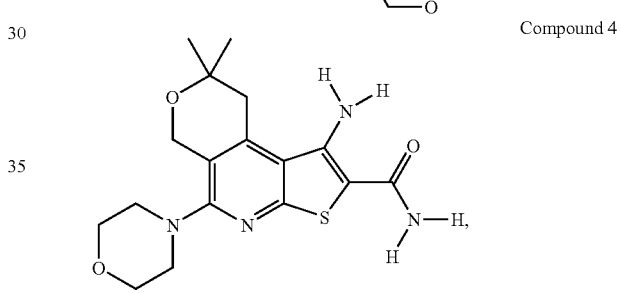

Compound 51

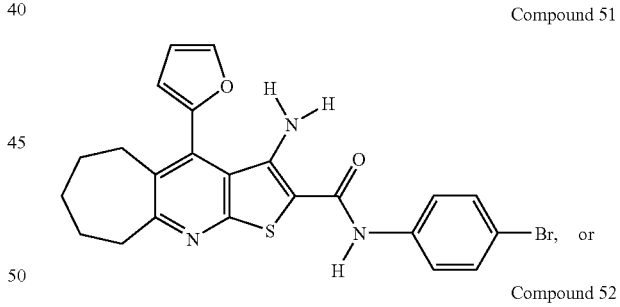

Compound 52

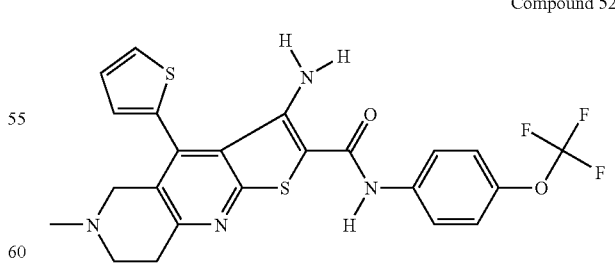

As used herein, the term "alkyl" generally refers to saturated hydrocarbyl radicals of straight, branched or cyclic configuration, or combinations of cyclic and branched or straight, including methyl, ethyl, n-propyl, isopropyl, n-butyl, isobutyl, sec-butyl, tert-butyl, n-pentyl, n-hexyl, cyclohexyl, n-heptyl, octyl, n-octyl, and the like. In some embodiments, alkyl substituents may be $C_1$ to $C_8$ or $C_1$ to $C_6$ alkyl groups.

As used herein, "alkylene" generally refers to linear, branched or cyclic alkene radicals having one or more carbon-carbon double bonds, such as $C_2$ to $C_6$ alkylene groups including 3-propenyl.

As used herein, "aryl" refers to a carbocyclic aromatic ring structure. Included in the scope of aryl groups are aromatic rings having from five to twenty carbon atoms. Aryl ring structures include compounds having one or more ring structures, such as mono-, bi-, or tricyclic compounds. Examples of aryl groups that include phenyl, tolyl, anthracenyl, fluorenyl, indenyl, azulenyl, phenanthrenyl (i.e., phenanthrene), and napthyl (i.e., napthalene) ring structures. In certain embodiments, the aryl group may be optionally substituted.

As used herein, "heteroaryl" refers to cyclic aromatic ring structures in which one or more atoms in the ring, the heteroatom(s), is an element other than carbon. Heteroatoms are typically O, S or N atoms. Included within the scope of heteroaryl, and independently selectable, are O, N, and S heteroaryl ring structures. The ring structure may include compounds having one or more ring structures, such as mono-, bi-, or tricyclic compounds. In some embodiments, the heteroaryl groups may be selected from heteroaryl groups that contain two or more heteroatoms, three or more heteroatoms, or four or more heteroatoms. Heteroaryl ring structures may be selected from those that contain five or more atoms, six or more atoms, or eight or more atoms. Examples of heteroaryl ring structures include: acridine, benzimidazole, benzoxazole, benzodioxole, benzofuran, 1,3-diazine, 1,2-diazine, 1,2-diazole, 1,4-diazanaphthalene, furan, furazan, imidazole, indole, isoxazole, isoquinoline, isothiazole, oxazole, purine, pyridazine, pyrazole, pyridine, pyrazine, pyrimidine, pyrrole, quinoline, quinoxaline, thiazole, thiophene, 1,3,5-triazine, 1,2,4-triazine, 1,2,3-triazine, tetrazole and quinazoline.

As used herein, "heterocycle" refers to cyclic ring structures in which one or more atoms in the ring, the heteroatom(s), is an element other than carbon. Heteroatoms are typically O, S or N atoms. Included within the scope of heterocycle, and independently selectable, are O, N, and S heterocycle ring structures. The ring structure may include compounds having one or more ring structures, such as mono-, bi-, or tricyclic compounds. Example of heterocyclo groups include morpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl or tetrahydrothiopyranyl and the like. In certain embodiments, the heterocycle may optionally be substituted.

As used herein, "alkoxy" generally refers to a group with the structure —O—R. In certain embodiments, R may be an alkyl group, such as a $C_1$ to $C_8$ alkyl group.

For the purposes of this invention, halo substituents may be independently selected from the halogens such as fluorine, chlorine, bromine, iodine, and astatine. A haloalkyl is an alkyl group, as defined above, substituted with one or more halogens. A haloalkoxy is an alkoxy group, as defined above, substituted with one or more halogens.

For the purposes of this invention, where one or more functionalities encompassing X, Y, R, $R_1$ and $R_2$ are incorporated into a molecule of Formula (I), each functionality appearing at any location within the disclosed molecule may be independently selected, and as appropriate, independently substituted. Further, where a more generic substituent is set forth for any position in the molecules of the present invention, it is understood that the generic substituent may be replaced with more specific substituents, and the resulting molecules are within the scope of the molecules of the present invention.

By "substituted" or "optionally substituted" it is meant that the particular substituent may be substituted with a chemical group known to one of skill in the art to be appropriate for the referred to substituent, unless a chemical group is specifically mentioned.

Exemplary X substituents include the following, where the * indicates the bond of attachment of the scaffold molecule.

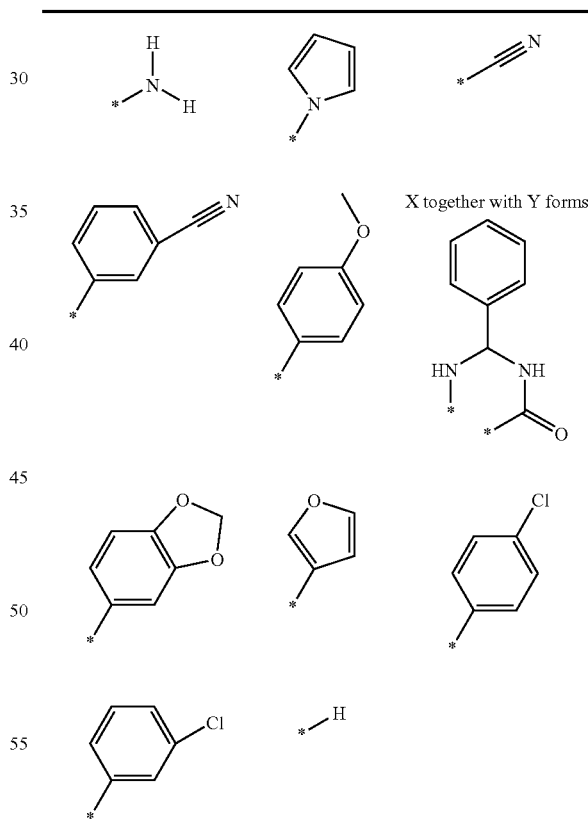

Preferred X substituents include an amino group or a hydrogen. Particularly preferred X substituents include an amino group.

Exemplary Y substituents include the following, where the * indicates the bond of attachment of the scaffold molecule.

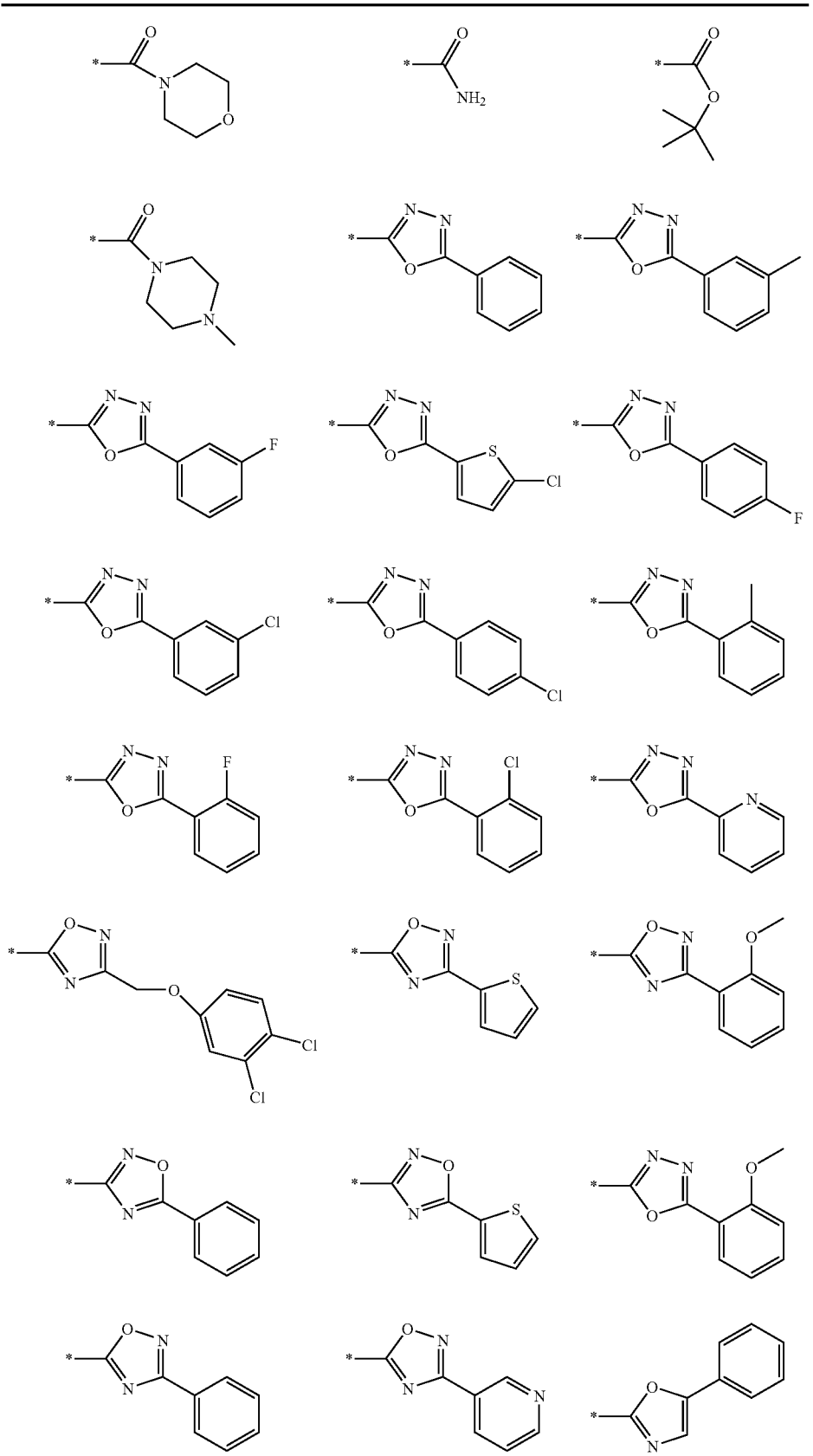

-continued
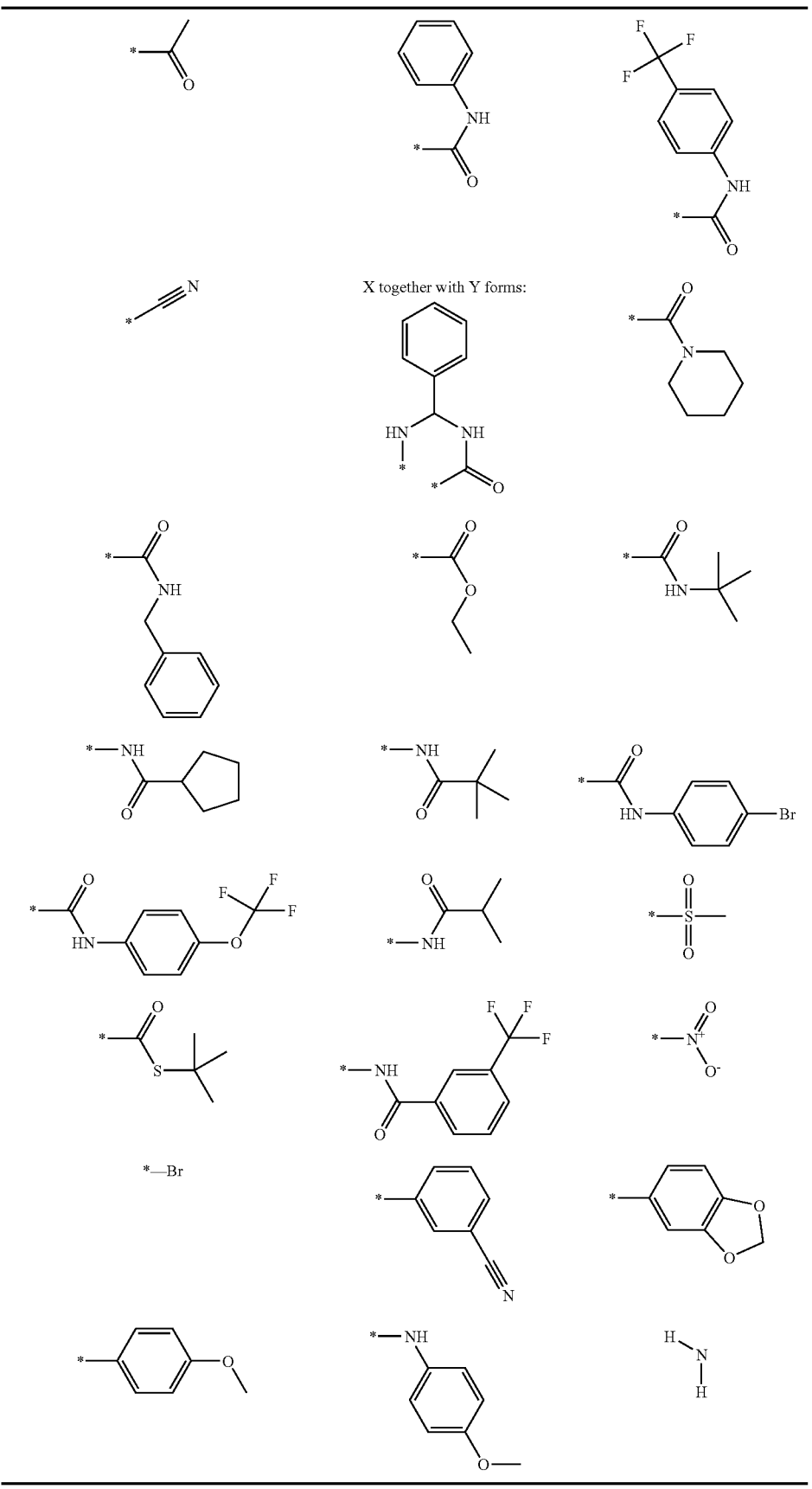

Preferred Y substituents include the following, where the * indicates the bond of attachment of the scaffold molecule.
Exemplary R substituents include the following, where the * indicates the bond of attachment of the scaffold molecule.
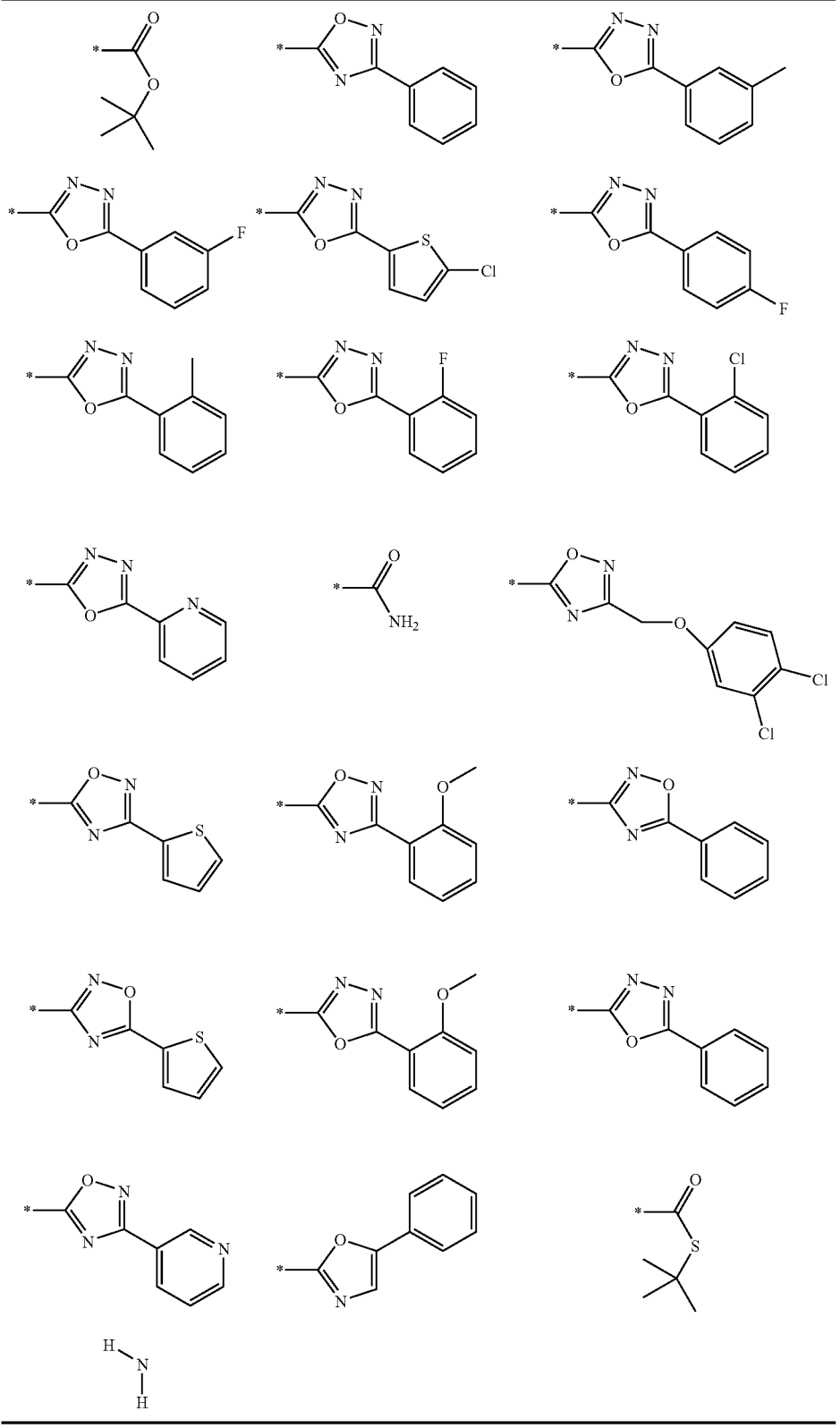

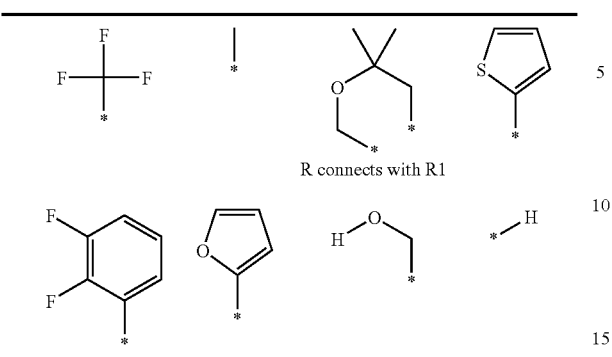
Preferred R substituents include $C_1$ to $C_6$ alkyl and more preferred R substituents include methyl.
Exemplary $R_1$ substituents include the following, where the * indicates the bond of attachment of the scaffold molecule.
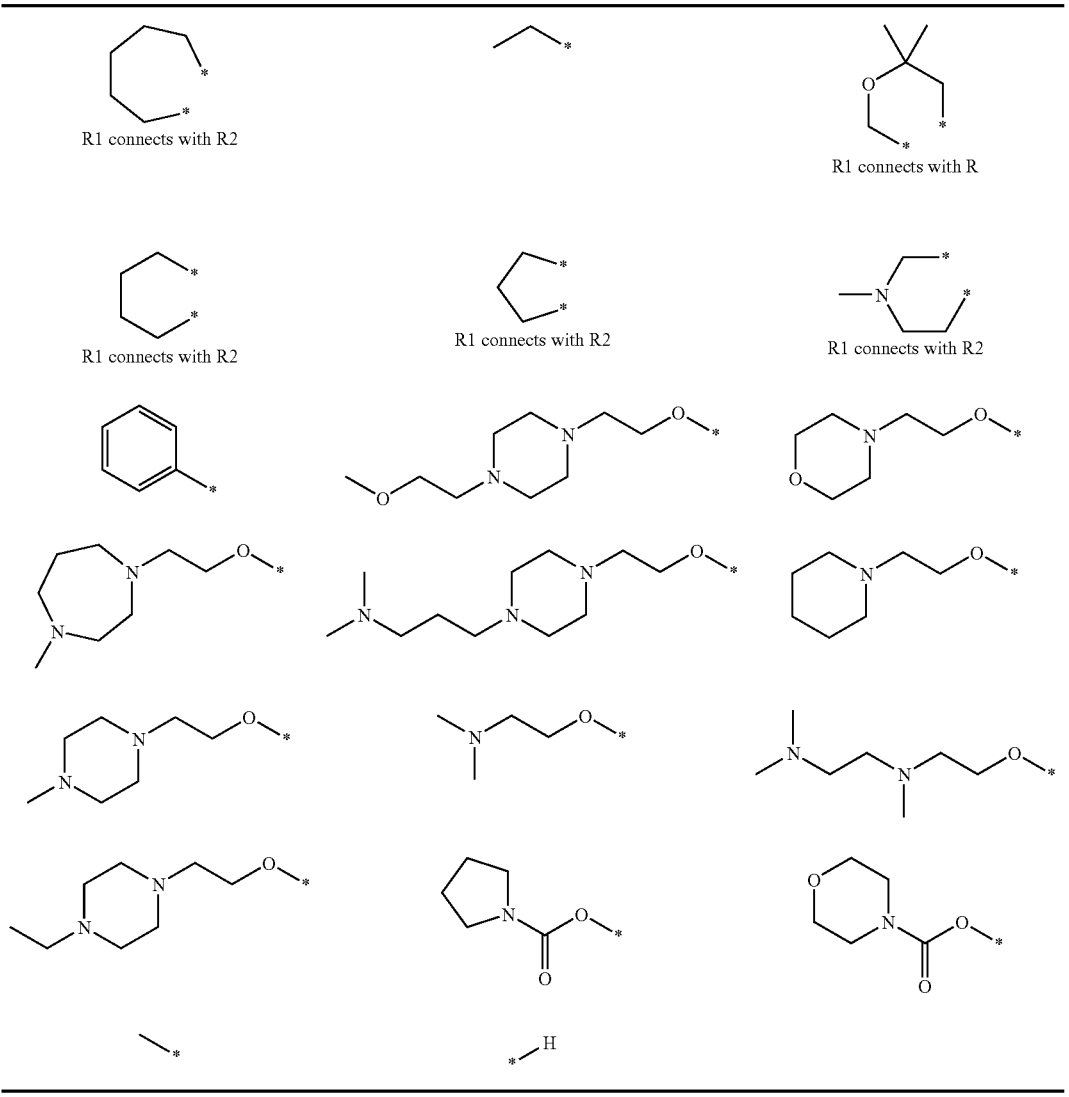

Preferred $R_1$ substituents include the following, where the * indicates the bond of attachment of the scaffold molecule.

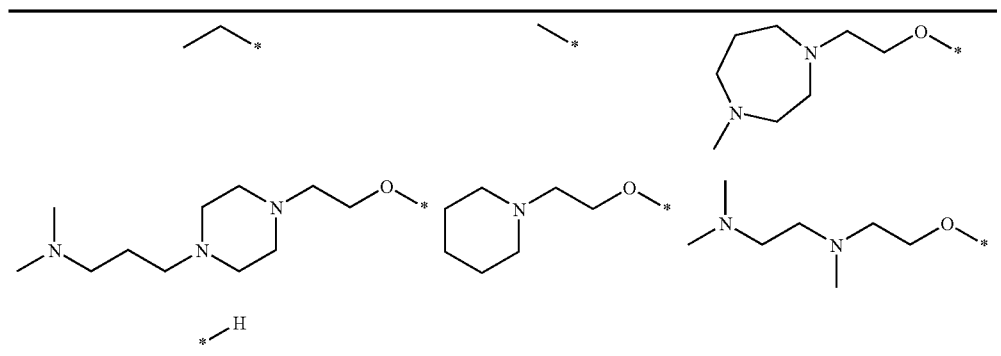

Exemplary $R_2$ substituents include the following, where the * indicates the bond of attachment of the scaffold molecule.

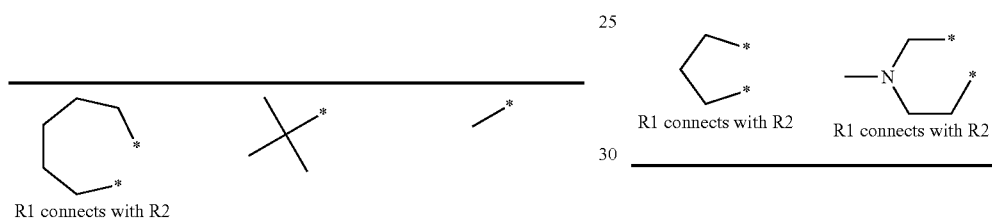

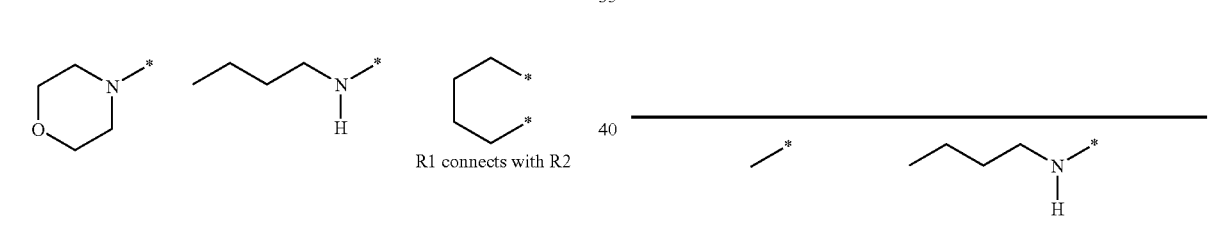

Preferred $R_2$ substituents include the following, where the * indicates the bond of scaffold molecule.

Compounds of the invention include the following:

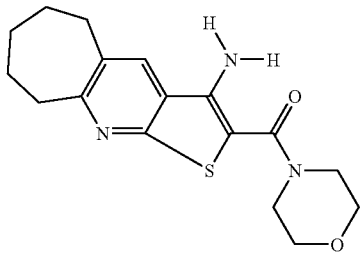

1

-continued
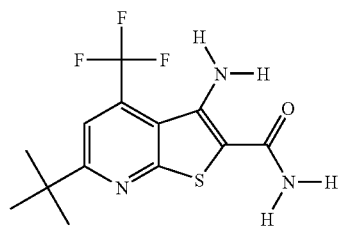
2
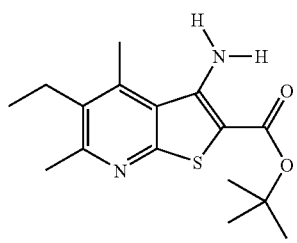
3
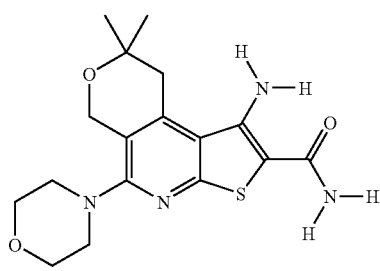
4
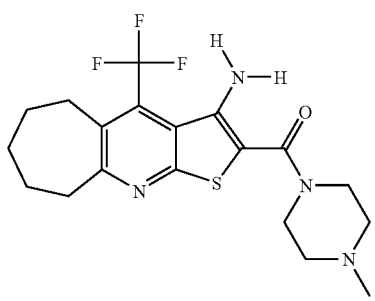
5
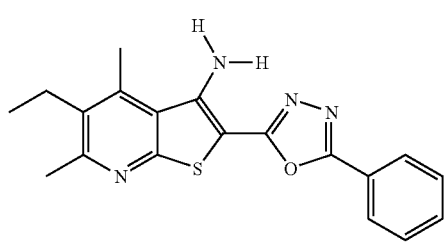
6

-continued
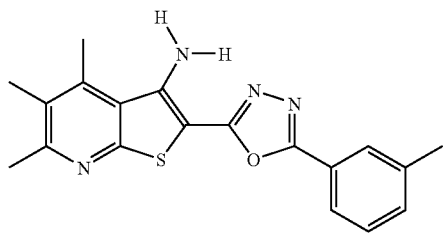
7
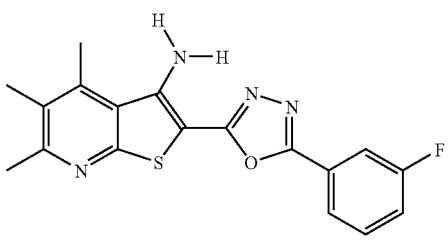
8
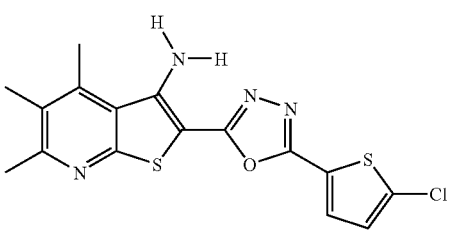
9
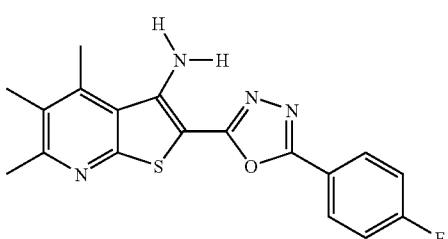
10
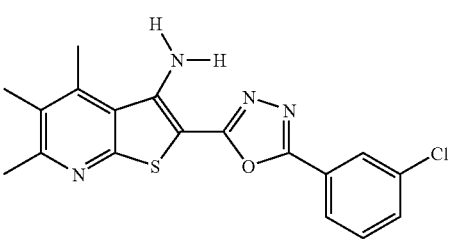
11

-continued
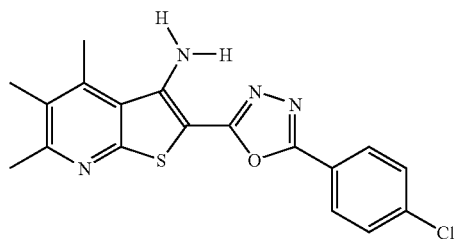
12
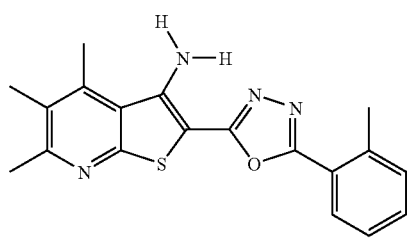
13
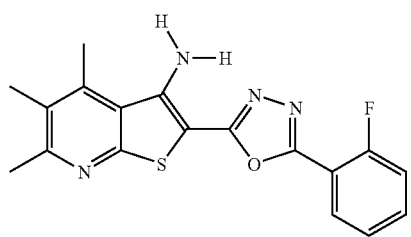
14
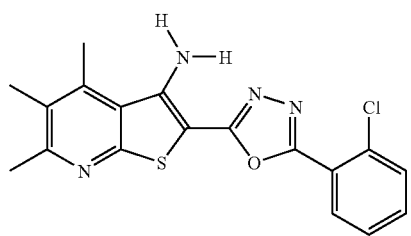
15
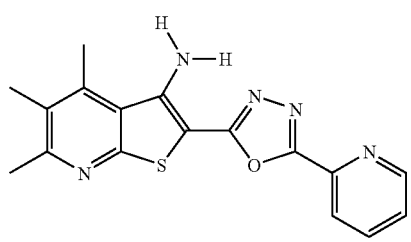
16

-continued
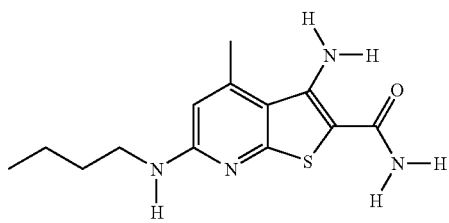
17
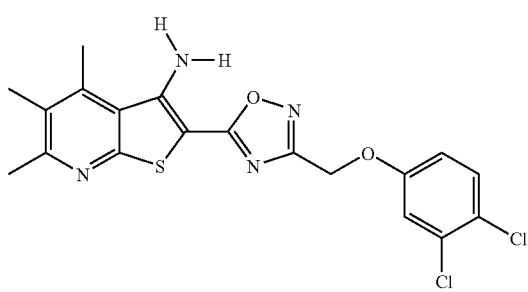
18
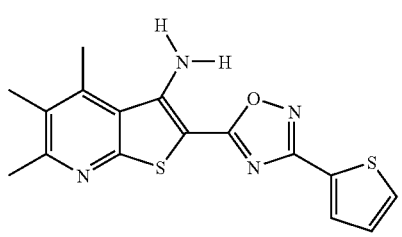
19
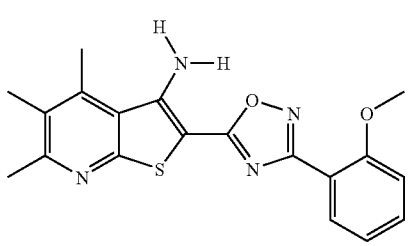
20
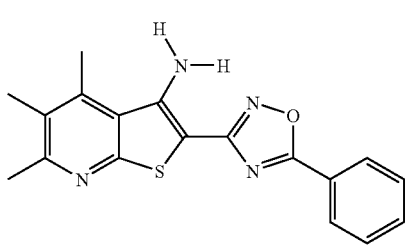
21

-continued
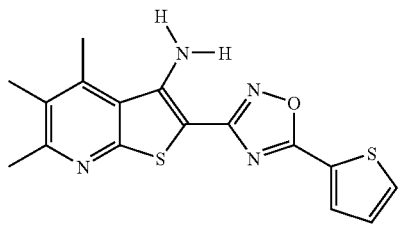
22
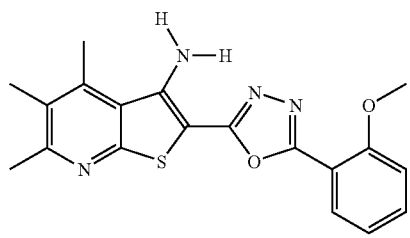
23
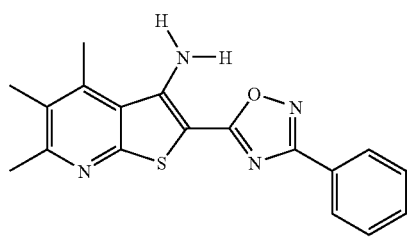
24
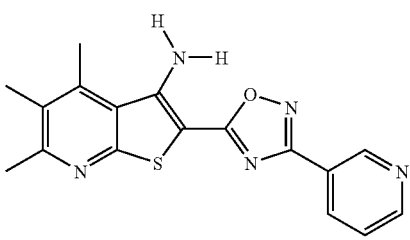
25
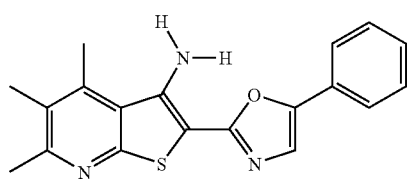
26
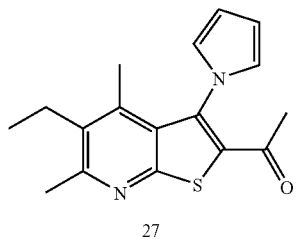
27

-continued
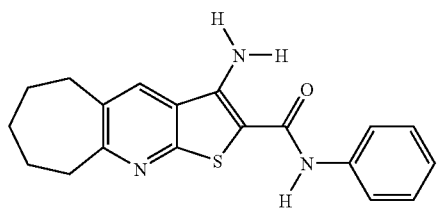
28
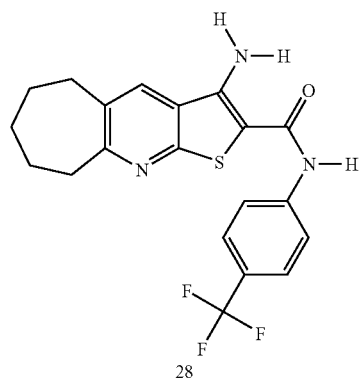
28
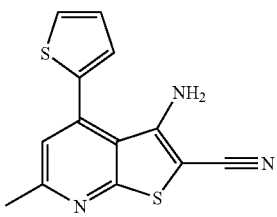
30
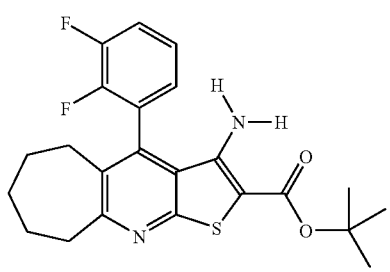
31
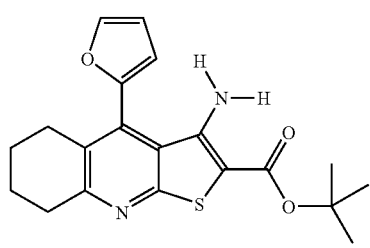
32

-continued
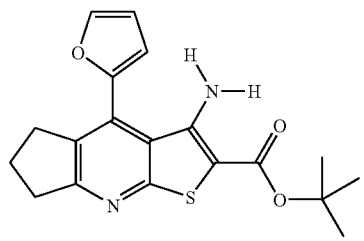
33
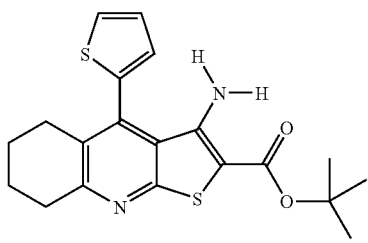
34
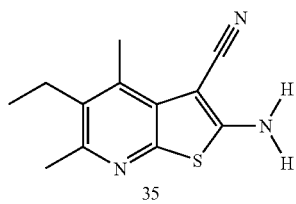
35
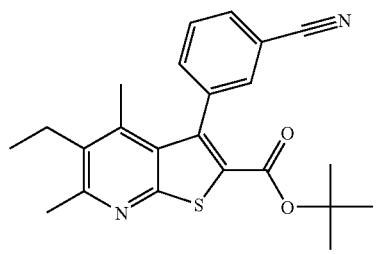
36
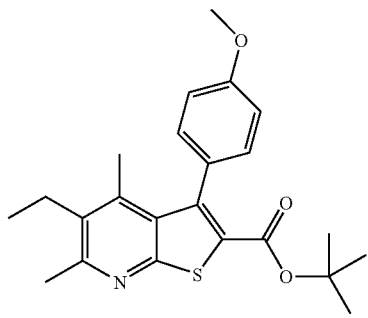
37

-continued
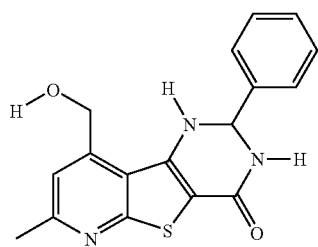
38
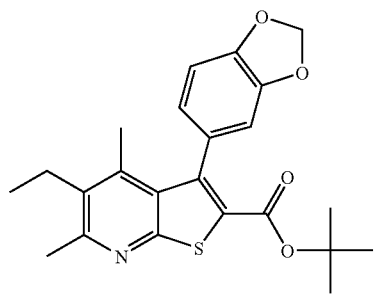
39
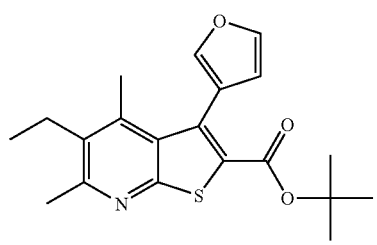
40
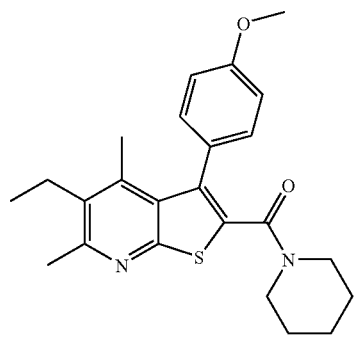
41

-continued
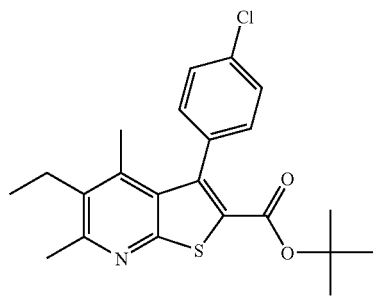
42
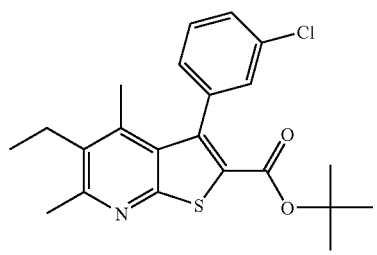
43
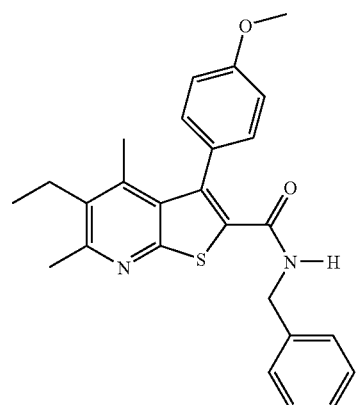
44
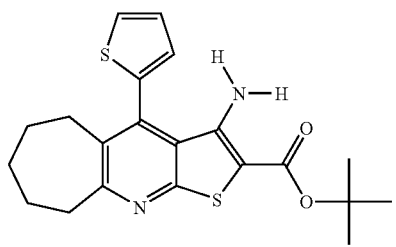
45

-continued
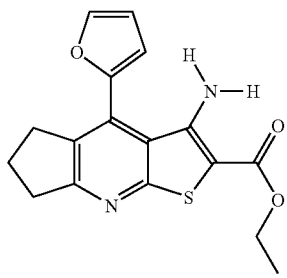
46
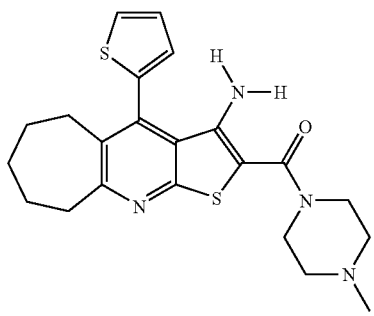
47
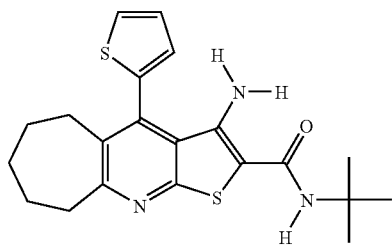
48
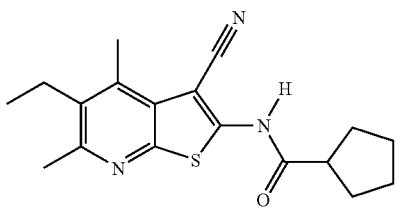
49
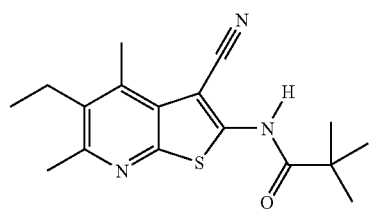
50

-continued
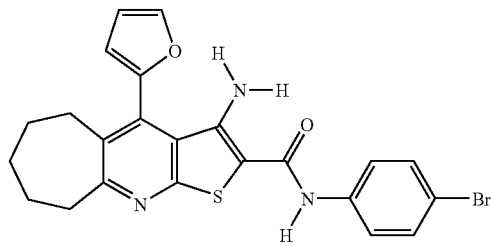
51
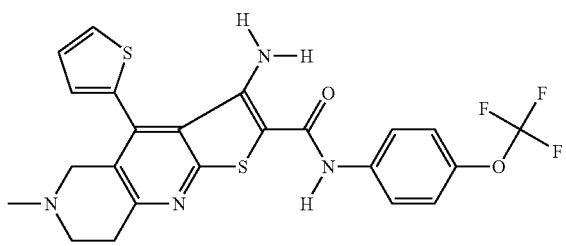
52
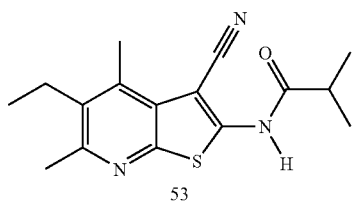
53
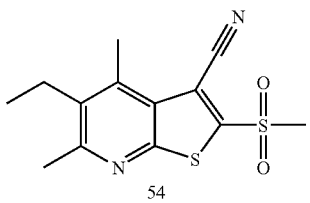
54
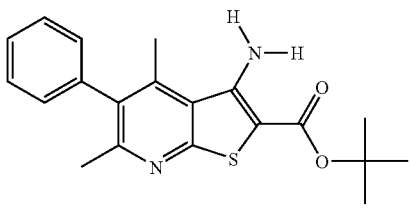
55
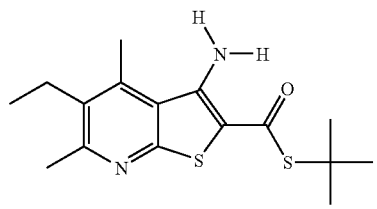
56

-continued
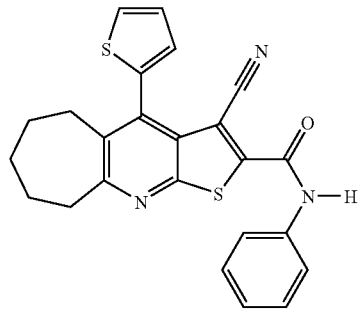
57
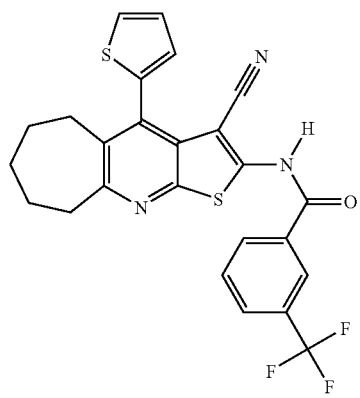
58
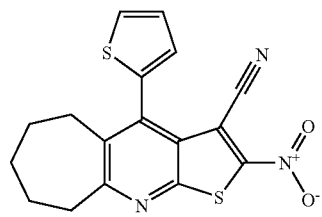
59
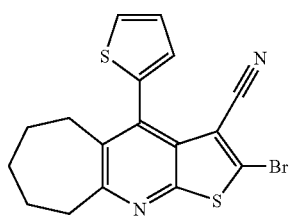
60
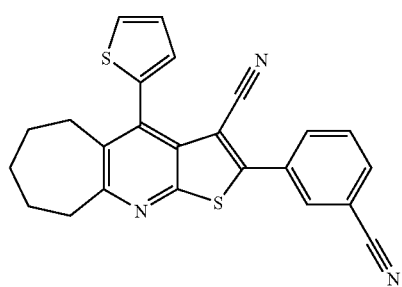
61

-continued
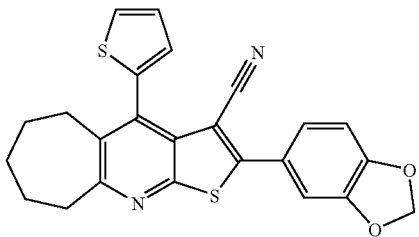
62
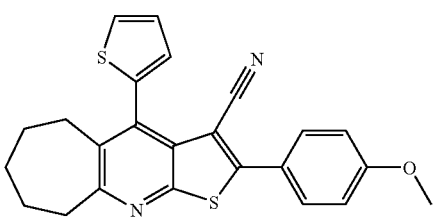
63
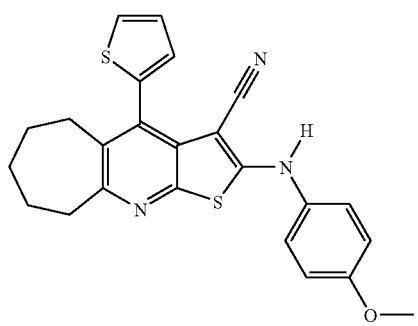
64
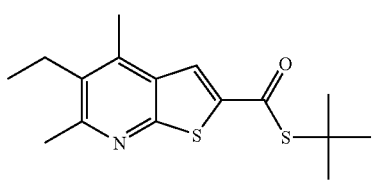
65
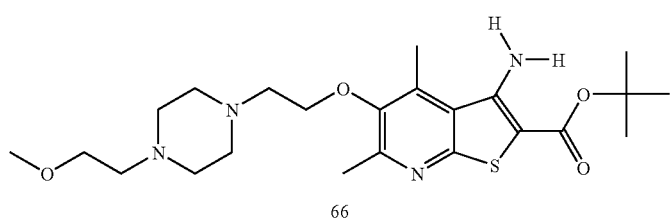
66
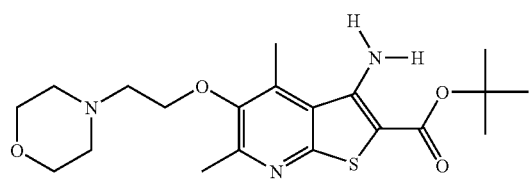
67

-continued
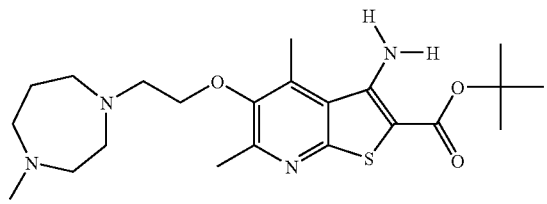
68
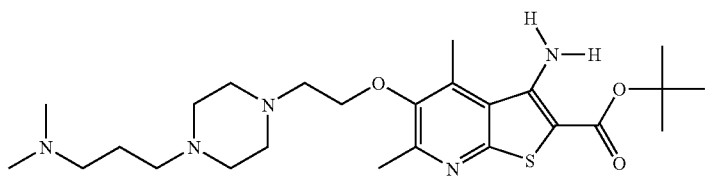
69
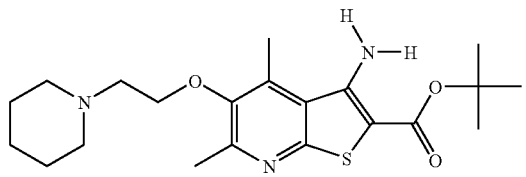
70
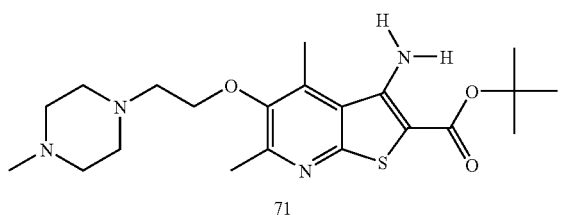
71
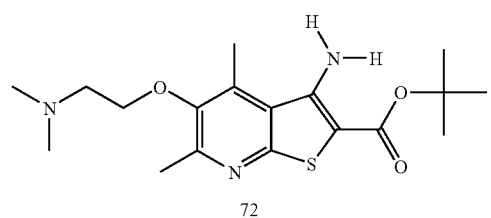
72
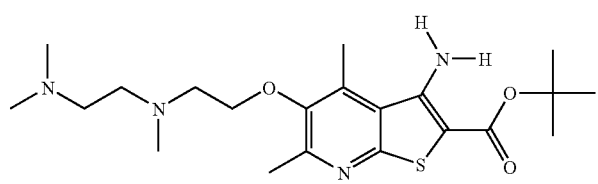
73

-continued
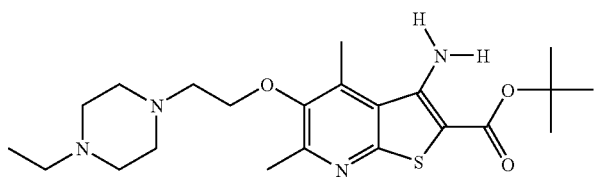
74
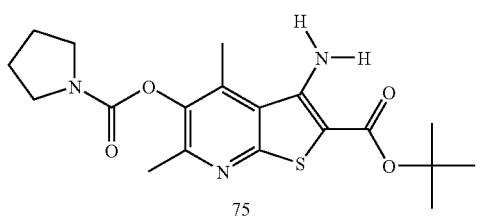
75
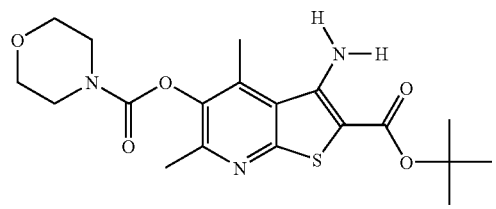
76
The above compounds were prepared using the schemes and examples set forth below. Other methods of producing these compounds are known to one of skill in the art.
Preferred compounds of the present invention include the following:
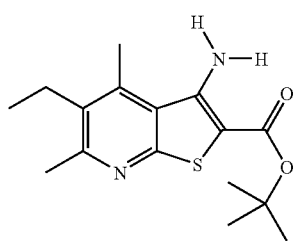
3
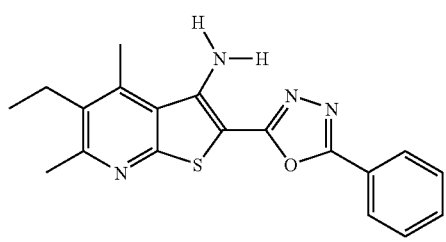
6

-continued
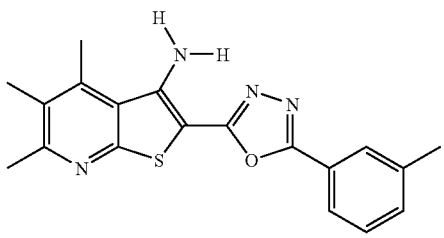
7
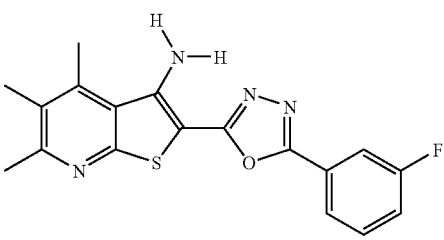
8
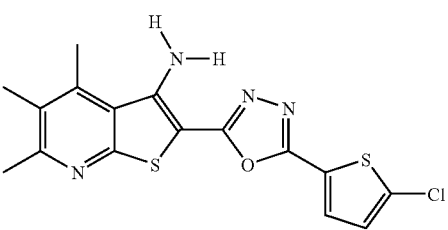
9
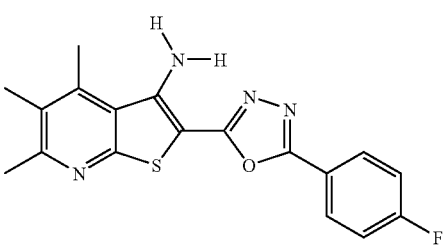
10
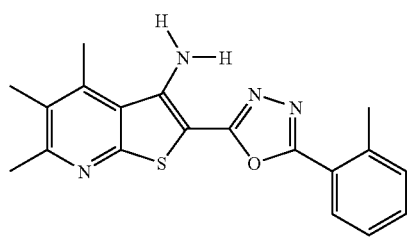
13

-continued
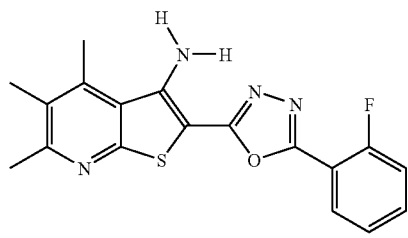
14
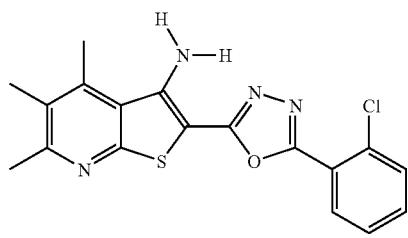
15
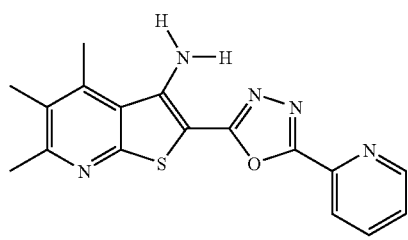
16
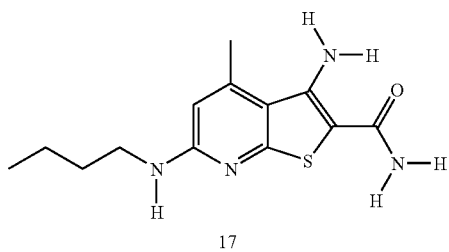
17
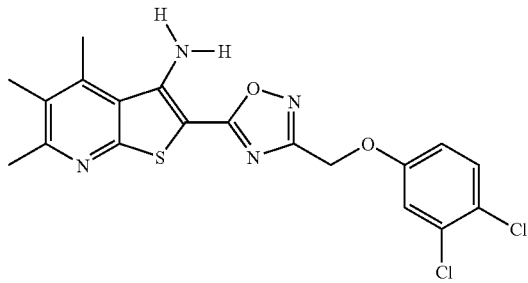
18

-continued
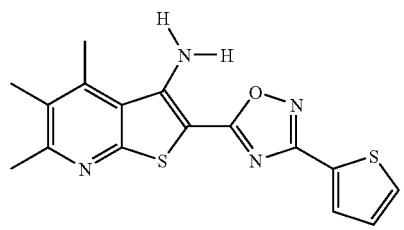
19
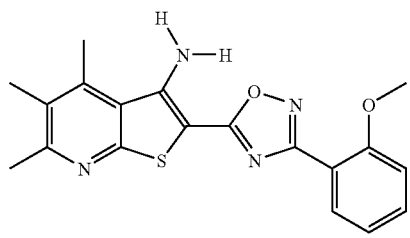
20
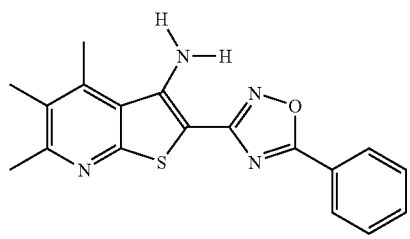
21
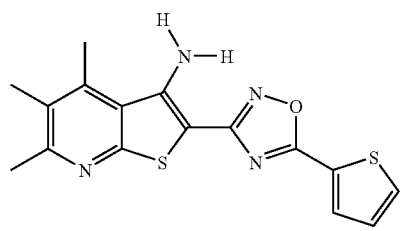
22
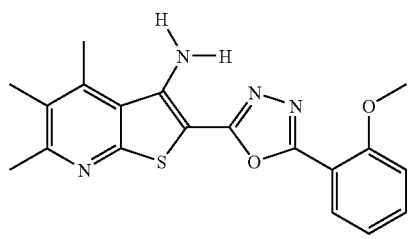
23

-continued
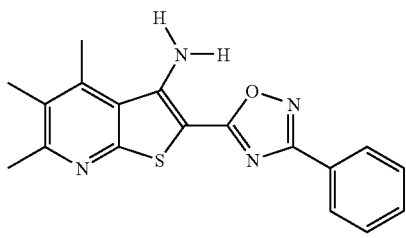
24
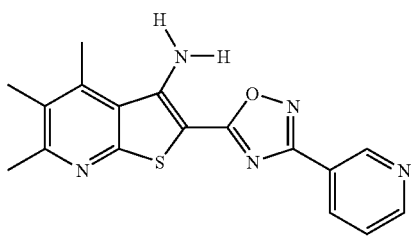
25
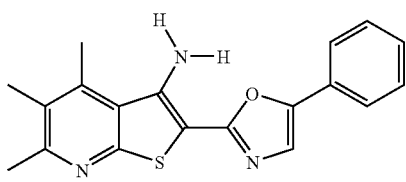
26
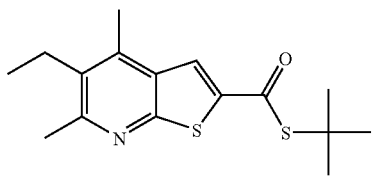
65
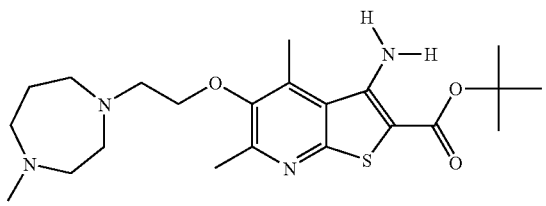
68
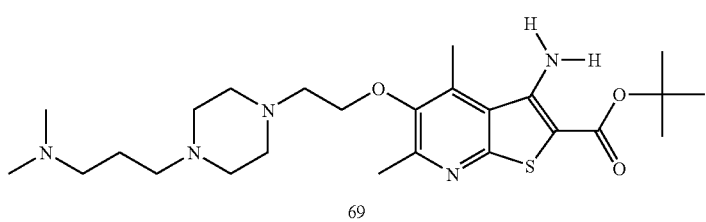
69

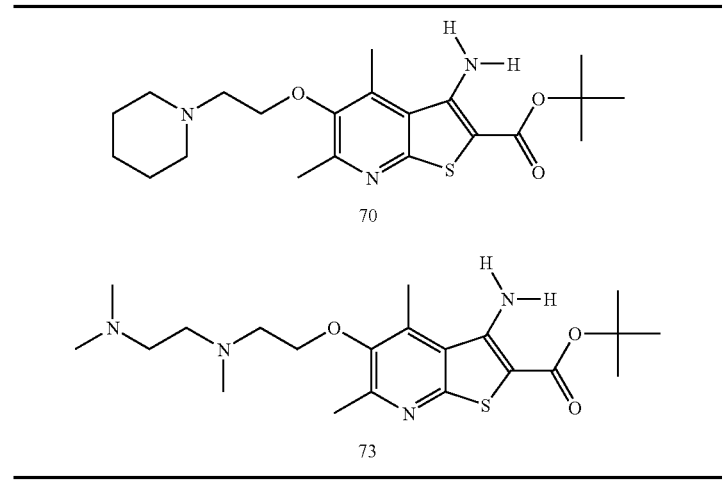

B. Preparation of Compounds of the Invention

Compounds of the invention may be produced in any manner known in the art. By way of example, compounds of the invention may be prepared according to the following general schemes.

Thienopyridine compounds of the present invention can be obtained via standard, well known synthetic methodology. All the starting materials and intermediates for preparing the compounds in the invention are commercially available or can be prepared from commercially available materials using known synthetic methods and reagents.

Compounds of formula I, represented by structure II, where $R_3$ represents an electron deficient group, such as aryl, heteroaryl, cyano, $COOR_c$, $COR_d$, $CONR_aR_b$, $NO_2$, $CONR_aSO_2R_e$, $SO_2R_e$ and $SO_2NR_aR_b$, can be prepared using the method depicted in Scheme A.

I. Scheme A

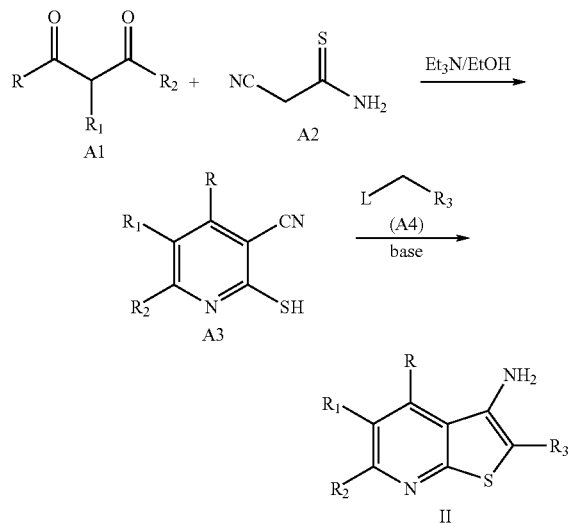

Treatment of 1,3-diketones A1 with 2-cyanothioacetamide A2 in a suitable solvent, such as alcohol or a polar aprotic solvent, in the presence of an organic or inorganic base, such as triethylamine at a temperature from ambient to 80° C. gives the intermediate 2-mercapto-3-cyanopyridine A3. A3 can be treated directly with A4, where L represents a suitable leaving group, which is attached to an activated methylene, in the presence of a base, such as sodium methoxide (NaOMe), to give compounds of formula II.

Preferably, A3 can be isolated using a standard aqueous work-up procedure, then treated with A4 in a polar solvent, such as dimethylformamide (DMF), in the presence of a base, such as potassium carbonate ($K_2CO_3$), at an elevated temperature, e.g., 50-90° C., to give compounds of formula II. Sodium hydride can also be deployed for the transformation of less reactive substrates.

Alternatively, compounds of formula I, represented by structure II can be prepared using the method depicted in Scheme B.

II. Scheme B

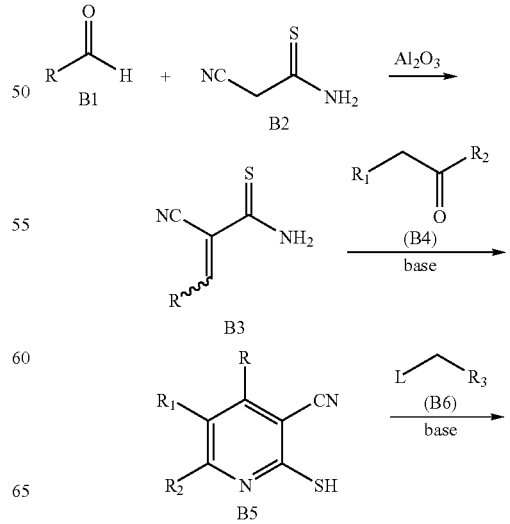

-continued

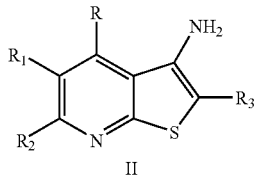
II

Condensation of aldehydes B1 and 2-cyanothioacetamide B2 in a suitable solvent, such as alcohol, in the presence of aluminium oxide gives the intermediate B3. Condensation of B3 with ketones B4 in the presence of a base, e.g., piperidine or potassium hexamethyldisilazane (KHMDS), followed by ring-closure and self-oxidation gives the intermediates, 2-mercapto-3-cyanopyridines B5. Conversion of B5 to compounds of formula II can be realized by the treatment of B5 with B6 using the method described previously.

Compounds of formula I, represented by structure III can also be prepared using the method depicted in Scheme C.

III. Scheme C

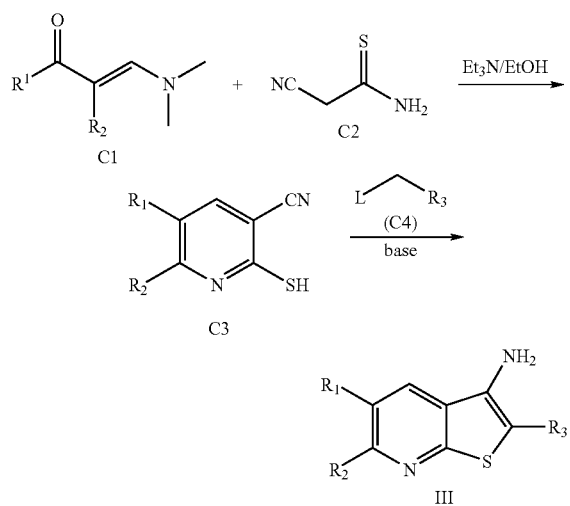
III

Treatment of ketoenamines C1 with 2-cyanothioacetamide C2 in a suitable solvent, such as alcohol or a polar aprotic solvent, in the presence of an organic or inorganic base, such as triethylamine at a temperature from ambient to 80° C. gives the intermediate 2-mercapto-3-cyanopyridines C3. Compounds C3 can then be converted to formula III compounds using the method described previously.

Compounds of formula I, represented by structure IV can be prepared using the method depicted in Scheme D.

IV. Scheme D

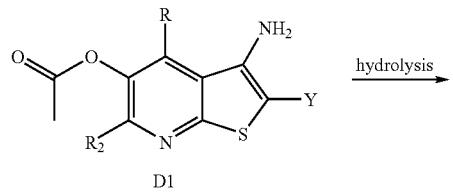
D1

-continued

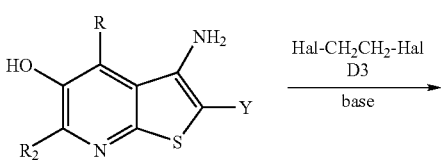
D2

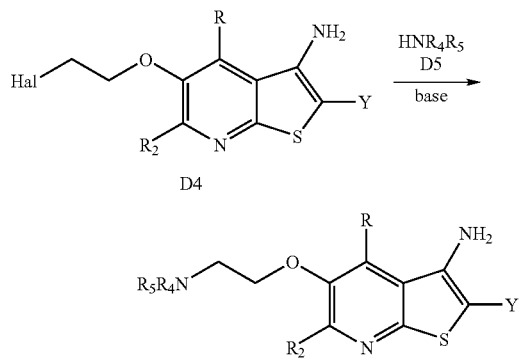
D4

IV

5-Thienopyridinyl acetate D1, prepared using the method depicted in Schemes A and B (where $R_1$=OAc), can be converted to D2 by a standard basic hydrolysis. Compounds D2 can be treated with 1,2-dihaloethane D3, such as 1-bromo-2-chloroethane, in a suitable solvent such as acetonitrile, in the presence of a base, eg., potassium carbonate, at an elevated temperature, typically 50~90° C., to compounds D4. Treatment of D4 with a primary or a secondary amine D5, in a suitable solvent in the presence of a base gives compounds of formula IV.

Compounds of formula I, represented by structure V can be prepared using the method depicted in Scheme E.

V. Scheme E

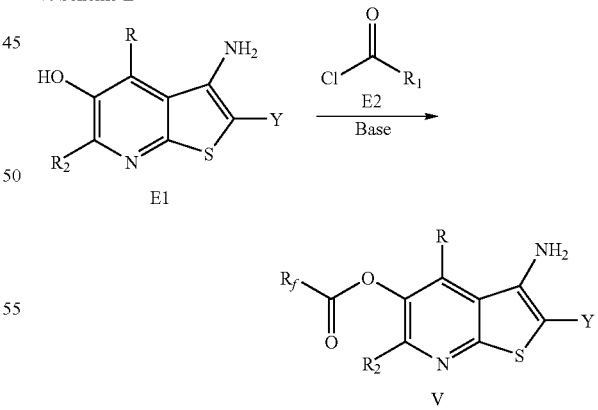
V

5-Hydroxythienopyridine E1, prepared using the method depicted in Scheme D, can be acetylated with compounds of type E2 in the presence of a base to give compounds of formula V.

Compounds of formula I, represented by structure VI can be prepared using the method depicted in Scheme F.

VI. Scheme F

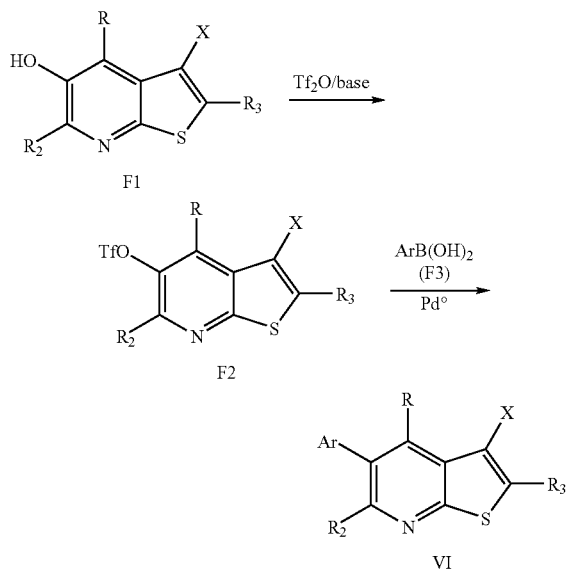

Compound F1 can be treated with trifluoromethylsulfonic anhydride in a suitable solvent such as dichloromethane in the presence of a base, eg., 4-dimethylaminopyridine, to give triflate F2. Treatment of F2 with arylboronic acids F3 using Suzuki coupling methodology in the presence of a palladium catalyst gives compounds of formula VI.

Compounds of formula I, represented by structure VII can be prepared using the method depicted in Scheme G.

VII. Scheme G

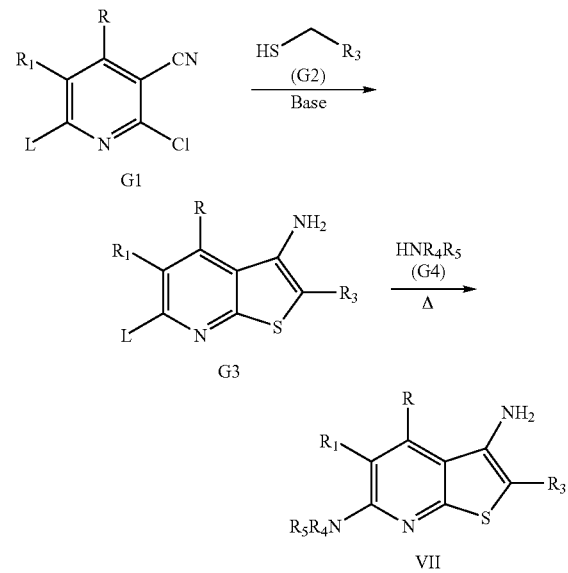

Thienopyridines of type G3, where L represents a suitable leaving group, preferably halogen, such as Cl and Br, can be prepared by the treatment of G1 with G2, in the presence of a base. Treatment of G3, with a variety of amines G4 at an elevated temperature gives compounds of formula VII.

Compounds of formula I, represented by structure VIII can be prepared using the method depicted in Scheme H.

VIII. Scheme H

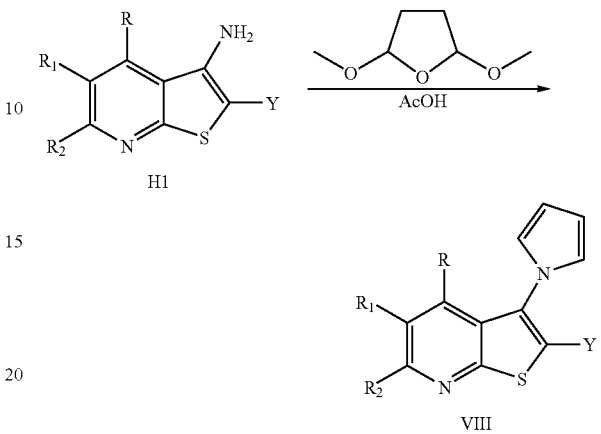

Treatment of 3-aminothienopyridines H1, prepared using the method depicted in Schemes A, or B, with 2,5-dimethoxytetrahydrofuran in the presence of an inorganic or organic acid, such as acetic acid, in a suitable solvent, or use of acetic acid as the solvent at a temperature from 20 to 90° C., gives compounds of formula VIII.

Compounds of formula I, represented by structure IX can be prepared using the method depicted in Scheme I.

IX. Scheme I

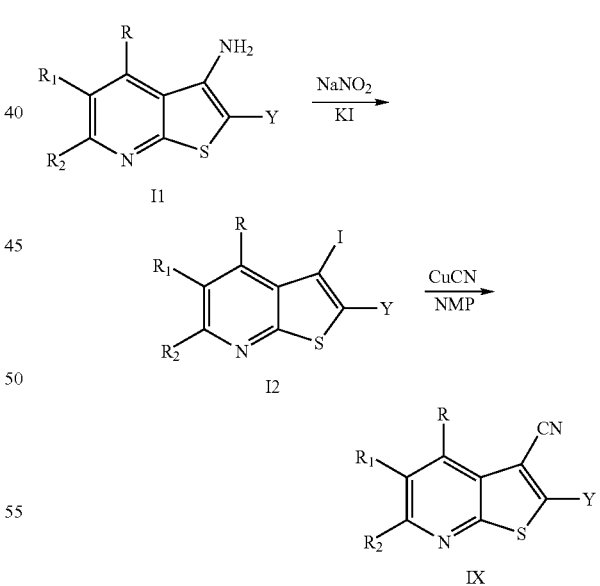

3-Aminothienopyridines I1, prepared using the method depicted in Schemes A or B, can be converted to 3-iodothienopyridines I2 with KI or CuI, via a diazonium salt intermediate, generated in situ using standard diazotization methods, such as sodium nitrite in aqueous acid media, or using an organic nitrite, such as BuONO in a suitable solvent, such as acetonitrile. The iodide I2 can then be treated with CuCN in a suitable solvent, e.g., N-methylpyrrolidinone, at temperature of 25-180° C. to give the compounds of formula IX.

Compounds of formula I, represented by structure X can be prepared using the method depicted in Scheme J.

X. Scheme J
XI.

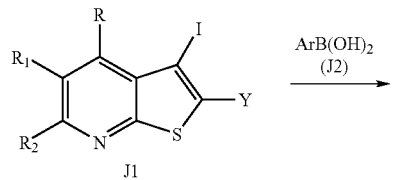

3-iodothienopyridines J1, prepared using the method depicted in Scheme I, can be reacted with aryl or heteroaryl-boronic acids J2 in the presence of a palladium catalyst under standard Suzuki coupling condition to give the compounds of formula X.

Compounds of formula I, represented by structure XI, can be prepared using the method depicted in Scheme K.

XII. Scheme K

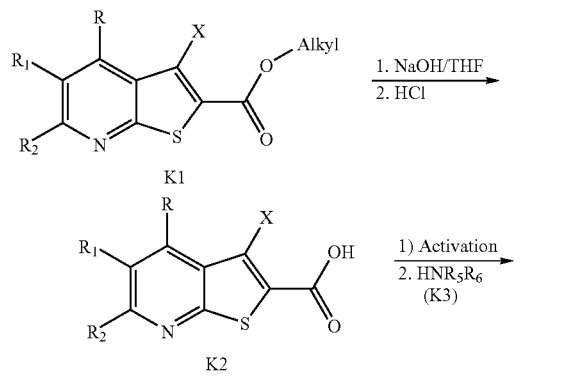

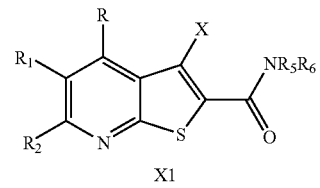

Thienopyridine-2-carboxylates K1, prepared using methods described previously, can be converted to the corresponding acids K2 using standard hydrolysis or de-alkylation methods. For example, K1 can be treated with sodium hydroxide solution in a suitable solvent, such as THF at an elevated temperature from 50-80° C., to give K2. Alternatively, K2 can be obtained from K1 using a selective de-alkylation method, such as standard trifluoroacetic acid de-t-butylation, e.g., when K1 is a t-butyl ester; or standard de-methylation using $BBr_3$ or trimethylsilyl iodide, e.g., when K1 is a methyl ester. K2 then can be activated as an acid chloride by the treatment of the acids with thionyl chloride or oxalyl chloride, or alternatively, activated as an active ester or active anhydride using standard peptide coupling chemistry, for example, PyBOP in DMF, followed by the treatment with amines K3 to give the compounds of formula XI.

Compounds of formula I, represented by structure XII, where $R_7$ represents phenyl optionally substituted with a C 1 to C6 alkyl or a 5 or 6 membered heteroaryl optionally substituted with a C1 to C6 alkyl, can be prepared using the method depicted in Scheme L.

XIII. Scheme L

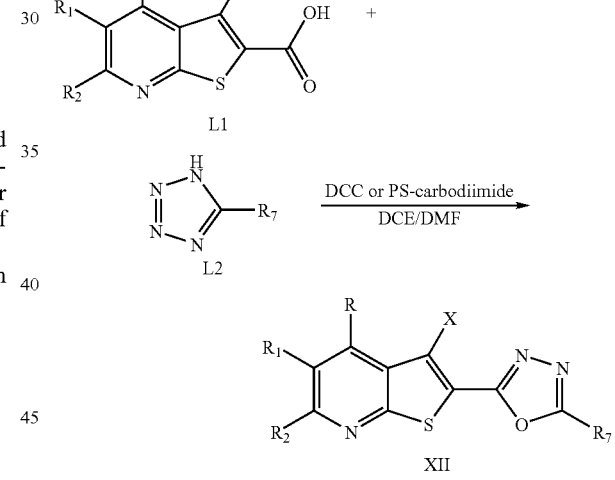

Thienopyridine-2-carboxylic acids L1, prepared using methods depicted in previous Schemes, can be activated with DCC or PS-carbodiimide in a suitable solvent system, such as dichloroethane-DMF, followed by the treatment with tetrazoles L2. Heating the reaction at an elevated temperature, e.g., 50-150° C. gives the compounds of formula XII.

Compounds of formula I, represented by structure XIII, can be prepared using the method depicted in Scheme M.

XIV. Scheme M

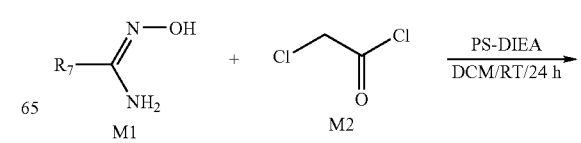

-continued

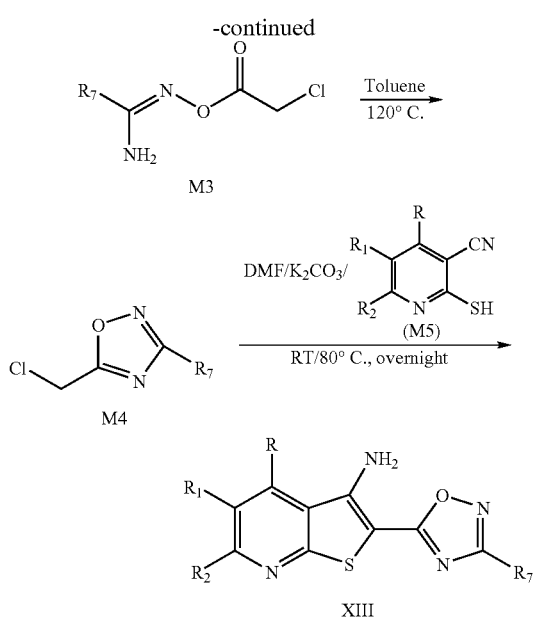

Hydroxyamidines of type M1, commercially available, can be reacted with 2-chloroacetyl chloride M2 in a suitable aprotic solvent, such as dichloromethane, in the presence of a base, e.g. PS-DIEA, to give O-acylated hydroxyamines M3. Heating M3 in a suitable solvent at temperature from 80-110° C. gives 5-chloromethyl-1,2,4-oxadiazoles of type M4. Treatment of M4 with M5, which can be obtained using the chemistry described in Scheme A, in a suitable solvent, preferably polar protic, or aprotic solvent, such as MeOH or DMF in the presence of a base, e.g. NaOMe or $K_2CO_3$ at an elevated temperature 50-80° C. to give the compounds of formula XIII.

Compounds of formula I, represented by structure XIV, can be prepared using the method depicted in Scheme N.

XV. Scheme N

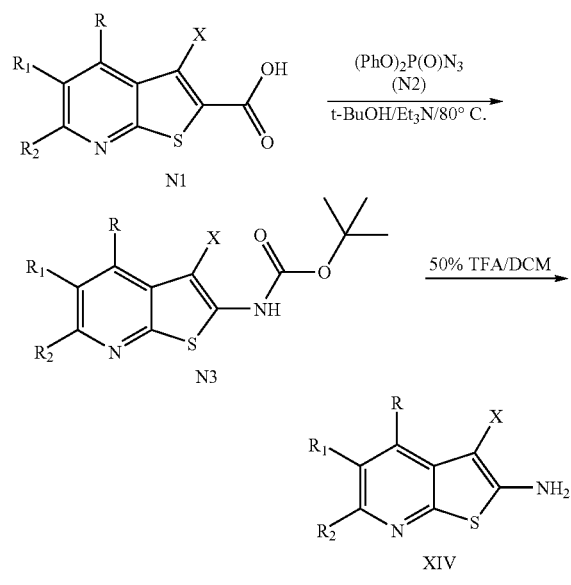

Thienopyridine-2-carboxylic acids N1, prepared using the method depicted in the previous Schemes, upon reaction with diphenylphosphoryl azide (DPPA) (N2) in the presence of an organic base, such as triethylamine in tert-butanol undergo Curtis rearrangement at an elevated temperature, to give N3, which can be converted to 2-amino thienopyridines in 50% TFA in dichloromethane, to give the compounds of formula XIV.

Compounds of formula I, represented by structure XV, can be prepared using the method depicted in Scheme O.

XVI. Scheme O

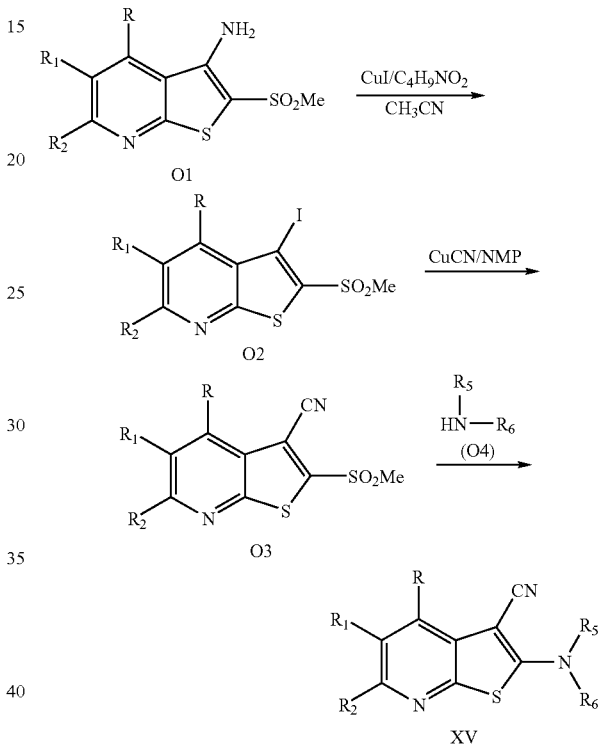

3-Amino-2-methylsulfonylthienopyridines O1, prepared using the method described previously in Scheme A, can be converted to 3-iodo-2-methylsulfonylthienopyridines O2 by the treatment of O1 with butylnitrite and CuI in acetonitrile at an elevated temperature, for example, 50-70° C. Treatment of O2 with CuCN in NMP at temperatures between ambient and 60° C. gives 3-cyano derivatives O3. The 2-methylsulfonyl group of O3 can then be reacted with amines of type O4 in a suitable solvent, such as acetonitrile at a temperature between 25-85° C. to give compounds of structure XV.

Compounds of formula I, represented by structure XVI, can be prepared using the method depicted in Scheme P.

XVII. Scheme P

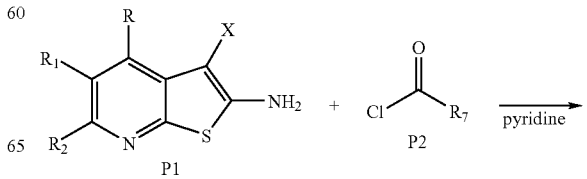

-continued

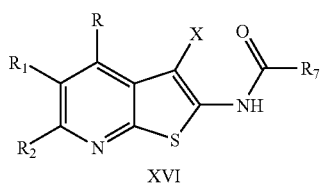

XVI

2-Aminothienopyridines P1, prepared using the methods described previously, can be treated with an acid chloride (P2) in the presence of a base, such as triethyl amine, in a suitable organic solvent, such as dichloromethane, or pyridine as the base and the solvent at temperature from ambient to 110° C. to give compounds of structure XVI.

Compounds of formula I, represented by structures XVII can be prepared using the method depicted in Scheme Q.

XVIII. Scheme Q

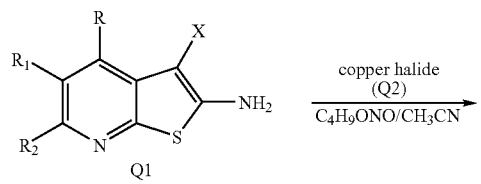

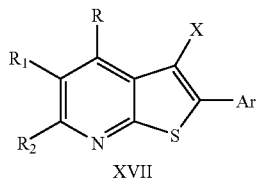

XVII

2-Aminothienopyridines Q1, prepared using the method described previously can be converted to 2-halothienopyridines Q3, where halogen is preferably, bromo or iodo, using standard Sandmeyer diazonium chemistry, by the treatment of Q1 with $NaNO_2$ in aqueous acidic media, such as concentrated HCl, followed by the addition of copper halide Q2. Alternatively, Q3 can also be obtained by the treatment of Q1 with an organic nitrite, such as butylnitrite in the presence of copper halide in a suitable solvent, preferably, acetonitrile at an elevated temperature from 50-70° C. Compounds Q3 can then be subjected to Suzuki type coupling using a palladium catalyst with various aryl- or heteroarylboronic acids Q4, in a suitable solvent system to give compounds of structure XVII.

Compounds of formula I, represented by structures XVIII can be prepared using the method depicted in Scheme R.

XIX. Scheme R

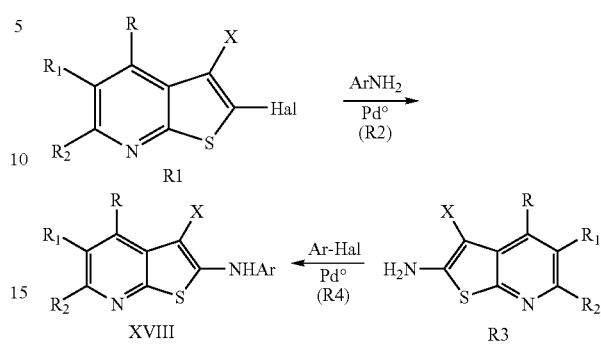

XVIII

2-Halothienopyridines R1, prepared using the method described in the previous Scheme S, where halogen is preferably, chloro, bromo or iodo, can be subjected to palladium catalyzed amination reaction with various substituted anillines (R2), in the presence of a base, such as potassium tert-butoxide, in a suitable solvent system, such as toluene, to give compounds of structure XVIII. Alternatively, XVIII can be prepared by adopting the similar chemistry from R3, which can be synthesized using the chemistry described in scheme P and halo-aryl compounds, R4.

Compounds of formula I, represented by structures XIX can be prepared using the method depicted in Scheme S.

XX. Scheme S

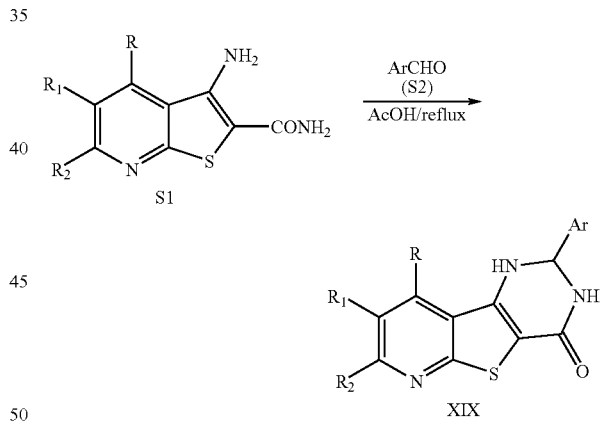

XIX

Treatment of compounds of type S1 can then be reacted with an aryl aldehyde (S2), for example benzaldehyde, in refluxing acetic acid to provide compounds of structure XIX.

C. Methods of the Invention

The methods of the invention generally comprise administering a therapeutically effective amount of at least one compound of the present invention to a subject in need of treatment for HCV infection. In a preferred embodiment, a therapeutically effective amount of a composition comprising a compound of Formula I as described herein is administered to a subject in need of treatment. In another preferred embodiment, a compound or a composition used in the methods of the present invention includes a compound of Formula I as described herein wherein the compound of Formula I is not In another preferred embodiment, a compound or a composition of the present invention comprises a compound of Formula I, wherein the compound of Formula I is not

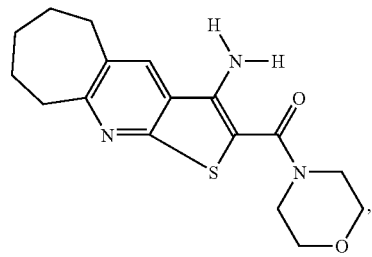
Compound 1

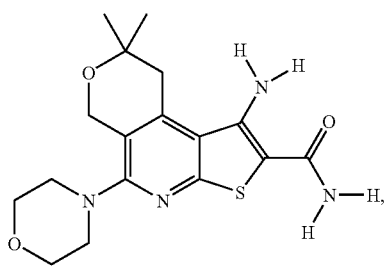
Compound 4

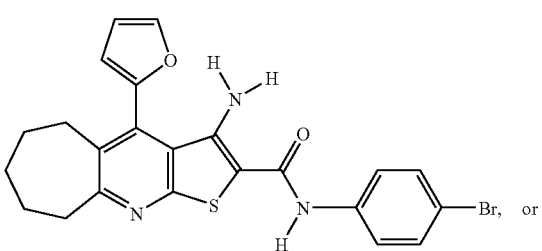
Compound 51

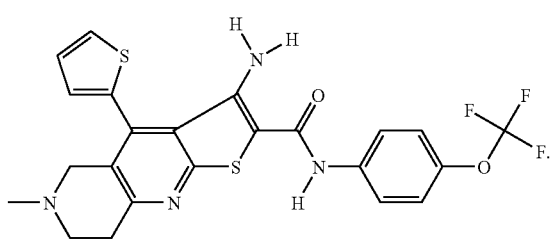
Compound 52

The compound(s) of the present invention may be administered to the subject via any drug delivery route known in the art. Specific exemplary administration routes include oral, ocular, rectal, buccal, topical, nasal, ophthalmic, subcutaneous, intramuscular, intraveneous (bolus and infusion), intracerebral, transdermal, and pulmonary. Individuals infected with HCV can be treated with the compounds of the present invention to prevent or reduce further replication of HCV.

The term therapeutically effective amount, as used herein, refers to an amount of a compound of the present invention effective to inhibit HCV translation, thereby effectively treating or ameliorating the HCV infection. The effect of the compound can be determined by analyzing (1) the presence of HCV-RNA; (2) the presence of anti-HCV antibodies; (3) the level of serum alanine amino transferase (ALT) and aspartate aminotransferase (AST) (ALT and AST are elevated in patients chronically infected with HCV); or (4) hepatocellular damage or any combination thereof. The precise effective amount for a subject will depend upon the subject's body weight, size and health. Therapeutically effective amounts for a given patient can be determined by routine experimentation that is within the skill and judgment of the clinician.

For any compound, the therapeutically effective amount can be estimated initially either in cell culture assays or in relevant animal models, such as marmosets and tamarins. The animal model may also be used to determine the appropriate concentration range and route of administration. Such information can then be used to determine useful doses and routes for administration in humans. Therapeutic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $LD_{50}/ED_{50}$. Pharmaceutical compositions that exhibit large therapeutic indices are preferred. The dosage contained in such compositions is preferably within a range of circulating concentrations that include an $ED_{50}$ with little or no toxicity. The dosage may vary within this range depending upon the dosage form employed, sensitivity of the patient, and the route of administration.

More specifically, the concentration-biological effect relationships observed with regard to the compound(s) of the present invention indicate an initial target plasma concentration ranging from approximately 0.1 µg/ml to approximately 100 µg/mL, preferably from approximately 1 µg/mL to approximately 50 µg/mL, more preferably from approximately 5 µg/mL to approximately 50 µg/mL, even more preferably from approximately 10 µg/mL to approximately 25 µg/mL. To achieve such plasma concentrations, the compounds of the invention may be administered at doses that vary from 0.1 µg to 100,000 mg, depending upon the route of administration. Guidance as to particular dosages and methods of delivery is provided in the literature and is generally available to practitioners in the art. In general the dose will be in the range of about 1 mg/day to about 10 g/day, or about 0.1 g to about 3 g/day, or about 0.3 g to about 3 g/day, or about 0.5 g to about 2 g/day, in single, divided, or continuous doses for a patient weighing between about 40 to about 100 kg (which dose may be adjusted for patients above or below this weight range, particularly children under 40 kg).

The exact dosage will be determined by the practitioner, in light of factors related to the subject that requires treatment. Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

D. Metabolites of the Compounds of the Invention

Also falling within the scope of the present invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammalian tissue or a mammal for a period of time sufficient to yield a metabolic product thereof. Such products typically are identified by preparing a radio-labeled (e.g. $C^{14}$ or $H^3$) compound of the invention, administering it in a detectable dose (e.g., greater than about 0.5 mg/kg) to a mammal such as rat, mouse, guinea pig, monkey, or to man, allowing sufficient time for metabolism to occur (typically about 30 seconds to 30 hours), and isolating its conversion products from urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites may be done in the same way as conventional drug metabolism studies well-known to those skilled in the art. The conversion products, so long as they are not otherwise found in vivo, are useful in diagnostic assays for therapeutic dosing of the compounds of the invention even if they possess no biological activity of their own.

E. Pharmaceutical Compositions of the Invention

While it is possible for the compounds of the present invention to be administered neat, it may be preferable to formulate the compounds as pharmaceutical compositions. As such, in yet another aspect of the invention, pharmaceutical compositions useful in the methods of the invention are provided. The pharmaceutical compositions of the invention may be formulated with pharmaceutically acceptable excipients such as carriers, solvents, stabilizers, adjuvants, diluents, etc., depending upon the particular mode of administration and dosage form. The pharmaceutical compositions should generally be formulated to achieve a physiologically compatible pH, and may range from a pH of about 3 to a pH of about 11, preferably about pH 3 to about pH 7, depending on the formulation and route of administration. In alternative embodiments, it may be preferred that the pH is adjusted to a range from about pH 5.0 to about pH 8.0.

More particularly, the pharmaceutical compositions of the invention comprise a therapeutically or prophylactically effective amount of at least one compound of the present invention, together with one or more pharmaceutically acceptable excipients. A therapeutically or prophylactically effective amount of a compound of the present invention includes a viral inhibitory amount of said compound. By "viral inhibitory amount" it is meant an amount sufficient to inhibit viral replication or infectivity. Optionally, the pharmaceutical compositions of the invention may comprise a combination of compounds of the present invention, or may include any additional active ingredient useful in the treatment of viral infections, such as anti-viral agents that include, but are not limited to: pegylated interferon, including by way of non-limiting example alpha-interferon; un-pegylated interferon, including by way of non-limiting example alpha-interferon; ribavirin or prodrugs or derivatives thereof; a glucosidase inhibitor; protease inhibitors; polyermase inhibitors; p7 inhibitors; entry inhibitors, including fusion inhibitors such as Fuzeon™ (Trimeris); helicase inhibitors; anti-fibrotics; caspase inhibitors; Toll-like receptor agonists; drugs that target IMPDH (inosine monophosphate dehydrogenase inhibitors), such as Merimepodib™ (Vertex Pharmaceuticals Inc.); synthetic thymosin alpha 1 (ZADAXIN™, SciClone Pharmaceuticals Inc.); prophylactic vaccines, therapeutic viral vaccines, such as those produced by Chiron, and therapeutic antibodies such as those produced by Innogenetics and XTL; and immunomodulators, such as histamine.

Formulations of the present invention, e.g., for parenteral or oral administration, are most typically solids, liquid solutions, emulsions or suspensions, while inhaleable formulations for pulmonary administration are generally liquids or powders, with powder formulations being generally preferred. A preferred pharmaceutical composition of the invention may also be formulated as a lyophilized solid that is reconstituted with a physiologically compatible solvent prior to administration. Alternative pharmaceutical compositions of the invention may be formulated as syrups, creams, ointments, tablets, and the like.

The term "pharmaceutically acceptable excipient" refers to an excipient for administration of a pharmaceutical agent, such as the compounds of the present invention. The term refers to any pharmaceutical excipient that may be administered without undue toxicity. Pharmaceutically acceptable excipients are determined in part by the particular composition being administered, as well as by the particular method used to administer the composition. Accordingly, there exists a wide variety of suitable formulations of pharmaceutical compositions of the present invention (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants such as ascorbic acid; chelating agents such as EDTA; carbohydrates such as dextrin, hydroxyalkylcellulose, hydroxyalkylmethylcellulose, stearic acid; liquids such as oils, water, saline, glycerol and ethanol; wetting or emulsifying agents; pH buffering substances; and the like. Liposomes are also included within the definition of pharmaceutically acceptable excipients.

The pharmaceutical compositions of the invention may be formulated in any form suitable for the intended method of administration. When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as croscarmellose sodium, cross-linked povidone, maize starch, or alginic acid; binding agents, such as povidone, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, pharmaceutical compositions of the invention may be formulated as suspensions comprising a compound of the present invention in an admixture with at least one pharmaceutically acceptable excipient suitable for the manufacture of a suspension. In yet another embodiment, pharmaceutical compositions of the invention may be formulated as dispersible powders and granules suitable for preparation of a suspension by the addition of suitable excipients.

Excipients suitable for use in connection with suspensions include suspending agents, such as sodium carboxymethylcellulose, methylcellulose, hydroxypropyl methylcelluose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); and thickening agents, such as carbomer, beeswax, hard paraffin or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions of the invention may be in the form of a sterile injectable preparation, such as a sterile injectable aqueous emulsion or oleaginous suspension. This emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,2-propane-diol. The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or di-glycerides. In addition, fatty acids such as oleic acid may likewise be used in the preparation of injectables.

Generally, the compounds of the present invention useful in the methods of the present invention are substantially insoluble in water and are sparingly soluble in most pharmaceutically acceptable protic solvents and in vegetable oils. However, the compounds are generally soluble in medium-chain fatty acids (e.g., caprylic and capric acids) or triglycerides and have high solubility in propylene glycol esters of medium-chain fatty acids. Also contemplated in the invention are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In a preferred embodiment, the compounds of the present invention may be formulated for oral administration in a lipid-based formulation suitable for low solubility compounds. Lipid-based formulations can generally enhance the oral bioavailability of such compounds. As such, a preferred pharmaceutical composition of the invention comprises a therapeutically or prophylactically effective amount of a compound of the present invention, together with at least one pharmaceutically acceptable excipient selected from the group consisting of: medium chain fatty acids or propylene glycol esters thereof (e.g., propylene glycol esters of edible fatty acids such as caprylic and capric fatty acids) and pharmaceutically acceptable surfactants such as polyoxyl 40 hydrogenated castor oil.

In an alternative preferred embodiment, cyclodextrins may be added as aqueous solubility enhancers. Preferred cyclodextrins include hydroxypropyl, hydroxyethyl, glucosyl, maltosyl and maltotriosyl derivatives of $\alpha$-, $\beta$, and $\gamma$-cyclodextrin. A particularly preferred cyclodextrin solubility enhancer is hydroxypropyl-$\beta$-cyclodextrin (HPBC), which may be added to any of the above-described compositions to further improve the aqueous solubility characteristics of the compounds of the present invention. In one embodiment, the composition comprises 0.1% to 20% hydroxypropyl-$\beta$-cyclodextrin, more preferably 1% to 15% hydroxypropyl-$\beta$-cyclodextrin, and even more preferably from 2.5% to 10% hydroxypropyl-$\beta$-cyclodextrin. The amount of solubility enhancer employed will depend on the amount of the compound of the present invention in the composition.

F. Combination Therapy

It is also possible to combine any compound of the present invention with one or more other active ingredients useful in the treatment of HCV infection, including compounds, in a unitary dosage form, or in separate dosage forms intended for simultaneous or sequential administration to a patient in need of treatment. When administered sequentially, the combination may be administered in two or more administrations. In an alternative embodiment, it is possible to administer one or more compounds of the present invention and one or more additional active ingredients by different routes.

The skilled artisan will recognize that a variety of active ingredients may be administered in combination with the compounds of the present invention that may act to augment or synergistically enhance the viral inhibiting activity of the compounds of the invention. Such active ingredients include anti-HCV agents. Anti-HCV agents include agents that target the virus as well as agents that have an immunomodulatory effect. For example, anti-HCV agents include, but are not limited to, interferon, including, for example without limitation, IFN-$\alpha$, ribavirin or prodrugs or derivatives thereof; a glucosidase inhibitor, protease inhibitors, polymerase inhibitors, helicase inhibitors, a Toll-like receptor agonist, a caspase inhibitor and a glucosidase inhibitor. Furthermore, the compounds of the invention may also be administered in combination with other compounds that affect IRES activity known to one of skill in the art.

According to the methods of the invention, the combination of active ingredients may be: (1) co-formulated and administered or delivered simultaneously in a combined formulation; (2) delivered by alternation or in parallel as separate formulations; or (3) by any other combination therapy regimen known in the art. When delivered in alternation therapy, the methods of the invention may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

To assist in understanding the present invention, the following Examples are included. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

EXAMPLES

The present invention is described in more detail with reference to the following non-limiting examples, which are offered to more fully illustrate the invention, but are not to be construed as limiting the scope thereof. The examples illustrate the preparation of certain compounds of the invention, and the testing of these compounds in vitro and/or in vivo. Those of skill in the art will understand that the techniques described in these examples represent techniques described by the inventors to function well in the practice of the invention, and as such constitute preferred modes for the practice thereof. However, it should be appreciated that those of skill in the art should in light of the present disclosure, know that many changes can be made in the specific methods that are disclosed and still obtain a like or similar result without departing from the spirit and scope of the invention.

Example 1

Preparation of Compounds of the Invention

Example 1A

Preparation of tert-Butyl 3-amino-5-ethyl-4,6-dimethylthieno[2,3-B]pyridine-2-carboxylate (compound 3)

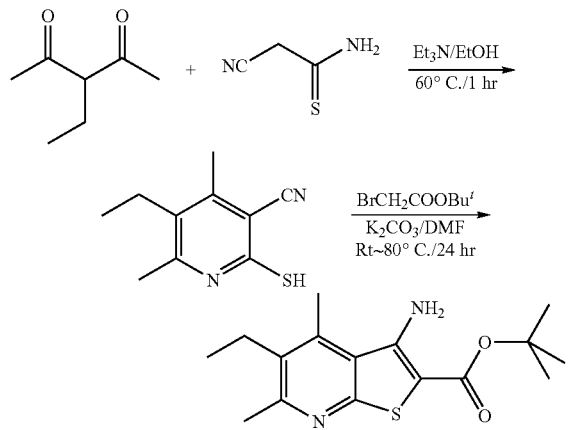

Step A: To a mixture of 2-cyanothioacetamide (6.33 g, 63.3 mmol) and triethylamine (6.39 g, 8.81 mL, 63.3 mmol) in ethanol (100 mL) at room temperature was added 3-ethylpentane-2,4-dione (8.1 g, 8.50 mL, 63.3 mmol). After stirring at 60° C. for 1 h, the mixture was cooled to room temperature and poured into cold water (800 mL). The precipitate, 5-ethyl-2-mercapto-4,6-dimethylnicotinonitrile, was collected by filtration, washed with hexanes (30 mL×2) and dried in air to give a yellow powder (10.87 g, 89%). LC/MS reveals a single component (MS ES+m/z: 193) that was used without additional purification.

Step B: A mixture of 5-ethyl-2-mercapto-4,6-dimethylnicotinonitrile (3.84 g, 20.0 mmol) prepared above, tert-butyl bromoacetate (4.29 g, 22.0 mmol) and $K_2CO_3$ powder (6.90 g, 50.0 mmol) in DMF (50 mL) was stirred at room temperature for 20 min. and then at 80° C. for 24 h. The mixture was then poured into cold water (500 mL). The precipitate was collected by filtration, washed with water and dried in air to give a yellow powder (5.90 g, 96%) to give the title compound, tert-butyl 3-amino-5-ethyl-4,6-dimethylthieno[2,3-B]pyridine-2-carboxylate.

The following compounds were prepared in the same fashion as described above, by using various 1,3-diketones and 2-haloacetic acid derivatives, or 2-haloacetonitrile and 2-halomethylheteroaromatics: Compounds 2, 18, 19, 20, 21, 22, 26, 28, 29, 30, and 56.

Example 1B

Preparation of tert-butyl 3-amino-4-thiophen-2-yl-6,7,8,9-tetrahydro-5H-1-thia-10-aza-cyclohepta[f]indene-2-carboxylate (compound 45)

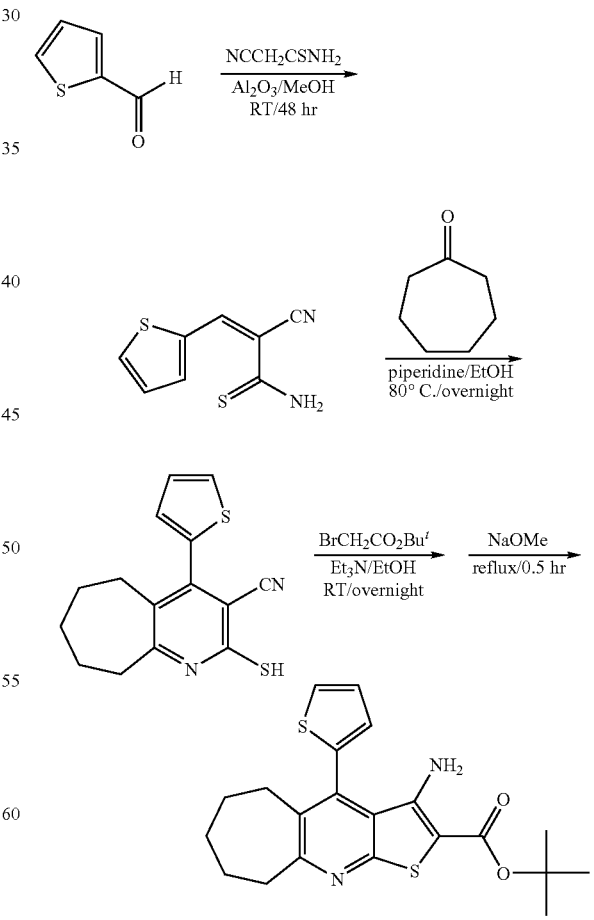

Step A: To a solution of thiophene-2-carbaldehyde (20.0 g, 0.18 mol) and 2-cyanothioacetamide (17.8 g, 0.18 mol) in methanol (400 mL), was added neutral Al₂O₃ (106 g). The suspension was stirred at room temperature for 48 hrs, and then filtered. The solid was washed with methanol and the filtrates were combined and the solvent was then removed by evaporation to afford 2-cyano-3-thien-2-ylprop-2-enethioamide (30 g, 87%).

Step B: A mixture of 2-cyano-3-thien-2-ylprop-2-enethioamide (4.2 g, 21 mmol), cycloheptene (2.4 g, 21 mmol) and piperidine (1.8 g, 22 mmol) in ethanol (100 mL) was heated to 80° C. overnight. After removal of the solvent, the residue was treated with water and extracted with ethyl acetate. The organic phase was washed with brine and dried over anhydrous sodium sulfate. The crude product, obtained after removal of the solvent, was purified by flash chromatography to afford 2-mercapto-4-thien-2-yl-6,7,8,9-tetrahydro-5H-cyclohepta[b]pyridine-3-carbonitrile (1.6 g, 25%).

Step C: A mixture of 2-mercapto-4-thien-2-yl-6,7,8,9-tetrahydro-5H-cyclohepta[b]pyridine-3-carbonitrile (143 mg, 0.5 mmol), tert-butyl bromoacetate (97 mg, 0.5 mmol) and triethyl amine (51 mg, 0.5 mmol) in ethanol (20 mL) was stirred at room temperature overnight, followed by the addition of NaOMe (30 mg, 0.56 mmol). The mixture was then refluxed for 30 min., and poured onto ice. The precipitate is filtered and washed with water to furnish pure t-butyl 3-amino-4-thiophen-2-yl-6,7,8,9-tetrahydro-5H-1-thia-10-aza-cyclohepta[f]indene-2-carboxylate.

The following compounds were prepared in the same fashion as described above, using various aldehydes, ketones and 2-haloacetic acid derivatives: Compounds 31, 32, 33, 34, and 46.

Example 1C

Preparation of t-butyl 3-amino-4,6-dimethyl-5-(2-morpholin-4-yl-ethoxy)-thieno[2,3-b]pyridine-2-carboxylate (compound 67)

extracted with EtOAc (800 mL×3). The combined organic layers were washed with brine, dried over anhydrous MgSO₄ and concentrated under reduced pressure to give crude 1-acetyl-2-oxo-propyloxy acetate (64 g, 60%).

Step B: To a solution of the above compound (40 g, 25.3 mmol) in ethanol (1 L) was added Et₃N (25.6 g, 25.3 mmol). After stirring for 0.5 h, a solution of 2-cyanothioacetamide (25.3 g, 25.3 mmol) in ethanol (150 mL) was added dropwise. The reaction mixture was stirred at room temperature overnight. Then, the reaction was quenched by water (600 mL) and the aqueous layer was extracted with EtOAc (600 mL×3). The combined organic layer was washed with brine, dried over anhydrous MgSO₄ and concentrated under reduced pressure to give a crude product, which was dissolved with ethanol (800 mL) and treated with Et₃N (17.3 g, 17.1 mmol) and stirring for an additional 0.5 h. To this solution, a solution of t-butyl chloroacetate (25.7 g, 17.2 mmol) in ethanol (150 mL) was added dropwise, and then the reaction mixture was heated to reflux and stirred for 3 h. The solvent was evaporated under reduced pressure, the residue was treated with water (800 mL), and the precipitate was collected and dissolved in ethanol (500 mL). Sodium methoxide (2.4 g) was added to the solution potionwise, the mixture was heated to reflux for 3 h and then concentrated. The residue that was obtained was then treated with water (800 mL), and the solid was collected via filtration to give tert-butyl 5-acetoxy-3-amino-4,6-dimethyl-thieno[2,3-b]pyridine-2-carboxylate (19.6 g, 78%).

Step C: To a solution of tert-butyl 5-acetoxy-3-amino-4,6-dimethyl-thieno[2,3-b]pyridine-2-carboxylate (19.6 g, 5.8 mmol) in methanol (300 mL), was added a 5% solution of aqueous LiOH (150 mL) and the mixture was stirred overnight. The precipitate was collected and washed with water to provide tert-butyl 3-amino-5-hydroxy-4,6-dimethyl-thieno[2,3-b]pyridine-2-carboxylate (12 g, 71%).

Step D: The tert-butyl 3-amino-5-hydroxy-4,6-dimethyl-thieno[2,3-b]pyridine-2-carboxylate obtained above (12 g, 40 mmol) was dissolved in CH₃CN (300 mL), followed by the addition of K₂CO₃ (11 g, 80 mmol) and 1-bromo-2-chloroet-

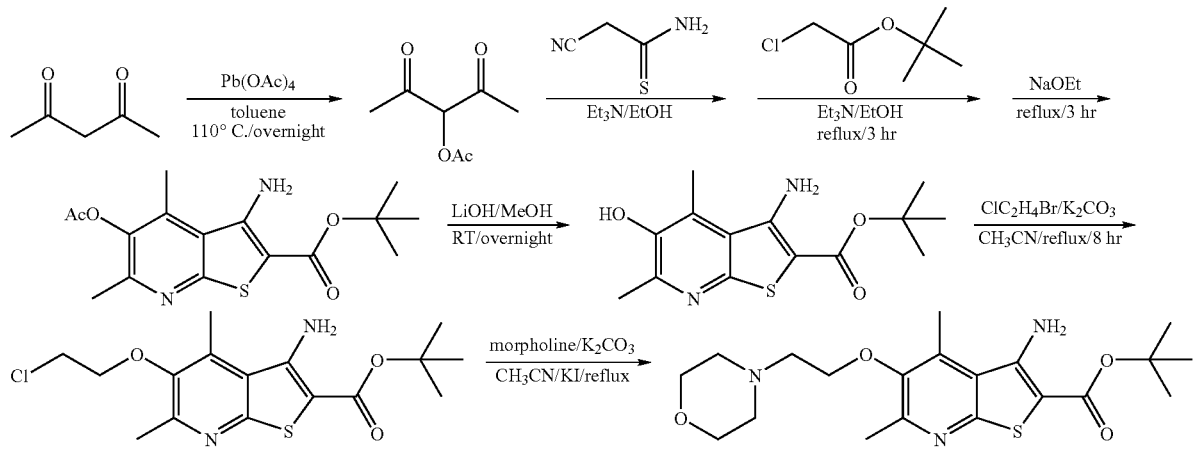

Step A: To a solution of pentane-2,4-dione (67.5 g, 67.5 mmol) in toluene (1.5 L) was added portionwise, Pb(OAc)₄ (300 g, 67.5 mmol) at room temperature. The reaction mixture was then heated to 110° C. and stirred overnight. After cooling to room temperature, the reaction mixture was quenched by water (800 mL). The aqueous layer was hane (5.7 g, 40 mmol). The mixture was heated to reflux for 8 h, water (100 mL) was added and the mixture was extracted with ethyl acetate (60 mL× 3). The organic layers were washed with 0.5% aqueous sodium hydroxide (150 mL) and brine, dried over anhydrous Na₂SO₄ and then concentrated to give tert-butyl 3-amino-5-(2-chloroethoxy)-4,6-dimethylthieno[2,3-b]pyridine-2-carboxylate as a yellow solid (6.9 g, 50%).

Step E: tert-Butyl 3-amino-5-(2-chloroethoxy)-4,6-dimethyl-thieno[2,3-b]pyridine-2-carboxylate, prepared above (50 mg, 0.22 mmol), was dissolved in $CH_3CN$ (5 mL), followed by the addition of $K_2CO_3$ (41 mg, 0.30 mmol), morpholine (26 mg, 0.30 mmol) and a catalytic amount of KI. The mixture was heated to reflux overnight, the solvent was removed under reduced pressure, water was added and the residue was extracted with ethyl acetate (10 mL), and the organic phases were washed with water (5 mL×3), brine, dried over anhydrous $Na_2SO_4$, concentrated and purified by preparative HPLC to furnish the title compound, tert-butyl 3-amino-4,6-dimethyl-5-(2-morpholin-4-yl-ethoxy)-thieno[2,3-b]pyridine-2-carboxylate (20 mg, 30%).

The following compounds were prepared in the same fashion as described above: Compounds 66, 68, 69, 70, 71, 72, 73, and 74.

Example 1D

Preparation of tert-butyl 3-amino-4,6-dimethyl-5-(pyrrolidine-1-carbonyloxy)-thieno[2,3-b]pyridine-2-carboxylate (compound 75)

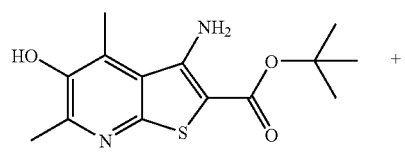

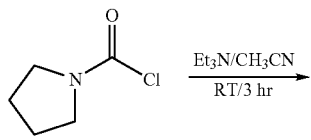

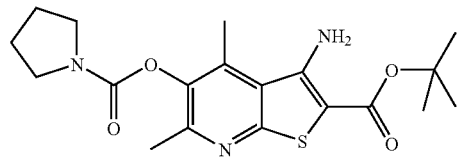

tert-Butyl 3-amino-5-hydroxy-4,6-dimethyl-thieno[2,3-b]pyridine-2-carboxylate, prepared in example 1C, Step C, (40 mg, 0.14 mmol) in $CH_3CN$ (1 mL) was combined with $Et_3N$ (52 mg, 0.52 mmol) and pyrrolidine-1-carbonyl chloride (51 mg, 0.39 mmol) at room temperature. After stirring for 3 h, the mixture was evaporated under reduced pressure, water was added and extracted with ethyl acetate (3 mL), washed with water (3 mL×3), brine, dried over anhydrous $Na_2SO_4$ and concentrated under reduced pressure. The residue was purified by preparative HPLC to provide tert-butyl 3-amino-4,6-dimethyl-5-(pyrrolidine-1-carbonyloxy)-thieno[2,3-b]pyridine-2-carboxylate (41 mg, 52%).

The following compound was prepared in the same fashion as described above: Compound 76.

Example 1E

Preparation of 5-ethyl-4,6-dimethyl-2-(5-phenyl-[1,3,4]oxadiazol-2-yl)-thieno[2,3-b]pyridin-3-yl amine (compound 6)

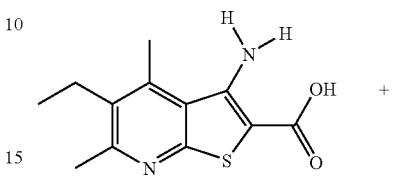

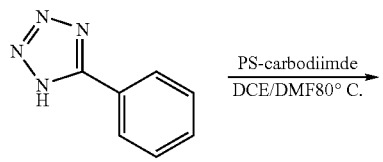

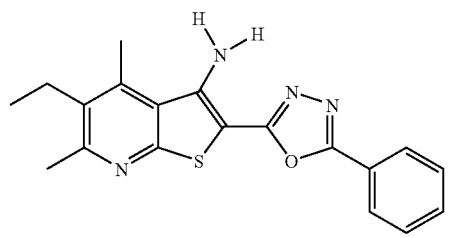

To a solution of 3-amino-5-ethyl-4,6-dimethyl-thieno[2,3-b]pyridine-2-carboxylic acid (0.16 g, 0.63 mmol) in a mixture of dichloroethane (8 mL) and DMF (2 mL) was added PS-carbodiimide (1.0 g, 1.26 mmol). The mixture was shaken for 15 min at room temperature, followed by the addition of 5-phenyltetrazole (0.042 g, 0.32 mmol). Then, the mixture was shaken at 80° C. overnight. The resin was then removed by filtration and washed with hot chloroform (2×5 mL). The filtrate was evaporated in vacuum to dryness and purified by chromatography (silica gel, dichloromethane/ethyl acetate, 9/1) to furnish the product 5-ethyl-4,6-dimethyl-2-(5-phenyl-[1,3,4]oxadiazol-2-yl)-thieno[2,3-b]pyridin-3-yl amine (0.063 g, 56%).

The following compounds were prepared in the same fashion as described above: Compounds 7, 8, 9, 10, 11, 12, 13, 14, 15, 16, 23.

Example 1F

Preparation of 4,5,6-trimethyl-2-(3-phenyl-[1,2,4]oxadiazol-5-yl)-thieno[2,3-b]pyridin-3-ylamine (compound 24)

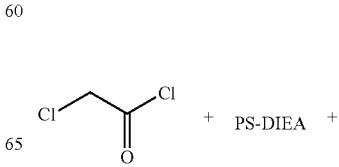

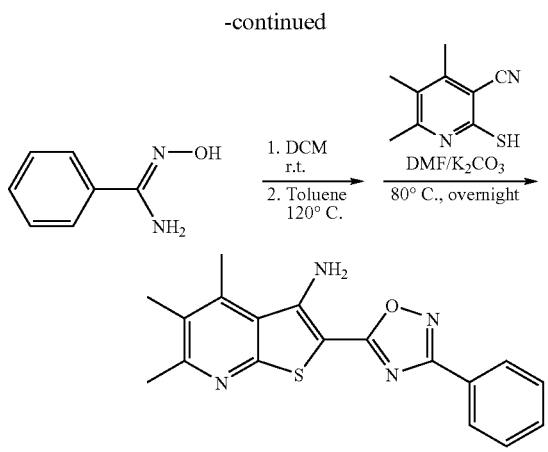

To a solution of N-hydroxy-benzamidine (41 mg, 0.30 mmol) in DCM (10 mL) was added PS-DIEA (240 mg, 0.90 mmol), followed by the addition of chloroacetyl chloride (0.36 mL, 0.45 mmol). The mixture was shaken at room temperature for 24 hr and filtered to remove the resin. The solvent was then replaced with toluene and the mixture obtained was stirred at 120° C. in a sealed tube overnight. The toluene was then replaced with DMF (10 mL) and to the solution was added $K_2CO_3$ (124 mg, 0.90 mmol) and 2-mercapto-4,5,6-trimethyl-nicotinonitrile (54 mg, 0.30 mmol). The mixture was stirred at 80° C. overnight before pouring it into water. The precipitate was collected and purified via flash chromatography to provide the title product, 4,5,6-trimethyl-2-(3-phenyl-[1,2,4]oxadiazol-5-yl)-thieno[2,3-b]pyridin-3-yl amine (21 mg, 21%).

The following compound was prepared in samilar fashion as described above: Compound 25.

Example 1G

Preparation of cyclopentanecarboxylic acid (3-cyano-5-ethyl-4,6-dimethyl-thieno[2,3-b]pyridin-2-yl) amide (compound 49)

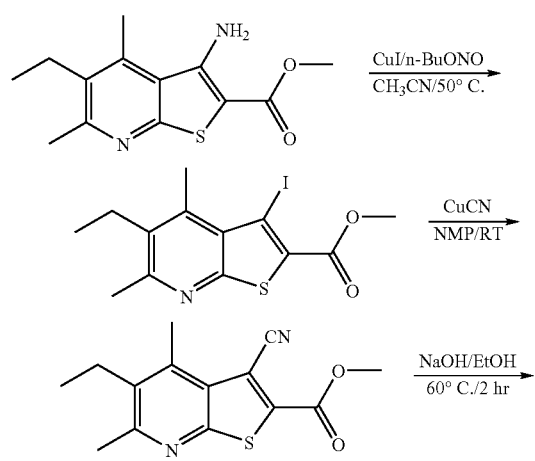

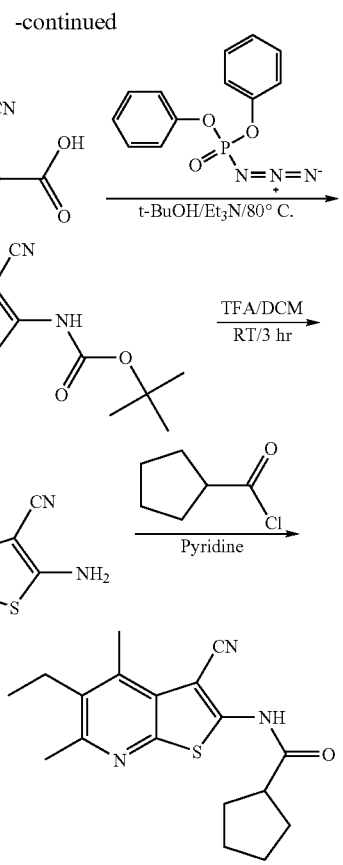

Step A: To a mixture of methyl 3-amino-5-ethyl-4,6-dimethylthieno[2,3-b]pyridine-2-carboxylate (7.92 g, 30.0 mmol), prepared analogously to the procedure described in example 1A, and CuI (11.40 g, 60.0 mmol) in acetonitrile (150 mL), was added n-butyl nitrite (6.18 g, 7.12 mL, 60.0 mmol). The mixture was stirred at 50° C. for 24 h, and then poured into water (500 mL). To this mixture was added dichloromethane (100 mL), followed by the addition of concentrated ammonium hydroxide dropwise with stirring, until all the precipitate had dissolved. The dichloromethane layer was separated and washed with water, brine and dried over anhydrous $Na_2SO_4$. The crude product was obtained after the removal of the solvent and chromatographed ($CH_2Cl_2$/hexanes, 1/9) to give methyl 3-iodo-5-ethyl-4,6-dimethylthieno[2,3-b]pyridine-2-carboxylate (5.18 g, 46%). MS (ES$^+$) m/z: 376.

Step B: To the solution of methyl 3-iodo-5-ethyl-4,6-dimethylthieno[2,3-b]pyridine-2-carboxylate prepared above (5.18 g, 13.8 mmol) in NMP (100 mL), was added CuCN (2.47 g, 27.6 mmol). The mixture was stirred at room temperature overnight. Work-up was conducted as above and the crude product was chromatographed (EtOAc/$CH_2Cl_2$, 2.5/97.5) to give pure methyl 3-cyano-5-ethyl-4,6-dimethylthieno[2,3-b]pyridine-2-carboxylate (2.70 g, 71%). MS (ES+) m/z: 275.

Step C: To a solution of methyl 3-cyano-5-ethyl-4,6-dimethylthieno[2,3-b]pyridine-2-carboxylate (2.70 g, 9.9 mmol), prepared above, in ethanol (100 mL), was added aqueous NaOH (1.25 N, 15.7 mL, 19.6 mmol), and the mixture was stirred for 2 h at 60° C. The volatiles were removed under reduced pressure and the residue was dissolved in water (150 mL) and then acidified using concentrated HCl until the pH was adjusted to 5-6. The precipitate was collected via filtration and washed thoroughly with water, dried in air to give 3-cyano-5-ethyl-4,6-dimethylthieno[2,3-b]pyridine-2-carboxylic acid (2.38 g, 93%). MS (ES⁻) m/z: 259.

Step D: 3-Cyano-5-ethyl-4,6-dimethylthieno[2,3-b]pyridine-2-carboxylic acid (1.00 g, 3.85 mmol) was mixed with triethylamine (0.78 g, 1.07 mL, 7.69 mmol), diphenylphosphoryl azide (2.12 g, 7.69 mmol) and anhydrous t-butanol (15 mL). The mixture was stirred at 80° C. for 8 h, followed by the removal of the volatiles under vacuum. To the residue was added dichloromethane (150 mL) and saturated NaHCO₃ (40 mL), and the mixture was filtered after stirring at room temperature for 0.5 h. The organics were separated from the filtrate and dried over anhydrous Na₂SO₄. After removal of the solvent, the residue was chromatographed to give (3-cyano-5-ethyl-4,6-dimethyl-thieno[2,3-b]pyridin-2-yl)-carbamic acid tert-butyl ester. MS (ES⁺) m/z: 332.

Step E: The t-butylcarbamate obtained above was treated with TFA (20 mL) at room temperature for 3 h, and then evaporated to dryness under vacuum. The residue was stirred in aqueous K₂CO₃ (50 mL) for 2 h. The precipitate was collected by filtration, washed and dried in air to furnish essentially pure product, 2-amino-5-ethyl-4,6-dimethylthieno[2,3-b]pyridine-3-carbonitrile, compound 35, (0.59 g, 66% from the carboxylic acid in step C). MS (ES⁺) m/z: 232.

Step F: To a solution of 2-amino-5-ethyl-4,6-dimethylthieno[2,3-b]pyridine-3-carbonitrile (23 mg, 0.10 mmol) in pyridine (2.5 mL) was added cyclopentanecarbonyl chloride (15 mg, 0.11 mmol). The mixture was stirred at room temperature overnight, poured into water (10 mL) and extracted with DCM (10 mL). The organic layer was separated and washed with HCl (2 N, 2×3 mL), water (3×3 mL) and brine (3 mL), dried over anhydrous Na₂SO₄. The solvent was removed under reduced pressure to provide essentially pure cyclopentanecarboxylic acid (3-cyano-5-ethyl-4,6-dimethyl-thieno[2,3-b]pyridin-2-yl)amide (28 mg, 86%).

The following compounds were prepared in the same fashion as described above: Compounds 50 and 53.

Example 1H

Preparation of 2-(4-methoxyphenyl)-4-thiophen-2-yl-6,7,8,9-tetrahydro-5H-1-thia-10-aza-cyclohepta[f]indene-3-carbonitrile (compound 63)

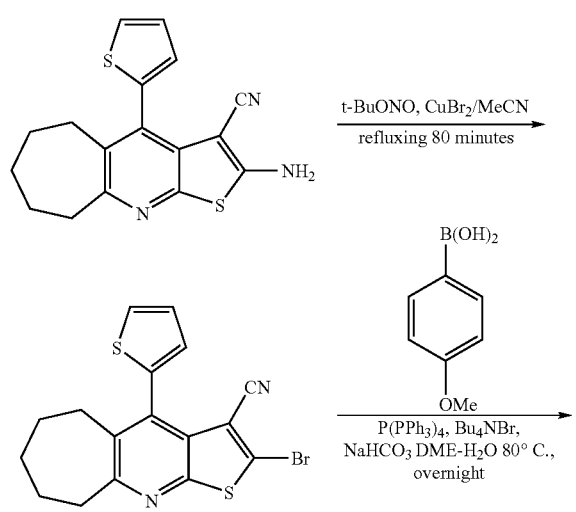

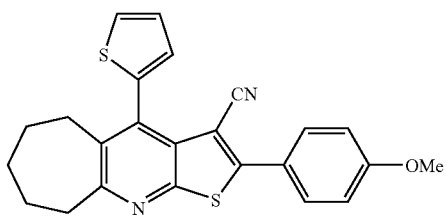

Step A: tert-Butyl nitrite (1.66 mL, 0.0138 mol) and CuBr₂ (2.5 g, 0.011 mol) were heated in acetonitrile (80 mL) to reflux. 2-Amino-4-thiophen-2-yl-6,7,8,9-tetrahydro-5H-1-thia-10-aza-cyclohepta[f]indene-3-carbonitrile (3.0 g, 0.0092 mol) in 10 mL of acetonitrile was then added to the mixture. The mixture was refluxed for 80 minutes, after which the solvent was removed and the residue was partitioned between 500 mL of EtOAc and 100 mL of aqueous ammonia. The organic layer was separated, washed with brine and dried over MgSO₄. Then, the residue was purified by chromatography to provide ca. 1 g of 2-bromo-4-thiophen-2-yl-6,7,8,9-tetrahydro-5H-1-thia-10-aza-cyclohepta[f]indene-3-carbonitrile.

Step B: To a Schlenk tube was added 2-bromo-4-thiophen-2-yl-6,7,8,9-tetrahydro-5H-1-thia-10-aza-cyclohepta[f]indene-3-carbonitrile (45 mg, 0.116 mmol), p-methoxyphenyl boronic acid (21 mg, 0.138 mmol), NaHCO₃ (29 mg, 0.348 mmol), Bu4NBr (8 mg, 0.023 mmol) and 1 mL of DME/H₂O (4/1). After evacuating and back-filling with nitrogen twice, a catalytic amount of Pd(PPh₃)₄ was added. The sealed mixture was heated to 80° C. overnight. After pouring into water, the mixture was extracted with ethyl acetate. The organic phase was washed with brine, dried over anhydrous MgSO₄ and concentrated. The residue was purified by flash chromatography to provide 30 mg of the title compound, 2-(4-methoxyphenyl)-4-thiophen-2-yl-6,7,8,9-tetrahydro-5H-1-thia-10-aza-cyclohepta[f]indene-3-carbonitrile.

The following compounds were prepared in the same fashion as described above: Compounds 61 and 62.

Example 1I

Preparation of t-butyl 5-ethyl-3-(4-methoxy-phenyl)-4,6-dimethyl-thieno[2,3-b]pyridine-2-carboxylate (compound 37)

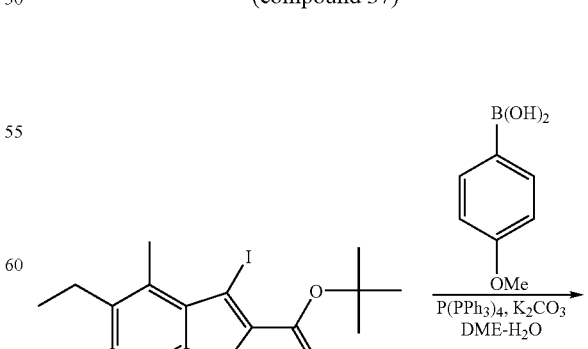

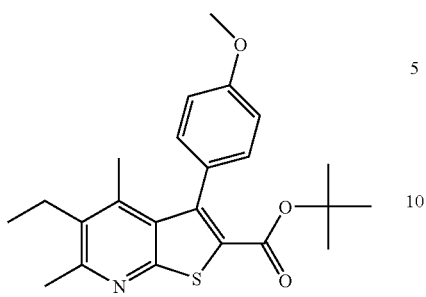

To a solution of compound tert-butyl 5-ethyl-3-iodo-4,6-dimethyl-thieno[2,3-b]pyridine-2-carboxylate (42 mg, 0.1 mmol) in 0.5 mL of DME/H$_2$O (1/1) was added K$_2$CO$_3$ (41 mg, 0.3 mmol), Pd(PPh$_3$)$_4$ (12 mg, 0.01 mmol), p-methoxyphenyl boronic acid (18 mg, 0.12 mmol). The mixture was then heated to reflux for 16 h. After cooling to room temperature, the solvent was evaporated under reduced pressure. The residue was dissolved with ethyl acetate (2 mL), washed with water (2 mL×3), brine, dried over anhydrous Na$_2$SO$_4$ and evaporated under reduced pressure. The crude solid was purified by preparative HPLC to provide t-butyl 5-ethyl-3-(4-methoxy-phenyl)-4,6-dimethyl-thieno[2,3-b]pyridine-2-carboxylate (12 mg, 30%).

The following compounds were prepared in the same fashion as described above: Compounds 36, 37, 39, 40, 42, and 43.

Example 1J

Preparation of N-(3-cyano-4-thiophen-2-yl-6,7,8,9-tetrahydro-5H-1-thia-10-aza-cyclohepta[f]inden-2-yl)-3-trifluoromethyl-benzamide (compound 58)

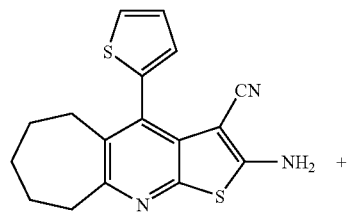

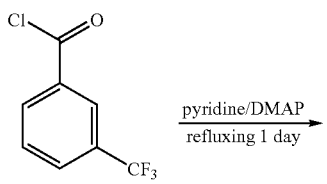

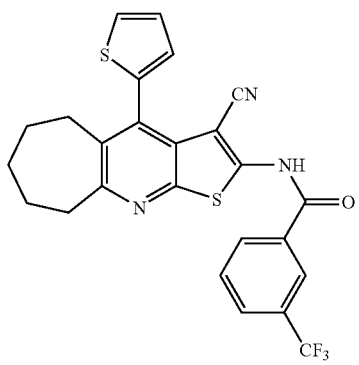

A mixture of 2-amino-4-thiophen-2-yl-6,7,8,9-tetrahydro-5H-1-thia-10-aza-cyclohepta[f]indene-3-carbonitrile, prepared using the chemistry described in Example 1G (100 mg, 0.31 mmol), 3-trifluoromethyl-benzoyl chloride (77 mg, 0.37 mmol) and a catalytic amount of DMAP in pyridine (20 mL) was heated under reflux for one day. After concentration, the residue was partitioned between EtOAc and H$_2$O. The organic layer was washed with brine, dried over MgSO$_4$ and concentrated. The residue was purified by chromatography to give N-(3-cyano-4-thiophen-2-yl-6,7,8,9-tetrahydro-5H-1-thia-10-aza-cyclohepta[f]inden-2-yl)-3-trifluoromethyl-benzamide (40 mg, 26%).

The following compound was prepared in the same fashion as described above: Compound 57.

Example 1K

Preparation of 4-hydroxymethyl-2-methyl-6-phenyl-6,7-dihydro-5H-9-thia-1,5,7-triaza-fluoren-8-one (compound 38)

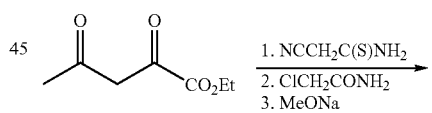

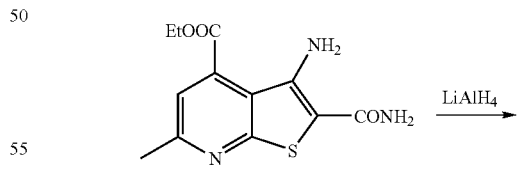

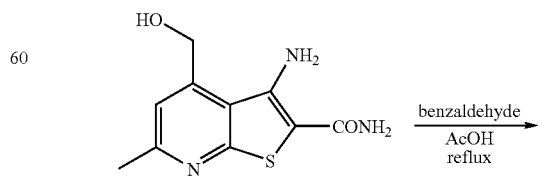

-continued

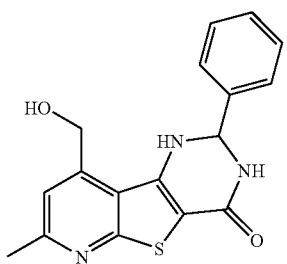

Step A: To a solution of ethyl acetoacetate (60 g, 0.38 mol) in ethanol (1.2 L) was added Et₃N (38.5 g, 0.38 mol). After stirring for 0.5 h, a solution of cyanothioacetamide (38.0 g, 0.38 mol) in ethanol (200 mL) was added dropwise. The reaction mixture was stirred at room temperature overnight after which it was quenched with water (750 mL). The aqueous layer was extracted with ethyl acetate (750 mL×3). The combined organic layers were washed with brine, dried over anhydrous MgSO₄ and concentrated under reduced pressure to give a crude product (55 g, 65%), which was dissolved in 800 mL of ethanol. Triethyl amine (25.3 g, 0.25 mol) was added and after stirring for 0.5 h, a solution of 2-chloroacetamide (23.3 g, 0.25 mol) in ethanol (250 mL) was added dropwise. After the addition, the reaction mixture was heated to reflux and stirred for 3 h. After cooling to room temperature, most of the solvent was evaporated under reduced pressure. To the approximately 50 mL of remaining solution, 900 mL of water was added, and after filtration, the crude solid was collected (68%, 47 g). The solid was dissolved into 600 mL of ethanol. Solid sodium methoxide (3.0 g) was added potionwise, and the mixture was heated to reflux for 3 h. After cooling to room temperature, the reaction was concentrated under reduced pressure. Water (800) mL was added to the residue, and after filtration ethyl 3-amino-2-carbamoyl-6-methyl-thieno[2,3-b]pyridine-4-carboxylate was collected (85%, 40 g).

Step B: To a suspension of LiAlH4 (22 g, 0.57 mol) in anhydrous THF (250 mL) was added a solution of ethyl 3-amino-2-carbamoyl-6-methyl-thieno[2,3-b]pyridine-4-carboxylate (40 g, 143 mmol) in anhydrous THF (250 mL) at −40° C. dropwise. The reaction was then allowed to warm to room temperature and the mixture was heated to reflux and stirred for 5 h. After cooling to room temperature, the reaction was quenched by aqueous NaOH (2N, 22 mL) at 0° C., filtered through Celite and washed with THF (50 mL×5). The filtrate was collected and evaporated under reduced pressure to give crude 3-amino-4-hydroxymethyl-6-methyl-thieno[2,3-b]pyridine-2-carboxamide (74%, 25 g).

Step C: To a solution of 3-amino-4-hydroxymethyl-6-methyl-thieno[2,3-b]pyridine-2-carboxamide (100 mg, 0.42 mmol) in acetic acid (2 mL) was added benzaldehyde (53 mg, 0.50 mmol) and the mixture was heated to reflux for 16 h. After cooling to room temperature, water (2 mL) and ethyl acetate (2 mL) were added to it. The reaction was further extracted with ethyl acetate (2 mL×3). The combined organic layers were washed with brine, dried over Na₂SO₄ and evaporated under reduced pressure. The residue was purified by preparative HPLC to give the title compound, 4-hydroxymethyl-2-methyl-6-phenyl-6,7-dihydro-5H-9-thia-1,5,7-triaza-fluoren-8-one (16 mg, 12%).

Example 2

Screening of Low Molecular Weight Compounds Using a Cell-based HCV IRES Monocistronic Translation Assay Chemical libraries are screened using a cell-based monocistronic HCV IRES-regulated translation assay designed to closely mimic natural HCV mRNA translation and then compound analogs are made based on hits in the chemical libraries and screened as well. A DNA construct is prepared, termed pHCVIRESmono, in which HCV IRES sequences (HCV 2b, nucleotides 18-347) are inserted between a promoter and the firefly luciferase (Fluc) reporter gene. A stably transfected HepG 2 (hepatoblastoma) cell line (termed HepGmono-4) or a Huh cell line (termed Huhmono 7), or a Hela-cell line (termed Helamono), are established by transfection with the pHCVIRESmono DNA by selecting for resistance to hygromycin.

Example 3

Determination of Selectivity for HCV IRES-regulated Translation Using the Cell-based Cap-dependent Translation Assays Since translation assays are used to screen HCV IRES inhibitors, the selected hits may specifically act on HCV IRES-driven translation or may modulate general protein synthesis in mammalian cells. The compounds that act on general translation will most likely have significant toxicity. To address this possibility, various cell-based cap-dependent translation assays are established for the further evaluation of all selected compounds. Plasmid DNAs containing 130 nucleotides of vector sequence 5' to Fluc are constructed. This construct is referred to herein as pLuc. A stable cell line is established in cap-dependent translation assays using 293T cells (a human embryonic kidney cell line). HepGmono-4 and pLuc are treated with compound for 20 hours and activity is determined by quantifying the Fluc signal. A five-fold selectivity between the HCV IRES and cap-dependent translation is considered to be desirable. For example, using these cell-based cap-dependent translation assays, Applicants identified compounds that showed IC₅₀ values that were at least 5-fold greater in the cap-dependent translation assays than in the HCV IRES translation assay.

Additionally, western blotting assays are used to further demonstrate that the compounds selectively inhibit HCV IRES-driven translation. Both HepGmono-4 and pLuc cells are treated with the compounds as described above, following treatment with the test compounds for 20 hours, cells are collected and lysed in Laminin buffer containing 0.5% SDS. Proteins are separated on a 10% SDS-PAGE, then transferred onto a nitrocellulose membrane, and blotted using antibodies against Fluc (RDI) and β-actin (Oncogene). For example, some of the compounds of the present invention were tested in this manner and as expected, the compounds that selectively inhibited HCV IRES-driven translation in assays using Fluc signal as an end point showed comparable reductions of the luciferase reporter protein levels in HepGmono-4 cells and were relatively inactive against pLuc in the Western blot (data not shown). Importantly, these compounds did not inhibit the expression of endogenous β-actin, the translation of which is cap-dependent in both cell lines. Consistently, compounds that did not show selectivity in the translation assays inhibited protein accumulation in both the HCV IRES and cap-dependent translation assays (data not shown). As expected, the general protein translation inhibitor puromycin also inhibited both the HCV IRES-driven and cap-dependent protein production (data not shown). Therefore, the Western blot results confirm that the compounds of the present invention selectively inhibit HCV IRES-driven translation.

Testing conditions for these cell lines are optimized and the effects of mRNA level on activity of the compounds are controlled by quantifying Fluc mRNA levels by RT real-time PCR. For example, some of the compounds of the present invention were tested in this manner, and no significant differences in Fluc mRNA levels were observed between the HepGmono-4, or the Hela cells, or the Huh cells, and cap-dependent translation cell lines used (data not shown).

Example 4

Evaluation of the Selectivity for HCV IRES-driven Translation Using Cellular IRES-mediated Translation Assays A number of human mRNAs have been shown to harbor IRES elements (18, 19, 39, 44, 45, 91, 126, 130). Although the primary sequences and secondary structures of the HCV IRES are different from those of cellular IRESs, an important test for selectivity is to determine whether the selected compounds are active against cellular IRESs. The VEGF IRES has poor initiation activity in in vitro assays, but demonstrates substantial activity in cell-based translation assays (18, 45). For example, some of the compounds of the present invention were tested and all of the compounds that had good selectivity with respect to cap-dependent translation exhibited at least 5-fold higher $IC_{50}$ values against the VEGF IRES than against the HCV IRES (data not shown). These data indicate that the selected compounds have selectivity against viral IRESs. In addition to having different structures, the VEGF IRES also have different interactions with non-canonical cellular translation factors. These differences may contribute to the selectivity of the HCV IRES inhibitors that we have identified. Cellular IRESs appear to function under conditions, such as stress or hypoxia, when cap-dependent translation is blocked (19, 126). Therefore, the lack of selectivity with respect to cellular IRESs may not necessarily be predictive of clinical toxicity.

Example 5

Evaluation of Cytotoxicity

Effects on cell proliferation are a critical issue for any drug discovery effort. Therefore, a cell proliferation/cytotoxicity assay is used to eliminate any compounds that affect mammalian cell growth. The effects of the selected hits on cell proliferation are tested in human cell lines 293 T and Huh7 (a human hepatoblastoma cell line). Cells are grown in Dulbecco's modified Eagle's medium supplemented with 10% fetal bovine serum, L-glutamine, penicillin, and streptomycin. Cells in log phase are treated with test compounds for three days, with 250 μM being the highest concentration of test compound used. The effect of the compounds on cell proliferation is assessed by using the CellTiter 96 AQueous One Solution Cell Proliferation Assay (Promega, Madison, Wis.). Compounds that have at least 5-fold higher $CC_{50}$ values relative to $IC_{50}$ values in HepGmono-4 are considered to have a sufficient window between activity and cytotoxicity and, hence, are selected for further evaluation. For example, some of the compounds of the present invention were tested in this manner, and importantly, all compounds that had good selectivity with respect to cap-dependent translation also demonstrated a greater than 5-fold ratio of $CC_{50}$ to $IC_{50}$ values.

Example 6

Evaluation of the Efficacy of the Compounds in the HCV Replicon System

The lack of reliable and readily accessible cell-culture and small animal models permissive for HCV replication has limited the development of new anti-HCV agents. Self-replicating subgenomic HCV systems, termed HCV replicons, have recently been described and have been widely used to assess the efficacy of anti-HCV inhibitors (8, 70, 104). Interferon (IFN) a and inhibitors of the HCV protease and polymerase have been reported to be active in the HCV replicon system (8, 17, 32, 68, 69, 117).

HCV replicons that include bicistronic and monocistronic systems are identified and assays for testing the HCV IRES inhibitors are established. In the bicistronic replicons, the HCV IRES directs the expression of the selective marker (Neo and/or a Fluc reporter), and the EMCV IRES mediates the expression of viral non-structural proteins. In the monocistronic replicon, the HCV IRES directly mediates viral protein synthesis. The HCV IRES inhibitors are analyzed in the bicistronic replicon by quantifying the Fluc reporter signal. Replicon-containing cells are cultured with the compounds of the invention for 2 days. Interferon (IFN) α is used as a positive control. For example, some of the compounds of the present invention were tested in this manner, and the experiments showed that compounds that selectively inhibited HCV IRES-mediated translation inhibited Fluc expression in the bicistronic replicon in the micromolar range.

In the following table (Table 1),
*=replicon or HCV-PV IC50>2 uM
**=replicon or HCV-PV IC50 between 0.5 uM and 2 uM
***=replicon or HCV-PV IC50<0.5 uM
Replicon IC50 values are determined by firefly luciferase signal.
HCV-PV IC50 values are determined by viral RNA reduction.

TABLE 1

| Compound Number | Replicon IC50s μM | HCV-PV IC50 uM | Melting Point (° C.) | Mass Spec [M + H] | NMR Data |
|---|---|---|---|---|---|
| 1 | * | | 203-204 | | |
| 2 | * | | | 318.0 | |
| 3 | ** | | 135-136 | 307.18 | $^1$H NMR(CDCl$_3$, 300MHz) δ(ppm) 1.16(t, 3H), 1.59(s, 9H), 2.64(s, 3H), 2.72(s, 3H), 2.74-2.80(q, 2H), 6.13(s, b, 2H) |

TABLE 1-continued

| Compound Number | Replicon IC50s μM | HCV-PV IC50 uM | Melting Point (° C.) | Mass Spec [M + H] | NMR Data |
|---|---|---|---|---|---|
| 4 | * | | | | |
| 5 | * | ** | | 413.2 | |
| 6 | ** | | 306-307 | 351.29 | $^1$H NMR(CDCl$_3$, 300MHz) δ(ppm) 1.17(t, 3H), 2.68(s, 3H), 2.75-2.87(m, 5H), 6.25(s, br, 2H), 7.49-7.62(m, 3H), 8.08-8.20(m, 2H) |
| 7 | ** | | 268-270 | 351.29 | |
| 8 | ** | | 300-302 | 355.24 | |
| 9 | ** | | 284-286 | 377.18 | |
| 10 | ** | | 320-322 | 355.24 | |
| 11 | * | | 302-303 | 371.25 | |
| 12 | * | | 331-332 | 371.25 | |
| 13 | *** | | 261-262 | 351.29 | |
| 14 | *** | | 287-288 | 355.24 | |
| 15 | ** | | 284-286 | 371.25 | |
| 16 | *** | | 306-308 | 338.27 | |
| 17 | ** | | 169-170 | 279.1 | |
| 18 | ** | | 197-200 | 435.23 | |
| 19 | *** | | 281-282 | 343.25 | |
| 20 | ** | | 244-245 | 367.30 | |
| 21 | *** | | 248-250 | 337.28 | |
| 22 | *** | | 260-265 | 343.23 | |
| 23 | ** | | 238-240 | 367.30 | |
| 24 | *** | | 276-278 | 337.25 | $^1$H NMR(CD$_3$COCD$_3$, 300MHz) δ(ppm) 2.36(s, 3H), 2.60(s, 3H), 2.85(s, 3H), 7.02(s, br, 2H), 7.55-7.65(m, 3H), 8.13-8.21(m, 2H) |
| 25 | ** | | 278-280 | 338.27 | |
| 26 | ** | | 284-285 | 336.15 | |
| 27 | * | | 145-147 | 299.18 | |
| 28 | * | | | 338.14 | |
| 29 | * | ** | | 406.22 | |
| 30 | * | | | 272.18 | |
| 31 | * | | | 430.92 | |
| 32 | * | | | 370.89 | |
| 33 | * | | | 356.88 | |
| 34 | * | ** | | 386.87 | |
| 35 | * | *** | 223-225 | 232.23 | $^1$H NMR(CDCl$_3$, 300MHz) δ(ppm) 1.11-1.16(t, 3H), 2.56(s, 3H), 2.67(s, 3H), 2.67-2.74(q, 2H), 5.16(s, 2H) |
| 36 | * | | | 392.99 | |
| 37 | * | | | 397.99 | |
| 38 | * | | | 326.1 | |
| 39 | * | | 151-152 | 411.96 | |
| 40 | * | | 111-111.5 | 357.90 | |
| 41 | * | | | 409.31 | |
| 42 | * | | 117-118 | 401.91 | |
| 43 | * | | 152.1-152.6 | 401.92 | |
| 44 | * | | | 431.36 | |
| 45 | * | | 202.9-203.1 | 401.00 | |
| 46 | * | | 157.6-157.7 | 329.30 | |
| 47 | * | | 115-118 | 427.29 | |
| 48 | * | | 184-185 | 400.45 | |
| 49 | * | | 228-230 | 328.26 | $^1$H NMR(CDCl$_3$, 300MHz) δ(ppm) 1.17(t, 3H), 1.61-2.13(m, 8H), 2.64(s, 3H), 2.69-2.99(m, 6H), 8.52(s, 1H) |
| 50 | * | | 164-166 | 316.30 | |
| 51 | * | | | | |
| 52 | * | | | | |
| 53 | * | | 189-190 | 302.24 | |
| 54 | * | | 219-220 | | |
| 55 | * | | 212-3 | 354.98 | |
| 56 | * | | 206.3-203.8 | 323.02 | CDCl$_3$, 300MHz, δ=6.61(b, 2H), 2.75(q, J=7.5Hz, 2H), 2.71(s, 3H), 2.64(s, 3H), 1.59(s, 9H), 1.15(t, J=7.5Hz, 3H) |
| 57 | * | | 215.3-215.7 | 430.24 | |
| 58 | * | | 226.9-227.1 | 498.25 | |
| 59 | * | | 183-185 | 331.24 | |
| 60 | * | | 196.4-196.7 | 389.26 | |

TABLE 1-continued

| Compound Number | Replicon IC50s μM | HCV-PV IC50 uM | Melting Point (° C.) | Mass Spec [M + H] | NMR Data |
|---|---|---|---|---|---|
| 61 | * | | 159-162 | 412.36 | |
| 62 | * | | 210-211 | 431.34 | |
| 63 | * | | 179.2-179.6 | 417.34 | |
| 64 | * | | | 432.28 | |
| 65 | ** | | 109.6-110.2 | 307.8 | CDCl$_3$, 300MHz, δ=7.93(s, 1H), 2.78(q, J=7.8Hz, 2H), 2.67(s, 3H), 2.57(s, 3H), 1.61(s, 9H), 1.17(t, J=7.8Hz, 3H) |
| 66 | * | | 79-81 | 465.0 | CDCl$_3$, 300MHz, δ=4.09(s, 2H), 3.97(s, 4H), 3.47-3.33(m, 12H) 2.66(s, 3H), 2.61(s, 3H), 2.43(b, 3H), 1.57(s, 9H) |
| 67 | * | | 102-104 | 408.0 | CD$_4$O, 300MHz, δ=4.23(t, J=5.0Hz, 2H), 4.15-3.87(m, 4H), 3.72(t, J=5.1Hz, 2H), 3.460-3.40(m, 4H), 2.73(s, 3H), 2.58(s, 3H), 1.56(s, 9H) |
| 68 | ** | | | 435.1 | CDCl$_3$, 300MHz, δ=4.17(s, 2H), 4.06(s, 2H), 3.86-3.78(m, 4H) 3.58-3.56(m, 4H), 2.94(s, 3H), 2.66(s, 3H), 2.56(b, 5H), 1.57(s, 9H) |
| 69 | ** | | | 492.1 | CD$_4$O, 300MHz, δ=4.16(t, J=4.5Hz, 2H), 3.52(b, 6H), 3.35(b, 4H), 3.29(t, J=1.5Hz, 2H), 3.22(t, J=7.8Hz, 2H), 3.04(t, J=7.2Hz, 2H), 2.91(s, 6H), 2.74(s, 3H), 2.58(s, 3H), 2.13(b, 2H), 1.56(s, 9H) |
| 70 | ** | | | 406.0 | CD$_4$O, 300MHz, δ=4.19(t, J=5.1Hz, 2H), 3.74(d, J=12.3Hz, 2H), 3.64(t, J=4.8Hz, 2H), 3.18-3.08(m, 2H), 2.73(s, 3H), 2.57(s, 3H), 2.02-1.86(m, 6H), 1.56(s, 9H) |
| 71 | * | | 155.4-155.5 | 421.0 | CD$_4$O, 300MHz, δ=4.00(t, J=4.8Hz, 2H), 3.34-3.29(m, 8H), 3.02(t, J=5.1Hz, 2H), 2.91(s, 3H), 2.76(s, 3H), 2.58(s, 3H), 1.57(s, 9H) |
| 72 | * | | | 365.9 | CD$_4$O, 300MHz, δ=4.18(t, J=4.5Hz, 2H), 3.68(t, J=5.4Hz, 2H), 3.01(s, 6H), 2.76(s, 3H), 2.60(s, 3H), 1.57 (s, 9H) |
| 73 | ** | | | 423.0 | CDCl$_3$, 300MHz, δ=6.06(s, 2H), 3.86(t, J=4.8Hz, 2H), 2.86(t, J=4.5Hz, 2H), 2.69(s, 3H), 2.65-2.57(m, 5H), 2.49-2.46(m, 2H), 2.37(s, 3H), 2.28(s, 6H), 1.57(s, 9H) |
| 74 | * | | | 435.0 | CDCl$_3$, 300MHz, δ=4.16(t, J=4.5Hz, 2H), 3.76(b, 4H), 3.65(b, 4H), 3.46(t, J=4.8Hz, 2H) 3.21(q, J=6.9Hz, 2H), 2.70(s, 3H), 2.60(s, 3H), 1.57(s, 9H) 1.41(t, J=7.2Hz, 3H) |
| 75 | * | | decomposed | 391.9 (M − H) | (CDCl3, 300MHz), δ3.66(t, J=6.3Hz, 2H), 3.51(t, J=6.3Hz, 2H), 2.61(s, 3H), 2.54(s, 3H), 2.06-1.95(m, 6H), 1.58(s, 9H) |
| 76 | * | | decomposed | 407.9 | (CDCl3, 300MHz), δ3.78(b, 8H), 3.60(b, 2H), 2.57(s, 3H), 2.49(s, 3H), 1.57(s, 9H) |

Example 7

Evaluation of the Activity of Compounds Using an HCV-poliovirus Chimera

In an HCV-poliovirus (HCV-PV) chimera, the PV 5' UTR is replaced by the HCV 5' UTR and partial (the first 123 amino acids) core coding sequences (nucleotides 18 to 710 of HCV 1b) as shown in FIG. 1 (140). As a consequence, the expression of poliovirus proteins is under regulation of the HCV IRES. Poliovirus is a picornavirus in which protein translation initiation is mediated by an IRES element located in the 5' UTR. At the 5' end of the HCV-PV chimeric genome, there is the cloverleaf-like RNA structure of PV, an essential cis-acting replication signal ending with the genome-linked protein VPg. Replication kinetics of the HCV-PV chimera matches that of the parental poliovirus (Mahoney) and can result in cytopathic effects (CPE) in cell culture. Heptazyme, a ribozyme that targets the HCV IRES, was shown to be active against the chimeric virus in cell culture (76, 77).

To evaluate compounds for activity against the chimeric virus, HeLa cells are seeded and incubated at 37° C. under 5% $CO_2$ for 24 hours. The cells are then infected with HCV-PV at a multiplicity of infection (MOI) at 0.1 for 30 min and then treated with compound for 1 day. The activity of compounds is determined by a change in cytopathic effect, plaque assay, and/or viral RNA production (see e.g., Table 1) is then quantified by RT real-time PCR using the HCV IRES primers and probes.

Example 8

Evaluation of the Activity of Compounds Against a Wild-type Poliovirus (WT-PV) and the Poliovirus IRES Translation Assay (WT-PV mono luc)

A DNA construct is prepared, termed pPVIRESmono, in which PV IRES sequences are inserted (nucleotide number 1-742) between a promoter and the firefly luciferase (Fluc) reporter gene. A stably transfected 293 T cell line, is established by transfection with the pPVIRESmono DNA by selecting for resistance to hygromycin. As previously described, cells are treated with compounds for 20 hours, and activity is determined by quantifying the Fluc signal. Table 2 provides data obtained using some of the compounds of the present invention. Additionally, to evaluate activity of compounds against wild-type poliovirus, HeLa cells are seeded and incubated at 37° C. under 5% $CO_2$ for 24 hours. Cells are then infected with wild-type poliovirus at a MOI at 0.1 for 30 minutes, and then treated with compound for one day. The activity of compounds is determined by changes in cytopathic effect (see e.g., Table 2), plaque assay, and RNA production determined by RT real time PCR using poliovirus IRES primers and probes.

Furthermore, if compounds are active in the poliovirus IRES or other virus IRESs, then the compounds may also be useful for treating viral infection by other viruses containing an IRES.

TABLE 2

| Compound Number | WTPV CPE (100 µM) | WTPV CPE (11.1 µM) | WTPV CPE (1.2 µM) |
| --- | --- | --- | --- |
| 5 | 2 | 1 | 0 |
| 29 | 2 | 1 | 0 |
| 35 | 2 | 1 | 0 |
| 50 | 3 | 1 | 0 |

*A "1" in the WT-PV CPE columns indicates that the CPE (cytopathic effect) is decreased by 20-50%.
A "2" in the WT-PV CPE columns indicates that the CPE is decreased by 50-75%.
A "3" in the WT-PV CPE columns indicates that the CPE is decreased by 75-100%.

Example 9

In Vitro Translation Assay

In vitro translation assays can be used to distinguish between the compounds that act on HCV IRES RNA or cellular translation factors. In exemplary assays, the mRNA that will direct translation is a transcribed runoff product from the T7 RNA polymerase promoter of the pHCVIRESmono plasmid DNA generated with Ambion RNA MegaTranscript kit (Ambion, Inc., Austin, Tex.). In vitro translation is performed using HeLa cell lysates using methods known to one of skill in the art. Preliminary results indicate that at least one of the compounds of the present invention has significantly higher activity against HCV IRES regulated translation after preincubating the compound with the HCV IRES RNA transcripts than after preincubating with HeLa cell lysate for 30 min at 37° C. or without preincubation (data not shown). This suggests that this compound may interact with the HCV IRES RNA in the in vitro translation assay. To demonstrate whether the compounds selectively act on the HCV IRES, pLuc is used together with cellular IRES mRNA transcripts as controls for in vitro translation.

All publications and patent applications cited herein are incorporated by reference to the same extent as if each individual publication or patent application was specifically and individually indicated to be incorporated by reference.

Although certain embodiments have been described in detail above, those having ordinary skill in the art will clearly understand that many modifications are possible in the embodiments without departing from the teachings thereof. All such modifications are intended to be encompassed within the claims of the invention.

REFERENCES

1. Ali, N., G. J. Pruijn, D. J. Kenan, J. D. Keene, and A. Siddiqui. 2000. Human La antigen is required for the hepatitis C virus internal ribosome entry site-mediated translation. J Biol Chem 275:27531-27540.
2. Ali, N. and A. Siddiqui. 1995. Interaction of polypyrimidine tract-binding protein with the 5' noncoding region of the hepatitis C virus RNA genome and its functional requirement in internal initiation of translation. J Virol 69:6367-6375.
3. Ali, N. and A. Siddiqui. 1997. The La antigen binds 5' noncoding region of the hepatitis C virus RNA in the context of the initiator AUG codon and stimulates internal ribosome entry site-mediated translation. Proc Natl Acad Sci USA 94:2249-2254.
4. Anwar, A. N. Ali, R. Tanveer, and A. Siddiqui. 2000. Demonstration of functional requirement of polypyrimidine tract-binding protein by SELEX RNA during hepatitis C virus internal ribosome entry site-mediated translation initiation. J Biol Chem 275:34231-34235.
5. Beales, L. P., D. J. Rowlands, and A. Holzenburg. 2001. The internal ribosome entry site (IRES) of hepatitis C virus visualized by electron microscopy. RNA 7:661-670.
6. Belsham, G. J. and J. K. Brangwyn. 1990. A region of the 5' noncoding region of foot-and-mouth disease virus RNA directs efficient internal initiation of protein synthesis within cells: involvement with the role of L protease in translational control. J Virol 64:5389-5395.
7. Belsham, G. J. and R. J. Jackson. 2000. Translation initiation on picornavirus RNA., p. 869-900. Cold Spring Harbor Laboratory Press, New York.
8. Blight, K. J., A. A. Kolykhalov, and C. M. Rice. 2000. Efficient initiation of HCV RNA replication in cell culture. Science 290:1972-1974.
9. Blight, K. J., J. A. McKeating, and C. M. Rice. 2002. Highly permissive cell lines for subgenomic and genomic hepatitis C virus RNA replication. J Virol 76:13001-13014.
10. Borvjagin, G., T. Pestova, and I. Shatsky. 1994. Pyrimidine tract binding protein strongly stimulates in vitro encephalomyocarditis virus RNA translation at the level of the preinitiation complex formation. FEBS Lett 351:291-302.
11. Brown, E. A., H. Zhang, L. H. Ping, and S. M. Lemon. 1992. Secondary structure of the 5' nontranslated regions of hepatitis C virus and pestivirus genomic RNAs. Nucleic Acids Res 20:5041-5045.
12. Buck C B, Shen X, Egan M A, Pierson T C, Walker C M, and Siliciano R F. 2001. The human immunodeficiency virus type 1 gag gene encodes an internal ribosome entry site. J Virol 75:181-191.

13. Bukh, J., R. H. Purcell, and R. H. Miller. 1992. Sequence analysis of the 5' noncoding region of hepatitis C virus. Proc Natl Acad Sci USA 89:4942-4946.
14. Bukh, J., R. H. Purcell, and R. H. Miller. 1994. Sequence analysis of the core gene of 14 hepatitis C virus genotypes. Proc Natl Acad Sci USA 91:8239-8243.
15. Buratti, E., S. Tisminetzky, M. Zotti, and F. E. Baralle. 1998. Functional analysis of the interaction between HCV 5'UTR and putative subunits of eukaryotic translation initiation factor eIF3. Nucleic Acids Res 26:3179-3187.
16. Chappell, S. A., J. P. LeQuesne, F. E. Paulin, M. L. deSchoolmeester, M. Stoneley, R. L. Soutar, S. H. Ralston, M. H. Helfrich, and A. E. Willis. 2000. A mutation in the c-myc-IRES leads to enhanced internal ribosome entry in multiple myeloma: a novel mechanism of oncogene deregulation. Oncogene 19:4437-4440.
17. Chung, R. T., W. He, A. Saquib, A. M. Contreras, R. J. Xavier, A. Chawla, T. C. Wang, and E. V. Schmidt. 2001. Hepatitis C virus replication is directly inhibited by IFN-alpha in a full-length binary expression system.
18. Coldwell, M. J., S. A. Mitchell, M. Stoneley, M. MacFarlane, and A. E. Willis. 2000. Initiation of Apaf-1 translation by internal ribosome entry. Oncogene 19:899-905.
19. Creancier, L., D. Morello, P. Mercier, and A. C. Prats. 2000. Fibroblast growth factor 2 internal ribosome entry site (IRES) activity ex vivo and in transgenic mice reveals a stringent tissue-specific regulation. J Cell Biol 150:275-281.
20. Das, S., M. Ott, A. Yamane, A. Venkatesan, S. Gupta, and A. Dasgupta. 1998. Inhibition of internal entry site (IRES)-mediated translation by a small yeast RNA: a novel strategy to block hepatitis C virus protein synthesis. Front Biosci 3:D1241-D1252.
21. Dever, T. E. 2002. Gene-specific regulation by general translation factors. Cell 108:545-556.
22. Dumas, E., C. Staedel, M. Colombat, S. Reigadas, S. Chabas, T. Astier-Gin, A. Cahour, S. Litvak, and M. Ventura. 2003. A promoter activity is present in the DNA sequence corresponding to the hepatitis C virus 5' UTR. Nucleic Acids Res 31:1275-1281.
23. Fukushi, S., K. Katayama, C. Kurihara, N. Ishiyama, F. B. Hoshino, T. Ando, and A. Oya. 1994. Complete 5' noncoding region is necessary for the efficient internal initiation of hepatitis C virus RNA. Biochem Biophys. Res Commun. 199:425-432.
24. Fukushi, S., C. Kurihara, N. Ishiyama, F. B. Hoshino, A. Oya, and K. Katayama. 1997. The sequence element of the internal ribosome entry site and a 25-kilodalton cellular protein contribute to efficient internal initiation of translation of hepatitis C virus RNA. J Virol 71:1662-1666.
25. Fukushi, S., M. Okada, T. Kageyama, F. B. Hoshino, and K. Katayama. 1999. Specific interaction of a 25-kilodalton cellular protein, a 40S ribosomal subunit protein, with the internal ribosome entry site of hepatitis C virus genome. Virus Genes 19:153-161.
26. Fukushi, S., M. Okada, J. Stahl, T. Kageyama, F. B. Hoshino, and K. Katayama. 2001. Ribosomal protein S5 interacts with the internal ribosomal entry site of hepatitis C virus. J Biol Chem 276:20824-20826.
27. Funkhouser, A. W., D. E. Schultz, S. M. Lemon, R. H. Purcell, and S. U. Emerson. 1999. Hepatitis A virus translation is rate-limiting for virus replication in MRC-5 cells. Virology 254:268-278.
28. Glass, M. J., X. Y. Jia, and D. F. Summers. 1993 Identification of the hepatitis A virus internal ribosome entry site: in vivo and in vitro analysis of bicistronic RNAs containing the HAV 5' noncoding region. Virology. 193:842-852.
29. Gordon S. C., B. R. Bacon, I. M. Jacobson, M. I. Shiffman, N. H. Afdhal, J. G. McHutchison, T. J. Kwoh, and F. A. Dorr. 2002. A Phase II, 12-week study of ISIS 14803, an antisense inhibitor of HCV for the treatment of chronic hepatitis C. AASLD Abst. 795. Hepatology 36:362A.
30. Gosert, R., K. H. Chang, R. Rijnbrand, M. Yi, D. V. Sangar, and S. M. Lemon. 2000. Transient expression of cellular polypyrimidine-tract binding protein stimulates cap-independent translation directed by both picornaviral and flaviviral internal ribosome entry sites In vivo. Mol Cell Biol 20:1583-1595.
31. Gray, N, and M. Wickens. 1998. Control of translation initiation in animals. Annu Rev Cell Dev Biol 14:399-458.
31a. Griffith, A., and D. M. Coen. 2005. An unusual internal ribosome entry site in the herpes simplex virus thymidine kinase gene. Proc Natl Acad Sci USA. 102:9667-72.
32. Guo, J. T., V. V. Bichko, and C. Seeger. 2001. Effect of alpha interferon on the hepatitis C virus replicon. J Virol 75:8516-8523.
33. Hahm, B., Y. K. Kim, J. H. Kim, T. Y. Kim, and S. K. Jang. 1998. Heterogeneous nuclear ribonucleoprotein L interacts with the 3' border of the internal ribosomal entry site of hepatitis C virus. J Virol 72:8782-8788.
34. Haller, A. A., S. R. Stewart, and B. L. Semler. 1996. Attenuation stem-loop lesions in the 5' noncoding region of poliovirus RNA: neuronal cell-specific translation defects. J Virol 70:1467-1474.
35. Hellen, C. U. and T. V. Pestova. 1999. Translation of hepatitis C virus RNA. J Viral Hepat 6:79-87.
36. Hellen, C. U., G. W. Witherell, M. Schmid, S. H. Shin, T. V. Pestova, A. Gil, and E. Wimmer. 1993. A cytoplasmic 57-kDa protein that is required for translation of picornavirus RNA by internal ribosomal entry is identical to the nuclear pyrimidine tract-binding protein. Proc Natl Acad Sci USA 90:4672-7646
37. Hendrix, M., E. S. Priestley, G. F. Joyce, and C. H. Wong. 1997. Direct observation of aminoglycoside-RNA interactions by surface plasmon resonance. Journal of the American Chemical Society 119:3641-8.
38. Holcik, M. and R. G. Korneluk. 2000. Functional characterization of the X-linked inhibitor of apoptosis (XIAP) internal ribosome entry site element: role of La autoantigen in XIAP translation. Mol Cell Biol 20:4648-4657.
39. Holcik, M., C. Lefebvre, C. Yeh, T. Chow, and R. G. Korneluk. 1999. A new internal-ribosome-entry-site motif potentiates XIAP-mediated cytoprotection. Nat Cell Biol 1:190-192.
40. Honda, M., M. R. Beard, L. H. Ping, and S. M. Lemon. 1999. A phylogenetically conserved stem-loop structure at the 5' border of the internal ribosome entry site of hepatitis C virus is required for cap-independent viral translation. J Virol 1165-1174.
41. Honda, M., E. A. Brown, and S. M. Lemon. 1996. Stability of a stem-loop involving the initiator AUG controls the efficiency of internal initiation of translation on hepatitis C virus RNA. RNA 2:955-968.
42. Honda, M., L. H. Ping, R. C. Rijnbrand, E. Amphlett, B. Clarke, D. Rowlands, and S. M. Lemon. 1996. Structural requirements for initiation of translation by internal ribosome entry within genome-length hepatitis C virus RNA. Virology 222:31-42.
43. Honda, M., R. Rijnbrand, G. Abell, D. Kim, and S. M. Lemon. 1999. Natural variation in translational activities of the 5' nontranslated RNAs of hepatitis C virus genotypes 1a and 1b: evidence for a long-range RNA-RNA interaction outside of the internal ribosomal entry site. J Virol 73:4941-4951.

44. Huez, I., S. Bornes, D. Bresson, L. Creancier, and H. Prats. 2001. New vascular endothelial growth factor isoform generated by internal ribosome entry site-driven CUG translation initiation. Mol Endocrinol. 15:2197-2210.
45. Huez, I., L. Creancier, S. Audigier, M. C. Gensac, A. C. Prats, and H. Prats. 1998. Two independent internal ribosome entry sites are involved in translation initiation of vascular endothelial growth factor mRNA. Mol Cell Biol 18:6178-6190
46. Ikeda, M., M. Yi, K. L1, and S. M. Lemon. 2002. Selectable subgenomic and genome-length dicistronic RNAs derived from an infectious molecular clone of the HCV-N strain of hepatitis C virus replicate efficiently in cultured Huh7 cells. J Virol 76:2997-3006.
47. Irvine, J. D., L. Takahashi, K. Lockhart, J. Cheong, J. W. Tolan, H. E. Selick, and J. R. Grove. 1999. MDCK (Madin-Darby canine kidney) cells: A tool for membrane permeability screening. J Pharm Sci 88:28-33.
48. Isoyama, T., N. Kamoshita, K. Yasui, A. Iwai, K. Shiroki, H. Toyoda, A. Yamada, Y. Takasaki, and A. Nomoto. 1999. Lower concentration of La protein required for internal ribosome entry on hepatitis C virus RNA than on poliovirus RNA. J Gen Virol 80 (Pt 9):2319-2327.
49. Ito, T. and M. M. Lai. 1999. An internal polypyrimidine-tract-binding protein-binding site in the hepatitis C virus RNA attenuates translation, which is relieved by the 3'-untranslated sequence. Virology 254:288-296.
50. Jang, S. K., H. G. Krausslich, M. J. Nicklin, G. M. Duke, A. C. Palmenberg, and E. Wimmer. 1988. A segment of the 5' nontranslated region of encephalomyocarditis virus RNA directs internal entry of ribosomes during in vitro translation. J Virol 62:2636-2643.
51. Jubin, R., N. E. Vantuno, J. S. Kieft, M. G. Murray, J. A. Doudna, J. Y. Lau, and B. M. Baroudy. 2000. Hepatitis C virus internal ribosome entry site (IRES) stem loop IIId contains a phylogenetically conserved GGG triplet essential for translation and IRES folding. J Virol 74:10430-10437.
52. Kalliampakou, K. I., L. Psaridi-Linardaki, and P. Mavromara. 2002. Mutational analysis of the apical region of domain II of the HCV IRES. FEBS Lett 511:79-84.
53. Kaminski, A., S. L. Hunt, J. G. Patton, and R. J. Jackson. 1995. Direct evidence that polypyrimidine tract binding protein (PTB) is essential for internal initiation of translation of encephalomyocarditis virus RNA.RNA 1:924-938
54. Kamoshita, N., K. Tsukiyama-Kohara, M. Kohara, and A. Nomoto. 1997. Genetic analysis of internal ribosomal entry site on hepatitis C virus RNA: implication for involvement of the highly ordered structure and cell type-specific transacting factors. Virology 233:9-18.
55. Kieft, J. S., K. Zhou, R. Jubin, M. G. Murray, J. Y. Lau, and J. A. Doudna. 1999. The hepatitis C virus internal ribosome entry site adopts an ion-dependent tertiary fold. J Mol Biol 292:513-529.
56. Kieft, J. S., K. Zhou, R. Jubin, M. G. Murray, J. Y. Lau, and J. A. Doudna. 2001. Mechanism of ribosome recruitment by hepatitis C IRES RNA. RNA 7:194-206.
57. Klinck, R., E. Westhof, S. Walker, M. Afshar, A. Collier, and F. Aboul-E1a. 2000. A potential RNA drug target in the hepatitis C virus internal ribosomal entry site. RNA 6:1423-1431.
58. Kolupaeva V G, Pestova T V, and Hellen C U T. 2000. An enzymatic foot-printing analysis of the interaction of 40S ribosomal subunits with the internal ribosomal entry site of hepatitis C virus. J Virol 74:6242-6250.
59. Kolupaeva, V. G., C. U. Hellen, and I. N. Shatsky. 1996. Structural analysis of the interaction of the pyrimidine tract-binding protein with the internal ribosomal entry site of encephalomyocarditis virus and foot-and-mouth disease virus RNAs. RNA 2:1199-1212.
60. Kolupaeva, V. G., T. V. Pestova, C. U. Hellen, and I. N. Shatsky. 1998. Translation eukaryotic initiation factor 4G recognizes a specific structural element within the internal ribosome entry site of encephalomyocarditis virus RNA. J Biol Chem 273:18599-18604.
61. Kozak, M. 1999. Initiation of translation in prokaryotes and eukaryotes. Gene 234:187-208.
62. Kruger, M., C. Beger, P. J. Welch, J. R. Barber, M. P. Manns, and F. Wong-Staal. 2001. Involvement of proteasome alpha-subunit PSMA7 in hepatitis C virus internal ribosome entry site-mediated translation. Mol Cell Biol 21: 8357-8364
63. La Monica, N. and V. R. Racaniello. 1989. Differences in replication of attenuated and neurovirulent polioviruses in human neuroblastoma cell line SH-SY5Y. J Virol 63:2357-2360.
64. Le, S. Y., N. Sonenberg, and J. V. Maizel, Jr. 1995. Unusual folding regions and ribosome landing pad within hepatitis C virus and pestivirus RNAs. Gene 154:137-143.
65. Lerat, H., Y. K. Shimizu, and S. M. Lemon. 2000. Cell type-specific enhancement of hepatitis C virus internal ribosome entry site-directed translation due to 5' nontranslated region substitutions selected during passage of virus in lymphoblastoid cells. J Virol 74:7024-7031.
66. L1, K., T. M. Davis, C. Bailly, A. Kumar, D. W. Boykin, and W. D. Wilson. 2001. A heterocyclic inhibitor of the REV-RRE complex binds to RRE as a dimer. Biochemistry 40:1150-8.
67. Lipinski, J. 2000. J. Pharm. Tox. Meth. 44:235-249.
68. Llina's-Brunet M. 2002. NS3 serine protease inhibitors as potential antiviral agents for the treatment of hepatitis C virus infections. The 3rd internatl antiviral & vaccine discovery and development summit. March 13-14. Princeton, N.J.
69. Lohmann, V., F. Korner, A. Dobierzewska, and R. Bartenschlager. 2001. Mutations in hepatitis C virus RNAs conferring cell culture adaptation. J Virol 75:1437-1449.
70. Lohmann, V., F. Korner, J. Koch, U. Herian, L. Theilmann, and R. Bartenschlager. 1999. Replication of subgenomic hepatitis C virus RNAs in a hepatoma cell line. Science 285:110-113.
71. Lopez, d. Q., E. Lafuente, and E. Martinez-Salas. 2001. IRES interaction with translation initiation factors: functional characterization of novel RNA contacts with eIF3, eIF4B, and eIF4GII. RNA 7:1213-1226.
72. Lopez, d. Q. and E. Martinez-Salas. 2000. Interaction of the eIF4G initiation factor with the aphthovirus IRES is essential for internal translation initiation in vivo. RNA 6:1380-1392.
73. Lu, H. H. and E. Wimmer. 1996. Poliovirus chimeras replicating under the translational control of genetic elements of hepatitis C virus reveal unusual properties of the internal ribosomal entry site of hepatitis C virus. Proc Natl Acad Sci USA 93:1412-7.
74. Lukavsky, P. J., G. A. Otto, A. M. Lancaster, P. Sarnow, and J. D. Puglisi. 2000. Structures of two RNA domains essential for hepatitis C virus internal ribosome entry site function. Nat Struct Bio 7:1105-1110.
75. Lyons, A. J., J. R. Lytle, J. Gomez, and H. D. Robertson. Hepatitis C virus internal ribosome entry site RNA contains a tertiary structural element in a functional domain of stem-loop II. Nucleic Acids Res 29:2535-2546.

76. Macejak, D. G., K. L. Jensen, S. F. Jamison, K. Domenico, E. C. Roberts, N. Chaudhary, I. von_Carlowitz, L. Bellon, M. J. Tong, A. Conrad, P. A. Pavco, and L. M. Blatt. 2000. Inhibition of hepatitis C virus (HCV)-RNA-dependent translation and replication of a chimeric HCV poliovirus using synthetic stabilized ribozymes. Hepatology (Baltimore, Md.) 31:769-76.

77. Macejak, D. G., K. L. Jensen, P. A. Pavco, K. M. Phipps, B. A. Heinz, J. M. Colacino, and L. M. Blatt. 2001. Enhanced antiviral effect in cell culture of type 1 interferon and ribozymes targeting HCV RNA. J Viral Hepatitis 8:400-405.

78. Macejak, D. G. and P. Sarnow. 1991. Internal initiation of translation mediated by the 5' leader of a cellular mRNA. Nature 353:90-94.

79. Major M E, Rehermann B, and Feinstone. 2001. Hepatitis C viruses., p. 2535-2541. In D. Knipe and P. Howley (eds.), Fields Virology. Lippincott Williams and Wilkins, Philadelphia, Pa.

80. Manns M P, McHutchison J G, Gordon S C, Rustgi V K, Shiffman M, Reindollar R, Goodman Z D, Koury K, Ling M, and Albrecht J K. 2003. Peginterferon alfa-2b plus ribavirin compared with interferon alfa-2b plus ribavirin for initial treatment of chronic hepatitis C: a randomised trial. Lancet 358:958-965.

81. Martinez-Salas, E., R. Ramos, E. Lafuente, and d. Q. Lopez. 2001. Functional interactions in internal translation initiation directed by viral and cellular IRES elements. J Gen Virol 82:973-984.

82. Mazur, S., F. A. Tanious, D. Ding, A. Kumar, D. W. Boykin, I. J. Simpson, S. Neidle, and W. D. Wilson. 2000. A thermodynamic and structural analysis of DNA minor-groove complex formation. Journal of Molecular Biology 300:321-37.

83. McHutchison JG and Poynard T. 1999. Combination therapy with interferon plus ribavirin for the initial treatment of chronic hepatitis C. Semin. Liver Dis. 19 Suppl 1:57-65.

84. McHutchison, J. G., T. Poynard, R. Esteban-Mur, G. L. Davis, Z. D. Goodman, J. Harvey, M. H. Ling, J. J. Garaud, J. K. Albrecht, K. Patel, J. L. Dienstag, and T. Morgan. 2002. Hepatic HCV RNA before and after treatment with interferon alone or combined with ribavirin. Hepatology 35:688-693.

85. Meerovitch, K., J. Pelletier, and N. Sonenberg. 1989. A cellular protein that binds to the 5'-noncoding region of poliovirus RNA: implications for internal translation initiation. Genes Dev 3:1026-1034.

86. Meerovitch, K., Y. V. Svitkin, H. S. Lee, F. Lejbkowicz, D. J. Kenan, E. K. Chan, V. 1. Agol, J. D. Keene, and N. Sonenberg. 1993. La autoantigen enhances and corrects aberrant translation of poliovirus RNA in reticulocyte lysate. J Virol 67: 3798-3807.

87. Mercer, D. F., D. E. Schiller, J. F. Elliott, D. N. Douglas, C. Hao, A. Rinfret, W. R. Addison, K. P. Fischer, T. A. Churchill, J. R. Lakey, D. L. Tyrrell, and N. M. Kneteman. 2001. Hepatitis C virus replication in mice with chimeric human livers. Nature Medicine 7:927-33.

88. Michel, Y. M., A. M. Borman, S. Paulous, and K. M. Kean. 2001. Eukaryotic initiation factor 4G-poly(A) binding protein interaction is required for poly(A) tail-mediated stimulation of picornavirus internal ribosome entry segment-driven translation but not for X-mediated stimulation of hepatitis C virus translation. Mol Cell Biol 21: 4097-4109.

89. Mitchell, S. A., E. C. Brown, M. J. Coldwell, R. J. Jackson, and A. E. Willis. 2001. Protein factor requirements of the Apaf-1 internal ribosome entry segment: roles of polypyrimidine tract binding protein and upstream of N-ras. Mol Cell Biol 21:3364-3374.

90. Moriguchi, e. al. 1992. Chem Pharm Bull 40:127-130.

91. Nanbru, C., I. Lafon, S. Audigier, M. C. Gensac, S. Vagner, G. Huez, and A. C. Prats. 2003. Alternative translation of the proto-oncogene c-myc by an internal ribosome entry site. J Biol Chem 272:32061-32066.

92. Niepmann, M., A. Petersen, K. Meyer, and E. Beck. 1997. Functional involvement of polypyrimidine tract-binding protein in translation initiation complexes with the internal ribosome entry site of foot-and-mouth disease virus. J Virol 71:8330-8339.

93. Odreman-Macchioli, F., F. E. Baralle, and E. Buratti. 2001. Mutational analysis of the different bulge regions of hepatitis C virus domain II and their influence on internal ribosome entry site translational ability. J Biol Chem 276: 41648-41655.

94. Odreman-Macchioli, F. E., S. G. Tisminetzky, M. Zotti, F. E. Baralle, and E. Buratti. 2000. Influence of correct secondary and tertiary RNA folding on the binding of cellular factors to the HCV IRES. Nucleic Acids Res 28:875-885.

95. Ohlmann, T., M. Lopez-Lastra, and J. L. Darlix. 2000. An internal ribosome entry segment promotes translation of the simian immunodeficiency virus genomic RNA. J Biol Chem 275:11899-11906.

96. Pain VM. 1996. Initiation of protein synthesis in eukaryotic cells. Eur J Biochem 236:747-771.

97. Pelletier, J. and N. Sonenberg. 1988. Internal initiation of translation of eukaryotic mRNA directed by a sequence derived from poliovirus RNA. Nature 334:320-325.

98. Pelletier, J. and N. Sonenberg. 1989. Internal binding of eucaryotic ribosomes on poliovirus RNA: translation in HeLa cell extracts. J Virol 63:441-444.

99. Pestova, T. V., S. I. Borukhov, and C. U. Hellen. 1998. Eukaryotic ribosomes require initiation factors 1 and 1A to locate initiation codons. Nature 394:854-859.

100. Pestova, T. V., I. N. Shatsky, S. P. Fletcher, R. J. Jackson, and C. U. Hellen. 1998. A prokaryotic-like mode of cytoplasmic eukaryotic ribosome binding to the initiation codon during internal translation initiation of hepatitis C and classical swine fever virus RNAs. Genes Dev 12: 67-83.

101. Pestova, T. V., I. N. Shatsky, and C. U. Hellen. 1996. Functional dissection of eukaryotic initiation factor 4F: the 4A subunit and the central domain of the 4G subunit are sufficient to mediate internal entry of 43S preinitiation complexes. Mol Cell Biol 16:6870-6878.

102. Peytou, V., R. Condom, N. Patino, R. Guedj, A. M. Aubertin, N. Gelus, C. Bailly, R. Terreux, and D. Cabrol-_Bass. 1999. Synthesis and antiviral activity of ethidium-arginine conjugates directed against the TAR RNA of HIV-1. Journal of Medicinal Chemistry 42:4042-53.

103. Pietschmann, T., V. Lohmann, A. Kaul, N. Krieger, G. Rinck, G. Rutter, D. Strand, and R. Bartenschlager. 2002. Persistent and transient replication of full-length hepatitis C virus genomes in cell culture. J Virol 76:4008-4021.

104. Pietschmann, T., V. Lohmann, G. Rutter, K. Kurpanek, and R. Bartenschlager. 2001. Characterization of cell lines carrying self-replicating hepatitis C virus RNAs. J Virol 75:1252-1264.

105. Poole, T. L., C. Wang, R. A. Popp, L. N. Potgieter, A. Siddiqui, and M. S. Collett. 1995. Pestivirus translation initiation occurs by internal ribosome entry. Virology 206: 750-754.

106. Pringle, C. 1999. Virus taxonomy—1999. The universal system of virus taxonomy, updated to include the new 107. Psaridi, L., U. Georgopoulou, A. Varaklioti, and P. Mavromara. 1999. Mutational analysis of a conserved tetraloop in the 5' untranslated region of hepatitis C virus identifies a novel RNA element essential for the internal ribosome entry site function. FEBS Lett 453:49-53.

108. Reynolds, J. E., A. Kaminski, A. R. Carroll, B. E. Clarke, D. J. Rowlands, and R. J. Jackson. 1996. Internal initiation of translation of hepatitis C virus RNA: the ribosome entry site is at the authentic initiation codon. RNA 2:867-878.

109. Reynolds, J. E., A. Kaminski, H. J. Kettinen, K. Grace, B. E. Clarke, A. R. Carroll, D. J. Rowlands, and R. J. Jackson. 1995. Unique features of internal initiation of hepatitis C virus RNA translation. EMBO J. 14: 6010-6020.

110. Rijnbrand R, Bredenbeek P, van der Straaten T, Whetter L, Inchauspe G, Lemon S, and Spaan W. 1995. Almost the entire 5' non-translated region of hepatitis C virus is required for cap-independent translation. FEBS Lett 365: 115-119.

111. Rijnbrand R C and Lemon S M. 2000. Internal ribosome entry site-mediated translation in hepatitis C virus replication. Curr Top. Microbiol Immunol. 242:85-116.

112. Rijnbrand, R., P. J. Bredenbeek, P. C. Haasnoot, J. S. Kieft, W. J. Spaan, and S. M. Lemon. 2001. The influence of downstream protein-coding sequence on internal ribosome entry on hepatitis C virus and other flavivirus RNAs. RNA 7:585-597.

113. Rijnbrand, R. C., T. E. Abbink, P. C. Haasnoot, W. J. Spaan, and P. J. Bredenbeek. 1996. The influence of AUG codons in the hepatitis C virus 5' nontranslated region on translation and mapping of the translation initiation window. Virology 226:47-56.

114. Sachs, A. B., P. Sarnow, and M. W. Hentze. 1997. Starting at the beginning, middle, and end: translation initiation in eukaryotes. Cell 89:831-838.

115. Saito I, Miyamura T, Ohbayashi A, Harada H, Katayama T, Kikuchi S, Watanabe Y, Koi S, Onji M, Ohta Y, Choo Q, Houghton M, and Kuo G. 2003. Hepatitis C virus infection is associated with the development of hepatocellular carcinoma. Proc Natl Acad Sci U.S.A 87:6547-6549.

116. Schultz, D. E., M. Honda, L. E. Whetter, K. L. McKnight, and S. M. Lemon. 1996. Mutations within the 5' nontranslated RNA of cell culture-adapted hepatitis A virus which enhance cap-independent translation in cultured African green monkey kidney cells. J Virol 70:1041-1049.

117. Shimazaki, T., M. Honda, S. Kaneko, and K. Kobayashi. 2002. Inhibition of internal ribosomal entry site-directed translation of HCV by recombinant IFN-alpha correlates with a reduced La protein. Hepatology 35:199-208.

118. Simmonds, P. 2003. Variability of hepatitis C virus. Hepatology 21:570-583.

119. Sinha, R., P. Yang, S. Kodali, Y. Xiong, R. M. Kim, P. R. Griffin, H. R. Onishi, J. Kohler, L. L. Silver, and K. Chapman. 2001. Direct interaction of a vancomycin derivative with bacterial enzymes involved in cell wall biosynthesis. Chem Biol 8:1095-1106.

120. Sizova, D. V., V. G. Kolupaeva, T. V. Pestova, I. N. Shatsky, and C. U. Hellen. 1998. Specific interaction of eukaryotic translation initiation factor 3 with the 5' nontranslated regions of hepatitis C virus and classical swine fever virus RNAs. J Virol 72:4775-4782.

121. Smith. 1994. Eur J Drug Metab Pharm 3:193-199.

122. Smith, D. B., J. Mellor, L. M. Jarvis, F. Davidson, J. Kolberg, M. Urdea, P. L. Yap, and P. Simmonds. 1995. Variation of the hepatitis C virus 5' non-coding region: implications for secondary structure, virus detection and typing. The International HCV Collaborative Study Group. J Gen Virol 76 (Pt 7):1749-1761.

123. Sonenberg N, Mathews M B, and Hershey J W B. 2000. Translational control of gene expression. Cold Spring Harbor. Cold Spring Harbor Laboratory Press, New York.

124. Spahn, C. M., J. S. Kieft, R. A. Grassucci, P. A. Penczek, K. Zhou, J. A. Doudna, and J. Frank. 2001. Hepatitis C virus IRES RNA-induced changes in the conformation of the 40s ribosomal subunit. Science 291:1959-1962.

125. Spatzenegger, M. and W. Jaeger. 1995. Clinical importance of hepatic cytochrome P450 in drug metabolism. Drug Metab Rev 27:397-417.

126. Subkhankulova, T., S. A. Mitchell, and A. E. Willis. 2001. Internal ribosome entry segment-mediated initiation of c-Myc protein synthesis following genotoxic stress. Biochem J 359:183-192.

127. Tang, S., A. J. Collier, and R. M. Elliott. 1999. Alterations to both the primary and predicted secondary structure of stem-loop IIIc of the hepatitis C virus 1b 5' untranslated region (5'UTR) lead to mutants severely defective in translation which cannot be complemented in trans by the wild-type 5'UTR sequence. J Virol 73:2359-2364.

128. Thiel, V. and S. G. Siddell. 1994. Internal ribosome entry in the coding region of murine hepatitis virus mRNA 5. J Gen Virol. 75 (Pt 11):3041-3046.

129. Tsukiyama-Kohara, K., N. Iizuka, M. Kohara, and A. Nomoto. 1992. Internal ribosome entry site within hepatitis C virus RNA. J Virol 66:1476-1483.

130. Vagner, S., M. C. Gensac, A. Maret, F. Bayard, F. Amalric, H. Prats, and A. C. Prats. 1995. Alternative translation of human fibroblast growth factor 2 mRNA occurs by internal entry of ribosomes. Mol Cell Biol 15:35-44.

131. Varaklioti A, Georgopoulou U, Kakkanas A, Psaridi L, Serwe M, Caselmann W H, and Mavromara P. 1998. Mutational analysis of two unstructured domains of the 5, untranslated region of HCV RNA. Biochem Biophys. Res Commun. 253:678-685.

132. Wang, C., S. Y. Le, N. Ali, and A. Siddiqui. 1995. An RNA pseudoknot is an essential structural element of the internal ribosome entry site located within the hepatitis C virus 5' noncoding region. RNA 1:526-537.

133. Wang, C., P. Sarnow, and A. Siddiqui. 1993. Translation of human hepatitis C virus RNA in cultured cells is mediated by an internal ribosome-binding mechanism. J Virol 67:3338-3344.

134. Wang, C., P. Sarnow, and A. Siddiqui. 1994. A conserved helical element is essential for internal initiation of translation of hepatitis C virus RNA. J Virol 68:7301-7307.

135. Wang, S. M., S. C. Fears, L. Zhang, J. J. Chen, and J. D. Rowley. 2000. Screening poly(dA/dT)-cDNAs for gene identification. Proceedings of the National Academy of Sciences of the United States of America 97:4162-7.

136. Wang, T. H., R. C. Rijnbrand, and S. M. Lemon. 2000. Core protein-coding sequence, but not core protein, modulates the efficiency of cap-independent translation directed by the internal ribosome entry site of hepatitis C virus. J Virol 74:11347-11358.

137. Wimmer, E., C. U. Hellen, and X. Cao. 1993. Genetics of poliovirus. Annu Rev Genet 27:353-436.

138. Wong, J. B., T. Poynard, M. H. Ling, J. K. Albrecht, and S. G. Pauker. 2000. Cost-effectiveness of 24 or 48 weeks of interferon alpha-2b alone or with ribavirin as initial treatment of chronic hepatitis C. International Hepatitis Interventional Therapy Group. Am. J. Gastroenterol. 95:1524-1530.

139. Zhao, W. D. and E. Wimmer. 2001. Genetic analysis of a poliovirus/hepatitis C virus chimera: new structure for domain II of the internal ribosomal entry site of hepatitis C virus. J Virol 75:3719-3730.
140. Zhao, W. D., E. Wimmer, and F. C. Lahser. 1999. Poliovirus/Hepatitis C virus (internal ribosomal entry site-core) chimeric viruses: improved growth properties through modification of a proteolytic cleavage site and requirement for core RNA sequences but not for core-related polypeptides. Journal of Virology 73:1546-54.

What is claimed is:

1. A compound having the following formula:

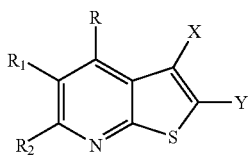

wherein:
X is:
an amino;
Y is:
an oxadiazolyl substituted with:
  a $C_6$ aryl optionally substituted with:
    an alkoxy,
    a halogen, or
    a $C_1$ to $C_6$ alkyl; or
  a 5- or 6-membered heteroaryl optionally substituted with:
    an alkoxy,
    a halogen, or
    a $C_1$ to $C_6$ alkyl;
R is:
a haloalkyl;
a $C_1$ to $C_6$ alkyl optionally substituted with hydroxyl;
$R_1$ is:
a $C_6$ aryl;
a $C_1$ to $C_6$ alkyl;
a $OCOR_f$ where $R_f$ is a 5- or 6-membered heterocycle;
an alkoxy optionally substituted with an amino, wherein the amino is optionally substituted with one or two $C_1$ to $C_6$ alkyls, where the alkyls are optionally substituted with an amino optionally substituted with one or two $C_1$ to $C_6$ alkyls;
an alkoxy optionally substituted with a 5 to 8 membered heterocycle optionally substituted with a $C_1$ to $C_6$ alkyl, which is optionally substituted with:
  an alkoxy; or
  an amino, optionally substituted with one or two $C_1$ to $C_6$ alkyls;
$R_2$ is:
a $C_1$ to $C_6$ alkyl;
a 5- or 6-membered heterocycle;
an amino optionally substituted with a $C_1$ to $C_6$ alkyl;
or a pharmaceutically acceptable salt thereof.

2. The compound of claim 1, wherein Y is
an oxadiazolyl substituted with:
  a $C_6$ aryl optionally substituted with:
    an alkoxy,
    a halogen, or
    a $C_1$ to $C_6$ alkyl, or
  a 5- or 6-membered heteroaryl optionally substituted with a $C_6$ aryl optionally substituted with a halogen.

3. The compound of claim 1, wherein R, $R_1$ and $R_2$ are independently $C_1$ to $C_6$ alkyl.

4. The compound of claim 3, wherein said $C_1$ to $C_6$ alkyl in R, $R_1$ and $R_2$ is independently a methyl or an ethyl.

5. The compound of claim 1, wherein $R_1$ is selected from the group consisting of
a $C_1$ to $C_6$ alkyl; and
an alkoxy optionally substituted with an amino, wherein the amino is optionally substituted with one or two $C_1$ to $C_6$ alkyls, where the alkyls are optionally substituted with an amino optionally substituted with one or two $C_1$ to $C_6$ alkyls; and
an alkoxy optionally substituted with a 5 to 8 membered heterocycle optionally substituted with a $C_1$ to $C_6$ alkyl, which is optionally substituted with:
  an amino, optionally substituted with one or two $C_1$ to $C_6$ alkyls.

6. The compound of claim 1, wherein said compound is selected from the group consisting of:

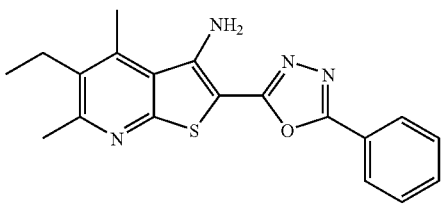

6

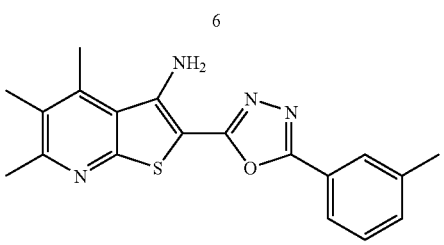

7

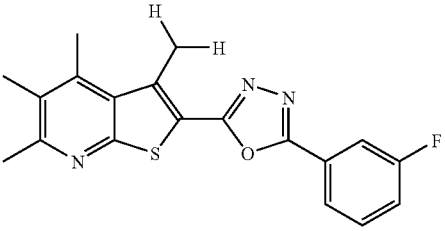

8

-continued
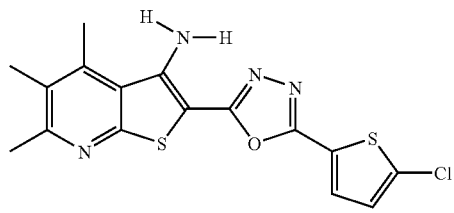
9
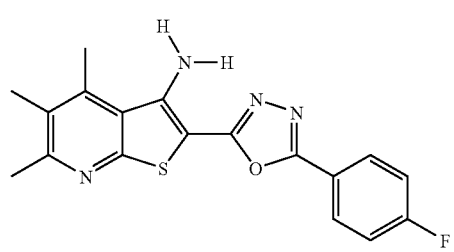
10
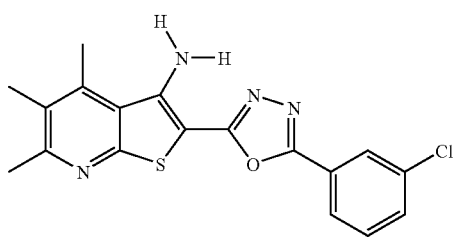
11
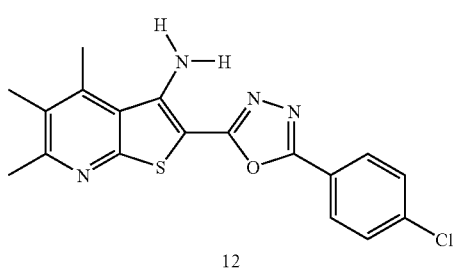
12
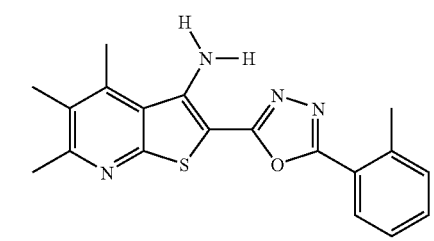
13
-continued
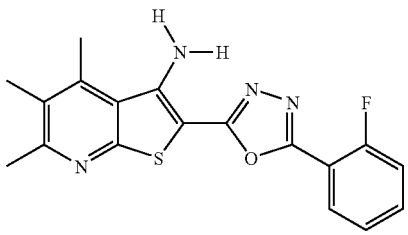
14
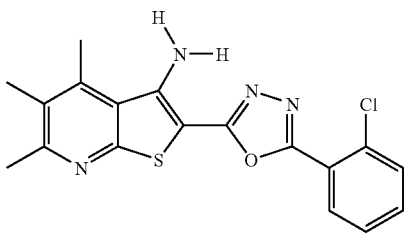
15
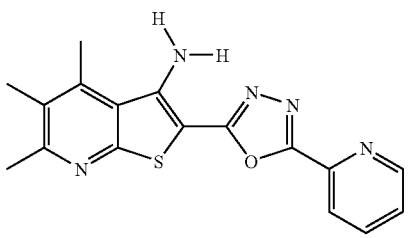
16
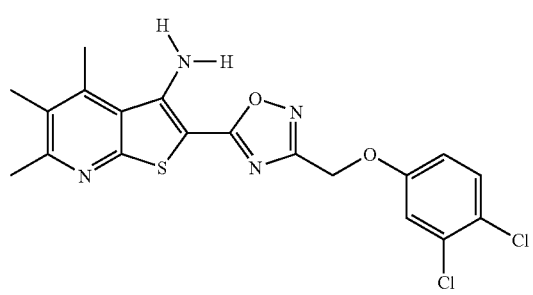
18
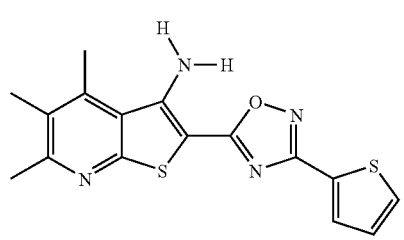
19

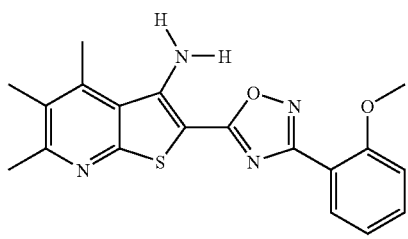

20

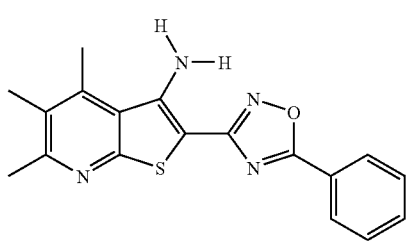

21

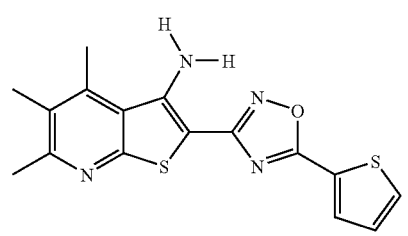

22

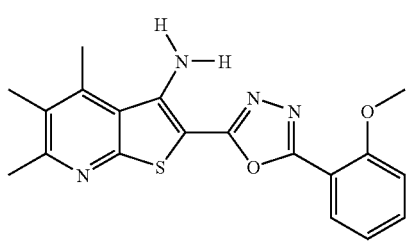

23

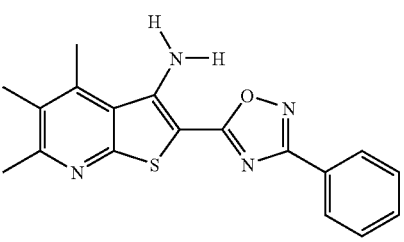

24

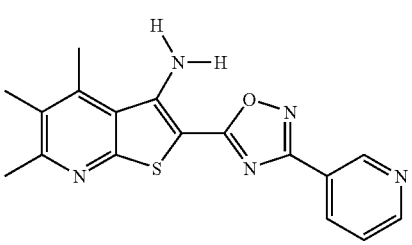

25 or a pharmaceutically acceptable salt thereof.

7. A pharmaceutical composition comprising a compound of claim 1, or a pharmaceutically acceptable salt thereof together with a pharmaceutically acceptable excipient.

8. A pharmaceutical composition comprising a compound of claim 2, or a pharmaceutically acceptable salt thereof, together with a pharmaceutically acceptable excipient.

9. A pharmaceutical composition comprising a compound of claim 6, or a pharmaceutically acceptable salt thereof, together with a pharmaceutically acceptable excipient.

10. A method of treating Hepatitis C viral infection in a subject in need thereof comprising administering an effective amount of a compound of claim 1 to the subject.

11. A method of treating Hepatitis C viral infection in a subject in need thereof comprising administering an effective amount of a compound of claim 2 to the subject.

12. A method of treating Hepatitis C viral infection in a subject in need thereof comprising administering an effective amount of a compound of claim 6 to the subject.

* * * * *

UNITED STATES PATENT AND TRADEMARK OFFICE
CERTIFICATE OF CORRECTION

PATENT NO. : 7,645,881 B2
APPLICATION NO. : 11/180779
DATED : January 12, 2010
INVENTOR(S) : Karp et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 324 days.

Signed and Sealed this

Twenty-eighth Day of December, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,645,881 B2 | Page 1 of 1 |
| APPLICATION NO. | : 11/180779 | |
| DATED | : January 12, 2010 | |
| INVENTOR(S) | : Karp et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 324 days.

Column 7, line 47, replace "COORX" with --$COOR_x$--;

Column 48, line 46, replace "acceptable" with --acceptable excipient--;

Column 148, line 27, replace "COOR5" with --$COOR_x$--;

Column 149, line 34, replace "a $OCOR_f$" with --a $COR_f$--;

Column 321, line 37, replace "was added potionwise" with --was added portionwise--;

Signed and Sealed this
Fourth Day of January, 2011

David J. Kappos
*Director of the United States Patent and Trademark Office*